United States Patent
Ausubel et al.

(10) Patent No.: US 11,690,824 B2
(45) Date of Patent: Jul. 4, 2023

(54) ANTIBACTERIAL COMPOUNDS

(71) Applicants: THE GENERAL HOSPITAL CORPORATION, Boston, MA (US); RHODE ISLAND HOSPITAL, A LIFESPAN-PARTNER, Providence, RI (US); EMORY UNIVERSITY, Atlanta, GA (US)

(72) Inventors: Frederick M. Ausubel, Newton, MA (US); Wooseong Kim, Providence, RI (US); Eleftherios Mylonakis, Providence, RI (US); William M. Wuest, Atlanta, GA (US)

(73) Assignees: The General Hospital Corporation, Boston, MA (US); Rhode Island Hospital, A Lifespan-Partner, Providence, RI (US); Emory University, Atlanta, GA (US)

( * ) Notice: Subject to any disclaimer, the term of this patent is extended or adjusted under 35 U.S.C. 154(b) by 0 days.

(21) Appl. No.: 17/046,463

(22) PCT Filed: Apr. 10, 2019

(86) PCT No.: PCT/US2019/026799
§ 371 (c)(1),
(2) Date: Oct. 9, 2020

(87) PCT Pub. No.: WO2019/199979
PCT Pub. Date: Oct. 17, 2019

(65) Prior Publication Data
US 2021/0251958 A1    Aug. 19, 2021

Related U.S. Application Data

(60) Provisional application No. 62/720,880, filed on Aug. 21, 2018, provisional application No. 62/655,362, filed on Apr. 10, 2018.

(51) Int. Cl.
A61K 31/404 (2006.01)
C07D 209/36 (2006.01)
(Continued)

(52) U.S. Cl.
CPC ............ *A61K 31/404* (2013.01); *A61K 31/41* (2013.01); *A61K 31/4439* (2013.01);
(Continued)

(58) Field of Classification Search
None
See application file for complete search history.

(56) References Cited

U.S. PATENT DOCUMENTS 3,634,402 A    1/1972   Yamamoto et al.
3,781,299 A   12/1973   Yamamoto et al.
(Continued)

FOREIGN PATENT DOCUMENTS

CA    1334415    2/1995
EP     275667    7/1988
(Continued)

OTHER PUBLICATIONS

Helaine et al., "Bacterial persisters: formation, eradication, and experimental systems" Trends in Microbiology vol. 22 no. 7 pp. 417-424 http://dx.doi.org/10.1016/j.tim.2014.03.008 (Year: 2014).*

(Continued)

*Primary Examiner* — Eric Olson
(74) *Attorney, Agent, or Firm* — Fish & Richardson P.C.

(57) ABSTRACT

The present application provides compounds of formula: Methods of using these compounds for killing bacterial growth and treating bacterial infections are also provided.

(Continued)

US 11,690,824 B2
Page 2

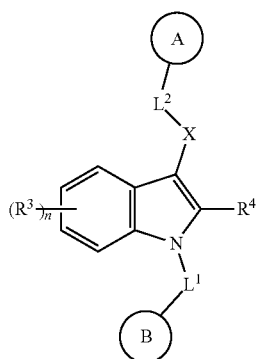

51 Claims, 45 Drawing Sheets

(51) Int. Cl.
| | |
|---|---|
| C07D 209/42 | (2006.01) |
| A61P 31/04 | (2006.01) |
| A61K 31/41 | (2006.01) |
| A61K 31/4439 | (2006.01) |
| A61K 31/7036 | (2006.01) |
| C07D 401/06 | (2006.01) |
| C07D 403/04 | (2006.01) |
| C07D 405/06 | (2006.01) |

(52) U.S. Cl.
CPC .......... *A61K 31/7036* (2013.01); *A61P 31/04* (2018.01); *C07D 209/36* (2013.01); *C07D 209/42* (2013.01); *C07D 401/06* (2013.01); *C07D 403/04* (2013.01); *C07D 405/06* (2013.01)

(56) References Cited

U.S. PATENT DOCUMENTS

| | | | |
|---|---|---|---|
| 4,013,641 | A | 3/1977 | Brown |
| 4,066,660 | A | 1/1978 | Brown |
| 4,117,129 | A | 9/1978 | Brown |
| 4,179,513 | A | 12/1979 | Brown |
| 4,675,332 | A | 6/1987 | Connor et al. |
| 4,814,345 | A | 3/1989 | Ohlendorf et al. |
| 5,081,138 | A | 1/1992 | Gillard et al. |
| 5,225,421 | A | 7/1993 | Gillard et al. |
| 5,399,699 | A | 3/1995 | Kolasa et al. |
| 5,482,960 | A | 1/1996 | Berryman et al. |
| 5,527,819 | A | 6/1996 | Williams et al. |
| 6,436,965 | B1 | 8/2002 | Labelle et al. |
| 6,469,046 | B1 | 10/2002 | Daines et al. |
| 6,787,651 | B2 | 9/2004 | Stolle et al. |
| 6,833,387 | B1 | 12/2004 | Fanil |
| 7,696,240 | B2 | 4/2010 | Banner et al. |
| 8,097,623 | B2 | 1/2012 | Pelcman et al. |
| 9,000,025 | B2 | 4/2015 | Roppe et al. |
| 9,849,109 | B2 | 12/2017 | Roppe et al. |
| 2002/0068756 | A1 | 6/2002 | Labelle et al. |
| 2003/0032581 | A1 | 2/2003 | Berger et al. |
| 2003/0232787 | A1 | 12/2003 | Dooley |
| 2004/0242459 | A1 | 12/2004 | Forrest et al. |
| 2010/0197687 | A1 | 8/2010 | Pelcman et al. |
| 2010/0240642 | A1 | 9/2010 | Oplinger et al. |
| 2011/0152225 | A1* | 6/2011 | Baroni ............. A61K 31/357 |
| | | | 514/342 |
| 2011/0190242 | A1 | 8/2011 | Gjorstrup |
| 2013/0019326 | A1* | 1/2013 | Spiegelman ......... C12Q 1/6883 |
| | | | 435/7.1 |
| 2013/0150326 | A1 | 6/2013 | Roppe et al. |
| 2013/0316989 | A1 | 11/2013 | Gjorstrup |
| 2015/0328198 | A1* | 11/2015 | Richardson ........ A61K 31/4439 |
| | | | 514/342 |
| 2018/0016314 | A1 | 1/2018 | Harley et al. |

FOREIGN PATENT DOCUMENTS

| | | |
|---|---|---|
| JP | 5393119 | 1/2014 |
| KR | 10-1343668 | 12/2013 |
| KR | 10-1350077 | 1/2014 |
| WO | WO 1993/005020 | 3/1993 |
| WO | WO 2001/091736 | 12/2001 |
| WO | WO 2011/091134 | 7/2011 |
| WO | WO 2012/081893 | 6/2012 |
| WO | WO 2016/029027 | 2/2016 |
| WO | WO 2017/155857 | 9/2017 |

OTHER PUBLICATIONS

Hansen et al., "One-day Workflow Scheme for Bacterial Pathogen Detection and Antimicrobial Resistance Testing from Blood Cultures" Journal of Visualized Experiments vol. 65 e3254 doi:10.3791/3254 https://www.jove.com/video/3254 (Year: 2012).*
DuPont, Herbert, "Approach to the patient with infectious colitis" Current Opinion in Gastroenterology vol. 28 pp. 39-408 DOI: 10.1097/MOG.0b013e32834d3208 (Year: 2012).*
Allison et al., "Metabolite-enabled eradication of bacterial persisters by aminoglycosides," Nature, May 2011; 473(7346):216-220.
Ambroggio et al., "Direct visualization of membrane leakage induced by the antibiotic peptides: maculatin, citropin, andaurein," Biophys. J., Sep. 2005, 89(3):1874-1881.
Anézo et al., "Methodological issues in lipid bilayer simulations," J. Phys. Chem. B, 2003, 107(35):9424-9433.
Baba et al., "Genome and virulence determinants of high virulence community-acquired MRSA," Lancet, May 2002, 359(9320):1819-1827.
Baba et al., "Genome sequence of *Staphylococcus aureus* strain Newman and comparative analysis of Staphylococcal genomes: polymorphism and evolution of two major pathogenicity islands," J Bacteriol., Jan. 2008, 190(1):300-310.
Beloin et al., "Novel approaches to combat bacterial biofilms," Curr Opin Pharmacol, 2014, 18:61-68.
Bennasar et al., "Regioselective Intramolecular Reactions of 2-Indolylacyl Radicals with Pyridines: A Direct Synthetic Entry to Ellipticine Quinones," J. Org. Chem., 2005, 70(22):9077-9080.
Berger et al., "Distinct properties and advantages of a novel peroxisome proliferator-activated protein [gamma] selective modulator," Mol. Endocrinol., Apr. 2003, 17(4):662-676.
Berger et al., "Molecular dynamics simulations of a fluid bilayer of dipalmitoylphosphatidylcholine at full hydration, constant pressure, and constant temperature," Biophys. J., 1997, 72(5):2002-2013.
Bhagwat et al., "Thromboxane receptor antagonism combined with thromboxane synthase inhibition. 8. N-Alkylation of indole ring using Mitsunobu reaction," Tetrahedron Letters, 1994, 35(12):1847-50.
Böttcher et al., "Indoxylic Acid Esters as Convenient Intermediates Towards Indoxyl Glycosides," Eur. J. Org. Chem., 2014, 564-574.
Bruemmer et al., "Peroxisome proliferator-activated receptor γ inhibits expression of minichromosome maintenance proteins in vascular smooth muscle cells," Molecular Endocrinology, 2003, 17(6):1005-1018.
Bruemmer et el., "A non-thiazolidinedione partial peroxisome proliferator-activated receptor γ ligand inhibits vascular smooth muscle cell growth," European Journal of Pharmacology, 2003, 466(3):225-234.
Bruning et al., "Partial Agonists Activate PPARγ Using a Helix 12 Independent Mechanism," Structure, 2007, 15(10), 1258-1271.
Buchholtz et al., "Severity of gentamicin's nephrotoxic effect on patients with infective endocarditis: a prospective observational cohort study of 373 patients," Clin, Infect. Dis., 2009, 48(1):65-71.

(56) References Cited

OTHER PUBLICATIONS

Bunker et al., "1-Benzyl-3-thioaryl-2-carboxyindoles as potent non-peptide endothelin antagonists," Bioorganic & Medicinal Chemistiy Letters, 1996, 6(12):1367-1370.
Carias et al., "Genetic linkage and cotransfer of a novel, vanB-containing transposon (Tn5382) and a low-affinity penicillin-binding protein 5 gene in a clinical vancomycin-resistant Enterococcus faecium isolate," J Bacterial., Sep. 1998, 180(17):4426-4434.
CAS No. 118414-59-8, "nTZDpa," Sigma Aldrich, retrieved on Dec. 31, 2020, retrieved from URL <https://www.sigmaaldrich.com/catalog/product/sigma/sm10616?lang=en&region=US>, 2 pages.
CAS No. 1332595-10-4, "1H-Indole-2-carboxylic acid, 5-bromo-1-[(4-bromophenyl)methyl]-3-(phenylthio)," STNEasy, retrieved on Feb. 23, 2021, 1 page.
CAS No. 1348104-31-3, "1H-Indole-2-carboxylic acid, 5-chloro-1-(4-chlorophenyl)-3-(phenylthio)," STNEasy, retrieved on Feb. 23, 2021, 1 page.
CAS No. 1349510-85-5, "1H-Indole-2-carboxamide, 5-chloro-1-(2-furanylmethyl)-3-(phenylthio)," STNEasy, retrieved on Feb. 23, 2021, 1 page.
CAS No. 1359982-43-6, "1H-Indole-2-carboxylic acid, 3-[(3-bromophenyl)thio]-6-chloro-1-(phenylmethyl)-, ethyl ester," STNEasy, retrieved on Feb. 23, 2021, 1 page.
CAS No. 1359982-44-7, "1H-Indole-2-carboxylic acid, 3-[(3-bromophenyl)thio]-6-chloro-1-(phenylmethyl)," STNEasy, retrieved on Feb. 23, 2021, 1 page.
CAS No. 148900-63-4, "1H-Indole-2-carboxamide, 5-chloro-3-(phenylthio)-1-(3-pyridinylmethyl)," STNEasy, retrieved on Feb. 23, 2021, 1 page.
CAS No. 155697-78-2, "1H-Indole-2-carboxylic acid, 3-[(4-chlorophenyl)methyl]-5-fluoro-1-[4-(3-pyridinyl)butyl]-, ethyl ester," STNEasy, retrieved on Feb. 23, 2021, 1 page.
CAS No. 359003-51-3, "1H-Indole-2-carboxylic acid, 5-bromo-1-[(4-fluorophenyl)methyl]-3-(phenylmethoxy)-, ethyl ester," STNEasy, retrieved on Feb. 23, 2021, 1 page.
CAS No. 36100-86-4, "1H-Indole-2-carboxylic acid, 5-chloro-1-(cyclopropylmethyl)-3-(phenylmethyl)-, ethyl ester," STNEasy, retrieved on Feb. 23, 2021, 1 page.
CAS No. 36100-87-5, "1H-Indole-2-carboxylic acid, 5-chloro-1-(cyclopropylmethyl)-3-(phenylmethyl)," STNEasy, retrieved on Feb. 23, 2021, 1 page.
CAS No. 36100-90-0, "1H-Indole-2-carboxamide, 5-chloro-1-(cyclopropylmethyl)-3-(phenylmethyl)," STNEasy, retrieved on Feb. 23, 2021, 1 page.
CAS No. 870459-68-0, "1H-Indole-2-carboxylic acid, 6-chloro-1-[4-(1,1-dimethylethyl)phenyl]-3-[3-(trifluoromethyl)phenoxy]," STNEasy, retrieved on Feb. 23, 2021, 1 page.
CAS No. 870459-69-1, "1H-Indole-2-carboxylic acid, 6-chloro-1-[4-(1,1-dimethylethyl)phenyl]-3-[3-(1-methylethyl)phenoxy]," STNEasy, retrieved on Feb. 23, 2021, 1 page.
CAS No. 870459-70-4, "1H-Indole-2-carboxylic acid, 5-chloro-1-[4-(1,1-dimethylethyl)phenyl]-3-[3-(trifluoromethyl)phenoxy]," STNEasy, retrieved on Feb. 23, 2021, 1 page.
CAS No. 870459-71-5, "1H-Indole-2-carboxylic acid, 3-[3,5-bis(trifluoromethyl)phenoxy]-5-chloro-1-[4-(1,1-dimethylethyl)phenyl]," STNEasy, retrieved on Feb. 23, 2021, 1 page.
CAS No. 870459-72-6, "1H-Indole-2-carboxylic acid, 5-chloro-3-[4-chloro-3-(trifluoromethyl)phenoxy]-1-[4-(1,1-dimethylethyl)phenyl]," STNEasy, retrieved on Feb. 23, 2021, 1 page.
CAS No. 870459-75-9, "1H-Indole-2-carboxylic acid, 1-[4-(1,1-dimethylethyl)phenyl]-5-hydroxy-3-[3-(trifluoromethyl)phenoxy]-, ethyl ester," STNEasy, retrieved on Feb. 23, 2021, 1 page.
CAS No. 870459-77-1, "1H-Indole-2-carboxylic acid, 1-[4-(1,1-dimethylethyl)phenyl]-5-hydroxy-3-[3-(trifluoromethyl)phenoxy]," STNEasy, retrieved on Feb. 23, 2021, 1 page.
CAS No. 911827-00-4, "1H-Indole-2-carboxylic acid, 6-chloro-1-[4-(1,1-dimethylethyl)phenyl]-3-[3-(trifluoromethyl)phenoxy]-, ethyl ester," STNEasy, retrieved on Feb. 23, 2021, 1 page.
CAS No. 911827-03-7, "1H-Indole-2-carboxylic acid, 6-chloro-1-[4-(1,1-dimethylethyl)phenyl]-3-[3-(1-methylethyl)phenoxy]-, ethyl ester," STNEasy, retrieved on Feb. 23, 2021, 1 page.
CAS No. 911828-97-2, "1H-Indole-2-carboxylic acid, 5-chloro-1-[4-(1,1-dimethylethyl)phenyl]-3-[3-(trifluoromethyl)phenoxy]-, ethyl ester," STNEasy, retrieved on Feb. 23, 2021, 1 page.
CAS No. 911829-13-5, "1H-Indole-2-carboxylic acid, 3-[3,5-bis(trifluoromethyl)phenoxy]-5-chloro-1-[4-(1,1-dimethylethyl)phenyl]-, ethyl ester," STNEasy, retrieved on Feb. 23, 2021, 1 page.
CAS No. 911829-14-6, "1H-Indole-2-carboxylic acid, 5-chloro-3-[4-chloro-3-(trifluoromethyl)phenoxy]-1-[4-(1,1-dimethylethyl)phenyl]-, ethyl ester," STNEasy, retrieved on Feb. 23, 2021, 1 page.
CAS No. 958868-85-4, "1H-Indole-2-carboxylic acid, 5-chloro-1-(phenylmethyl)-3-(phenylthio)," STNEasy, retrieved on Feb. 23, 2021, 1 page.
CAS No. 958868-86-5, "1H-Indole-2-carboxylic acid, 5-chloro-1-[(3-methoxyphenyl)methyl]-3-(phenylthio)," STNEasy, retrieved on Feb. 23, 2021, 1 page.
Cassat et al., "Investigation of biofilm formation in clinical isolates of *Staphylococcus aureus*," Methods Mol. Biol., 2007; 391(Chapter 10):127-144.
Chalmers et al., "Probing Protein Ligand Interactions by Automated Hydrogen/Deuterium Exchange Mass Spectrometry," Analytical Chemistiy, 2006, 78(4):1005-1014.
Chambers et al., "Waves of resistance: *Staphylococcus aureus* in the antibiotic era," Nat. Rev. Microbiol., Sep. 2009, 7(9):629-641.
Chen et al., "Interaction of daptomycin with lipid bilayers: lipid extracting effect," Biochem., 2014, 53(33):5384-5392.
Cheng et al, "Opioid ligands with mixed properties from substituted enantiomeric N-phenethyl-5-phenylmorphans. Synthesis of a T-agonist L-antagonist and L-inverse agonists," Org. Biomol. Chem., 2007, 5:1177-1190.
Chong et al., "Persistent *Staphylococcus aureus* bacteremia: a prospective analysis of risk factors, outcomes, and microbiologic and genotypic characteristics of isolates," Medicine, Mar. 2013, 92(2):98-108.
Chuang et al., "Synthesis and Cyclic Voltammetry Studies of Copper Complexes of Bromo- and Alkoxyphenyl-Substituted Derivatives of Tris(2-pyridylmethyl)amine: Influence of Cation-Alkoxy Interactions on Copper Redox Potentials," Inorg. Chem., 1997, 36:1967-1972.
Cieplak et al., "Molecular mechanical models for organic and biological systems going beyond the atom centered two body additive approximation: aqueous solution free energies of methanol and N-methyl acetamide, nucleic acid base, and amide hydrogen bonding and chloroform/water partition coefficients of the nucleic acid bases," J. Comput. Chem., 2001, 22(10):1048-1057.
Clinical and Laboratory Standards Institute, "Methods for dilution antimicrobial susceptibility tests for bacteria that grow aerobically; approved standard-ninth edition," CLSI document M07-A9, Jan. 2012, 32(2):1-88.
Conery et al., "High-throughput screening for novel anti-infectives using a C. elegans pathogenesis model," Curr. Protoc. Chem. Biol., 2014, 6(1):25-37.
Conlon et al., "Activated ClpP kills persisters and eradicates a chronic biofilm infection," Nature, Nov. 2013, 503(7476):365-370.
Conlon et al., "Persister formation in *Staphylococcus aureus* is associated with ATP depletion," Nat. Microbiol., May 2016, 1(5):16051.
Cosgrove et al., "Initial low-dose gentamicin for *Staphylococcus aureus* bacteremia and endocarditis is nephrotoxic," Clin. Infect. Dis., 2009, 48(6):713-721.
Creighton et al., "Three-dimensional graphene-based microbarriers for controlling release and reactivity in colloidal liquid phases," ACS Nano, 2016, 10(2):2268-2276.
Dimova et al., "A practical guide to giant vesicles. Probing the membrane nanoregime via optical microscopy," J Phys Condens Matter, 2006, 18(28):S1151-S1176.
Dropinski et al., "Synthesis and biological activities of novel arylindole-2-carboxylic acid analogs as PPARγ partial agonists," Bioorganic & Medicinal Chemistiy Letters, 2005, 15(22):5035-5038.

(56) References Cited

OTHER PUBLICATIONS

Einstein et al., "The differential interactions of peroxisome proliferator-activated receptor γ ligands with Tyr473 is a physical basis for their unique biological activities," Mol. Pharmacol., 2008, 73(1):62-74.
Elgharably et al., "Current hypotheses in cardiac surgery: biofilm in infective endocarditis," Semin. Thoracic Surg., 2016, 28(1):56-59.
Fey et al., "A genetic resource for rapid and comprehensive phenotype screening of nonessential *Staphylococcus aureus* genes," Mbio, 2013, 4(1):e00537-12, 8 pages.
Friedman et al., "Genetic changes that correlate with reduced susceptibility to daptomycin in *Staphylococcus aureus*," Antimicrob. Agents Chemother., Jun. 2006, 50(6):2137-2145.
Friedrich et al., "Antibacterial action of structurally diverse cationic peptides on Gram-positive bacteria," Antimicrob. Agents Chemother., Aug. 2000, 44(8):2086-2092.
Friedrich et al., "Structure and mechanism of action of an indolicidin peptide derivative with improved activity against gram-positive bacteria," J. Biol. Chem., Jun. 2001, 276(26):24015-24022.
Ganewatta et al., "Bio-inspired resin acid-derived materials as anti-bacterial resistance agents with unexpected activities," Chem. Sci., 2014, 5(5):2011-2016.
Garcia-Solache et al., "Genome sequence of the multiantibiotic-resistant Enterococcus faecium Strain C68 and insights on the pLRM23 colonization plasmid," Genome Announc., 2016, 4(3):e01719-15.
Garcia-Vallve et al., "Peroxisome Proliferator-Activated Receptor γ (PPARγ) and Ligand Choreography: Newcomers Take the Stage," Journal of Medicinal Chemistry, 2015, 58(14):5381-5394.
Garsin et al., "A simple model host for identifying Gram-positive virulence factors," Proc. Natl. Acad. Sci. U.S.A., Sep. 2001, 98(19):10892-10897.
Hamuro et al., "Hydrogen/deuterium-exchange (H/D-Ex) of PPARγ LBD in the presence of various modulators," Protein Science, 2006, 15(8):1883-1892.
Helaine et al., "Bacterial persisters: formation, eradication, and experimental systems," Trends Microbiol., 2014, 22(7):417-424.
Hess et al., "GROMACS 4: algorithms for highly efficient, load-balanced, and scalable molecular simulation," J Chem. Theory Comput., 2008, 4(3):435-447.
Hub et al., "g_wham—A free weighted histogram analysis implementation including robust error and autocorrelation estimates," J. Chem. Theory Comput., 2010, 6(12):3713-3720.
Hurdle et al., "Targeting bacterial membrane function: an underexploited mechanism for treating persistent infections," Nat. Rev. Microbiol., Jan. 2011, 9(1):62-75.
Isralewitz et al., "Steered molecular dynamics and mechanical functions of proteins," Curr. Opin. Struct. Biol., 2001, 11(2):224-230.
Joseph et al., "Synthesis of substituted indolo[1,2-a]quinoxalines," Synthetic Communications, 2003, 33(5):851-862.
Joshi et al., "N-terminal aromatic tag induced self-assembly of tryptophan-arginine rich ultra short sequences and their potent antibacterial activity," RSC Advances, 2015, 5(84):68610-68620.
Kaserer et al., "Evaluation of selected 3D virtual screening tools for the prospective identification of peroxisome proliferator-activated receptor (PPAR) γ partial agonists," European Journal of Medicinal Chemistiy 2016, 124:49-62.
Kaushik et al., "Biomedical Importance of indoles," Molecules, 2013, 18(6):6620-6662.
Kemnitz et al., "'Amide Resonance' correlates with a breadth of C-N rotation barriers," J Am Chem Soc, 2007, 129(9):2521-2528.
Keren et al., "Persister cells and tolerance to antimicrobials," FEMS Microbial. Lett., 2004, 230(1):13-18.
Khatib et al., "Persistent *Staphylococcus aureus* bacteremia: incidence and outcome trends over time," Scand. J. Infect. Dis., 2009, 41(1):4-9.
Kim et al., "A new class of synthetic retinoid antibiotics effective against bacterial persisters," Nature, 2018, 556(7699):103-107.
Kim et al., "An update on the use of C. elegans for preclinical drug discovery: screening and identifying anti-infective drugs," Expert Opin Drug Discov, 2017, 12(6):625-633.
Kim et al., "Discovery and Optimization of nTZDpa as an Antibiotic Effective Against Bacterial Persisters," ACS Infect. Dis., 2018, 4:1540-1545.
Kim et al., "Identification of an antimicrobial agent effective against methicillin-resistant *Staphylococcus aureus* persisters using a fluorescence-based screening strategy," PLoS One, Jun. 2015, 10(6):e0127640, 15 pages.
Kim et al., "NH125 kills methicillin-resistant *Staphylococcus aureus* persisters by lipid bilayer disruption," Future Med. Chem., Mar. 2016, 8(3):257-269.
Kim et al., "PPARγ agonists induce adipocyte differentiation by modulating the expression of Lipin-1, which acts as a PPARγ phosphatase," International Journal of Biochemistry & Cell Biology, 2016, 81(A):57-66.
Koenig et al., "A ligand-free, copper-catalyzed cascade sequence to indole-2-carboxylic esters," Tetrahedron Lett., Dec. 2010, 51(50):6549-6551.
Kofink et al., "Synthesis of functionalized diarylmethanes via a copper-catalyzed cross-coupling of arylmagnesium reagents withbenzylic phosphates," Organic Letters, 2006, 8(18):4121-4124.
Kogan, "3-Indolylphenylacetonitriles," Chem Heterocycl Compd., 1978, 14(11):1204-1208.
Kolasa et al., "Synthesis of indolylalkoxyiminoalkylcarboxylates as leukotriene biosynthesis inhibitors," Bioorganic & Medicinal Chemistiy, 1997, 5(3):507-514.
Kumar et al., "The weighted histogram analysis method for free-energy calculations on biomolecules. I. The method," J. Comput. Chem., 1992, 13(8):1011-1021.
La Cour Jansen et al., "Modeling the amide I bands of small peptides," J Chem Phys, 2006, 125(4):044312.
Lee et al., "Process of inducing pores in membranes by melittin," Proc. Natl. Acad. Sci. U.S.A., Aug. 2013, 110(35):14243-14248.
Lee et al., "Transmembrane pores formed by human antimicrobial peptide LL-37," Biophys. J., Apr. 2011, 100(7):1688-1696.
Lehar et al., "Novel antibody-antibiotic conjugate eliminates intracellular *S. aureus*," Nature, 2015, 527(7578):323-328.
Lew et al., "Osteomyelitis," The Lancet, Jul. 2004, 364(9431):369-379.
Lewis, "Persister cells," Annu. Rev. Microbial., 2010, 64(1):357-372.
Lewis, "Platforms for antibiotic discovery," Nat. Rev. Drug Discov., May 2013, 12(5):371-387.
Li et al., "Graphene microsheets enter cells through spontaneous membrane penetration at edge asperities and comer sites," Proc. Natl. Acad. Sci. U.S.A., Jul. 2013, 110(30):12295-12300.
Liu et al., "Clinical practice guidelines by the Infectious Diseases Society of America or the treatment of methicillin-resistant *Staphylococcus aureus* infections in adults and children," Clin. Infect. Dis., Feb. 2011, 52(3):e18-e55.
Mahmoud et al., "Structure- Activity Relationship Study of Indole-2-carboxamides Identifies a Potent Allosteric Modulator for the Cannabinoid Receptor 1 (CB1)," J. Med. Chem., Sep. 2013, 56(20):7965-7975.
Malde et al., "An automated force field topology builder (ATB) and repository: version 1.0," J. Chem. Theory Comput., 2011, 7(12):4026-4037.
Meinke et al., "Nuclear Hormone Receptor Modulators for the Treatment of Diabetes and Dyslipidemia," Annual Reports in Medicinal Chemistry, 2007, 41:99-126.
Miki et al., "Synthesis of 5H-benzo[b]carbazole-6,11-diones frombenzoylindolecarboxylie acids," Heterocycles, 2002, 57(9):1645-1651.
Miki et al., "Synthesis of naphth[3,2,1-cd]indole by Heck cyclization of 2-methoxycarbonyl-3-benzoylindoles," Heterocycles, 2003, 60(9):2095-2101.
Milner-White, "The partial charge of the nitrogen atom in peptide bonds," Protein Sci., 1997, 6(11):2477-2482.
Moy et al., "High-throughput screen for novel antimicrobials using a whole animal infection model," ACS Chem. Biol., Jul. 2009, 4(7):527-533.

(56) References Cited

OTHER PUBLICATIONS

Moy et al., "Identification of novel antimicrobials using a live-animal infection model," Proc. Natl. Acad. Sci. U.S.A., Jul. 2006, 103(27):10414-10419.
Ngemmeesri et al., "Formal synthesis of (±)-cladoniamide G," Tetrahedron Lett., Feb. 2014, 55(9):1621-1624.
Odds, "Synergy, antagonism, and what the chequerboard puts between them," J. Antimicrob. Chemother., Jul. 2003, 52(1):1.
Oostenbrink et al., "A biomolecular force field based on the free enthalpy of hydration and salvation: The GROMOS force-field parameter sets 53A5 and 53A6," J. Comput. Chem., 2004, 25(13):1656-1676.
PCT International Preliminary Report on Patentability in International Appln. No. PCT/US2019/026799, dated Oct. 22, 2020, 8 pages.
PCT International Search Report and Written Opinion in International Appln. No. PCT/US2019/026799, dated Aug. 20, 2019, 12 pages.
Petersen et al., ""Pharmacophore-driven identification of PPARγ agonists from natural sources,"" J. Comput. Aided Mol. Des., 2011, 25(2):107-116.
Racusen et al., "Cell lines with extended in vitro growth potential from human renal proximal tubule: characterization, response to inducers, and comparison with established cell lines," J. Lab. Clin. Med., 1997, 129(3):318-329.
Rahme et al., "Common virulence factors for bacterial pathogenicity in plants and animals," Science, Jun. 1995, 268(5219):1899-1902.
Rajamuthiah et al., "A defensin from the model beetle *Tribolium castaneum* acts synergistically with telavancin and daptomycin against multidrug resistant *Staphylococcus aureus*," PLoS One, Jun. 2015, 10(6):e0128576, 14 pages.
Rajamuthiah et al., "Whole animal automated platform for drug discovery against multi-drug resistant *Staphylococcus aureus*," PLoS One, Feb. 2014, 9(2):e89189, 11 pages.
Rice et al., "Enterococcus faecium low-affinity pbp5 is a transferable determinant," Antimicrob. Agents Chemother., Dec. 2005, 49(12):5007-5012.
Rizzo et al., "OPLS all-atom model for amines: resolution of the amine hydration problem," J. Am. Chem. Soc., 1999, 121(20):4827-4836.
Roth et al., "Bacterial viability and antibiotic susceptibility testing with SYTOX green nucleic acid stain," Appl. Environ. Microbial., Jun. 1997, 63(6):2421-2431.
Schmid et al., "Definition and testing of the GROMOS force-field versions 54A7 and 54B7," Eur. Biophys. J, 2011, 40(7):843-856.
Sharma et al., "Biological importance of the indole nucleus in recent years: A comprehensive review," J. Heterocyclic Chem., 2010, 47(3):491-502.
Shi et al., "Synthesis and preliminary cytotoxic evaluation of substituted indoles as potential anticancer agents," Chinese Chemical Letters, 2007, 18(8):899-901.
Shimoda et al., "Morphology of defensin-treated *Staphylococcus aureus*," Infect. Immun., Aug. 1995, 63(8):2886-2891.
Shvedov et al., "Synthesis of derivatives of 3-benzylindole," Pharm Chem J., 1969, 3:378-381.
Smith et al., "New insights into Acinetobacter baumannii pathogenesis revealed by high-density pyrosequencing and transposon mutagenesis," Genes Dev., 2007, 21(5):601-614.
Sudbrack et al., "Observing the solubilization of lipid bilayers by detergents with optical microscopy of GUVs," J. Phys. Chem. B, 2011, 115(2):269-277.
Sudhakara et al., "Efficient Synthesis of 2-Ethoxycarbonyl Indoles," Synth. Commun., 2009, 39(14):2506-2515.
Tamba et al., "Single giant unilamellar vesicle method reveals effect of antimicrobial peptide magainin 2 on membrane permeability," Biochemistry, 2005, 44(48):15823-15833.
Temple et al., Development of a Series of (1-Benzyl-3-(6-methoxypyrimidin-3-yl)-5-(trifluoromethoxy)-1H-indol-2-yl)methanols as Selective Protease Activated Receptor 4 (PAR4) Antagonists with in Vivo Utility and Activity Against γ-Thrombin, J. Med. Chem., Aug. 2016, 59(16):7690-7695.
Thorisdottir et al., "IS6770, an enterococcal insertion-like sequence useful for determining the clonal relationship of clinical enterococcal isolates," J Infect. Dis., 1994, 170(6):1539-1548.
Tong et al., "*Staphylococcus aureus* infections: epidemiology, pathophysiology, clinical manifestations, and management," Clin. Microbiol. Rev., Jul. 2015, 28(3):603-661.
Tsakovska et al., "Molecular modelling study of the PPARγ receptor in relation to the mode of action/adverse outcome pathway framework for liver steatosis," Int. J. Mol. Sci., 2014, 15(5):7651-7666.
Tu et al., "Destructive extraction of phospholipids from *Escherichia coli* membranes by graphene nanosheets," Nat. Nanotechnol., Aug. 2013, 8(8):594-601.
Unangst et al., "Novel indolecarboxamidotetrazoles as potential antiallergy agents," J. Med. Chem., 1989, 32(6): 1360-1366.
Unangst et al., "Synthesis of novel 1-phenyl-1H-indole-2-carboxylic acids. II. Preparation of 3-dialkylamino, 3-alkylthio, 3-alkylsulfinyl, and 3-alkylsulfonyl derivatives," Journal of Heterocyclic Chemistiy, 1987, 24(3):817-20.
Van Bambeke et al., "The bacterial envelope as a target for novel anti-MRSA antibiotics," Trends Pharmacol. Sci., Februaiy 2008, 29(3)424-134.
Vanommeslaeghe et al., "CHARMM general force field: A force field for drug-like molecules compatible with the CHARMM all-atom additive biological force fields," J. Comput. Chem., Mar. 2010, 31(4):671-690.
Vidovic et al., "A Combined Ligand- and Structure-Based Virtual Screening Protocol Identifies Submicromolar PPARy Partial Agonists," ChemMedChem, 2011, 6(1):94-103.
Wang et al., "Cellular entry of graphene nanosheets: the role of shickness, oxidation and surface adsorption," RSC Advances, 2013, 3(36): 15776-15782.
Wang et al., "Development and testing of a general amber force field," J. Comput. Chem., 2004, 25(9):1157-1174.
Wang et al., "Direct visualization of bactericidal action of cationic conjugated polyelectrolytes and oligomers," Langmuir, 2012, 28(1):65-70.
Watt et al., "Generalized concentration addition modeling predicts mixture effects of environmental PPARy agonists," Toxicological Sciences, 2016, 153(1): 18-27.
Werdan et al., "Mechanisms of infective endocarditis: pathogen-host interaction and risk states," Nat. Rev. Cardiol., Jan. 2014, 11(1):35-50.
Zhang et al., "A review on recent developments of indole-containing antiviral agents," Eur. J. Med. Chem., 2015, 89:421-441.
Zhu et al., "Nanomechanical mechanism for lipid bilayer damage induced by carbon nanotubes confined in intracellular vesicles," Proc. Natl. Acad. Sci. U.S.A., Nov. 2016, 113(44):12374-12379.
Zielonka et al., "Mitigation of NADPH Oxidase 2 Activity as a Strategy to Inhibit Peroxy nitrite Formation," Journal of Biological Chemistiy, 2016, 291(13):7029-7044.
Access.FDA.gov [online], "Highlights of Prescribing Information: ACTOS (pioglitazone hydrochloride) tablets for oral use," Jul. 2011, retrieved on Jun. 6, 2022, retrieved from URL<https://www.accessdata.fda.gov/drugsatfda_docs/label/2011/021073s043s0441b1.pdf,> 43 pages.
Access.FDA.gov [online], "Highlights of Prescribing Information: AVANDIA (rosiglitazone maleate) Tablets," 2007, retrieved on Jun. 6, 2022, retrieved from URL<https://www.accessdata.fda.gov/drugsatfda_docs/label/2007/021071s0311b1.pdf>, 42 pages.
Cir.Nii.Ac.jp [online], "Thermodynamic analysis of PPARγ-ligand interaction," 2010, retrieved on Jun. 7, 2022, retrieved from URL<https://cir.nii.ac.jp/crid/1570572700880716800,> 3 pages.
ClinicalTrials.gov [online], "An Evaluation of an Oral Antidiabetic Agent for the Treatment of Type 2 Diabetes," Jul. 2006, retrieved on Jun. 6, 2022, retrieved from URL<https://clinicaltrials.gov/ct2/show/NCT00065312>, 7 pages.
ClinicalTrials.gov [online], "GLAD: Dose-Finding, Efficacy, and Safety of AZ 242 (Tesaglitazar) in Subjects With Type 2 Diabetes," Jul. 2006, retrieved on Jun. 6, 2022, retrieved from URL<https://clinicaltrials.gov/ct2/show/NCT00280865>, 6 pages.

(56) References Cited

OTHER PUBLICATIONS

ClinicalTrials.gov [online], "Study of Muraglitazar Versus Pioglitazone in Type 2 Diabetes," Sep. 2010, retrieved on Jun. 6, 2022, retrieved from URL<https://clinicaltrials.gov/ct2/show/NCT00106808>, 5 pages.
Lipaglyn.com [online], "Product Monograph: Lipaglyn Saroglitazar," Aug. 2013, retrieved on Jun. 6, 2022, retrieved from URL<http://www.lipaglyn.com/downloads/Lipaglyn_Product_Monograph.pdf>, 64 pages.

* cited by examiner

FIG: 34

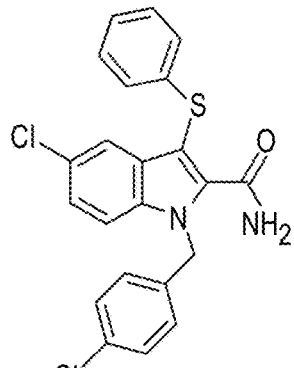
S1, MIC: >64, HC$_{50}$: >64
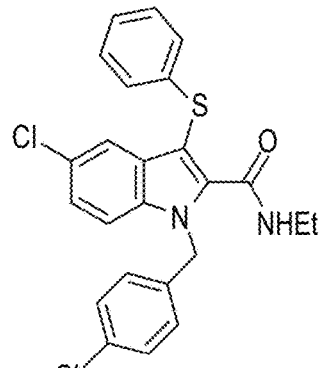
S2, MIC: >64, HC$_{50}$: >64
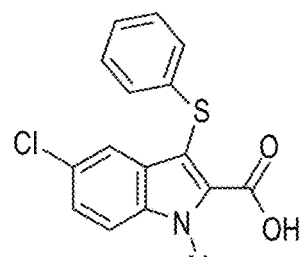
S3, MIC: 64, HC$_{50}$: >64
| # | R$^1$ | R$^2$ | R$^3$ | X | MIC | PKC | HC$_{50}$ | SI |
|---|---|---|---|---|---|---|---|---|
| 1 (nTZDpa) | 4-Cl | H | 5-Cl | S | 4 | 64 | 47 | 11.75 |
| S4 | 4-H | - | - | - | 16 | N.D. | >64 | >16 |
| S5 | 3-Cl | - | - | - | 4 | N.D. | 60 | 15.00 |
| S6 | 4-OMe | - | - | - | 8 | N.D. | >64 | >8 |
| S7 | - | Me | - | - | 4 | N.D. | 31 | 7.75 |
| S8 | - | OMe | - | - | 4 | N.D. | 33 | 8.25 |
| 4 | - | Cl | - | - | 2 | 16 | 34 | 17.00 |
| 5 | - | tBu | - | - | 2 | 8 | 26 | 13.00 |
| S9 | - | - | 6-Cl | - | 4 | N.D. | 50 | 12.50 |
| S10 | - | - | 5-F | - | 8 | N.D. | >64 | >8 |
| S11 | - | - | 5-CF$_3$ | - | 4 | N.D. | 37 | 9.25 |
| S12 | - | - | - | CH$_2$ | 8 | >64 | >64 | >8 |
FIG. 35

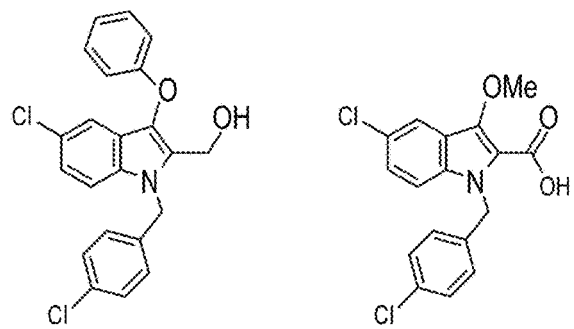
S13: MIC: >64, HC$_{50}$: >64     S14, MIC: 32, HC$_{50}$: >64
S15, MIC: 8, HC$_{50}$: >64     S16, MIC: 8, HC$_{50}$: >64     S17, MIC: 4, HC$_{50}$: >64
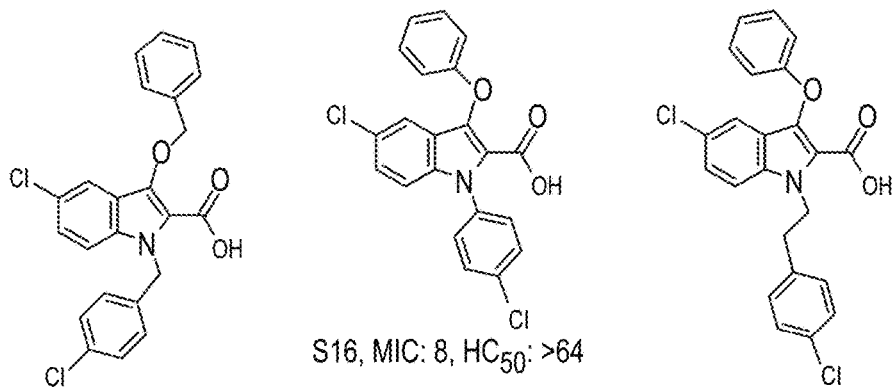
| # | R$^1$ | R$^2$ | R$^3$ | MIC | PKC | HC$_{50}$ | SI |
|---|---|---|---|---|---|---|---|
| 6 | 4-Cl | H | Cl | 4 | >64 | >64 | >16 |
| S18 | 3-Cl | - | - | 8 | N.D. | >64 | >8 |
| S19 | 4-F | - | - | 16 | N.D. | >64 | >4 |
| S20 | 4-Br | - | - | 4 | N.D. | >64 | >16 |
| S21 | 2,4-Cl | - | - | 2 | 32 | 47 | 23.50 |
| 10 | 3,4-Cl | - | - | 2 | 32 | >64 | >16 |
| S22 | - | 4-OH | - | 32 | N.D. | >64 | >2 |
| S23 | - | 4-OMe | - | 8 | >64 | >64 | >8 |
| S24 | - | 4-tBu | - | 2 | 16 | 26 | 13 |
| S25 | - | 4-F | - | 4 | N.D. | >64 | >16 |
| S26 | - | 4-CF$_3$ | - | 2 | 64 | 51 | 25.50 |
| 11 | - | 4-Cl | - | 2 | >64 | >64 | >32 |
| 12 | - | 3-Cl, 4-Cl | - | 1 | 8 | 38 | 38 |
| 13 | - | 4-Br | - | 2 | 32 | >64 | >32 |
| 14 | - | 4-I | - | 1 | 16 | >64 | >64 |
| S27 | - | - | OH | >64 | N.D. | >64 | N.D. |
| S28 | - | - | F | 16 | N.D. | >64 | >4 |
| S29 | - | - | Ph | 4 | N.D. | 35 | 8.50 |
| S30 | - | - | Br | 4 | N.D. | >64 | >16 |
FIG. 36

ANTIBACTERIAL COMPOUNDS

CLAIM OF PRIORITY

This application claims the benefit of U.S. Provisional Application Ser. Nos. 62/655,362, filed Apr. 10, 2018; and 62/720,880, filed Aug. 21, 2018. The disclosure of each application is incorporated herein by reference in its entirety.

FEDERALLY SPONSORED RESEARCH OR DEVELOPMENT

This invention was made with Government support under Grant Nos. P01 A1083214 and 1R35GM119426 awarded by the National Institutes of Health, and Grant Nos. CMMI-1562904 and NSF1755698 awarded by National Science Foundation. The Government has certain rights in the invention.

TECHNICAL FIELD

This invention relates to antibacterial compounds, and in particular to membrane-selective indole derivatives.

BACKGROUND

*Staphylococcus aureus* is a leading cause of both hospital and community-acquired infections, causing a wide range of diseases from mild skin abscesses to life-threatening infections such as endocarditis and osteomyelitis. The failure of antibiotic therapy against *S. aureus* is associated with both multi-drug resistant strains and its ability to adopt a dormant so-called persister lifestyle. Persisters tolerate high concentrations of other antibiotics due to their non-growing dormant state in which biosynthetic processes targeted by other antibiotics are inactive or significantly attenuated. Persisters are responsible for the antibiotic-tolerance of biofilms and the recalcitrance of chronic infections. Curing infections caused by multi-drug resistant or persistent bacteria is a formidable challenge.

SUMMARY

Other antibiotics are not effective in treating infections caused by drug-resistant bacteria or persistent non-growing bacteria. In contrast, the antibacterial compounds of the present disclosure kill both growing and persistent bacteria, e.g., by disruption of bacterial lipid bi-layer membrane. In one example, *S. aureus* exhibited no detectable development of resistance to the compounds of the present application, and the compounds acted synergistically with aminoglycosides such as gentamycin.

In one general aspect, the present disclosure provides a compound of Formula (I):

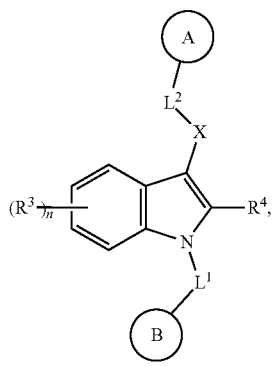

or a pharmaceutically acceptable salt thereof, wherein X, $L^1$, $L^2$, $R^3$, n, $R^4$, ring A, and ring B are as described herein.

In another general aspect, the present disclosure provides a pharmaceutical composition, comprising a compound of Formula (I), or a pharmaceutically acceptable salt thereof, and a pharmaceutically acceptable carrier.

In another general aspect, the present disclosure provides a method of treating a bacterial infection, the method comprising administering to a subject in need thereof a therapeutically effective amount of a compound of Formula (I), or a pharmaceutically acceptable salt thereof.

In another general aspect, the present disclosure provides a method of killing or inhibiting growth of bacteria, the method comprising contacting the bacteria with an effective amount of a compound of Formula (I), or a pharmaceutically acceptable salt thereof.

In another general aspect, the present disclosure provides a pharmaceutical composition, comprising (i) a compound of Formula (I), or a pharmaceutically acceptable salt thereof; (ii) at least one additional antibiotic, or a pharmaceutically acceptable salt thereof; and (iii) a pharmaceutically acceptable carrier.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 35 contains structures and biological activity data for compounds S1-S8, 4, 5, and S9-S12. "–" in the table means the substituent is the same as nTZDpa. MIC: minimum inhibitory concentration (µg/mL), PKC: persister killing concentration (µg/mL), HC50: median hemolysis concentration, SI: selectivity index ($HC_{50}$/MIC), N.D.: Not determined.

FIG. 36 contains structures and biological activity data for compounds S13-S21, 10, S22-S26, 11-14, and S27-S30. "–" in the table means the substituent is the same as 6. MIC: minimum inhibitory concentration (µg/mL), PKC: persister killing concentration (µg/mL), $HC_{50}$: median hemolytic concentration, SI: selectivity index ($HC_{50}$/MIC), N.D.: Not determined.

DETAILED DESCRIPTION

Introduction

Figure 1:
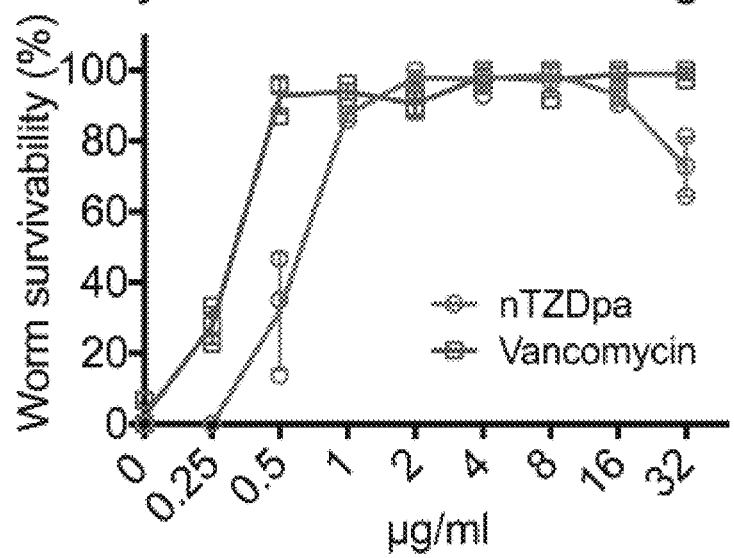
FIG. 1 shows dose-dependent *C. elegans* survival from MRSA infections in the presence of nTZDpa and vancomycin. MRSA-infected *C. elegans* glp-4(bn2);sek-1 (km4) animals were treated with the indicated concentrations of nTZDpa or vancomycin at 25° C. for 5 days. Percent survival of *C. elegans* was normalized to *C. elegans* treated with DMSO. Results are shown as means±s.d.; n=3.

The present application provides bacterial membrane-selective antibacterial compounds that—when compared to other antibiotics agents—advantageously retain potent antimicrobial activity (including, e.g., activity against multi-drug resistant and persistent bacteria) but show reduced cytotoxicity, improved pharmacokinetic profile, and low probability for developing resistance. Such exemplary antibacterial compounds, compositions containing these compounds and methods of making and using these compounds are described herein.

Antibacterial Compounds

In some embodiments, the present application provides a compound of Formula (I):

(I)

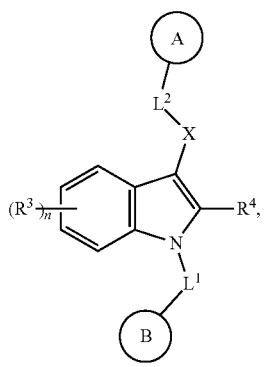

or a pharmaceutically acceptable salt thereof, wherein:

X is selected from S, O, and $C(R^5)_2$; wherein each $R^5$ is independently selected from H, $C_{1-3}$ alkyl, and $C_{1-3}$ haloalkyl;

$L^1$ is selected from a bond, C(=O), S(=O), $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

$L^2$ is selected from a bond, C(=O), S(=O), $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $C_{6-10}$ aryl, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, and $C_{6-10}$ aryl are each optionally substituted with 1, 2 or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

n is an integer selected from 1, 2, 3, and 4;

ring A is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^2$;

ring B is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^1$;

each $R^1$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^2$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

$R^4$ is selected from $C(O)OR^{a3}$, $C(O)NR^{c3}R^{d3}$, $C_{1-3}$ alkylene-$OR^{a3}$, and a 5-membered heteroaryl;

$R^{a1}$, $R^{b1}$, $R^{a2}$, $R^{b2}$, and $R^{a3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, $R^{d2}$, $R^{c3}$, $R^{d3}$, and $R^{c4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ $C(O)OR^{b7}$, $C(O)NR^{c7}R^{d7}$, $C(O)OR^{a7}$, $NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$; each $R^{a7}$, $R^{b7}$, $R^{c7}$, and $R^{d7}$ is in dependently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO-$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, X is S. In some embodiments, X is O. In some embodiments, X is $C(R^5)_2$. In some embodiments, both $R^5$ are the same. In other embodiments, both $R^5$ are different. In some embodiments, one $R^5$ is H, and the other is $C_{1-3}$ alkyl. In some embodiments, X is $CH_2$. In some embodiments, C is $CHCF_3$.

In some embodiments, X is S or O. In some embodiments, X is S, O, or $CH_2$.

In some embodiments, $L^1$ is a bond or $C_{1-6}$ alkylene. In some embodiments, $L^1$ is a bond. In some embodiments, $L^1$ is $C_{1-6}$ alkylene (e.g., methylene or ethylene).

In some embodiments, $L^2$ is a bond or $C_{1-6}$ alkylene. In some embodiments, $L^2$ is a bond. In some embodiments, $L^2$ is $C_{1-6}$ alkylene (e.g., methylene or ethylene).

In some embodiments, $L^1$ is a bond and $L^2$ is $C_{1-6}$ alkylene.

In some embodiments, $L^2$ is a bond and $L^1$ is $C_{1-6}$ alkylene.

In some embodiments, $L^1$ is a bond and $L^2$ is a bond.

In some embodiments, $L^2$ is $C_{1-6}$ alkylene and $L^1$ is $C_{1-6}$ alkylene.

In some embodiments, each $R^3$ is independently selected from halo, CN, $NO_2$, $C_{1-6}$ alkyl, $C_{1-6}$ haloalkyl, $C_{6-10}$ aryl, $OR^{a1}$, $C(O)R^{b1}$, $C(O)NR^{c1}R^{d1}$, $C(O)OR^{a1}$, and $NR^{c1}R^{d1}$, wherein said $C_{1-6}$ alkyl and $C_{6-10}$ aryl are each optionally substituted with 1, 2 or 3 independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, and $NR^{c1}R^{d1}$.

In some embodiments, each $R^3$ is independently selected from halo, $C_{1-6}$ alkyl, $C_{1-6}$ haloalkyl, $C_{6-10}$ aryl and $OR^{a1}$.

In some embodiments, each $R^3$ is independently selected from halo, $C_{1-6}$ haloalkyl, $C_{6-10}$ aryl and $OR^{a1}$.

In some embodiments, n is 1, 2, or 3. In some embodiments, n is 1 or 2. In some embodiments, n is 1. In some embodiments, n is 2.

In some embodiments, ring A is selected from $C_{6-10}$ aryl and $C_{3-10}$ cycloalkyl, each of which is optionally substituted with 1, 2, or 3 substituents independently selected from $R^2$. In some embodiments, ring A is $C_{6-10}$ aryl, optionally substituted with 1 or 2 substituents independently selected from $R^2$. In some embodiments, ring A is phenyl, optionally substituted with 1 or 2 substituents independently selected from $R^2$. In some embodiments, ring A is $C_{3-10}$ cycloalkyl, optionally substituted with 1 or 2 substituents independently selected from $R^2$. In some embodiments, ring A is an adamantyl of formula:

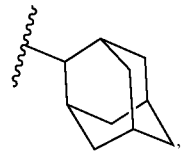 [SMILES: *C1C2CC3CC(C2)CC1C3]

optionally substituted with 1 or 2 substituents independently selected from $R^2$.

In some embodiments, ring B is selected from $C_{6-10}$ aryl and $C_{3-10}$ cycloalkyl, each of which is optionally substituted with 1, 2, or 3 substituents independently selected from $R^1$. In some embodiments, ring B is $C_{6-10}$ aryl, optionally substituted with 1 or 2 substituents independently selected from $R^1$. In some embodiments, ring B is phenyl, optionally substituted with 1 or 2 substituents independently selected from $R^1$. In some embodiments, ring B is $C_{3-10}$ cycloalkyl, optionally substituted with 1 or 2 substituents independently selected from In some embodiments, ring B is an adamantyl of formula:

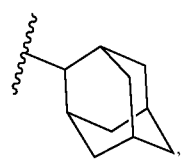 [SMILES: *C1C2CC3CC(C2)CC1C3]

optionally substituted with 1 or 2 substituents independently selected from $R^1$.

In some embodiments, ring A is $C_{6-10}$ aryl and ring B is $C_{6-10}$ aryl.

In some embodiments, ring A is $C_{3-10}$ cycloalkyl and ring B is $C_{3-10}$ cycloalkyl.

In some embodiments, ring A is $C_{6-10}$ aryl and ring B is $C_{3-10}$ cycloalkyl.

In some embodiments, ring A is $C_{3-10}$ cycloalkyl and ring B is $C_{6-10}$ aryl.

In some embodiments, each $R^1$ is independently selected from halo, CN, $NO_2$, $C_{1-6}$ alkyl, $C_{1-6}$ haloalkyl, $OR^{a2}$, $C(O)R^{b2}$, $C(O)OR^{a2}$, $C(O)NR^{c2}R^{d2}$, and $NR^{c2}R^{d2}$, wherein said $C_{1-6}$ alkyl is optionally substituted with 1, 2 or 3 substituents independently selected from halo, CN, $NO_2$, $OR^{a2}$, $C(O)R^{b2}$, $C(O)OR^{a2}$, $C(O)NR^{c2}R^{d2}$, and $NR^{c2}R^{d2}$.

In some embodiments, each $R^1$ is independently selected from halo and $OR^{a2}$. In some embodiments, $R^1$ is halo (e.g., Cl, I, or Br). In some embodiments, $R^1$ is Cl. In some embodiments, ring B is substituted with two $R^1$ both of which are halo. In some embodiments, $R^1$ is $OR^{a2}$. In some embodiments, $R^1$ is OH or $C_{1-6}$ alkoxy. In some embodiments, $R^1$ is $C_{1-6}$ alkoxy (e.g., methoxy or ethoxy). In some embodiments, $R^1$ is $C(O)OR^{a2}$. In some embodiments, $R^1$ is C(O)OH. In some embodiments, each $R^1$ is independently selected from halo, OH, and $C_{1-6}$ alkoxy.

In some embodiments, each $R^2$ is independently selected from halo, CN, $NO_2$, $C_{1-6}$ alkyl, $C_{1-6}$ haloalkyl, $OR^{a2}$, $C(O)R^{b2}$, $C(O)OR^{a2}$, $C(O)NR^{c2}R^{d2}$, and $NR^{c2}R^{d2}$; wherein said $C_{1-6}$ alkyl is optionally substituted with 1, 2 or 3 substituents independently selected from halo, CN, $NO_2$, $OR^{a2}$, $C(O)R^{b2}$, $C(O)NR^{c2}R^{d2}$, and $NR^{c2}R^{d2}$.

In some embodiments, each $R^2$ is independently selected from halo, $C_{1-6}$ alkyl, $C_{1-6}$ haloalkyl, $OR^{a2}$, and $C(O)OR^{a2}$. In some embodiments, each $R^2$ is independently selected from halo, $C_{1-6}$ alkyl, $C_{1-6}$ haloalkyl, and $OR^{a2}$. In some embodiments, $R^2$ is halo (e.g., Cl, I, or Br). In some embodiments, $R^2$ is Cl. In some embodiments, $R^2$ is I. In some embodiments, ring A is substituted with two or three $R^2$ all of which are halo. In some embodiments, ring A is a phenyl which is substituted with one $R^2$ in para position and $R^2$ is I. In some embodiments, X is O and $R^2$ is I. In some embodiments, $R^2$ is $C_{1-6}$ alkyl (e.g., methyl, ethyl, propyl, butyl, or t-butyl). In some embodiments, $R^2$ is $C_{1-6}$ haloalkyl (e.g., trifluoromethyl). In some embodiments, $R^2$ is $OR^{a2}$. In some embodiments, $R^2$ is OH or $C_{1-6}$ alkoxy. In some embodiments, $R^2$ is $C(O)OR^{a2}$. In some embodiments, $R^2$ is C(O)OH. In some embodiments, $R^2$ is selected from halo, $C_{1-6}$ alkyl, $C_{1-6}$ haloalkyl, $C_{1-6}$ alkoxy, and C(O)OH. In some embodiments, $R^2$ is selected from halo, $C_{1-6}$ alkyl, $C_{1-6}$ haloalkyl, and $C_{1-6}$ alkoxy.

In some embodiments, $R^4$ is $C(O)OR^{a3}$. In some embodiments, $R^4$ is C(O)OH.

In some embodiments, $R^4$ is $C(O)NR^{c3}R^{d3}$. In some embodiments, $R^4$ is $C(O)NH_2$.

In some embodiments, $R^4$ is $C(O)NH(C_{1-6}$ alkyl). In some embodiments, $R^4$ is $C(O)NH(C_{1-6}$ alkyl)$_2$.

In some embodiments, $R^4$ is $C_{1-3}$ alkylene-$OR^{a3}$. In some embodiments, $R^4$ is $C_{1-3}$ alkylene-OH. In some embodiments, $R^4$ is $CH_2$—OH. In some embodiments, $R^4$ is $CH_2CH_2$—OH.

In some embodiments, $R^4$ is a 5-membered heteroaryl. In some embodiments, $R^4$ is selected form pyrazolyl, imidazolyl, triazolyl, oxazolyl, isoxazolyl, and tetrazolyl. In some embodiments, $R^4$ is a tetrazolyl or formula:

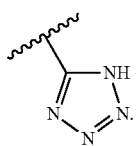 [SMILES: *c1nnn[nH]1]

In some embodiments:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
ring A is selected from $C_{6-10}$ aryl and $C_{3-10}$ cycloalkyl;
ring B is selected from $C_{6-10}$ aryl and $C_{3-10}$ cycloalkyl;
each $R^1$ is independently selected from halo and $OR^{a2}$; and
each $R^2$ is independently selected from halo, $C_{1-6}$ alkyl, $C_{1-6}$ haloalkyl, $OR^{a2}$; and $C(O)OR^{a2}$.

In some embodiments, each $R^{a1}$, $R^{b1}$, $R^{a2}$, $R^{b2}$, and $R^{d3}$ is independently selected from H, $C_{1-6}$ alkyl, $C_{1-4}$ haloalkyl. In some embodiments, each $R^{a1}$, $R^{b1}$, $R^{a2}$, $R^{b2}$, and $R^{d3}$ is independently selected from H and $C_{1-6}$ alkyl. In some embodiments, $R^{a1}$ is H. In some embodiments, $R^{a1}$ is $C_{1-6}$ alkyl. In some embodiments, $R^{a2}$ is H. In some embodiments, $R^{a2}$ is $C_{1-6}$ alkyl. In some embodiments, $R^{a3}$ is H. In some embodiments, $R^{a1}$ is $C_{1-6}$ alkyl.

In some embodiments, each $R^{c1}$, $R^{d1}$, $R^{c2}$, $R^{d2}$, $R^{c3}$, $R^{d3}$, and $R^{c4}$ is independently selected from H, $C_{1-6}$ alkyl and $C_{1-4}$ haloalkyl. In some embodiments, each $R^{c1}$, $R^{d1}$, $R^{c2}$, $R^{d2}$, $R^{c3}$, $R^{d3}$, and $R^{c4}$ is independently selected from H and $C_{1-6}$ alkyl.

In some embodiments:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
ring A is $C_{6-10}$ aryl;
ring B is $C_{6-10}$ aryl;
each $R^1$ is independently selected from halo and $OR^{a2}$; and
each $R^2$ is independently selected from halo, $C_{1-6}$ alkyl, $C_{1-6}$ haloalkyl, and $OR^{a2}$.

In some embodiments:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
n is 1 or 2; and at least one $R^3$ is selected from halo and $C_{1-6}$ haloalkyl;
ring A is selected from phenyl and adamantyl;
ring B is selected from phenyl and adamantyl;
each $R^1$ is independently selected from halo, OH, and $C_{1-6}$ alkoxy; and
each $R^2$ is independently selected from halo, $C_{1-6}$ alkyl, $C_{1-6}$ haloalkyl, $C_{1-6}$ alkoxy, and C(O)OH.

In some embodiments:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
n is 1 or 2; and at least one $R^3$ is selected from halo and $C_{1-6}$ haloalkyl;
ring A is phenyl;
ring B is phenyl;
each $R^1$ is independently selected from halo, OH, and $C_{1-6}$ alkoxy; and
each $R^2$ is independently selected from halo, $C_{1-6}$ alkyl, $C_{1-6}$ haloalkyl, and $C_{1-6}$ alkoxy.

In some embodiments, the compound of Formula (I) has formula:

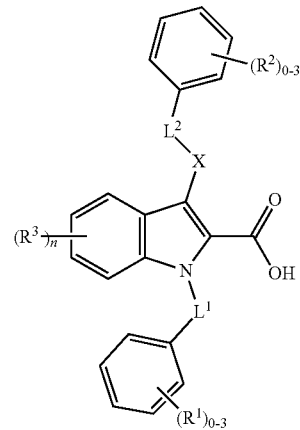

or a pharmaceutically acceptable salt thereof.

In some embodiments, the present disclosure provides a compound of Formula (I), or a pharmaceutically acceptable salt thereof, wherein X, $L^1$, $L^2$, $R^3$, n, $R^4$, ring A, and ring B are as described herein, wherein at least one $R^3$ is selected from halo and $C_{1-6}$ haloalkyl; with the proviso that the compound of Formula (II) is not any one of the compounds of Table C.

In some embodiments, the compound of Formula (I) has formula:

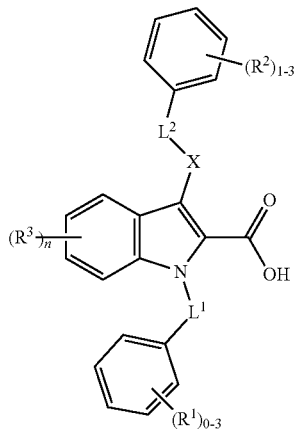

or a pharmaceutically acceptable salt thereof, wherein:

at least one $R^2$ is selected from halo and $C_{1-6}$ haloalkyl; and $L^1$ is $C_{1-6}$ alkylene; and the compound is not:

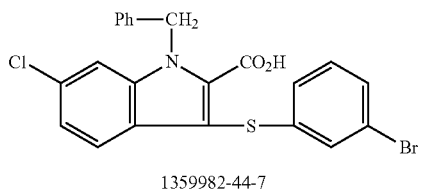 [SMILES: O=C(O)c1c(Sc2cccc(Br)c2)c2ccc(Cl)cc2n1Cc1ccccc1]

1359982-44-7

In some embodiments, the compound of Formula (I) has formula:

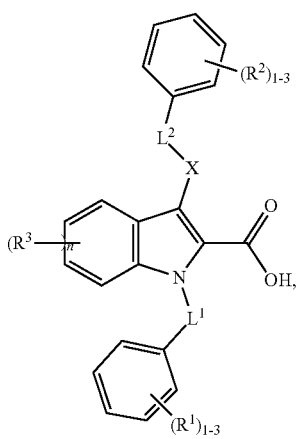

or a pharmaceutically acceptable salt thereof, wherein:

at least one $R^2$ is selected from halo and $C_{1-6}$ haloalkyl; and at least one $R^3$ is selected from halo and $C_{1-6}$ haloalkyl.

In some embodiments, the compound of Formula (I) has formula:

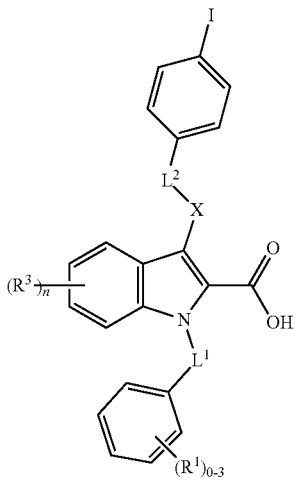

or a pharmaceutically acceptable salt thereof.

In some embodiments, the present disclosure provides a compound selected from:

| Structure | Compound No. |
|---|---|
| ![S14 structure: 5-chloro-3-methoxy-1-(4-chlorobenzyl)-1H-indole-2-carboxylic acid] | S14 (analog 4) |
| ![S3 structure: 5-chloro-1-methyl-3-(phenylthio)-1H-indole-2-carboxylic acid] | S3 (analog 5) | or a pharmaceutically acceptable salt thereof.

In some embodiments, the compound of Formula (I) is any one of the compounds in Table A, or a pharmaceutically acceptable salt thereof.

TABLE A
| Structure | Compound No. |
|---|---|
| 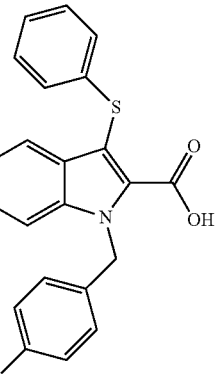 | nTZDpa |
| 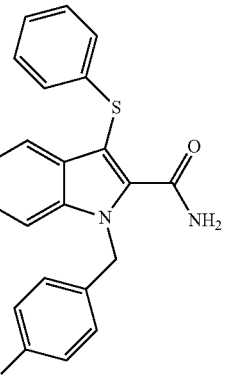 | S1 (analog 1) |
| 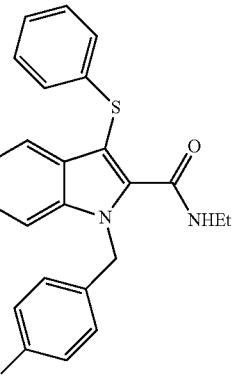 | S2 (analog 1a) |
| 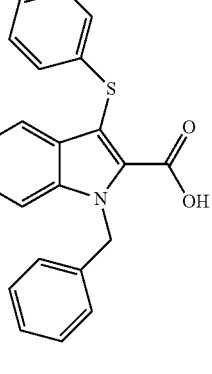 | S4 (analog 2) |
TABLE A-continued
| Structure | Compound No. |
|---|---|
| 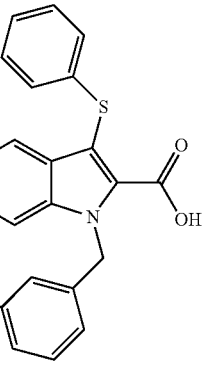 | S5 (analog 2b) |
| 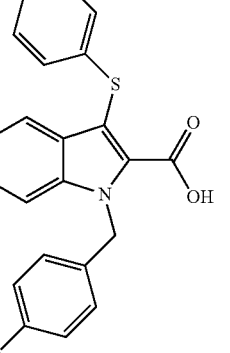 | S6 |
| 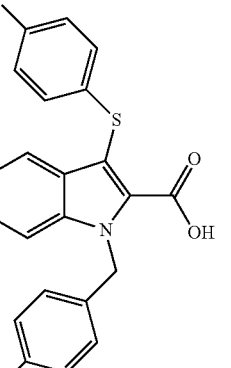 | S7 |
| 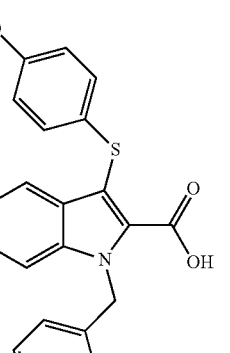 | S8 |

TABLE A-continued
| Structure | Compound No. |
|---|---|
| 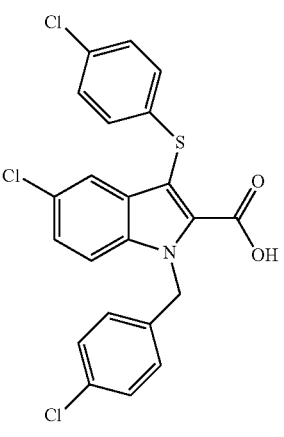 [SMILES: O=C(O)c1c(Sc2ccc(Cl)cc2)c2cc(Cl)ccc2n1Cc1ccc(Cl)cc1] | 4 (analog 3) |
| 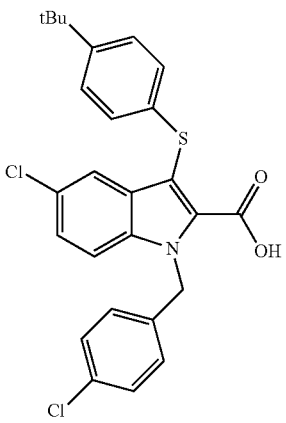 [SMILES: CC(C)(C)c1ccc(Sc2c(C(=O)O)n(Cc3ccc(Cl)cc3)c3ccc(Cl)cc23)cc1] | 5 |
| 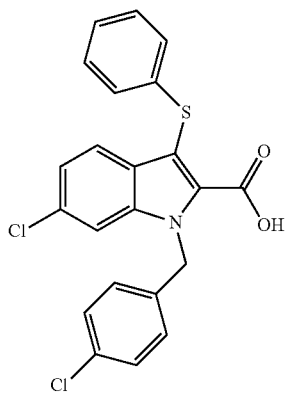 [SMILES: O=C(O)c1c(Sc2ccccc2)c2ccc(Cl)cc2n1Cc1ccc(Cl)cc1] | S9 (analog 2a) |
| 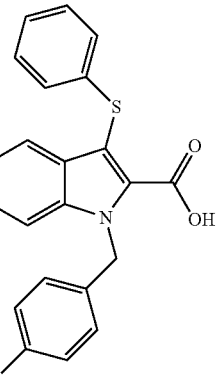 | S10 |
| 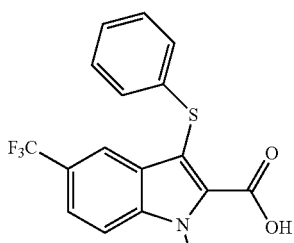 | S11 |
| 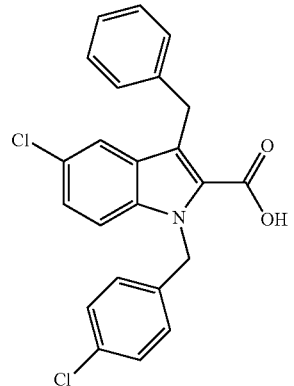 | S12 |
| 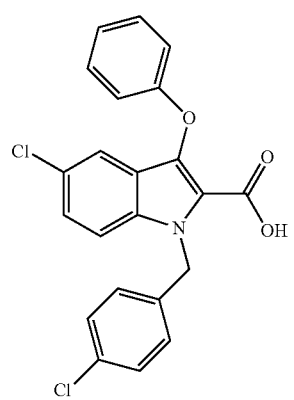 [SMILES: O=C(O)c1c(Oc2ccccc2)c2cc(Cl)ccc2n1Cc1ccc(Cl)cc1] | 6 |

TABLE A-continued
| Structure | Compound No. |
|---|---|
| 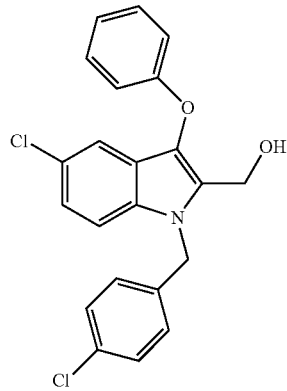 [SMILES: OCc1c(Oc2ccccc2)c2cc(Cl)ccc2n1Cc1ccc(Cl)cc1] | S13 |
| 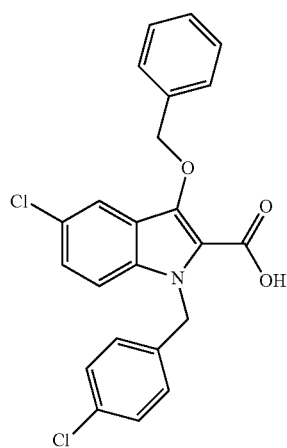 [SMILES: O=C(O)c1c(OCc2ccccc2)c2cc(Cl)ccc2n1Cc1ccc(Cl)cc1] | S15 |
| 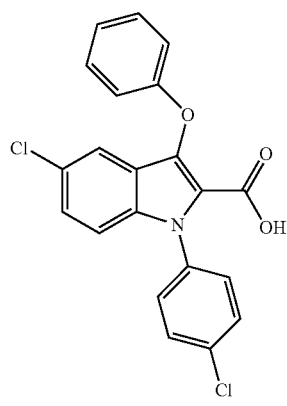 [SMILES: O=C(O)c1c(Oc2ccccc2)c2cc(Cl)ccc2n1-c1ccc(Cl)cc1] | S16 |
| | S17 |
| | S18 |
| | S19 |

TABLE A-continued

| Structure | Compound No. |
|---|---|
| (5-chloro-3-phenoxy-1-(4-bromobenzyl)-1H-indole-2-carboxylic acid) | S20 |
| (5-chloro-3-phenoxy-1-(2,4-dichlorobenzyl)-1H-indole-2-carboxylic acid) | S21 |
| (5-chloro-3-phenoxy-1-(3,4-dichlorobenzyl)-1H-indole-2-carboxylic acid) | 10 |
| (5-chloro-3-(4-hydroxyphenoxy)-1-(4-chlorobenzyl)-1H-indole-2-carboxylic acid) | S22 |
| (5-chloro-3-(4-methoxyphenoxy)-1-(4-chlorobenzyl)-1H-indole-2-carboxylic acid) | S23 |
| (5-chloro-3-(4-tert-butylphenoxy)-1-(4-chlorobenzyl)-1H-indole-2-carboxylic acid) | S24 |
| (5-chloro-3-(4-fluorophenoxy)-1-(4-chlorobenzyl)-1H-indole-2-carboxylic acid) | S25 |

TABLE A-continued
| Structure | Compound No. |
|---|---|
| 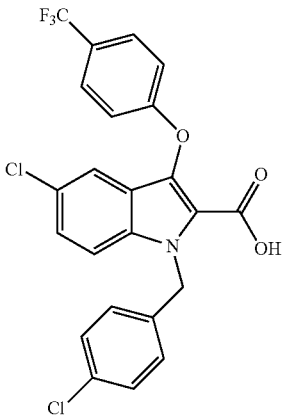 [SMILES: O=C(O)c1c(Oc2ccc(C(F)(F)F)cc2)c2cc(Cl)ccc2n1Cc1ccc(Cl)cc1] | S26 |
| 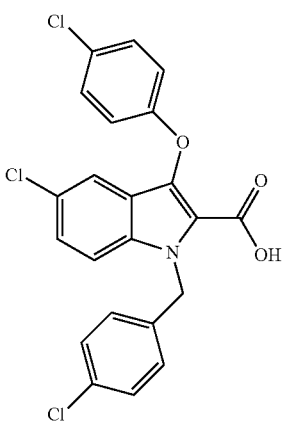 | 11 |
| 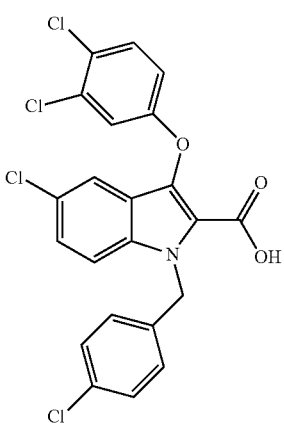 [SMILES: O=C(O)c1c(Oc2ccc(Cl)c(Cl)c2)c2cc(Cl)ccc2n1Cc1ccc(Cl)cc1] | 12 |
TABLE A-continued
| Structure | Compound No. |
|---|---|
| 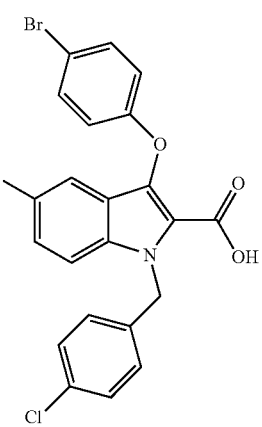 | 13 |
| 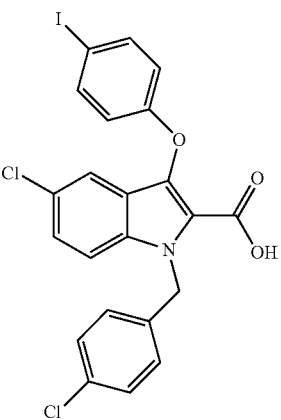 | 14 |
| 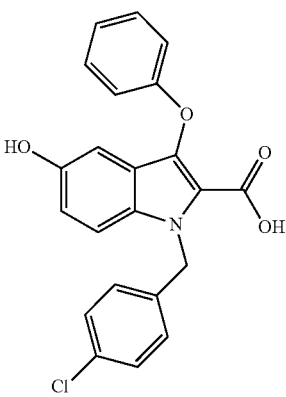 [SMILES: O=C(O)c1c(Oc2ccccc2)c2cc(O)ccc2n1Cc1ccc(Cl)cc1] | S27 |

TABLE A-continued
| Structure | Compound No. |
|---|---|
| 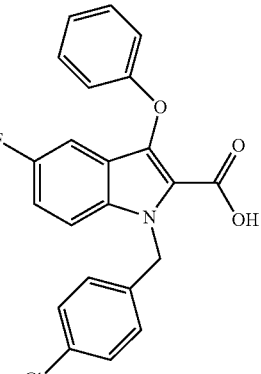 | S28 |
| 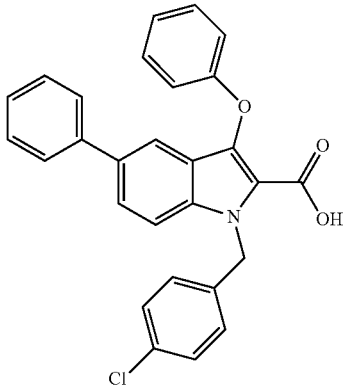 [SMILES: O=C(O)c1c(Oc2ccccc2)c2cc(-c3ccccc3)ccc2n1Cc1ccc(Cl)cc1] | S29 |
| 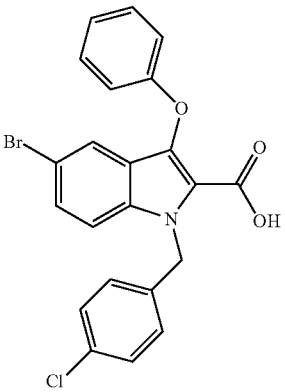 | S30 |
TABLE B
| Structure |
|---|
| 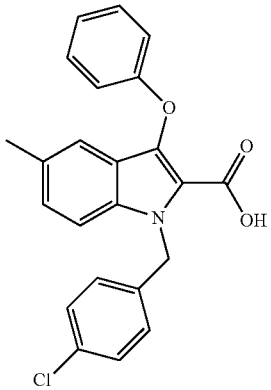 [SMILES: Cc1ccc2c(c1)c(Oc1ccccc1)c(C(=O)O)n2Cc1ccc(Cl)cc1] |
| 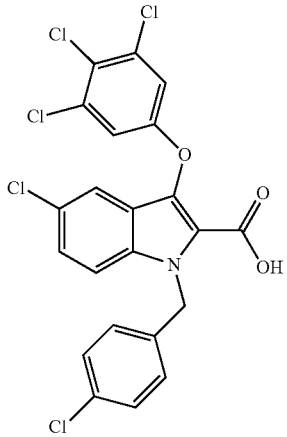 [SMILES: O=C(O)c1c(Oc2cc(Cl)c(Cl)c(Cl)c2)c2cc(Cl)ccc2n1Cc1ccc(Cl)cc1] |
| 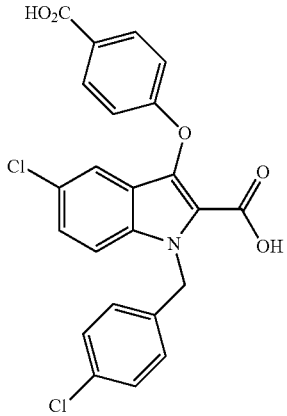 [SMILES: O=C(O)c1ccc(Oc2c(C(=O)O)n(Cc3ccc(Cl)cc3)c3ccc(Cl)cc23)cc1] |
In some embodiments, the compound of Formula (I) is any one of the compounds in Table A, with the proviso that the compound is not nTZDpa or analog 2.
In some embodiments, the compound of Formula (I) is any one of the compounds in Table B, or a pharmaceutically acceptable salt thereof.

TABLE B-continued
Structure
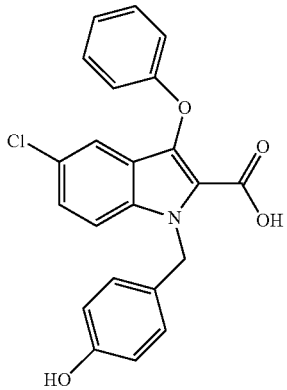 [SMILES: O=C(O)c1c(Oc2ccccc2)c2cc(Cl)ccc2n1Cc1ccc(O)cc1]
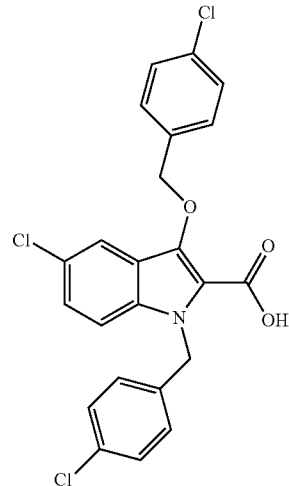
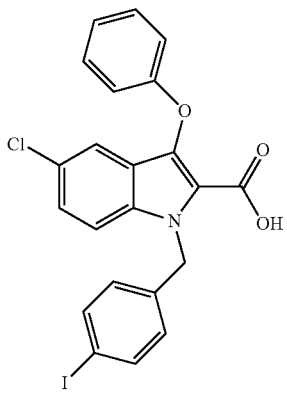 [SMILES: O=C(O)c1c(Oc2ccccc2)c2cc(Cl)ccc2n1Cc1ccc(I)cc1]
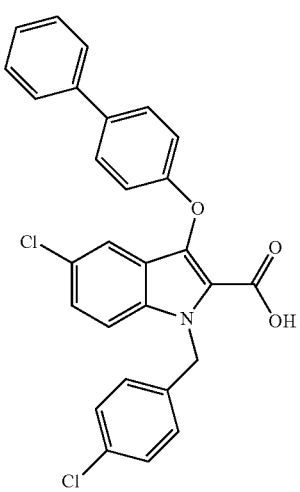
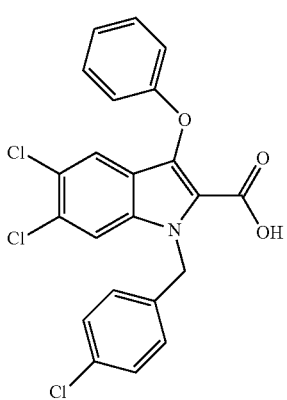 [SMILES: O=C(O)c1c(Oc2ccccc2)c2cc(Cl)c(Cl)cc2n1Cc1ccc(Cl)cc1]
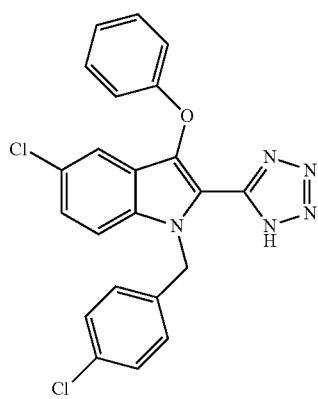 [SMILES: Clc1ccc(Cn2c(-c3nnn[nH]3)c(Oc3ccccc3)c3cc(Cl)ccc32)cc1]

TABLE B-continued

Structure

[Chemical structure: 5-chloro-3-(adamantan-2-yloxy)-1-(4-chlorobenzyl)-1H-indole-2-carboxylic acid]

[Chemical structure: 5-chloro-1-(adamantan-2-ylmethyl)-3-phenoxy-1H-indole-2-carboxylic acid]

In some embodiments, the compound of Formula (I) is any one of the compounds in Table C, or a pharmaceutically acceptable salt thereof.

TABLE C

| Structure | CAS Reg. No. |
|---|---|
| [5-chloro-1-(4-chlorobenzyl)-3-(phenylthio)-1H-indole-2-carboxylic acid] | 118414-59-8 |
| [5-chloro-1-benzyl-3-(phenylthio)-1H-indole-2-carboxylic acid] | 958868-85-4 |
| [5-chloro-1-(furan-2-ylmethyl)-3-(phenylthio)-1H-indole-2-carboxamide] | 1349510-85-5 |
| [5-bromo-1-(4-bromobenzyl)-3-(phenylthio)-1H-indole-2-carboxylic acid] | 1332595-10-4 |
| [5-chloro-3-(phenylthio)-1H-indole-2-carboxylic acid with R groups, 4-chlorophenyl] | 1348104-31-3 |
| [5-chloro-1-(3-methoxybenzyl)-3-(phenylthio)-1H-indole-2-carboxylic acid] | 958868-86-5 |
| [6-chloro-1-benzyl-3-(3-bromophenylthio)-1H-indole-2-carboxylic acid ethyl ester] | 1359982-43-6 |
| [6-chloro-1-benzyl-3-(3-bromophenylthio)-1H-indole-2-carboxylic acid] | 1359982-44-7 |
| [5-bromo-1-(4-fluorobenzyl)-3-(benzyloxy)-1H-indole-2-carboxylic acid ethyl ester] | 359003-51-3 |

TABLE C-continued
| Structure | CAS Reg. No. |
|---|---|
| 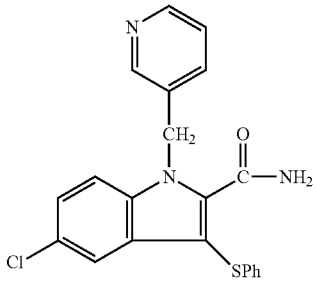 | 148900-63-4 |
| 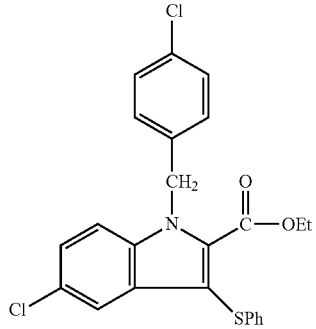 | 118414-58-7 |
| 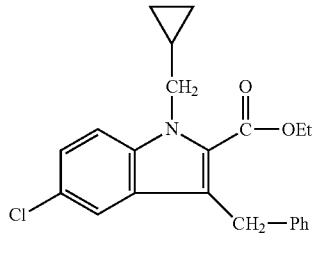 [SMILES: CCOC(=O)c1c(Cc2ccccc2)c2cc(Cl)ccc2n1CC1CC1] | 36100-86-4 |
| 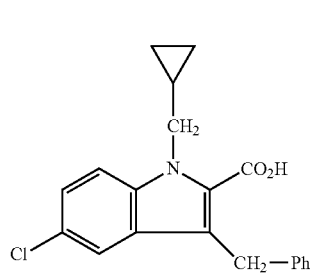 [SMILES: O=C(O)c1c(Cc2ccccc2)c2cc(Cl)ccc2n1CC1CC1] | 36100-87-5 |
| 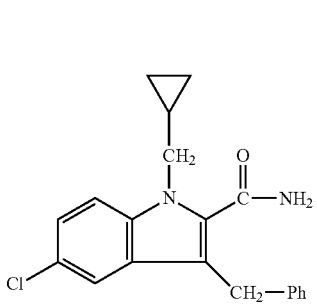 [SMILES: NC(=O)c1c(Cc2ccccc2)c2cc(Cl)ccc2n1CC1CC1] | 36100-90-0 |
| 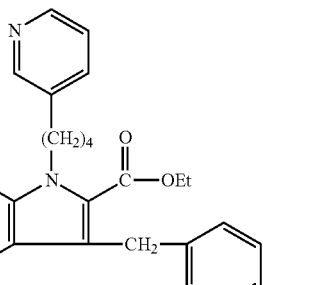 | 155697-78-2 |
| 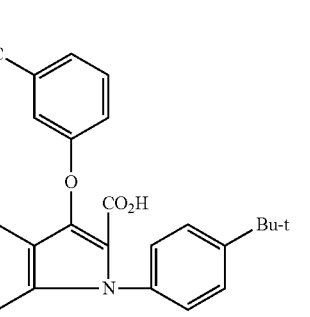 | 870459-68-0 |
| 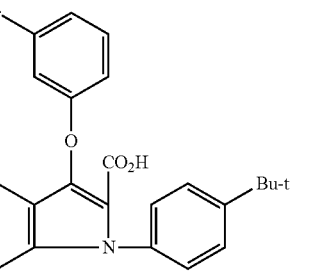 | 870459-69-1 |
| 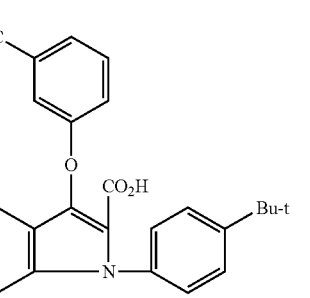 | 870459-70-4 |
| 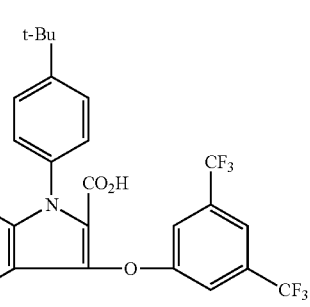 | 870459-71-5 |

TABLE C-continued

| Structure | CAS Reg. No. |
|---|---|
| (indole with t-Bu-phenyl N-substituent, CO₂H, 5-Cl, 3-O-(4-Cl-3-CF₃-phenyl)) | 870459-72-6 |
| (indole with 3-O-(3-CF₃-phenyl), CO₂H, 5-HO, N-(4-t-Bu-phenyl)) | 870459-77-1 |
| (indole with 3-O-(3-CF₃-phenyl), 5-HO, 2-R, N-(4-t-Bu-phenyl); R–C(O)–OEt) | 870459-75-9 |
| (indole with 3-O-(3-CF₃-phenyl), 6-Cl, 2-R, N-(4-t-Bu-phenyl); R–C(O)–OEt) | 911827-00-4 |
| (indole with 3-O-(3-i-Pr-phenyl), 6-Cl, 2-R, N-(4-t-Bu-phenyl)) | 911827-03-7 |

TABLE C-continued

| Structure | CAS Reg. No. |
|---|---|
| R–C(O)–OEt; (indole with 3-O-(3-CF₃-phenyl), 5-Cl, 2-R, N-(4-t-Bu-phenyl)) | 911828-97-2 |
| R–C(O)–OEt; (indole with N-(4-t-Bu-phenyl), 5-Cl, 2-C(O)OEt, 3-O-(3,5-bis-CF₃-phenyl)) | 911829-13-5 |
| (indole with N-(4-t-Bu-phenyl), 5-Cl, 2-C(O)OEt, 3-O-(4-Cl-3-CF₃-phenyl)) | 911829-14-6 |

In some embodiments, the compound of Formula (I) is not any of the compounds disclosed in Table C.

In some embodiments, a salt (e.g., pharmaceutically acceptable salt) of a compound of Formula I is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formula I include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formula I include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH-($C_1$-$C_6$)-alkylamine), such as N,N-dimethyl-N-(2-hydroxyethyl)amine or tri-(2-hydroxyethyl)amine; N-methyl-D-glutamine; morpholine; thiomorpholine; piperidine; pyrrolidine; and amino acids such as arginine, lysine, and the like.

In some embodiments, the compounds of Formula I, or pharmaceutically acceptable salts thereof, are substantially isolated.

Methods of Use

Inhibition of Bacterial Pathogens

In some embodiments, the present application is directed to a method of killing or inhibiting growth of bacteria, the method comprising contacting the bacteria with an effective amount of a compound of Formula I, or a pharmaceutically acceptable salt thereof, as described herein. In some embodiments, the compound kills the bacteria by disrupting the bacterial membrane.

In some embodiments, the bacteria (e.g., any one of bacteria described herein) is resistant to one or more other antibiotic agents (e.g., antibiotic agents disclosed herein). In some embodiments, the bacteria is at least 2-fold, 4-fold, 8-fold, 10-fold, 24-fold, 48-fold, 100-fold, 256-fold, 512-fold or 1000-fold resistant to one or more of other antibiotic agents. In some embodiments, the bacteria is multi-drug resistant (MDR). In one example, a bacterium that is antibiotic-resistant exhibits a minimum inhibitory concentration (MIC) for the antibiotic of >2 µg/ml. In some embodiments, any one of bacteria described herein is resistant to methicillin, vancomycin, rifampicin, linezolid, daptomycin, gentamicin and/or ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, linezolid, daptomycin, gentamicin and/or ciprofloxacin. In some embodiments, any one of bacteria described herein is resistant to an antibiotic selected from methicillin, vancomycin, rifampicin, gentamicin and ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, gentamicin and ciprofloxacin. In some embodiments, any one of bacteria described herein is resistant to methicillin, vancomycin, rifampicin, gentamicin and ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, gentamicin and ciprofloxacin. In some embodiments, the bacteria is not resistant (or at most 1.5-fold resistant) to a compound of Formula I. In some embodiments, any one of bacteria described herein is resistant to one or more of other antibiotic agents and is not resistant to a compound of Formula I. In some embodiments, the bacteria is a persister.

In some embodiments, the bacteria is Gram-positive bacteria.

In some embodiments, the bacteria is a member of a genus selected from the group consisting of *Staphylococcus* (including coagulase negative and coagulase positive), *Streptococcus*, *Peptococcus*, *Enterococcus*, and *Bacillus*.

In some embodiments, the bacteria is a member of *Staphylococcus* genus and the species of bacteria is selected from the group consisting of *S. aureus*, methicillin-susceptible *S. aureus* (MSSA), coagulase negative *staphylococci*, methicillin-resistant *S. aureus* (MRSA), vancomycin-resistant *S. aureus* (VRSA), *S. arlettae*, *S. agnetis*, *S. auricularis*, *S. capitis*, *S. caprae*, *S. carnosus*, *S. caseolyticus*, *S. chromogenes*, *S. cohnii*, *S. condimenti*, *S. delphini*, *S. devriesei*, *S. epidermidis*, *S. equorum*, *S. felis*, *S. fleurettii*, *S. gallinarum*, *S. haemolyticus*, *S. hominis*, *S. hyicus*, *S. intermedius*, *S. kloosii*, *S. leei*, *S. lentils*, *S. lugdunensis*, *S. lutrae*, *S. massiliensis*, *S. micron*, *S. muscae*, *S. nepalensis*, *S. pasteuri*, *S. pettenkoferi*, *S. piscifennentans*, *S. pseudintermedius*, *S. pseudolugdunensis*, *S. pulvereri*, *S. rostri*, *S. saccharolyticus*, *S. saprophyticus*, *S. schleiferi*, *S. sciuri*, *S. simiae*, *S. simulans*, *S. stepanovicii*, *S. succinus*, *S. vitulinus*, *S. warneri*, and *S. xylosus*.

In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, linezolid, daptomycin, gentamicin and ciprofloxacin. In one example, a bacterium that is antibiotic-resistant exhibits a minimum inhibitory concentration (MIC) for the antibiotic of >2 µg/ml.

In some embodiments, the bacteria is a member of *Peptococcus* genus and the species of bacteria is *P. magnus*.

In some embodiments, the bacteria is a member of *Streptococcus* genus and the species of bacteria is selected from the group consisting of *S. agalactiae*, *S. anginosus*, *S. bovis*, *S. canis*, *S. constellatus*, *S. dysgalactiae*, *S. equinus*, *S. iniae*, *S. intermedius*, *S. milleri*, *S. mitis*, *S. mutans*, *S. oralis*, *S. parasanguinis*, *S. peroris*, *S. pneumoniae*, *S. pseudopneumoniae*, *S. pyogenes*, *S. ratti*, *S. salivarius*, *S. tigurinus*, *S. thermophilus*, *S. sanguinis*, *S. sobrinus*, *S. suis*, *S. uberis*, *S. vestibularis*, *S. viridans*, and *S. zooepidemicus*.

In some embodiments, the bacteria is a member of *Enterococcus* genus and the species of bacteria is selected from the group consisting of *E. avium*, *E. durans*, *E. faecalis*, *E.* gallinarum, *E. haemoperoxidus*, *E. hirae*, *E. malodoratus*, *E. moraviensis*, *E. mundtii*, *E. pseudoavium*, *E. raffinosus*, *E. solitaries*, and *E. faecium*.

In some embodiments, the bacteria is a member of *Propionibacterium* genus. In such embodiments, the bacteria is *P. acnes*.

In some embodiments, the bacteria is Gram-negative bacteria. In some embodiments, Gram-negative bacteria is antibiotic resistant. In one example, a Gram-negative bacterium that is antibiotic-resistant exhibits a minimum inhibitory concentration (MIC) for the antibiotic of >2 µg/ml.

In some embodiments, the bacteria is a member of a family selected from the group consisting of *Enterobacteriaceae*, *Helicobacteraceae*, *Campylobacteraceae*, *Neisseriaceae*, *Pseudomonadaceae*, *Moraxellaceae*, *Xanthomonadaceae*, *Pasteurellaceae*, and *Legionellaceae*.

In some embodiments, the bacteria is a member of a genus selected from the group consisting of *Citrobacter*, *Enterobacter*, *Escherichia*, *Klebsiella*, *Pantoea*, *Proteus*, *Salmonella*, *Serratia*, *Shigella*, *Yersinia*, *Helicobacter*, *Wolinella*, *Campylobacter*, *Arcobacter*, *Neisseria*, *Francisella*, *Pseudomonas*, *Acinetobacter*, *Moraxella*, *Stenotrophomonas*, *Haemophilus*, *Pasteurella*, and *Legionella*.

In some embodiments, the bacteria is a member of *Citrobacter* genus and the species of bacteria is selected from the group consisting of *C. amalonaticus*, *C. braakii*, *C. diversus*, *C. farmer*, *C. freundii*, *C. gillenii*, *C. koseri*, *C. murliniae*, *C. rodentium*, *C. sedlakii*, *C. werkmanii*, and *C. youngae*.

In some embodiments, the bacteria is a member of *Enterobacter* genus and the species of bacteria is selected from the group consisting of *E. aerogenes*, *E. amnigenus*, *E. agglomerans*, *E. arachidis*, *E. asburiae*, *E. cancerogenous*, *E. cloacae*, *E. cowanii*, *E. dissolvens*, *E. gergoviae*, *E. helveticus*, *E. hormaechei*, *E. intermedius*, *E. kobei*, *E. ludwigii*, *E. mori*, *E. nimipressuralis*, *E. oryzae*, *E. pulveris*, *E. pyrinus*, *E. radicincitans*, *E. taylorae*, *E. turicensis*, *E. sakazakii*, and *E. spp*.

In some embodiments, the bacteria is a member of *Escherichia* genus and the species of bacteria is selected from the group consisting of *E. albertii*, *E. blattae*, *E. coli*, *E. fergusonii*, *E. hermannii*, and *E. vulneris*.

In some embodiments, the bacteria is a member of *Klebsiella* genus and the species of bacteria is selected from the group consisting of *K. granulomatis*, *K. oxytoca*, *K. pneumoniae*, *K. terrigena*, and *K. planticola*.

In some embodiments, the bacteria is a member of *Pantoea* genus and the species of bacteria is selected from the group consisting of *P. agglomerans*, *P. ananatis*, *P. citrea*, *P. dispersa*, *P. punctata*, *P. stewartii*, *P. terrea*, and *P. vagans*.

In some embodiments, the bacteria is a member of *Proteus* genus and the species of bacteria is selected from the group consisting of *P. hauseri*, *P. mirabilis*, *P. myxofaciens*, *P. penneri*, and *P. vulgaris*.

In some embodiments, the bacteria is a member of *Salmonella* genus and the species of bacteria is selected from the group consisting of *S. bongori*, and *S. enterica*.

In some embodiments, the bacteria is a member of *Serratia* genus and the species of bacteria is selected from the group consisting of *S. entomophila*, *S. ficaria*, *S. fonticola*, *S. grimesii*, *S. liquefaciens*, *S. marcescens*, *S. odorifera*, *S. plymuthica*, *S. proteamaculans*, *S. quinivorans*, *S. rubidaea*, and *S. symbiotica*.

In some embodiments, the bacteria is a member of *Shigella* genus and the species of bacteria is selected from the group consisting of *S. boydii*, *S. dysenteriae*, *S. flexneri*, and *S. sonnei*.

In some embodiments, the bacteria is a member of *Yersinia* genus and the species of bacteria is selected from the group consisting of *Y. pestis*, *Y. pseudotuberculosis*, and *Y. enterocolitica*.

In some embodiments, the bacteria is a member of *Helicobacter* genus and the species of bacteria is selected from the group consisting of *H. acinonychis*, *H. anseris*, *H. aurati*, *H. baculiformis*, *H. bilis*, *H. bizzozeronii*, *H. brantae*, *H. canadensis*, *H. canis*, *H. cetorum*, *H. cholecystus*, *H. cinaedi*, *H. cynogastricus*, *H. equorum*, *H. felis*, *H. fennelliae*, *H. ganmani*, *H. heilmannii*, *H. hepaticus*, *H. mesocricetorum*, *H. macacae*, *H. marmotae*, *H. mastomyrinus*, *H. mesocricetorum*, *H. muridarum*, *H. mustelae*, *H. pametensis*, *H. pullorum*, *H. pylori*, *H. rappini*, *H. rodentium*, *H. salomonis*, *H. suis*, *H. trogontum*, *H. typhlonius*, and *H. winghamensis*.

In some embodiments, the bacteria is a member of *Campylobacter* genus and the species of bacteria is selected from the group consisting of *C. avium*, *C. butzleri*, *C. canadensis*, *C. cinaedi*, *C. coli*, *C. concisus*, *C. corcagiensis*, *C. cryaerophilus*, *C. cuniculorum*, *C. curvus*, *C. fennelliae*, *C. fetus*, *C. gracilis*, *C. helveticus*, *C. hominis*, *C. hyoilei*, *C. hyointestinalis*, *C. insulaenigrae*, *C. jejuni*, *C. lanienae*, *C. lari*, *C. mucosalis*, *C. mustelae*, *C. nitrofigilis*, *C. peloridis*, *C. pylori*, *C. rectus*, *C. showae*, *C. sputorum*, *C. subantarcticus*, *C. upsaliensis*, *C. ureolyticus*, and *C. volucris*.

In some embodiments, the bacteria is a member of *Arcobacter* genus and the species of bacteria is selected from the group consisting of *A. bivalviorum*, *A. butzleri*, *A. cibarius*, *A. cryaerophilus*, *A. defluvii*, *A. ellisii*, *A. halophilus*, *A. marinus*, *A. molluscorum*, *A. mytili*, *A. nitrofigilis*, *A. skirrowii*, *A. thereius*, *A. trophiarum*, and *A. venerupis*.

In some embodiments, the bacteria is a member of *Neisseria* genus and the species of bacteria is selected from the group consisting of *N. bacilliformis*, *N. cinerea*, *N. denitrificans*, *N. elongata*, *N. flavescens*, *N. gonorrhoeae*, *N. lactamica*, *N. macacae*, *N. meningitidis*, *N. mucosa*, *N. pharyngis*, *N. polysaccharea*, *N .sicca*, *N. subflava*, and *N. weaver*.

In some embodiments, the bacteria is a member of *Francisella* genus and the species of bacteria is selected from the group consisting of *F. tularensis*, *F. novicida*, *F. hispaniensis*, *W. persica*, *F. noatunensis*, *F. philomiragia*, *F. halioticida*, *F. endociliophora*, and *F. guangzhouensis*.

In some embodiments, the bacteria is a member of *Pseudomonas* genus and the species of bacteria is selected from the group consisting of *P. aeruginosa*, *P. oryzihabitans*, and *P. plecoglossicida*.

In some embodiments, the bacteria is a member of *Acinetobacter* genus and the species of bacteria is *A. baumannii*.

In some embodiments, the bacteria is a member of *Moraxella* genus and the species of bacteria is selected from the group consisting of *M. catarrhalis*, *M. lacunata*, and *M. bovis*.

In some embodiments, the bacteria is a member of *Stenotrophomonas* genus and the species of bacteria is *S. maltophilia*.

In some embodiments, the bacteria is a member of *Haemophilus* genus and the species of bacteria is selected from the group consisting of *H. aegyptius*, *H. aphrophilus*, *H. avium*, *H. ducreyi*, *H. felis*, *H. haemolyticus*, *H. influenzae*, *H. parainfluenzae*, *H. paracuniculus*, *H. parahaemolyticus*, *H. pittmaniae*, *Haemophilus segnis*, and *H. somnus*.

In some embodiments, the bacteria is a member of *Pasteurella* genus and the species of bacteria is selected from the group consisting of *P. multocida, P. stomatis, P. dagmatis, P. canis, P. bettyae*, and *P. anatis*.

In some embodiments, the bacteria is a member of *Legionella* genus and the species of bacteria is selected from the group consisting of *L. pneumophila, L. anisa, L. bozemanae, L. cincinnatiensis, L. gormanii, L. jordani, L. longbeachae, L. maceachernii, L. micdadei, L. sainthelensi, L. wadsworthii*, and *L. waltersii*.

In some embodiments, the bacteria is a member of *Mycobacterium* genus and the species of bacteria is selected from a group consisting of *M. tuberculosis* and *M. smegmatic*.

In some embodiments, the bacteria is a member of a genus selected from: *Acinetobacter, Burkholderia, Acinetobacter, Burkholderia, Klebsiella, Pseudomonas*, and *Escherichia*. In such embodiments, the bacteria is a member of a species selected from: *K. pneumoniae, P. aeruginosa, Enterobacteriaceae*, and *E. coli*.

Treating Bacterial Infections

In some embodiments, the present application is also directed to a method of treating a bacterial infection in a subject, the method comprising administering to the subject in need thereof a therapeutically effective amount of a compound of Formula I, or a pharmaceutically acceptable salt thereof, as described herein. In some embodiments, the bacterial infection is resistant to treatment by one or more other antibiotic agents (e.g., any one of antibiotic agents described herein).

In some embodiments, the bacterial infection is caused by any one of the bacteria described herein (e.g., *P. acnes*, or MRSA). In some embodiments, the bacterial infection is resistant to treatment with one or more of the antibiotic agents described herein (e.g., bacterial infection is resistant to treatment with methicillin, vancomycin, rifampicin, gentamicin and/or ciprofloxacin). In these embodiments, the bacterial infection is characterized as persistent to treatment with one or more available antibiotic agents.

In some embodiments, the bacterial infection is a skin infection. In some aspects of these embodiments, the skin infection is selected from the group consisting of acne, pimples, impetigo, boils, cellulitis, folliculitis, carbuncles, scalded skin syndrome, skin abscesses, atopic dermatitis, and typhoid fever. In some embodiments, the bacterial infection is skin infection caused by *P. acnes*. In such embodiments, the skin infection is acne. In some embodiments, the bacterial infection is a skin and soft tissue infection (e.g., acne).

In some embodiments, the bacterial infection is a respiratory infection. In some aspects of these embodiments, the respiratory infection is selected from the group consisting of upper respiratory tract infection, bronchopneumonia, atypical pneumonia, tuberculosis, mycobacterium tuberculosis, pneumonia, anaerobic pleuropulmonary infection, ventilator-associated pneumonia, aspiration pneumonia, lung abscess, bronchitis, chronic obstructive pulmonary disease, obstructive pulmonary disease, Pontiac fever, and legionellosis.

In some embodiments, the bacterial infection is a wound infection. In some aspects of these embodiments, the wound infection is a postsurgical wound infection. In some embodiments, the bacterial infection is a blood stream infection. In some aspects of these embodiments, the blood stream infection is bacteremia or sepsis. In some embodiments, the bacterial infection is a pelvic infection. In some aspects of the embodiments, the pelvic infection is bacterial vaginosis.

In some embodiments, the bacterial infection is a gastrointestinal infection. In some aspects of these embodiments, the gastrointestinal infection is selected from the group consisting of peptic ulcer, chronic gastritis, duodenitis, gastroenteritis, diarrhea, dysentery, diphtheria, food poisoning and foodborne illness.

In some embodiments, the bacterial infection is a bone, joint or muscle infection. In some aspects of these embodiments, the bone, joint or muscle infection is selected from the group consisting of tetanus, secondary meningitis, meningitis, neonatal meningitis, sinusitis, laryngitis, arthritis, septic arthritis, Bartholin gland abscess, chancroid, osteomyelitis, endocarditis, mediastinitis, pericarditis, peritonitis, otitis media, blepharoconjunctivitis, keratoconjunctivitis, and conjunctivitis.

In some embodiments, the bacterial infection is selected from the group consisting of a dental infection, a zoonotic infection, an invasive systemic infection, a urinary tract infection, an abdominal infection, a CNS infection, an endovascular infection, and a nosocomial infection. In some embodiments, the bacterial infection is selected from the group consisting of syphilis, leprosy, abscesses, sepsis, empyema, and tularemia.

In some embodiments, the bacterial infection is associated with implanted devices (e.g., catheter, ballon catheter, stent, pacer etc). In some embodiments, the bacterial infection is osteomyelitis, endocarditis, or an infection associated with an implanted device, which is caused by a *S. aureus* persister.

In some embodiments, the bacterial infection is a connective tissue infection, or a joint or muscle infection. In some embodiments, the connective tissue or joint infection is caused by *P. acnes*. In such embodiments, the joint infection is an infection of a shoulder, a knee, a hip, or an elbow. In some embodiments, the bacterial infection is septic arthritis (e.g., septic arthritis caused by *P. acnes* or septic arthritis caused by *S. aureus*).

In some embodiments, any one of the bacterial infections described herein is caused by *S. aureus* (e.g., MRSA). In other embodiments, any one of the bacterial infections described herein is caused by *P. acnes*.

As the present disclosure shows, in one example, *S. aureus* exhibited no detectable development of resistance to the antibacterial compounds of the application, such as nTZDpa, which acted synergistically with aminoglycosides against both growing and persistent *S. aureus* cells. In combination with gentamicin, antibacterial compounds of the present disclosure (e.g., nTZDpa) significantly reduced bacterial burden in a mouse deep-seated chronic thigh infection without detectable toxicity. The compound of the present disclosure show a distinct membrane-active mechanism (disruption of bacterial lipid membrane) and good in vivo efficacy with a low relative cytotoxic profile.

Cleaning Compositions

In some embodiments, any one of compounds of Formula (I), or a salt thereof, may be used for killing bacteria on a surface (e.g., for disinfecting or sanitizing a surface). The surface may be metallic, plastic, ceramic, or wooden, for example, the surface is a floor, a table, a kitchen counter, a cutting board, or a medical instrument. Hence, any one of the compounds of the present application may be used in a commercial setting for general disinfecting, e.g., in medical and food industries. For these purposes, the compound may be provided in a cleaning composition comprising an acceptable carrier. The carrier(s) are "acceptable" in the sense of being compatible with the other ingredients of the cleaning composition. Acceptable carriers that may be used in a cleaning composition of the present application include, but are not limited to, alcohols, water, surfactants, emollients, stabilizers, thickeners, viscosifiers, and fragrances.

Compositions, Formulations, and Routes of Administration

In some embodiments, the present application also provides pharmaceutical compositions comprising an effective amount of a compound of any one of Formulae described herein, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and U.S. patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compound any one of Formulae described herein, or a pharmaceutically acceptable salt thereof, is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are otherly employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components.

Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application (e.g., skin and soft tissues).

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form, as a cream or a paste.

In some embodiments, the topical composition comprises a combination of a compound of any one of Formulae described herein, or a pharmaceutically acceptable salt thereof, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety. In some embodiments, diluents, carriers, and excipients may include, but are not limited to, polyethylene glycols (such as PEG200, PEG300, PEG400, PEG540, PEG600, PEG1450 or mixtures thereof) and coconut oils (such as propylene glycol dicaprate, coco-caprylate/caprate, propylene glycol dicaprylate/dicaprate, caprylic/capric triglyceride, caprylic/capric/lauric triglyceride, caprylic/capric/linoleic triglyceride, tricaprin, tricaprylin, glyceryl trioleate, neopentyl glycol dicaprylate/dicaprate, caprylic/capric/palmitic/stearic triglceride, or mixtures thereof). In some embodiments, suitable carriers include, but are not limited to, mineral oil, sorbitan monostearate, polysorbate 60, cetyl esters wax, cetearyl alcohol, 2-octyldodecanol, benzyl alcohol, and water. In some embodiments, preservatives may include, but are not limited to, 1,2-hexanediol, benzoic acid, benzothonium chloride, borax, bronopol, butylparaben, caprylyl glycol, chlorophene, chloroxylenol, chlorphenesin, dehydroacetic acid, diazolidinyl urea, DMDM hydantoin, ethylhexylglycerin, ethylparaben, formaldehyde-releasing preservative, Germaben II, hoelen, imidazolidinyl urea, iodopropynyl butylcarbamate, isobutylparaben, methylchloroisothiazolinone, methyldibromo glutaronitrile, Methylisothiazolinone, methylparaben, o-cymen-5-ol, phenoxyethanol, phenoxyisopropanol, phytosphingosine, polyaminopropyl biguanide, potassium sorbate, propylparaben, quaternium-15, sodium benzoate, sodium citrate, sodium dehydroacetate, sodium hexametaphosphate, sodium hydroxymethylglycinate, sodium lactobionate, sodium metabisulfite, sodium sulfite, sorbic acid, and styrax benzoin. In some embodiments, slip agents may include, but are not limited to, amodimethicone, bis-PEG-18 methyl ether dimethyl silane, bis-phenylpropyl dimethicone, butylene glycol, cetyl dimethicone, cetyl dimethicone copolyol, cetyl PEG/PPG-10/1-dimethicone, cyclohexasiloxane, cyclomethicone, cyclopentasiloxane, cyclotetrasiloxane, decylene glycol, diisostearoyl trimethylolpropane siloxy silicate, dimethicone, dimethicone copolyol, dimethicone crosspolymer, dimethiconol, dipropylene glycol, hexylene glycol, hydrolyzed silk, isododecane, methicone, methyl trimethicone, methylsilanol mannuronate, methylsilanol PEG-7 glyceryl cocoate, PEG-10 dimethicone, PEG-10 dimethicone/vinyl dimethicone crosspolymer, PEG-12 dimethicone, PEG/PPG-18/18 dimethicone, PEG/PPG-20/15 dimethicone, pentylene glycol, phenyl trimethicone, polymethylsilsesquioxane, PPG-3 benzyl ether myristate, silica dimethyl silylate, silk powder, siloxane, simethicone, sorbitol, stearyl dimethicone, stearyl methicone, triethoxycaprylylsilane, trimethylsiloxysilicate, xylitol, and zinc stearate. In some embodiments, sunscreen actives may include, but are not limited to, avobenzone, benzephenone-3, benzophenones, bumetrizole, butyl methoxydibenzoylmethane, ecamsule, ensulizole, ethylhexyl methoxycinnamate, homosalate, menthyl anthranilate, meradmiate, Mexoryl SX, octinoxate, octisalate, octocrylene, octyl methoxycinnamate, octyl salicylate, oxybenzone, padimate O, para-aminobenzoic acid (PABA), Parsol 1789, terephthalylidine dicamphor sulfonic acid, Tinosorb M, Tinosorb S, and titanium dioxide. In some embodiments, emulsifiers, surfactants, and detergents may include, but are not limited to, ammonium laureth sulfate, ammonium lauryl sulfate, arachidyl glucoside, behenic acid, bis-PEG-18 methyl ether dimethyl silane, $C_{20-40}$ pareth-40, cocamidopropyl betaine, cocamidopropyl dimethylamine, cocamidopropyl hydroxysultaine, coco-glucoside, coconut oil, decyl glucoside, dicetyl phosphate, dihydrocholeth-30, disodium cocoamphodiacetate, disodium cocoyl glutamate, disodium lauraminopropionate, glyceryl behanate, hydrogenated vegetable glycerides citrate, isohexadecane, isostearamide DEA, lauramphocarboxyglycinate, laureth-23, laureth-4, laureth-7, lauryl PEG-9 polydimethylsiloxyethyl dimethicone, lauryl alcohol, lauryl glucoside, magnesium laureth sulfate, magnesium oleth sulfate, myristic acid, nonoxynols, oleic acid, oleth 10, palm kernel acid, palmitic acid, PEG-60 almond glycerides, PEG-75 shea butter glycerides, PEG 90M, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-20 methyl glucose sesquistearate, PEG-40 stearate, PEG-60 hydrogenated castor oil, PEG-7 glyceryl cocoate, PEG-8, PEG-80 sorbitan laurate, PEG/PPG-17/6 copolymer (polyethylene glycol/polypropylene glycol-17/6 copolymer), PEG/PPG-18/18 dimethicone, PEG/PPG-20/15 dimethicone, poloxamer 184, Poloxamer 407, poloxamers, polyglyceryl-3 beeswax, polyglyceryl-4 isostearate, polyglyceryl-6 isostearate, polysorbate 20, polysorbate 60, polysorbate 80, potassium cetyl phosphate, potassium hydroxide, potassium myristate, PPG-12 buteth-16, PPG-26-Buteth-26, *Salvia officinalis, Saponaria officinalis* extract, soapwort, sodium $C_{14-16}$ olefin sulfonate, sodium cetearyl sulfate, sodium cocoamphoacetate, sodium cocoate, sodium cocoyl glutamate, sodium cocoyl isethionate, sodium dilauramidoglutamide lysine, sodium hexametaphosphate, sodium hydroxide, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium methyl cocoyl taurate, sodium methyl taurate, sodium myreth sulfate, sodium palm kernelate, sodium palmate, sodium PEG-7 olive oil carboxylate, sodium trideceth sulfate, steareth-20, TEA-lauryl sulfate (triethanolamine-lauryl sulfate), and tribehenin PEG-20 esters.

Application of the subject therapeutics may be local, so as to be administered at the site of interest (e.g., infected area of skin, or an infected joint or other connective tissue). Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides a method of coating an implantable medical device comprising the step of contacting said device with the coating composition described above. It will be obvious to those skilled in the art that the coating of the device will occur prior to implantation into a mammal.

According to another embodiment, the present application provides a method of impregnating an implantable drug release device comprising the step of contacting said drug release device with a compound or composition of the present application. Implantable drug release devices include, but are not limited to, biodegradable polymer capsules or bullets, non-degradable, diffusible polymer capsules and biodegradable polymer wafers.

According to another embodiment, the present application provides an implantable medical device coated with a compound or a composition comprising a compound of the present application, such that said compound is therapeutically active.

Where an organ or tissue is accessible because of removal from the subject, such organ or tissue may be bathed in a medium containing a composition of the present application, a composition of the present application may be painted onto the organ, or a composition of the present application may be applied in any other convenient way.

In the pharmaceutical compositions of the present application, a compound of any one of Formulae described herein, or a pharmaceutically available salt thereof, is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In some embodiments, a pharmaceutical composition comprising a compound of Formulae described herein, or a pharmaceutically acceptable salt thereof, also optionally contains at least one additional therapeutic agent, or a pharmaceutically acceptable salt thereof. Such composition is suitable for parenteral administration (e.g., a lyophilized powder or a sterile injection solution). In other aspects of these embodiments, the pharmaceutical composition is suitable for topical application (e.g., an aerosol spray, a cream, an emulsion, a foam, an oil, a gel, a lotion, a mousse, an ointment, or a patch).

In some embodiments, an effective amount of a compound of any one of Formulae described herein, or a pharmaceutically acceptable salt thereof, can range, for example, from about 1 mg to about 200 mg, from about 1 to about 100 mg, from about 1 to about 50 mg, from about 1 mg to about 30 mg, from about 1 mg to about 15 mg, from about 10 mg to about 2000 mg, from about 10 mg to about 1900 mg, from about 10 mg to about 1800 mg, from about 10 mg to about 1700 mg, from about 10 mg to about 1600 mg, from about 10 mg to about 1500 mg, from about 10 mg to about 1400 mg, from about 10 mg to about 1300 mg, from about 10 mg to about 1200 mg, from about 10 mg to about 1100 mg, from about 10 mg to about 1000 mg, from 10 mg about to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, and from about 10 mg to about 50 mg. In some embodiments, an effective amount of a compound of any one of Formulae described herein, or a pharmaceutically acceptable salt thereof, is 1 mg, 2 mg, 3 mg, 4 mg, 5 mg, 6 mg, 7 mg, 8 mg, 9 mg, or 10 mg. In some aspects of these embodiments, the composition containing an effective amount of a compound of any one of Formulae described herein, or a pharmaceutically acceptable salt thereof, is administered once daily. In some aspects of these embodiments, the composition containing an effective amount of a compound of any one of Formulae described herein, or a pharmaceutically acceptable salt thereof, is administered twice daily. In some aspects of these embodiments, the composition containing an effective amount of a compound of any one of Formulae described herein, or a pharmaceutically acceptable salt thereof, is administered thrice daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. In some embodiments, an effective dose of a compound of any one of Formulae disclosed herein does not cause cardiac, renal, and/or hepatic toxicity. In some embodiments, an effective dose of a compound of any one of Formulae disclosed herein does not cause hemolysis in a subject.

Combination Therapies

In some embodiments, an antibacterial compound of the present disclosure is administered to the subject in combination with an additional therapeutic agent. The additional therapeutic agent may be selected from any compound or therapeutic agent known to have or that demonstrates advantageous properties when administered with a compound of any one of Formulae described herein.

The second therapeutic agent may be administered to the subject in a therapeutically effective amount. Typically, an effective amount of the additional therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these additional therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000).

In some embodiments, the additional therapeutic agent is an antibiotic.

In some embodiments, the antibiotic is a cationic antimicrobial peptide (CAMP). In some aspects of these embodiments, the cationic antimicrobial peptide is a defensin peptide (e.g., defensin 1 such as beta-defensin 1 or alpha-defensin 1), or cecropin, andropin, moricin, ceratotoxin, melittin, magainin, dermaseptin, bombinin, brevinin (e.g., brevinin-1), esculentin, buforin II (e.g., from amphibians), CAP18 (e.g., from rabbits), LL37 (e.g., from humans), abaecin, apidaecins (e.g., from honeybees), prophenin (e.g., from pigs), indolicidin (e.g., from cattle), brevinins, protegrin (e.g., from pig), tachyplesins (e.g., from horseshoe crabs), or drosomycin (e.g., from fruit flies).

In some embodiments, the antibiotic is selected from the quinolone class of antibiotic compounds. In some aspects of these embodiments, the antibiotic is selected from the group consisting of levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, and besifloxacin.

In some embodiments, the antibiotic is selected from a β-lactam, a monobactam, oxazolidinone, and lipopeptide.

In some embodiments, the antibiotic is selected from the cephalosporin class of antibiotic compounds. In some aspects of these embodiments, the antibiotic is selected from the group consisting of cefazolin, cefuroxime, ceftazidime, cephalexin, cephaloridine, cefamandole, cefsulodin, cefonicid, cefoperazine, cefoprozil, and ceftriaxone.

In some embodiments, the antibiotic is selected from the penicillin class of antibiotic compounds. In some aspects of these embodiments, the antibiotic is selected from the group consisting of penicillin G, penicillin V, procaine penicillin, and benzathine penicillin, ampicillin, and amoxicillin, benzylpenicillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, and pivampicillin.

In some embodiments, the antibiotic is selected from the carbapenem class of antibiotic compounds. In some aspects of these embodiments, the antibiotic is selected from the group consisting of thienamycin, tomopenem, lenapenem, tebipenem, razupenem, imipenem, meropenem, ertapenem, doripenem, panipenem (betamipron), and biapenem.

In some embodiments, the antibiotic is selected from the lipopeptide class of antibiotic compounds. In some aspects of these embodiments, the antibiotic is selected from the group consisting of polymyxin B, colistin (polymyxin E), and daptomycin.

In some embodiments, the antibiotic is selected from the aminoglycoside class of antibiotic compounds. In some aspects of these embodiments, the antibiotic is selected from the group consisting of gentamicin, amikacin, tobramycin, debekacin, kanamycin, neomycin, netilmicin, paromomycin, sisomycin, spectinomycin, and streptomycin. When the second therapeutic agent is an aminoglycoside antibiotic (e.g., gentamicin, tobramycin, neomycin, kanamycin, or streptomycin), the compound of any one of Formulae described here in the aminoglycoside antibiotic act synergistically. In some embodiments, when the additional therapeutic agent is gentamicin, the effective amount of gentamicin is lower than the amount that causes nephrotoxicity in a subject.

In some embodiments, the antibiotic is selected from the glycopeptide class of antibiotic compounds. In some aspects of these embodiments, the antibiotic is selected from the group consisting of vancomycin, teicoplanin, telavancin, ramoplanin, daptomycin, decaplanin, and bleomycin.

In some embodiments, the antibiotic is selected from the macrolide class of antibiotic compounds. In some aspects of these embodiments, the antibiotic is selected from the group consisting of azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin and cineromycin B.

In some embodiments, the antibiotic is selected from the ansamycin class of antibiotic compounds. In some aspects of these embodiments, the antibiotic is selected from the group consisting of streptovaricin, geldanamycin, herbimycin, rifamycin, rifampin, rifabutin, rifapentine and rifamixin.

In some embodiments, the antibiotic is selected from the sulfonamide class of antibiotic compounds. In some aspects of these embodiments, the antibiotic is selected from the group consisting of sulfanilamide, sulfacetarnide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole and phthalylsulfathiazole.

In some embodiments, the antibiotic is selected from the group consisting of quinolones, fluoroquinolones, β-lactams, cephalosporins, penicillins, carbapenems, lipopeptide antibiotics, glycopeptides, macrolides, ansamycins, sulfonamides, and combinations of two or more thereof.

The additional therapeutic agent may be administered to the subject in the same pharmaceutical composition or dosage form as the compound of any one of Formulae disclosed herein; or the additional therapeutic agent and the compound of any one of Formulae disclosed herein may be administered to the subject in separate pharmaceutical compositions or dosage forms (e.g., any one of the compositions, formulation, routes and dosage forms described herein). The separate dosage forms may be administered together consecutively (e.g., within less than 24 hours of one another) or simultaneously (e.g., administered to the patient at the same time or within less than 5 minutes of one another).

Some of the second therapeutic agents referenced above will act synergistically with the compounds of the present application. In some embodiments, some of the second therapeutic agents referenced above will show additive effect. When this occurs, it will allow the effective dosage of the second therapeutic agent and/or the compound of the present application to be reduced from that required in a monotherapy. This has the advantage of minimizing toxic side effects of either the second therapeutic agent of a compound of the present application, synergistic improvements in efficacy, improved ease of administration or use and/or reduced overall expense of compound preparation or formulation.

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methylpropan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —C(O)NH$_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —(O)$_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula -($C_{1-3}$ alkylene)—CN.

As used herein, the term "HO-$C_{1-3}$ alkyl" refers to a group of formula -($C_{1-3}$ alkylene)—OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{2-10}$). In some embodiments, the cycloalkyl is a $C_{3-10}$ monocyclic or bicyclic cycloalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen.

In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, N=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the bacteria with a compound of the invention includes the administration of a compound of the present invention to an individual or patient, such as a human, infected with a bacteria, as well as, for example, introducing a compound of the invention into a sample containing a cellular or purified preparation containing the bacteria.

As used herein, the term "persister" refers to bacteria in non-growing dormant state in which biosynthetic process related to bacteria growth are inactive or significantly attenuated. Typically, persisters tolerate high concentrations of other antibiotics. In some embodiments, persisters are responsible for the antibiotic-tolerance of biofilms and the recalcitrance of chronic infections. Persistent bacteria may also be resistant to antibiotic drugs.

As used herein, the term "resistant" refers to bacterial strains that exhibit a high level of tolerance to one or more antibiotics. In some embodiments, the bacterial strain is resistant when the MIC of the bacterial strain is at least 2× (2-fold) of the MIC for the same strain prior to developing resistance. The x-fold resistant bacterial strain may be determined by the following steps: (i) MIC is determined for a non-resistant bacterial strain; (ii) the non-resistant bacterial strain is treated in a multi-well plate with an antibiotic at 2×, 5×, 10×etc, of the minimal inhibitory concentration (MIC); (iii) bacterial culture treated with the highest concentration that permitted bacterial growth is taken for serial passage for 100 days; and (iv) MIC of the bacterial culture after 100 days of serial passage is determined. If MIC of the bacterial culture after 100 days of serial passage is at least 2× of the MIC of the non-resistant strain, then the bacterial culture is at least 2× resistant to the antibiotic As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

EXAMPLES

Methods

Bacterial strains, growth conditions, and persister isolation. Methicillin-resistant *S. aureus* strains, MW2 BAA-1707, ATCC 33591, and JE2, methicillin-susceptible *S. aureus* strains, NCTC 8325, Newman, and ATCC 29213, vancomycin-resistant *S. aureus* strain, VRS1, *Enterococcus faecium* E007, vancomycin-resistant *E. faecium* strains, C68,[7] WB312, and WC196, Klebsiella pneumoniae WGLW2 (BEI Resources, Manassas, Va., USA), Acinetobacter baumannii ATCC 17978, Pseudomonas aeruginosa PA14, and Enterobacter aerogenes ATCC 13048 were used to test antimicrobial activity (Table 1). *S. aureus* strains were grown in tryptic soy broth (TSB) (BD, Franklin Lakes, N.J., USA), and *E. faecium* was grown in brain-heart infusion (BHI) broth (BD, Franklin Lakes, N.J., USA) at 37° C. *K. pneumoniae, A. baumannii, P. aeruginosa*, and *E. aerogenes* were grown in Luria Bertani (LB) broth (BD, Franklin Lakes, N.J., USA) at 37° C.

Antimicrobial agents and chemicals. Vancomycin, oxacillin, gentamicin, tobramycin, neomycin, kanamycin, streptomycin, ciprofloxacin, rifampicin, and tetracycline were purchased from Sigma-Aldrich (St Louis, Mo., USA). nTZDpa was purchased from R&D Systems (Minneapolis, Minn., USA). All compounds were dissolved in DMSO or ddH$_2$O to make 10 mg/mL stocks.

Minimal inhibitory concentration (MIC) assay. The MICS of antibiotics were determined by the standard micro-dilution method recommended by the Clinical and Laboratory Standards Institute. MIC assays were conducted in biological triplicate.

*C. elegans*-MRSA liquid killing assay. The *C. elegans*-MRSA infection assay was conducted as described in a previous study. Briefly, a black, clear-bottom 384-well plate (Corning no. 3712) was filled with 20 μL M9 buffer including the desired concentrations of nTZDpa, 1% DMSO (negative control), or 10 μg/mL vancomycin (positive control). After adding 15 young adult *C. elegans* glp-4(bn2); sek-1(km4) animals to the wells using a COPAS large particle sorter (Union Biometrica, Mass., USA), 35 μL of MRSA MW2 suspension was added (OD$_{600}$ 0.08). The assay plate was sealed with a gas-permeable membrane (Breathe-Easy, Diversified Biotech, Dedham, Mass., USA), and then incubated in a humidified chamber at 25° C. for 5 days. After washing the plate 8-times with M9 buffer using a microplate washer (BioTek ELx405, BioTek, Vt., USA), worms were stained with 0.7 μM SYTOX Orange. To evaluate worm survivability, the worms were imaged using an Image Xpress Micro automated microscope (Molecular Devices), capturing both transmitted light and TRITC (535 nm excitation, 610 nm emission) fluorescent images with a 2× objective. Only dead worms stain with SYTOX Orange. The assay was conducted in biological triplicate.

Killing kinetics assay. An MRSA MW2 overnight culture was diluted 1:10,000 in 25 mL TSB (~10$^5$ CFU/mL) in a 250 mL flask and incubated at 37° C. with shaking at 200 rpm for 4.5 h until it reached exponential-phase (~2×10$^7$ CFU/mL). 1 mL of the exponential phase cell culture was mixed with 1 mL of pre-warmed TSB containing twice the desired concentrations of antibiotics in a 96-well assay block (Corning Costar 3960). The assay block was incubated at 37° C. with shaking at 200 rpm. At every hour, 400 μl aliquots were taken, washed once with phosphate buffered saline (PBS), serially diluted and spot-plated onto tryptic soy agar (TSA, BD) plates. After incubation at 37° C. for overnight, colonies were counted to enumerate the number of cells. These experiments were conducted in biological triplicate.

Serial passage resistance development. Serial-passage of *S. aureus* cultures in sub-inhibitory concentrations of nTZDpa or ciprofloxacin as a control was carried out to determine the rate of resistance development following the methodology described in a previous study. Briefly, an extended range of concentrations of nTZDpa was generated by two-fold serial dilution with cation-adjusted Mueller Hinton (CaMH) broth (Difco, Detroit, USA) from three different starting concentrations (20, 24, and 32 μg/mL) covering 0.1875 to 32.0 μg/mL, which extended over three rows of the 96-well plate. Three sets of the extended gradient of nTZDpa were created in the 96-well plate to provide triplicates of the experiment. The same extended range of concentrations of ciprofloxacin was used. MRSA MW2 overnight cultures were adjusted to 1×10$^6$ CFU/mL in CaMH broth, and 50 μL of the diluted cultures were dispensed into the 96-well plates containing 50 μL of the extended gradient of antibiotics. After incubation for 24 h at 35° C., bacterial growth was determined by measuring optical density at 600 nm using a SpectraMax plate reader (Molecular Devices, Sunnyvale, Calif.), and growth was defined as an optical density reading of ≥0.1. Bacterial cells growing at the highest concentration of the antimicrobial (just below the MIC) were diluted 1:1000 in CaMH broth and then used to inoculate the next day's serial-passage plate. The remaining bacterial cells were stored at −80° C. in CaMH broth with 16% glycerol. This process was repeated for 25 days.

SYTOX Green membrane permeability assay. Exponential-phase MRSA MW2 cells prepared as described above under Killing kinetics assay were washed 3 times with the same volume of PBS. The washed cells were adjusted to $OD_{600}$=0.4 with PBS. SYTOX Green (Molecular Probes, Waltham, Mass., USA) was added to 10 mL of the diluted bacterial suspension to a final concentration of 5 μM and incubated for 30 min at room temperature in the dark. 50 μL of the bacteria/SYTOX Green suspension was mixed with 50 μl of PBS containing twice the desired concentrations of compounds in black, clear-bottom, 96-well plates (Corning no. 3904). Fluorescence was measured at room temperature using a spectrophotometer (SpectraMax M2, Molecular Devices), with excitation and emission wavelengths of 485 nm and 525 nm, respectively. All experiments were conducted in biological triplicate.

Transmission electron microscopy. Exponential-phase MRSA MW2 cells prepared as described above under Killing kinetics assay were treated with 16 μg/mL (4× MIC) nTZDpa or 0.1% DMSO (control) for 2 h. 1 mL of the treated cells was fixed with the same volume of a 2× fixative, a mixture of 5% glutaraldehyde, 2.5% paraformaldehyde and 0.06% picric acid in 0.2 M sodium cacodylate buffer (pH 7.4). Fixed cells were washed in 0.1 M cacodylate buffer and post-fixed with 1% Osmiumtetroxide ($OsO_4$)/ 1.5% Potassiumferrocyanide ($KFeCN_6$) for 1 h. The cells were then washed twice in water and once in maleate buffer (MB). After incubation in 1% uranyl acetate in MB for 1 h, the cells were washed twice in water and subsequently dehydrated in an alcohol gradient series (10 min each; 50%, 70%, 90%, 2×10 min 100%). The cells were treated with propyleneoxide for 1 h and then infiltrated overnight in a 1:1 mixture of propylene oxide and Spurr's low viscosity resin (Electron Microscopy sciences, Hatfield, Pa.). The cells were embedded in Spurr's resin and polymerized at 60° C. for 48 h. The polymerized samples were sectioned using a Reichert Ultracut-S microtome (Leica Microsystem, Wetzlar, Germany). The samples were stained with lead citrate and micrographs of the cells were taken using a JEOL 1200EX transmission electron microscope (Harvard Medical School EM facility).

Preparation of giant unilamellar vesicles (GUVs) and observation of compound effects on GUVs. GUVs were prepared by the electroformation method described previously. Dioleoyl-glycero-phosphocholine (DOPC), Dioleoyl-glycero-phosphoglycerol (DOPG) and Dioleoyl-glycero-phosphoethanolamine-N-lissamine rhodamine B sulfonyl (18:1 Liss Rhod PE) were purchased from Avanti Polar Lipids (Alabaster, Ala., USA). 4 mM of a lipid mixture consisting of DOPC/DOPG/18:1 Liss Rhod PE (7:3:0.005) was dissolved in chloroform. Indium tin oxide (ITO)-coated slides (50×75×1.1 mm, Delta Technologies, Loveland, Colo., USA) were coated with 40 μL of the lipid mixture and dried in a vacuum chamber for 2 h to remove chloroform. An electroformation chamber was made by placing a 2 mm thick Teflon spacer between the two lipid-coated ITO slides. After adding 2 mL of 100 mM sucrose into the electroformation chamber, the chamber was sealed with binder clips, and then connected to an AC field function generator. The swelling of the lipid bilayers was facilitated by applying an electric AC-field (10 Hz). The field strength was gradually increased from 0 to 0.5 kV/m for 30 min, and then maintained at a constant strength for 30 min. GUVs were detached from surfaces by reducing the AC-field from 10 Hz to 5 Hz for 20 min. The GUV suspension was diluted (1:30) in a 100 mM glucose solution. 49 μL of the diluted GUV suspension (~100 vesicles) was added to a black, clear-bottom 384-well plate (Corning no. 3712). The plate was left in the dark at room temperature for 30 min until all of the GUVs settled on the bottom of the plates. After adding 1 μL of compound solution to a well (final compound concentration: 1× MIC), the GUVs were observed and imaged with an optical microscope equipped with fluorescence contrast and a digital camera (40× or 63× objectives, Axio Observer. Al & AxioCam MRm, Zeiss, Germany). Images and movies are representative of three independent experiments.

All-atom molecular dynamics (MD) simulations. All-atom MD simulations were based on the GROMACS package (version 4.6.7) and were performed to investigate nTZDpa and its analogs interacting with the plasma membrane of S. aureus. The Gromos54a7 force field with Automated Topology Builder (ATB) was employed for the partial atomic charges, non-bonded and bonded parameters of the nTZDpa and its analogs in our simulations. The plasma membrane of S. aureus was represented by a mixed lipid bilayer composed of 88 neutrally charged DOPC and 40 negatively-charged DOPG lipids (~7:3 ratio) with dimensions of 5.96 nm×5.96 nm. This mixture of lipids has been widely used to mimic anionically-charged bacterial membranes and to elucidate the mechanism of the interactions between membrane-targeting antimicrobials and membrane lipid bilayers, including daptomycin and S. aureus lipid bilayers. A pure DOPC lipid bilayer (128 DOPC lipids) was used as a control to study the electronegative effects of hydroxyl and amine groups. The DOPC and DOPG lipids were modeled with Berger's lipid force field, which is an extensively validated all-atom lipid model for membrane-related simulations. The system was modeled as an NPT ensemble, with periodic boundary conditions in all directions, under constant pressure P (1 atm) and constant temperature T (300 K). After initial equilibration of solvated lipid systems for 500 ns, nTZDpa or its analogs were introduced into the water phase above the membrane. After 100 ns of re-equilibration, the inserted molecules were released and their interactions with the membrane, including attachments, penetrations and equilibrium configurations, were further simulated for 500 ns, similar to a previous study. The free energy profiles for the translocations of nTZDpa and its analogs were calculated by steered molecular dynamics, umbrella sampling and weighted histogram analysis method, with results giving the transfer energies and energy barriers associated with membrane penetration.

Human blood hemolysis. Hemolytic activity was evaluated as described in a previous study. Briefly, 100 μL of 4% human erythrocytes (Rockland Immunochemicals, Limerick, Pa., USA) was added to 100 μL of 2-fold serial dilutions of compounds in PBS, 0.2% DMSO (negative control), or 2% Triton-X 100 (positive control) in a 96-well plate. The 96-well plate was incubated at 37° C. for 1 h and then centrifuged at 500× g for 5 min. 50 μL of the supernatant was transferred to a fresh 96-well plate, and absorbance of supernatants was measured at 540 nm. Percent hemolysis was calculated using the following equation: ($A_{540}$ nm of compound treated sample−$A_{540\ nm}$ of 0.1% DMSO treated sample)/($A_{540\ nm}$ of 1% Triton X-100 treated sample−$A_{540\ nm}$ of 0.1% DMSO treated sample)×100. $HC_{50}$ (concentration of a compound causing 50% hemolysis) was determined using SigmaPlot 10.0 (Systat Software Inc., San Jose, Calif., USA).

Cytotoxicity. Cytotoxicity was evaluated using human hepatoma G2 (HepG2, ATCC HB 8065; ATCC, Manassas, Va., USA) or human renal proximal tubular epithelial cells (HKC-8). HepG2 and HKC-8 cells were grown in Dulbecco's modified Eagle F-12 media mixed 1:1 with Ham's F-12 (DMEM/F-12, Life Technologies, Carlsbad, Calif., USA) supplemented with 10% FBS and 4 mM L-glutamine at 37° C. in 5% $CO_2$. For cytotoxicity assays, HepG2 or HKC-8 was cultured in 96-well plates in 100 µL/well of the proper media to reach 70-80% confluence. The cells were then treated with a range of concentrations of nTZDpa or its analogs for 72 h. 10 µL of WST-1 (Roche, Mannheim, Germany) was added per well for the last 4 h of the 72 h period. WST-1 reduction was measured at absorbance 450 nm. The percent fluorescence relative to that of the no-treatment control was calculated. The assay was carried out in biological triplicate.

Antibiotic synergy test. Antibiotic synergism was evaluated by the checkerboard method. Briefly, 2-fold serial dilutions of nTZDpa were combined with 2-fold serial dilutions of each other antibiotic, which created an 8×8 matrix in a 96-well microtiter plate. The fractional inhibitory concentration index (FICI) was calculated as follows: FICI=MIC of compound A in combination/MIC of compound A alone+MIC of compound B in combination/MIC of compound B alone. The interaction between two compounds was defined, as follows: synergy if FICI≤0.5, no interaction if 0.5<FICI≤4, and antagonism if FICI>4.

Persister killing assay. As has been previously demonstrated, stationary-phase cells of *S. aureus* are tolerant to other antibiotics, and it was shown previously that MRSA MW2 cells become persisters when grown to stationary phase, which are tolerant to 100× MICS of other antibiotics such as gentamicin, ciprofloxacin and vancomycin. Persister cells of MRSA MW2 were prepared by growing cultures overnight to stationary phase at 37° C. at 200 rpm and washing 3 times with PBS. 1 mL of ~2×10⁸ CFU/mL MRSA persisters was added to 1 mL of PBS containing 2-fold of the desired concentration of antibiotics in a 96-well assay block (Corning Costar 3960). The assay block was incubated at 37° C., with shaking at 200 rpm. At specific times, 4000 aliquots were removed, washed once with PBS, serially diluted and spot-plated on TSA plates. Colonies were counted to enumerate the number of live cells after overnight incubation at 37° C. These experiments were conducted in biological triplicate.

Biofilm persister killing assay. An overnight culture of cells was diluted 1:200 with TSB supplemented with 0.2% glucose and 3% NaCl. A 13 mm-diameter Millipore mixed cellulose ester membrane (EMD Millipore GSWP01300) was placed at the bottom of each well of a 12-well plate (Falcon 353043). 1 mL of the diluted culture was added to each well and incubated statically at 37° C. for 24 h. The membranes were washed 3-times with PBS and transferred to a fresh 12-well plate. 1 mL of PBS containing the desired concentration of antibiotics was added to each well, and then the plate was incubated statically at 37° C. for 24 h. The membranes were washed 3 times with PBS, placed in 2-mL microcentrifuge tubes containing 1 mL PBS, and sonicated in an ultrasonic bath (Fisher Scientific FS 30) for 10 min. The sonicated samples were serially diluted and spot-plated on TSA to enumerate the number of live cells. The experiment was conducted in biological triplicate.

Deep-seated mouse thigh infection model. In vivo efficacy of nTZDpa alone or in combination with gentamicin against MRSA persisters was evaluated by a previously described neutropenic mouse thigh infection model with modifications. Six-week-old female CD-I mice (20-25 g, Charles River Laboratories, Wilmington, Mass., USA) were obtained from Charles River Laboratories (Wilmington, Mass., USA). The CD-I mice were rendered neutropenic by administering 150 mg/kg and 100 mg/kg of cyclophosphamide intraperitoneally (i.p.) at 4 days and 1 day before infection, respectively. On the day of infection, overnight culture of MRSA MVV2 was washed 3-time with sterile saline and diluted to $10^7$ CFU/ml in the saline. 50 µl of the diluted culture (5×10⁵ CFU per mouse) was injected to the right thigh of each mouse. nTZDpa was dissolved in Kolliphor EL (Sigma-Aldrich, St Louis, Mo., USA)/ethanol 1:1 and then diluted 1:10 in saline to a final concentration of 50 mg/kg. At 24 h post-infection, groups of mice (n=10) were treated with 30 mg/kg gentamicin subcutaneously (s.c.) every 12 h, 25 mg/kg vancomycin i.p. every 24 h, 50 mg/kg nTZPpa i.p. every 24 h, or the combination of 50 mg/kg nTZDpa i.p. every 24 h and 30 mg/kg gentamicin s.c. every 12 h for 5 days. Control mice were injected with 250 µl of 10% Kolliphor EL/ethanol in saline i.p. every 24 h for 5 days. Mice were euthanized at 96 h post-infection. Blood was collected by cardiac puncture, and the infected thighs were aseptically excised, weighed, and stored at 4° C. until homogenization. To evaluate hepatic and renal toxicities, the levels of alanine aminotransferase and blood urea nitrogen were analyzed with commercially available kits, following the manufacturer's protocol (Pointe Scientific, Canton, Mich., USA). Thighs were homogenized in PBS, serially diluted with PBS, and spot-plated on TSA plates. After incubating the TSA plates at 37° C. overnight, the number of colonies were enumerated to calculate CFU/g thigh tissue. This study and all experiments were performed in accordance with guidelines approved by the Rhode Island Hospital Institutional Animal Care and Use Committee (RIH IACUC). Statistical significance among each group was analyzed by one-way ANOVA with post-hoc Tukey test using PASW Statistics 18 (SPSS Inc. Chicago, Ill., USA).

Example 1—Antibacterial Activity of nTZDpa nTZDpa, previously known to be a non-thiazolidinedione peroxisome proliferator-activated receptor gamma (PPARγ) partial agonist, has been previously investigated in vivo for diabetes therapy.

To show the anti-infective activity of nTZDpa against MRSA, *C. elegans* survival was evaluated following MRSA infection for a range of nTZDpa concentrations. Treatment with 2 µg/ml to 16 µg/ml of nTZDpa rescued ~90% of *C. elegans* from MRSA-mediated lethality with an $EC_{50}$ (median effective concentration) of ~0.6 µg/mL (FIG. 1), which is 2-fold higher than the $EC_{50}$ of vancomycin.

Figure 10:
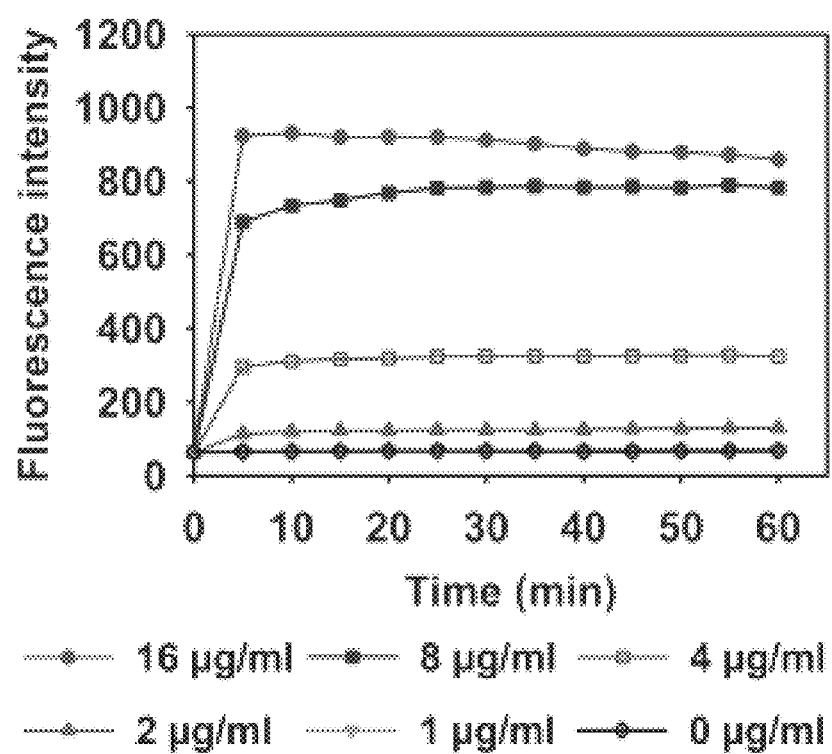
FIG. 10 contains line plot showing membrane permeabilization of MRSA by nTZDpa monitored with SYTOX Green dye uptake. Results are shown as means of triplicates. Error bars (s.d.) are excluded for clarity.

In vitro, nTZDpa exhibited antimicrobial activity against a panel of both *S. aureus* and *Enterococcus faecium* clinical strains, including the multidrug-resistant *S. aureus* strains MW2 and VRS1, with a minimal inhibitory concentration (MIC) of ~4 µg/mL (Table 1). nTZDpa was not effective against Gram-negative bacteria (Table 1). The MIC is 2-fold higher than the concentration at which nTZDpa rescues over 90% of the *C. elegans* animals from an MRSA infection (FIG. 1). These data indicate that nTZDpa most likely functions as an antibiotic that targets bacterial growth and/or viability, and are consistent with the observation that treatment of MRSA MVV2 cells with nTZDpa allows SYTOX Green permeabilization (FIG. 10).

TABLE 1

Minimum inhibitory concentration (μg/mL) of nTZDpa against major pathogenic bacteria

| Bacterial strains | nTZDpa | Van[1] | Oxa[2] | Gm[3] | Cipro[4] |
|---|---|---|---|---|---|
| S. aureus (MRSA) MW2 | 4 | 1 | 64 | 1 | 0.5 |
| S. aureus NCTC 8325 | 4 | 1 | 0.5 | 2 | 0.125 |
| S. aureus Newman | 4 | 2 | 0.5 | 2 | 0.25 |
| S. aureus ATCC 29213 | 4 | 1 | 0.5 | 2 | 0.5 |
| S. aureus ATCC 33591 | 4 | 2 | >64 | 8 | 0.25 |
| S. aureus JE2 | 4 | 1 | 64 | 4 | 16 |
| S. aureus VRS1 | 4 | >64 | >64 | 64 | 64 |
| E.faecium E007 | 4 | 1 | >64 | >64 | >64 |
| E. faecium C68 | 4 | 64 | >64 | >64 | >64 |
| E. faecium WB312 | 4 | 16 | >64 | 32 | 32 |
| E. faecium WC196 | 4 | 64 | >64 | 64 | 1 |
| K. pneumoniae WGLW2 | >64 | >64 | >64 | 1 | 0.031 |
| A. baumannii ATCC 17978 | >64 | >64 | >64 | 1 | 0.25 |
| P. aeruginosa PA14 | >64 | >64 | >64 | 2 | 0.063 |
| E. aerogenes ATCC 13048 | >64 | >64 | >64 | 2 | 0.031 |

Figure 3:
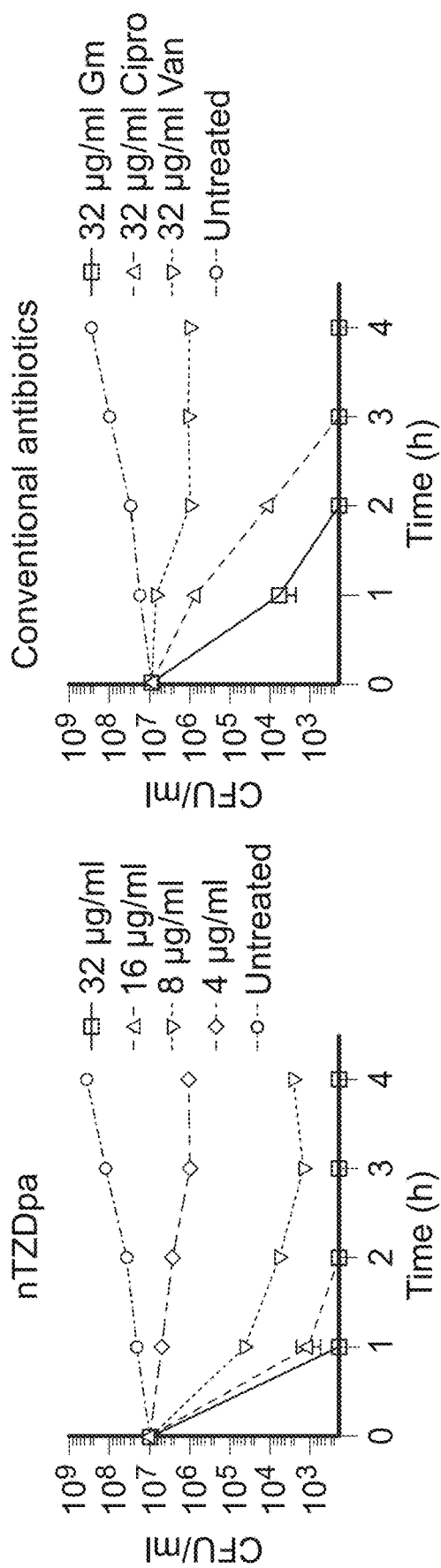
FIG. 3 shows killing kinetics of nTZDpa against growing and persistent MRSA and its cytotoxicity. Exponential phase MRSA MW2 cells were treated with the indicated concentrations of nTZDpa, gentamicin (Gm), ciprofloxacin (Cipro), or vancomycin (Van) for 4 hours. Colony forming unit (CFU) counts of persisters were measured by serial dilution and plating on TSA plates. The data points on the x-axis are below the level of detection (2×102 CFU/mL). Results are shown as mean±s.d.; n=3.

[1]Van: vancomycin, [2]Oxa: oxacillin, [3]Gm: gentamicin, [4]Cipro: ciprofloxacin Effective against MRSA resistant strains: Unexpectedly, 16 μg/ml nTZDpa completely eradicated ~10[7] CFU/mL exponential-phase MRSA MW2 within 2 hours, which was similar to 32 μg/ml gentamicin and faster than 32 μg/ml ciprofloxacin or 32 μg/ml vancomycin (FIG. 3).

Figure 4:
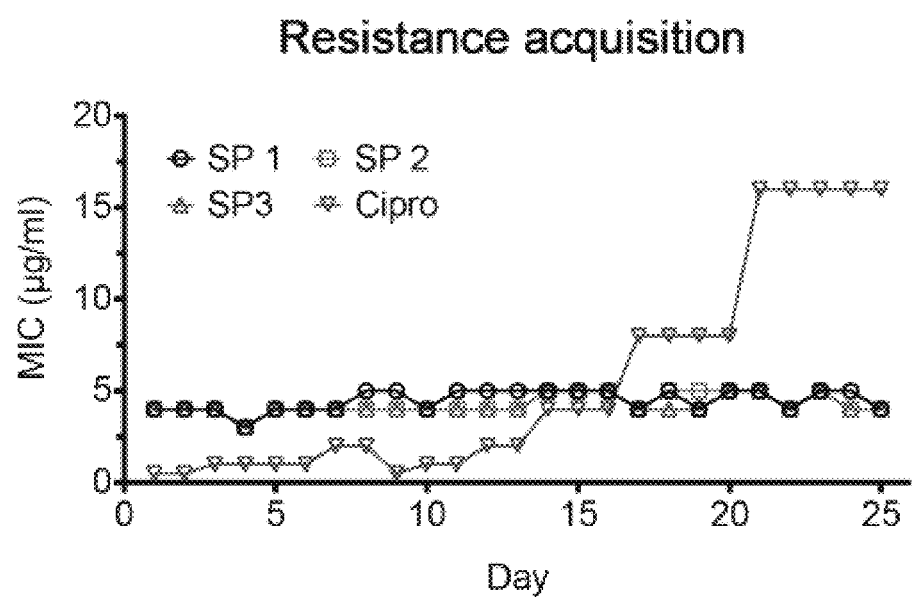
FIG. 4 shows three attempts to develop MRSA resistance to nTZDpa (SP 1, 2, and 3) and to ciprofloxacin over 25 days.

MRSA does not acquire resistance to nTZDpa: Further, nTZDpa exhibited extremely low probabilities of resistance development (FIG. 4). Whereas MRSA MW2 showed a 32-fold higher MIC to ciprofloxacin than wild-type after 25 days of serial passage in sub-MIC concentrations, MW2 did not acquire resistance to nTZDpa (FIG. 4). Three independent cultures of MW2 (SP1, SP2, and SP3) were serially passaged in sub-MIC levels of nTZDpa for 25 days (see Methods for details). Ciprofloxacin was used as a control. MRSA MW2 strains exhibiting a 32-fold higher MIC to ciprofloxacin than the wild-type strain were generated after 25 days of serial passage in sub-MIC concentrations. In contrast, no increase in the nTZDpa MIC was observed during the same time frame. Because membrane-active antimicrobials typically exhibit fast-killing rates and low probabilities of resistance, these results support the conclusion that nTZDpa targets bacterial membranes.

Figure 5:
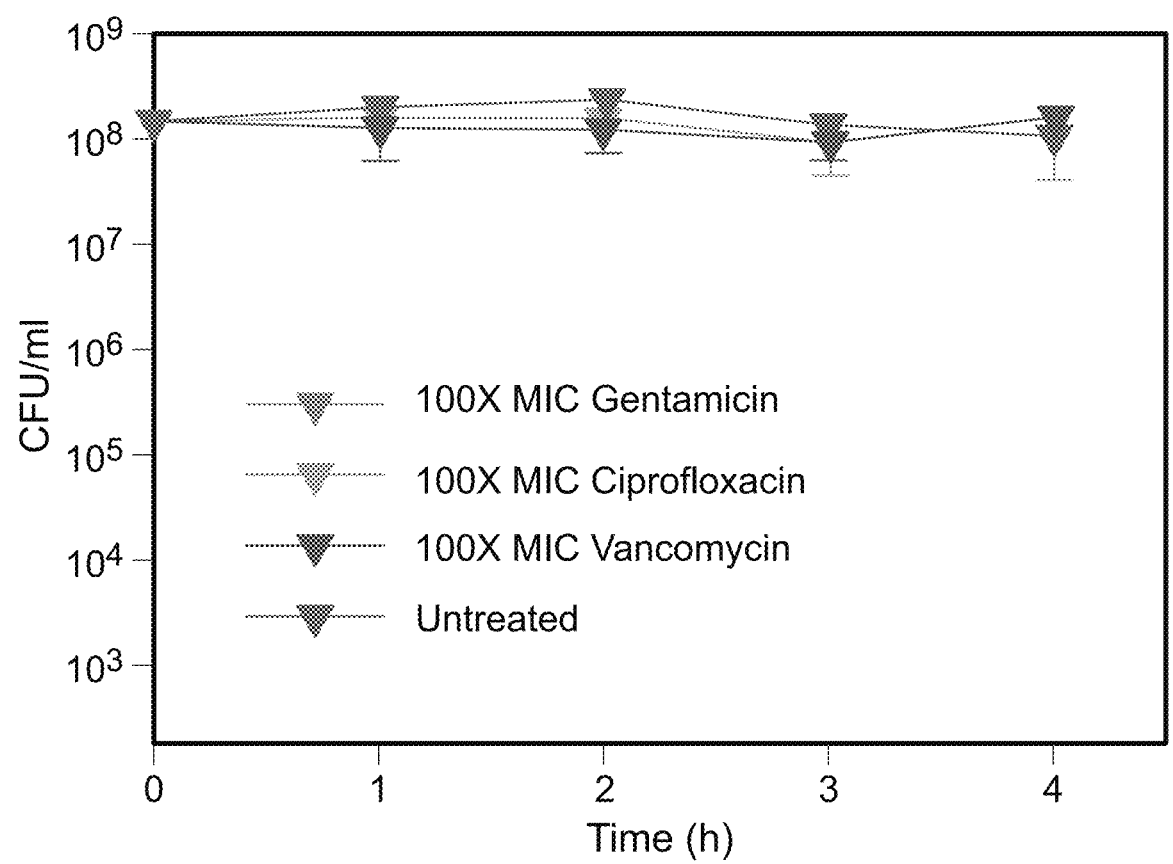
FIG. 5 contains a line plot showing that MRSA MW2 persisters were treated with 100× MIC other antibiotics, 0.1% DMSO (Control), 10× MIC aminoglycosides in combination with 4× MIC nTZDpa.
Figure 6:
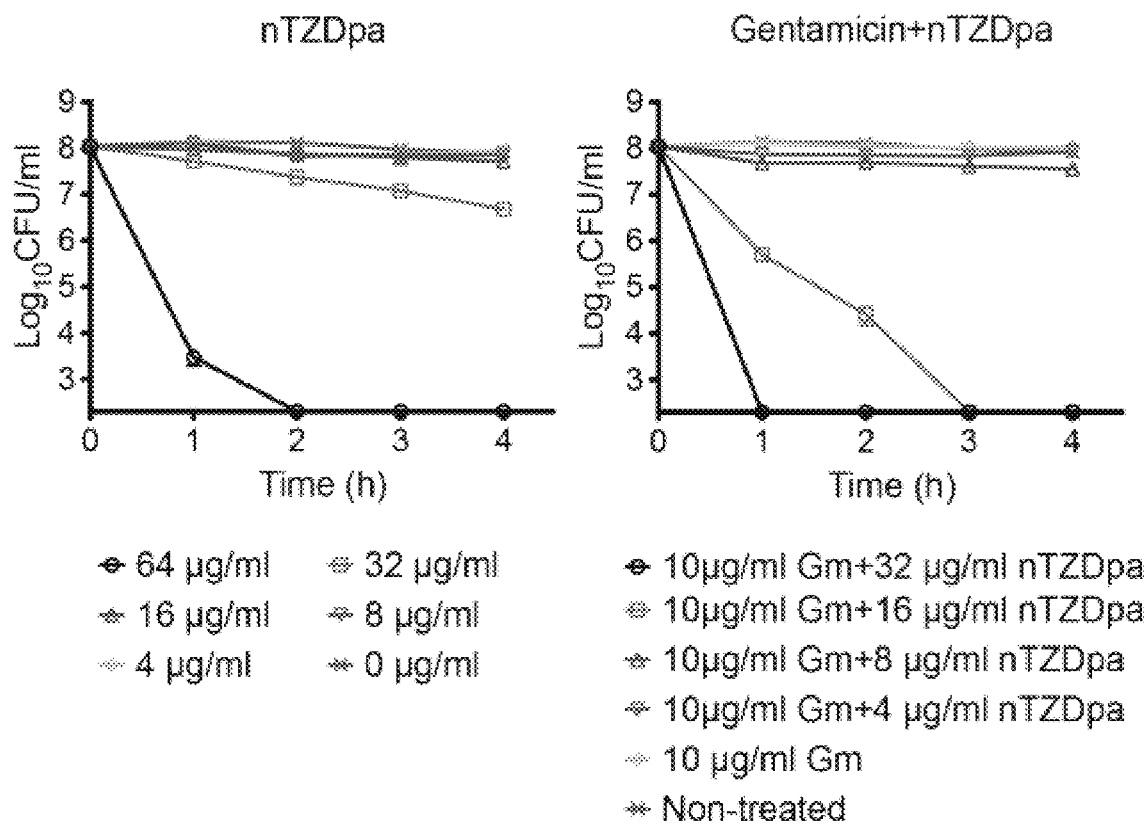
FIG. 6 contains line plots showing time-dependent killing of MRSA persister cells by nTZDpa and nTZDpa/gentamicin combinations.

MRSA persisters: Notably, nTZDpa was also potent against MRSA persisters. High concentrations of other antibiotics had no effect on the viability of MRSA persisters (FIG. 5), whereas nTZDpa caused a ~2-log reduction at 32 μg/mL and completely eradicated ~5×10[7] CFU/mL persisters within 2 hours at 64 μg/mL (FIG. 6).

Summary: Although the MIC of nTZDpa is 4-fold higher than the MIC of vancomycin (Table 1), nTZDpa showed superior bactericidal activity; 16 μg/ml (4× MIC). nZTDpa completely eradicated 10[7] CPU/ml MRSA MW2 within 2 hours, whereas 32 μg/ml (32× MIC) vancomycin only led to a 2-log decrease in viability after 4 hours. nTZDpa exhibited a similar level of antimicrobial activity against a variety of S. aureus clinical strains in addition to MRSA MW2 including the multidrug-resistant S. aureus strain VRS 1 (Table 1). nTZDpa also exhibited antimicrobial activity against vancomycin-resistant Enterococcus faecium strains with an MIC of 4μg/ml (Table 1). In contrast to nTZDpa, two other PPARγ agonists, pioglitazone and rosiglitazone:

(pioglitazone)

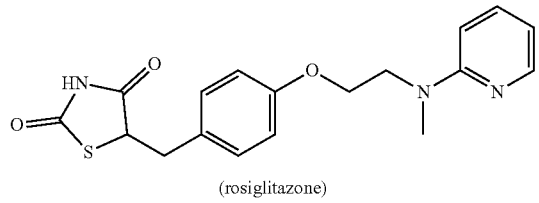

(rosiglitazone)

did not show antimicrobial activity against, indicating that nTZDpa's PPARγ agonistic-related activity is unlikely to be responsible for its antimicrobial activity (antimicrobial activity against S. aureus MW2 MICS>64 μg/ml).

Figure 11:
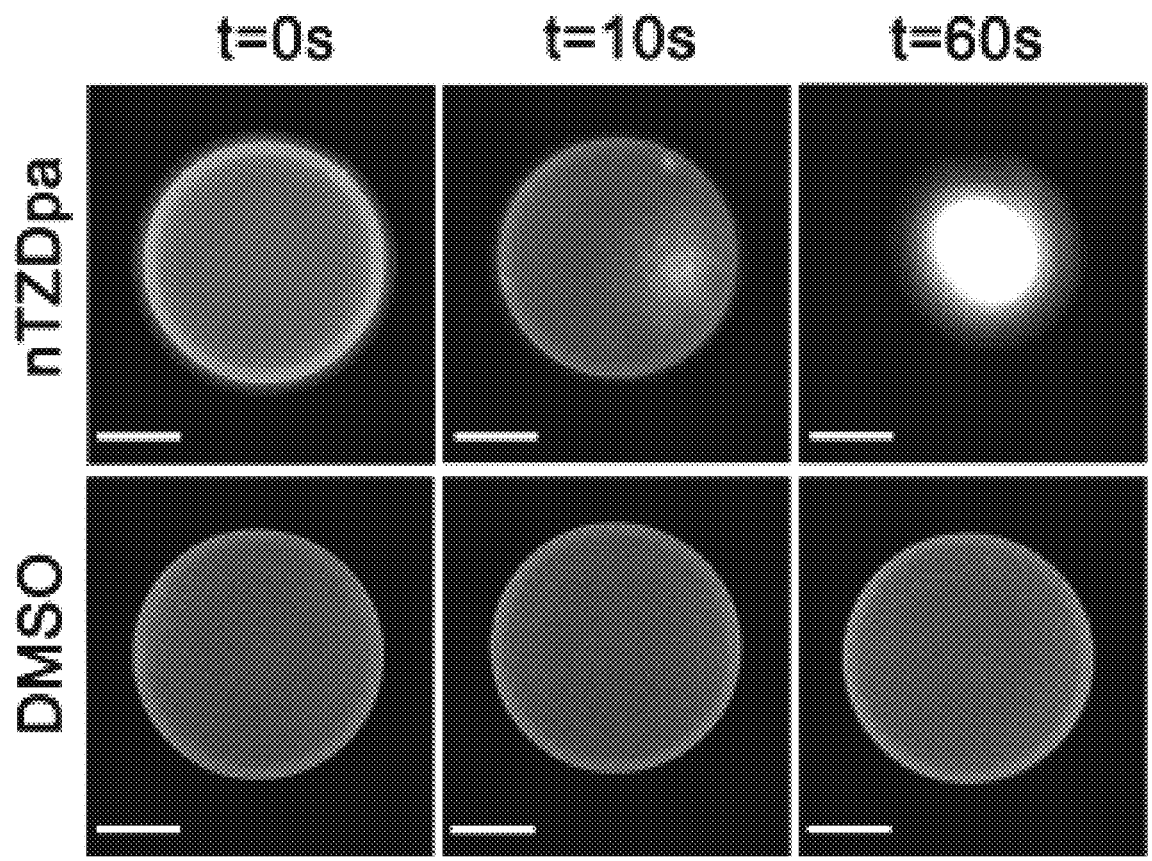
FIG. 11 shows GUVs consisting of DOPC/DOPG (7:3) labeled with 0.05% Liss Rhod PE were treated with 1× MIC (4 µg/ml) nTZDpa or 0.1% DMSO and were monitored over time using fluorescence microscopy. DMSO was used as a negative control. Scale bars=20 µm.

Example 2—nTZDpa is A Membrane-Active Compound nTZDpa induced membrane permeabilization of MRSA cells (FIG. 10) and disrupted S. aureus biomembrane-mimicking giant unilamellar vesicles (GUVs) (7:3 DOPC/DOPG 1,2-dioleoyl-sn-glycero-3-phosphocholine/glycerol (FIG. 11). As shown in FIG. 10, SYTOX Green fluorescence increased in a dose-dependent manner following treatment with 2 to 16 μg/ml nTZDpa. These results demonstrate that nTZDpa disrupts the physical integrity of the cell membranes rather than targeting membrane proton motive force (PMF) because ionophores dissipating PMF do not induce SYTOX Green membrane permeability or the killing of MRSA persisters. This assay takes advantage of the fact that SYTOX Green is a membrane-impermeable DNA-binding dye that only stains bacteria with damaged membranes.

Figure 9:
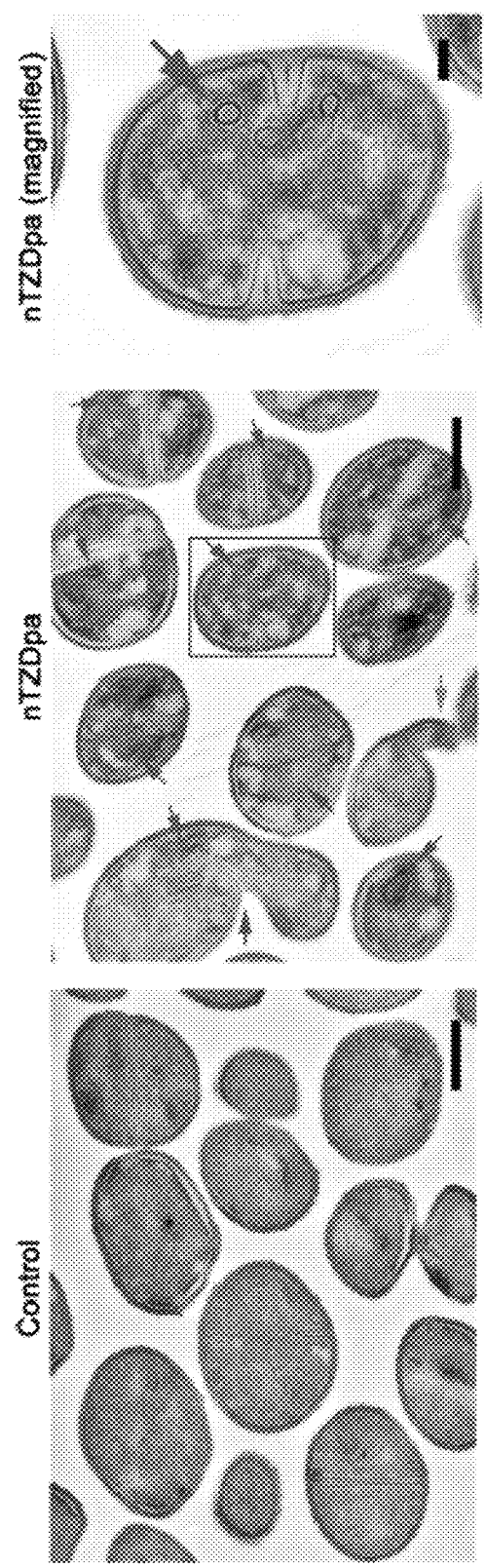
FIG. 9 contains TEM micrographs showing the formation of intracellular mesosome-like structures (dark arrow), abnormal cell division (lighter arrow, left hand side of the middle image), and cell lysis (light arrow bottom of the middle image) in MRSA MW2 treated with nTZDpa. A cell containing mesosome-like structures (in box) was magnified in the right panel. Exponential phase MRSA MW2 was treated with 4× MIC (16 µg/ml) nTZDpa or 0.1% DMSO (control) for 2 h. Scale bars for the "control" and 'nTZDpa' images represent 500 nm, and the one for the 'nTZDpa (magnified)' image is 100 nm.

Transmission electron microscopy showed that treatment of MRSA MW2 with nTZDpa at 4× MIC for 2 h caused the formation of mesosome-like structures in most cells, abnormal cell division, and cell lysis (FIG. 9). To further explore the effects of nTZDpa on bacterial lipid bilayers, biomembrane-mimicking giant unilamellar vesicles (GUVs) were challenged with nTZDpa. GUVs are artificial spherical vesicles made up of a single lipid bilayer with a diameter of 10-100 μm. Their relatively large size enables direct observation of dynamic morphology changes through optical microscopy. Therefore, GUVs have been employed to investigate the modes of action of several membrane-active antibacterial agents including daptomycin. To mimic the negatively charged S. aureus membrane, GUVs were created consisting of a mixed DOPC/DOPG lipid bilayer at a ratio of 7:3, which have been used for monitoring the effects of daptomycin and other membrane-active antimicrobial agents on S. aureus lipid bilayers. When GUVs were treated with 4 μg/ml (1× MIC) nTZDpa, the formation of lipid aggregates was noted on the surface of the GUVs after 10 s, followed by rupture at 60 s, indicating that nTZDpa directly interacts with and disrupts lipid bilayers.

Figure 14:
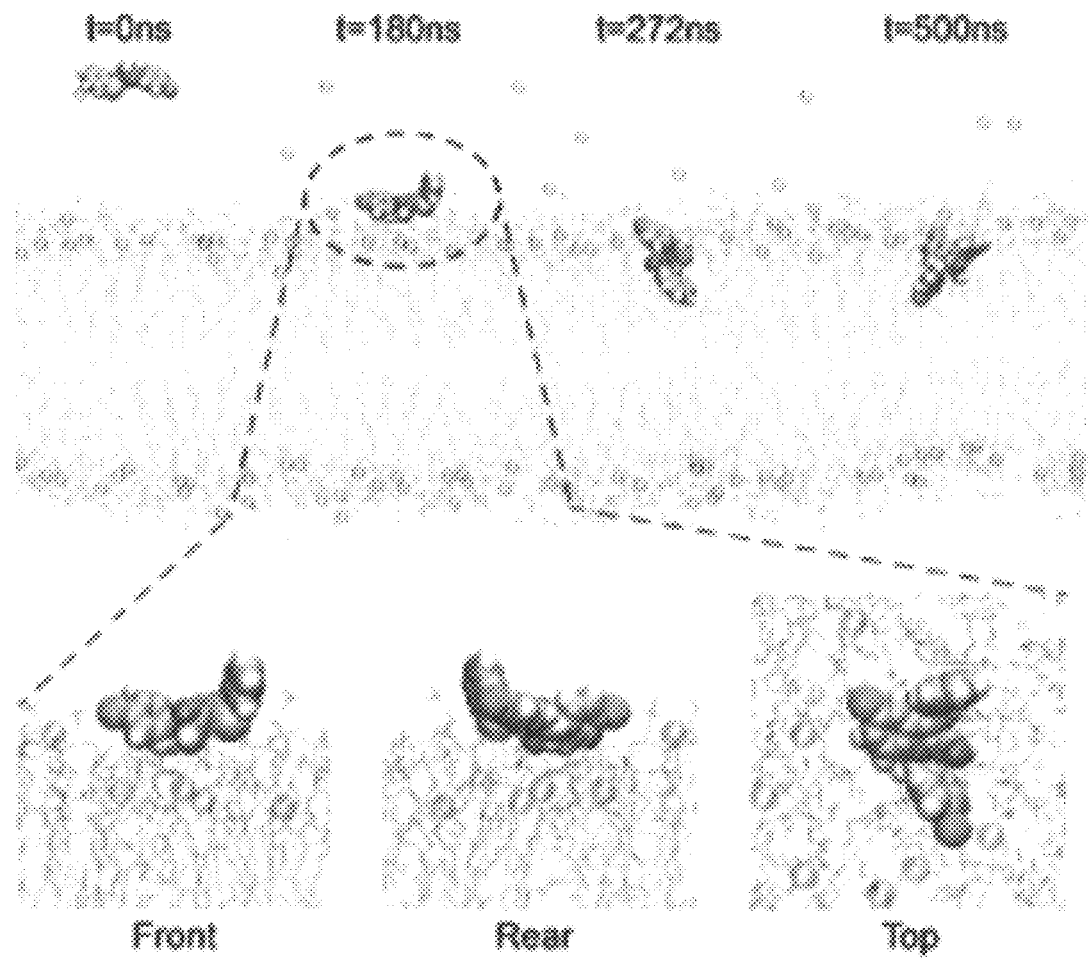
FIG. 14 contains an image showing representative configurations of MD simulations of nTZDpa at onset, membrane attachment, membrane penetration and equilibrium. The attachment configuration is magnified and shown in front, rear and top views. nTZDpa and sodium ions are depicted as large spheres, and phospholipids are represented as chains. The atoms in nTZDpa, phospholipids and sodium ions are colored as follows: hydrogen, white; oxygen, red; nitrogen, blue; sulfur, yellow; chlorine, green; carbon, cyan; phosphorus, orange; sodium, purple. Water molecules are set to be transparent for clarity.
Figure 15:
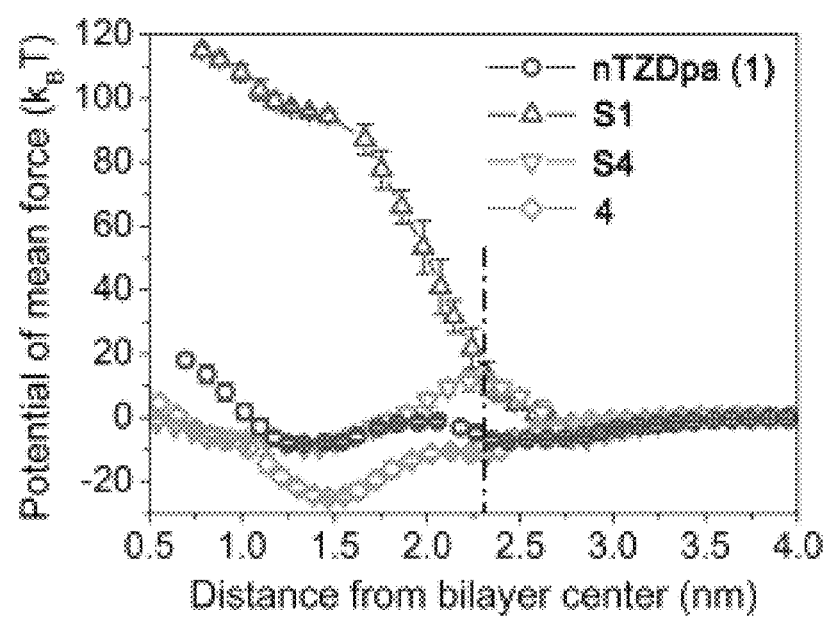
FIG. 15 contains a line plot showing the free energy profile of nTZDpa and three analogs penetrating into the membrane as a function of the center-of-mass (COM) distance to the bilayer. The dot-dashed line marks the membrane surface, averaged from the COM location of phosphate groups in the lipids of the outer leaflet.
Figure 16:
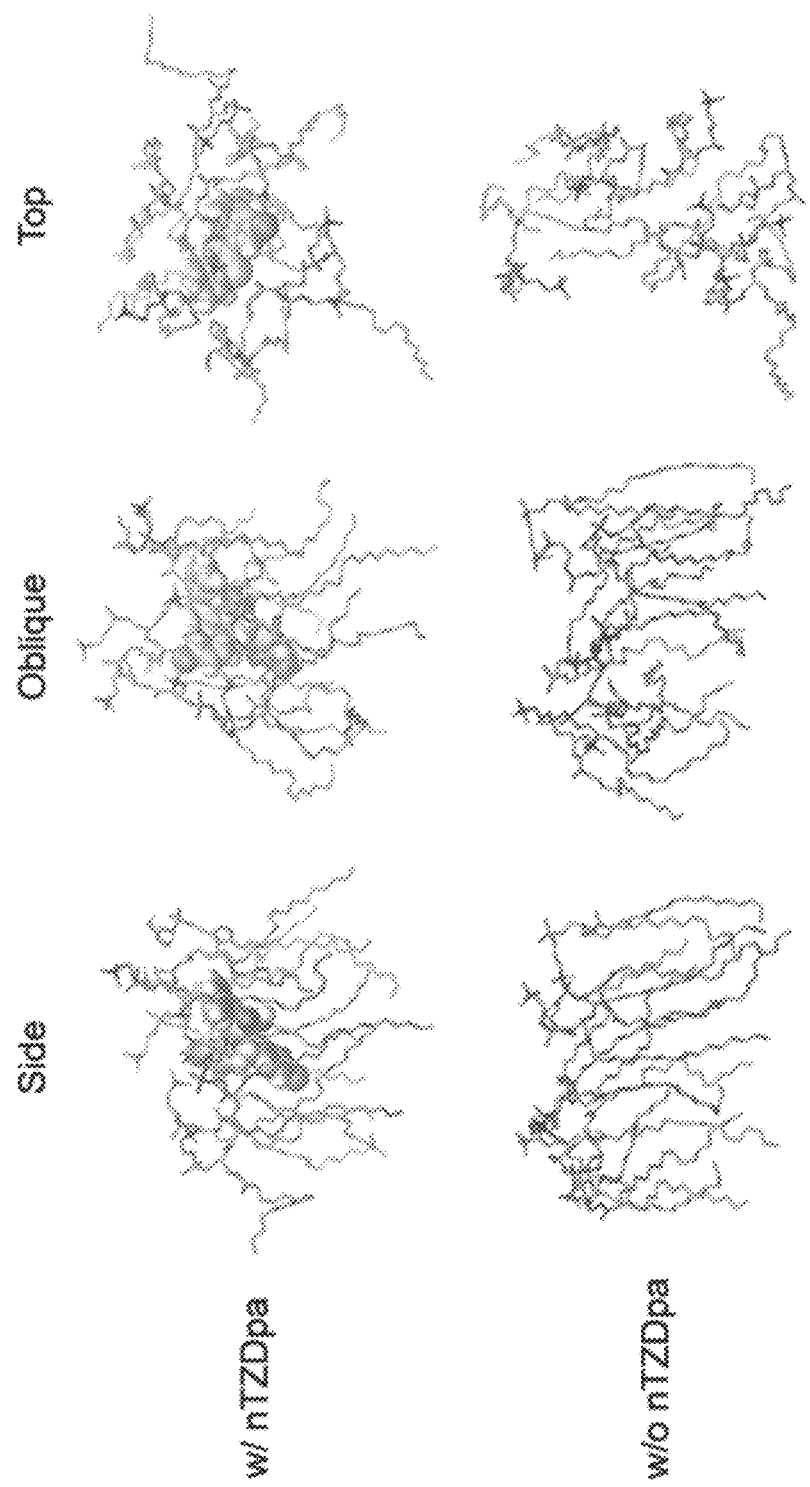
FIG. 16 contains an image showing detailed configurations of nearest neighboring lipids around an embedded nTZDpa molecule. nTZDpa is highlighted as large spheres. Phospholipids before and after the insertion of nTZDpa (1 nm around nTZDpa) are shown as chains of atoms. Water molecules are set to be transparent for clarity.

Molecular dynamics (MD) simulations demonstrated that nTZDpa interacts with the membrane surface via the carboxylic acid moiety and two chlorine atoms that bind strongly to hydrophilic lipid heads (FIG. 14). These contacts enable nTZDpa to overcome the energy barrier for penetration into the outer leaflet of the membrane via hydrophobic interactions between its aromatic rings and the hydrophobic tails of membrane lipids (FIG. 14). FIG. 15 shows that membrane penetration of nTZDpa involves a transfer energy of −0.81 kBT and an energy barrier of 6.14 kBT (FIG. 15), suggesting that the membrane penetration of nTZDpa is spontaneous and rapid at ambient temperature. At equilibrium, nTZDpa molecules are embedded in the outer leaflet of the membrane with an inclined orientation with respect to the acyl chains of lipids. As a result, the neighboring lipids deform to accommodate the invading nTZDpa molecules, inducing significant membrane perturbation. The binding affinities of these three polar groups conferred persistent attachment of the chlorinated benzene and chlorinated indole groups to the membrane surface, while the remaining unchlorinated benzene group dangled from the membrane due to entropic repulsion (FIG. 14). The transfer energy is favorable and the energy barrier is on the same order-of-magnitude as the thermal fluctuation energy, kBT, suggesting that the membrane penetration of nTZDpa is spontaneous and rapid at ambient temperature.

Example 3—Toxicity of nTZDpa and Its Analogs

Figure 12A:
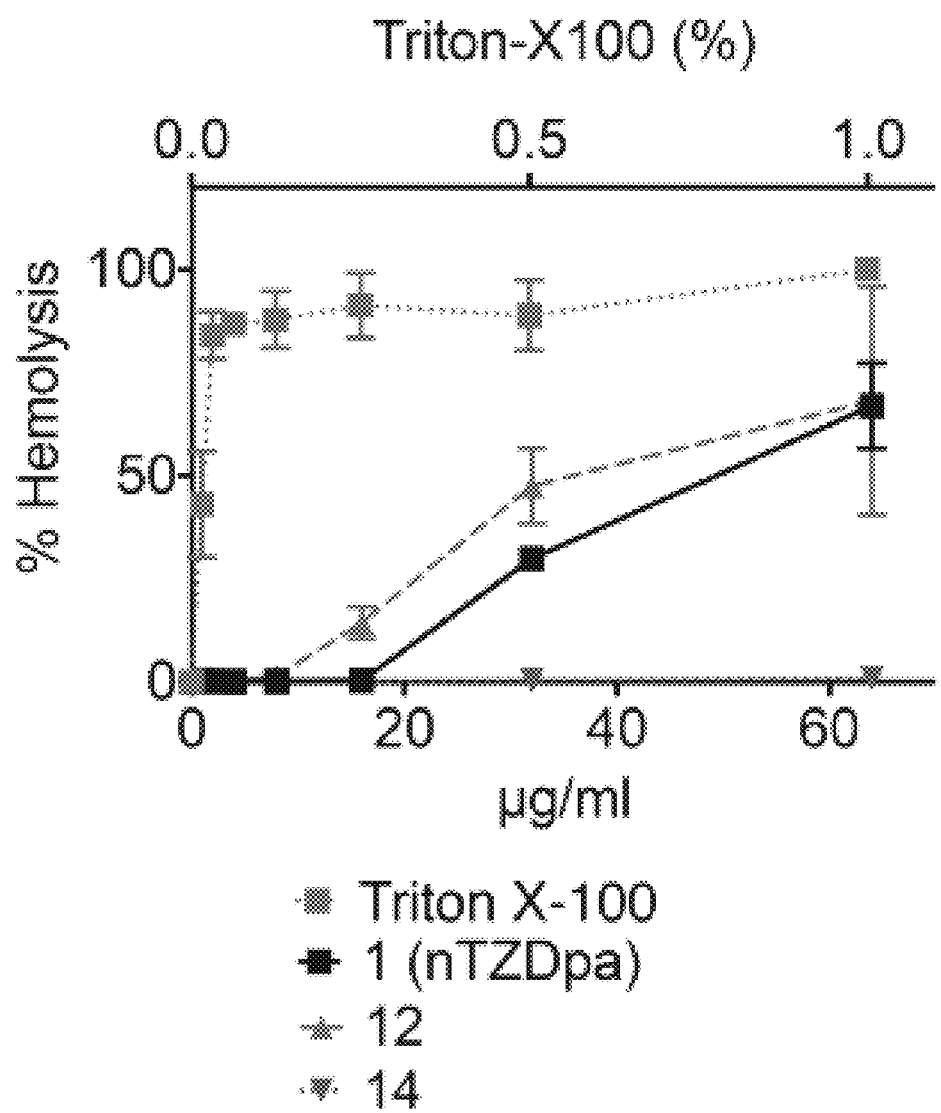
FIG. 12A contains a line plot showing nTZDpa hemolysis assay with human erythrocytes using 1% Triton X-100 as a positive control (12 and 14 refer to the compounds 12 and 14). Error bars denote s.d. (n=3).
Figure 12B:
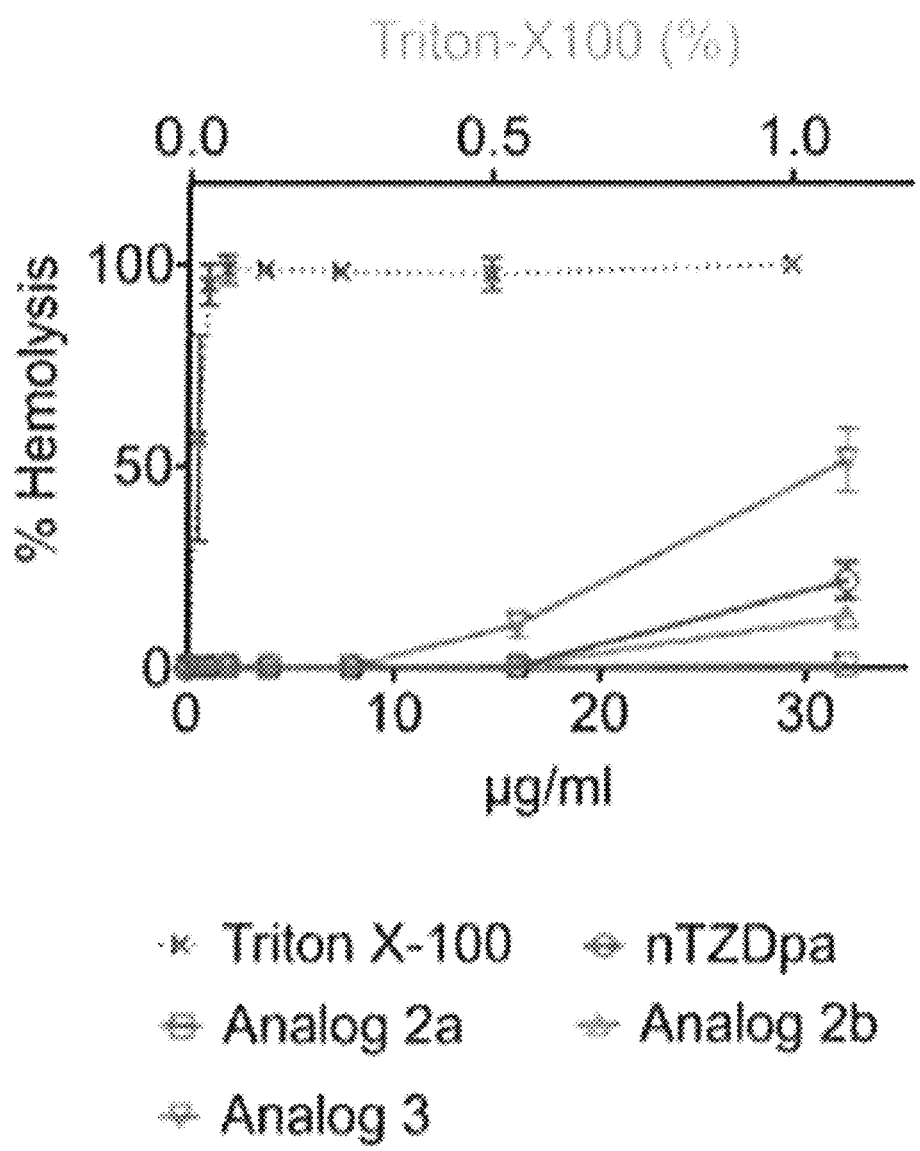
FIG. 12B contains a line plot showing results of hemolysis assay after 2% human erythrocytes were treated with two-fold serially diluted concentration of nTZDpa or its analogs 2a (S9), 2b (S5), and 3 (compound 4) for 1 h at 37 20 C. A sample treated with 1% Triton-X 100 was used as the control for 100% hemolysis. Results are shown as means±s.d.; n=3.

Membrane active agents are typically toxic to mammalian cells. To evaluate the membrane activity of nTZDpa on mammalian cell membranes, human erythrocytes were treated with a range of nTZDpa concentrations. Consistent with the apparent lack of toxicity of nTZDpa in *C. elegans*, nTZDpa did not show significant toxicity at or below 16 µg/mL, but significant hemolysis was observed above this threshold (FIGS. 12A and 12B); 32 µg/ml caused <25% hemolysis of human erythrocytes.

Analog 2b (compound S5) exhibited a similar level of hemolytic activity as nTZDpa, Analog 2a (compound S9) did not significantly cause hemolysis at 32 µg/ml. Analog 3, which exhibits improved antimicrobial activity, induced app. 51% hemolysis at 32 µg/ml, which is app. 2-fold higher than nTZDpa.

Figure 13A:
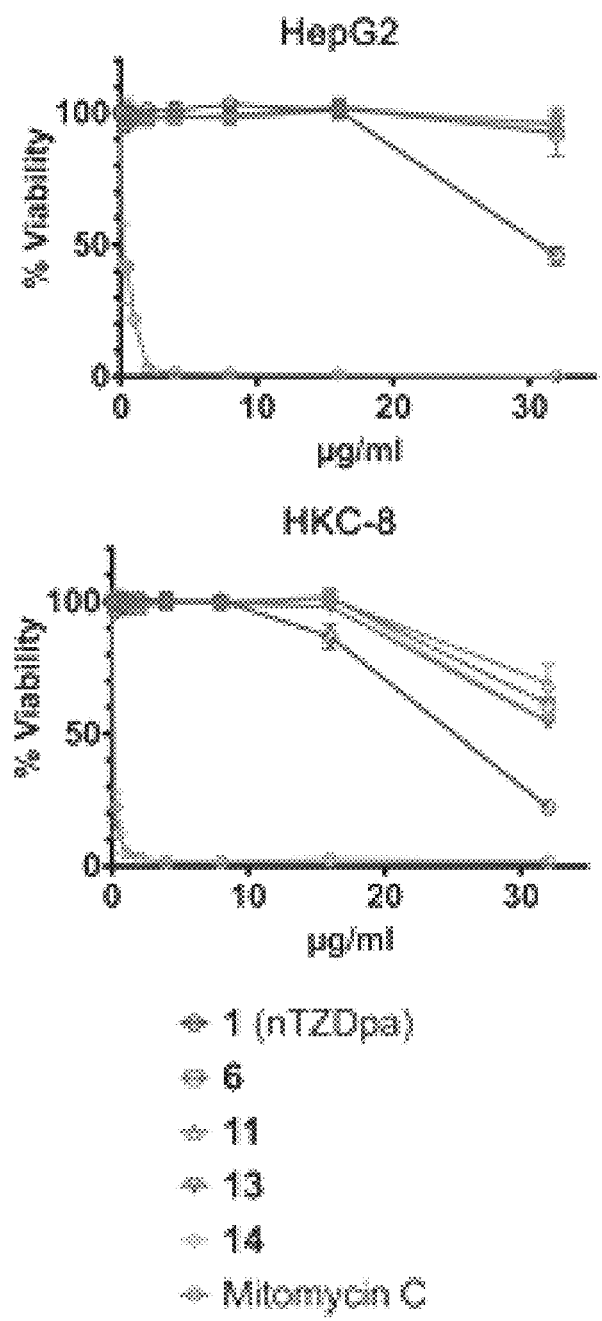
FIG. 13A contains line plots showing cell viability of human hepatoma cell line HepG2 and human renal proximal tubular epithelial cell line HKC-8 after treatment with 2-fold serially diluted concentrations of nTZDpa or its analogs 6, 11, 13, and 14 for 72 h at 37° C. An anticancer agent, mitomycin C showing bactericidal activity against MRSA persisters was used as a positive control. Cell viability was calculated based on the absorbance readings at 450 nm at 4 h after adding WST-1 using the following equation: % viability=(Abs sample−Abs blank)/(Abs non-treated−Abs blank)×100. Results are shown as means±s.d.; n=3.
Figure 13B:
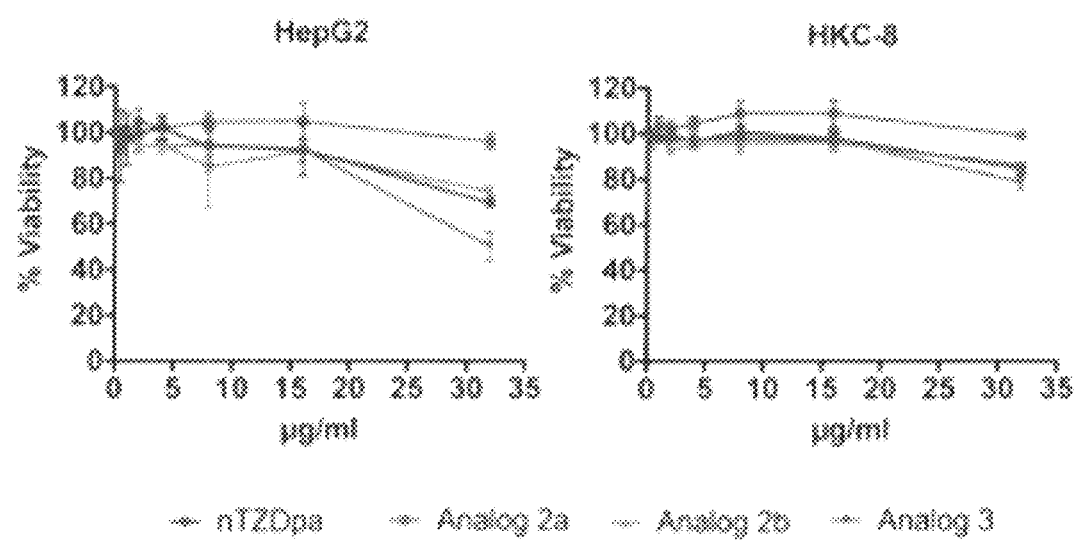
FIG. 13B contains a line plots showing cell viability of HepG2 and HKC-8 cell lines after treatment with two-fold serially diluted concentrations of nTZDpa, analog 2a (S9), analog 2b (S5), and analog 3 (compound 4) for 24 h at 37° C. Cell viability was calculated based on the absorbance readings at 450 nm at 4 h after adding WST-1 using the following equation: % viability=(Abs sample−Abs blank)/(Abs non-treated−Abs blank)×100. Results are shown as means±s.d.; n=3.

The observed hemolytic activity of nTZDpa at high concentrations was reflected by its toxicity toward two mammalian cell lines at 32 µg/mL (HepG2 and HKC-8, FIGS. 13A and 13B). nTZDpa led to app. 30% cell death of the human liver cell line HepG2 and app. 16% cell death of the human renal proximal tubular epithelial cell line HKC-8 at 32 µg/ml. Analog 2b showed a similar level of cytotoxicity as nTZDpa against HepG2 and HKC-8 cells, whereas Analog 2a did not display a significant level of cytotoxicity to those cell lines. Although Analog 3 induced app. 50% killing in HepG2 cells at 32 µg/ml, it exhibited a similar level of cytotoxicity as nTZDpa against HKC-8 cells.

Figure 2:
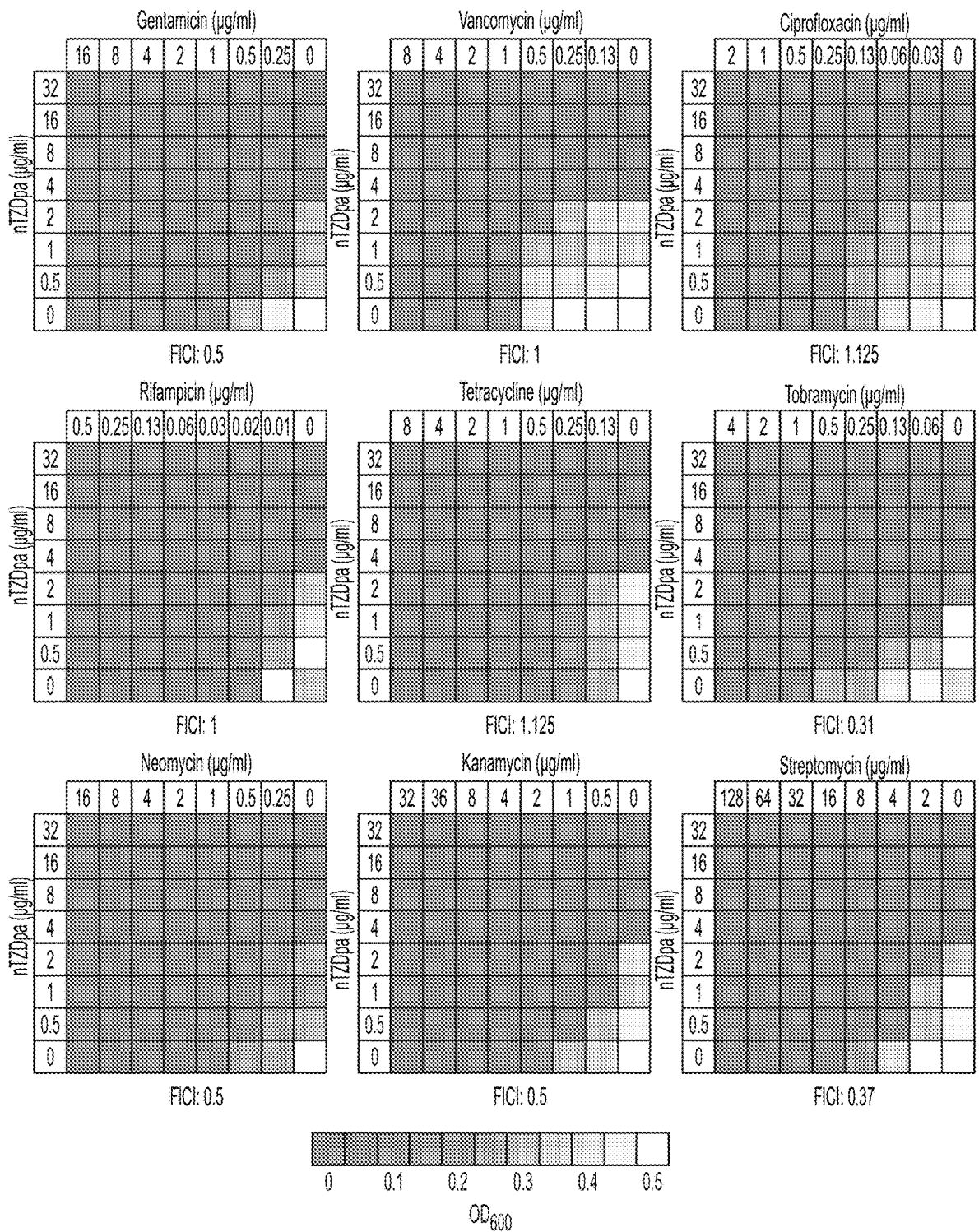
FIG. 2 shows antimicrobial synergism of nTZDpa with aminoglycosides against MRSA. Optical densities at 600 nm were measured after 18 h incubation of MRSA MW2 at 37° C. The results represent three independent experiments. The fractional inhibitory concentration index (FICI) was calculated as follows: FICI=MIC of compound A in combination/MIC of compound A alone+MIC of compound B in combination/MIC of compound B alone. The interaction between two compounds was defined, as follows: synergy if FICI≤0.5, no interaction if 0.5<FICI≤4, and antagonism if FICI>4.

Example 4—nTZDpa Shows Synergism with Aminoglycoside Antibiotics nTZDpa acted synergistically with aminoglycosides (gentamicin, tobramycin, neomycin, kanamycin, and streptomycin) with a fractional inhibitory concentration index ≤0.5, but not with vancomycin, ciprofloxacin, rifampicin, or tetracycline (FIG. 2). Antibiotic synergism refers to the phenomenon in which two antibiotics given together have a greater antimicrobial effect than each agent individually. Synergism not only increases an antibiotic's potency, but also allows for a lower dose of a potentially toxic antibiotic, thereby mitigating cytotoxic side-effects.

TABLE 2 antimicrobial synergy testing of nTZDpa against MRSA MW2.

| Antibiotics | FICI[1] |
|---|---|
| Gentamicin | 0.5 |
| Vancomycin | 1 |
| Ciprofloxacin | 1.125 |
| Rifampicin | 1 |
| Tetracycline | 1.125 |
| Tobramycin | 0.31 |
| Neomycin | 0.5 |
| Kanamycin | 0.5 |
| Streptomycin | 0.37 |

Figure 7:
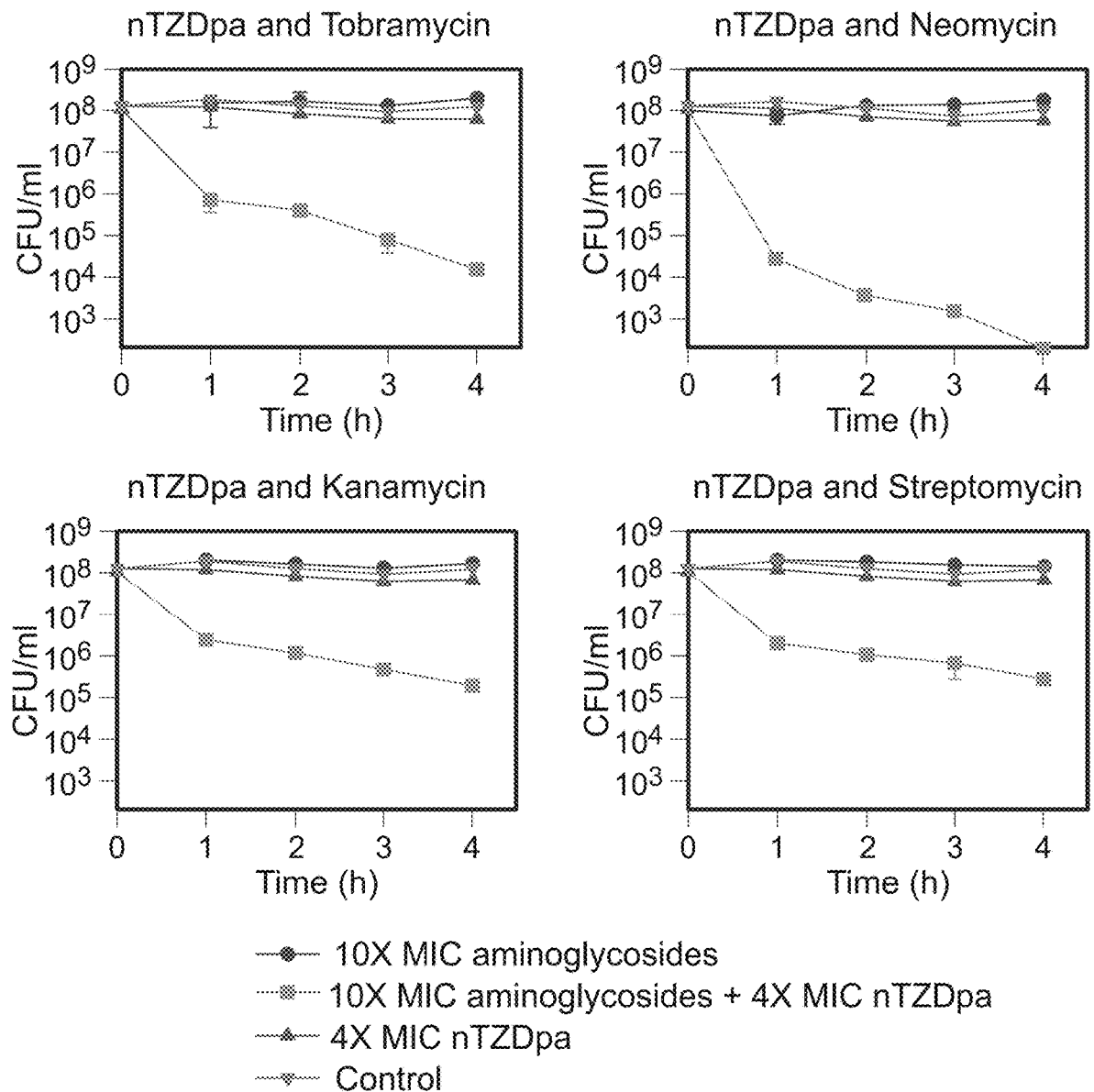
FIG. 7 contains line plots showing synergistic bactericidal activity of nTZDpa with aminoglycosides tobaramysin, neomycin, kanamysin, and streptomycin against both stationary-phase and biofilm MRSA persisters.
Figure 8:
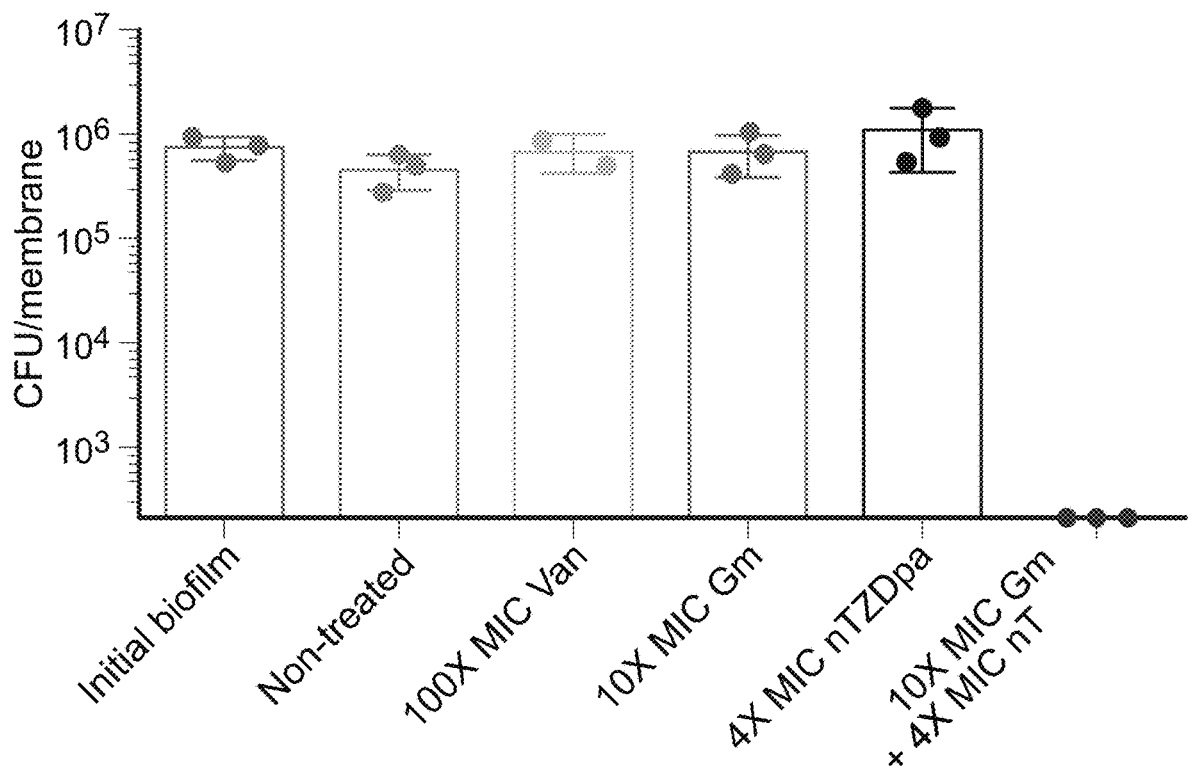
FIG. 8 contains a bar graph showing the number of viable cells in biofilms that was measured by CFU counting after MRSA MW2 biofilms formed on 13 mm cellulose ester membranes were treated with 0.1% DMSO (Control), 100× MIC (100 µg/ml) vancomycin (Van), 10× MIC (10 µg/ml) gentamicin (Gm), 4× MIC (16 µg/ml) nTZDpa, or their combination for 24 h. The data points on the x axis are below the level of ($2 \times 10^2$ CFU/membrane). Individual data points (n=3) and mean±s.d. are shown.

[1]FICI = MIC of compound A in combination/MIC of compound A alone + MIC of compound B in combination/MIC of compound B alone (82). The interaction between two compounds was defined, as follows: synergy if FICI ≤ 0.5, no interaction if 0.5 < FICI ≤ 4, antagonism if FICI > 4.

nTZDpa also exhibited synergistic bactericidal activity with aminoglycosides against both stationary-phase and biofilm MRSA persisters (FIGS. 6, 7, and 8).

Figure 25:
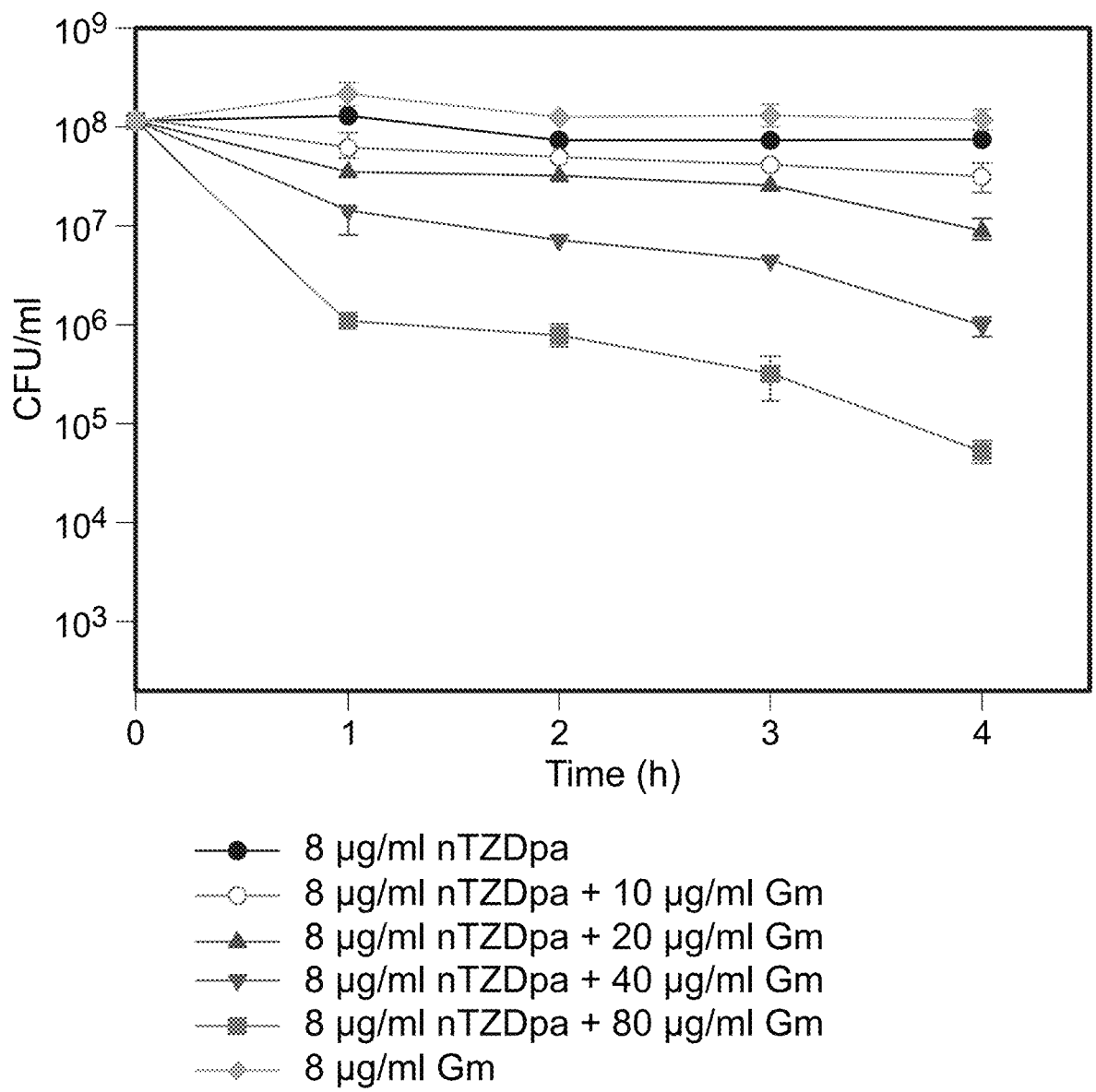
FIG. 25 contains a line plot showing results of testing of 8 µg/ml nTZDpa in combination with various concentrations of gentamicin (Gm) for 4 hours. Colony forming unit counts of persisters was measured by serial dilution and plating on TSA plates. The data points on the x-axis are below the level of detection ($2\times10^2$ CFU/mL). Results are shown as means±s.d.; n=3.
Figure 26:
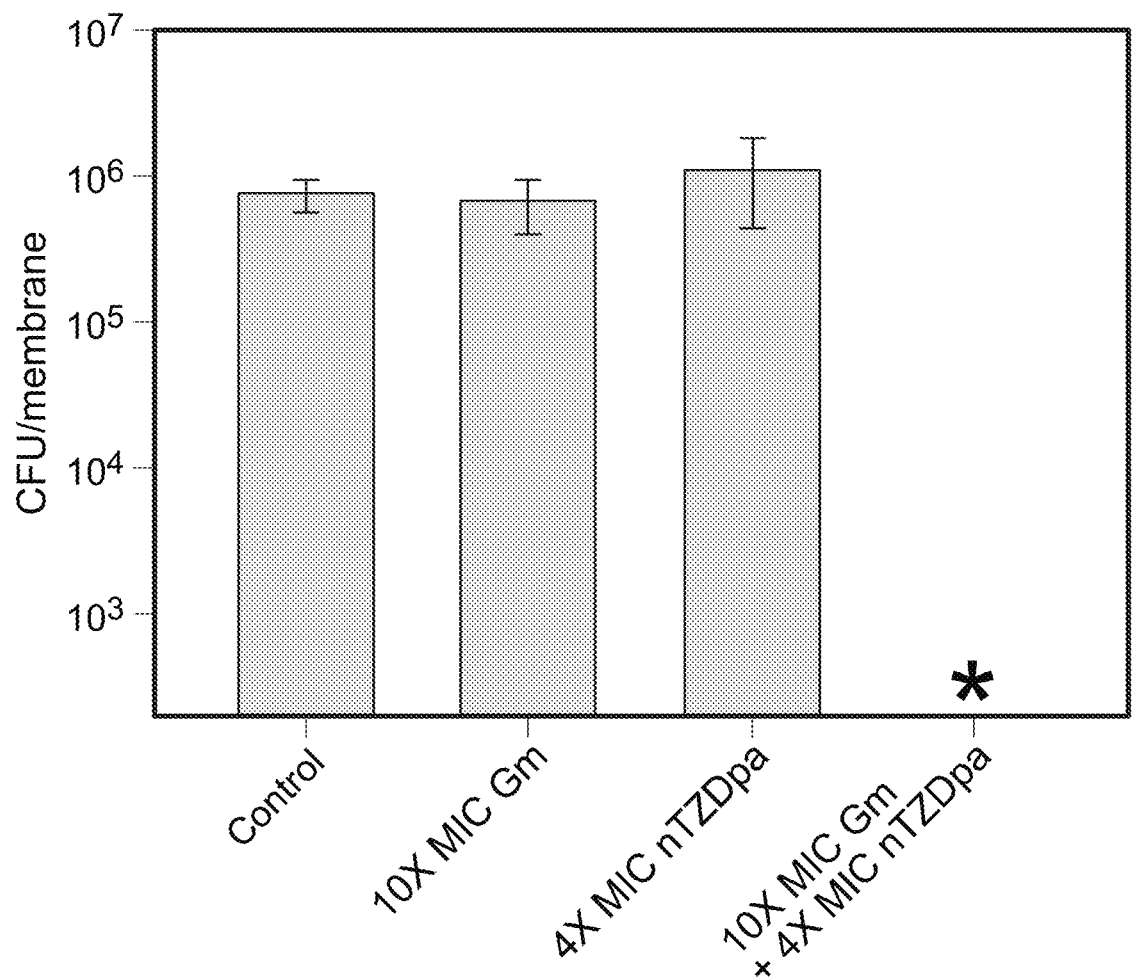
FIG. 26 contains a line plot showing results of cell viability assay when MRSA MW2 biofilms formed on 13 mm cellulose ester membranes were treated with 0.1% DMSO (Control), 10× MIC (10 µg/ml) Gentamicin (Gm), 4× MIC (16 µg/ml) nTZDpa, or their combination for 24 h. The number of viable cells in biofilms was measured by CFU counting. Results are shown as means±s.d.; n=3. The asterisk on the x-axis 1 s below the level of detection ($2\times10^2$ CPU/membrane).

Although nTZDpa is toxic to mammalian cells in vitro at or above 32 µg/ml, it was found by testing a range of nTZDpa concentrations combined with 10 µg/ml gentamicin as well as a range of gentamicin concentrations combined with 8 µg/ml nTZDpa, that 100% of persisters could be eradicated within 3 hours with 16 µg/ml nTZDpa and 10 µg/ml gentamicin (FIG. 8) and that 3 logs of persister killing could be achieved with 8 µg/ml nTZDpa and 80 µg/ml gentamicin (FIG. 25). Further, 16 µg/ml nTZDpa combined with 10× MIC of other aminoglycosides also exhibited synergistic killing of MRSA persisters. Importantly, persisters also exist in biofilms, which contributes to their antibiotic-tolerance. Consistent with the results for stationary-phase persisters described above, 16 µg/ml nTZDpa combined with 10 µg/ml gentamicin completely eradicated MRSA persisters formed in biofilms (FIG. 26). Considering that nTZDpa did not cause significant toxicity at 16 µg/ml, these data indicate that synergism with aminoglycosides may be an effective strategy to identify an efficacious non-toxic therapeutic dosing window for nTZDpa. In any case, gentamicin is clinically employed to treat chronic and severe staphylococcal infections, such as endocarditis, despite its dose-dependent nephrotoxicity.

Figure 27:
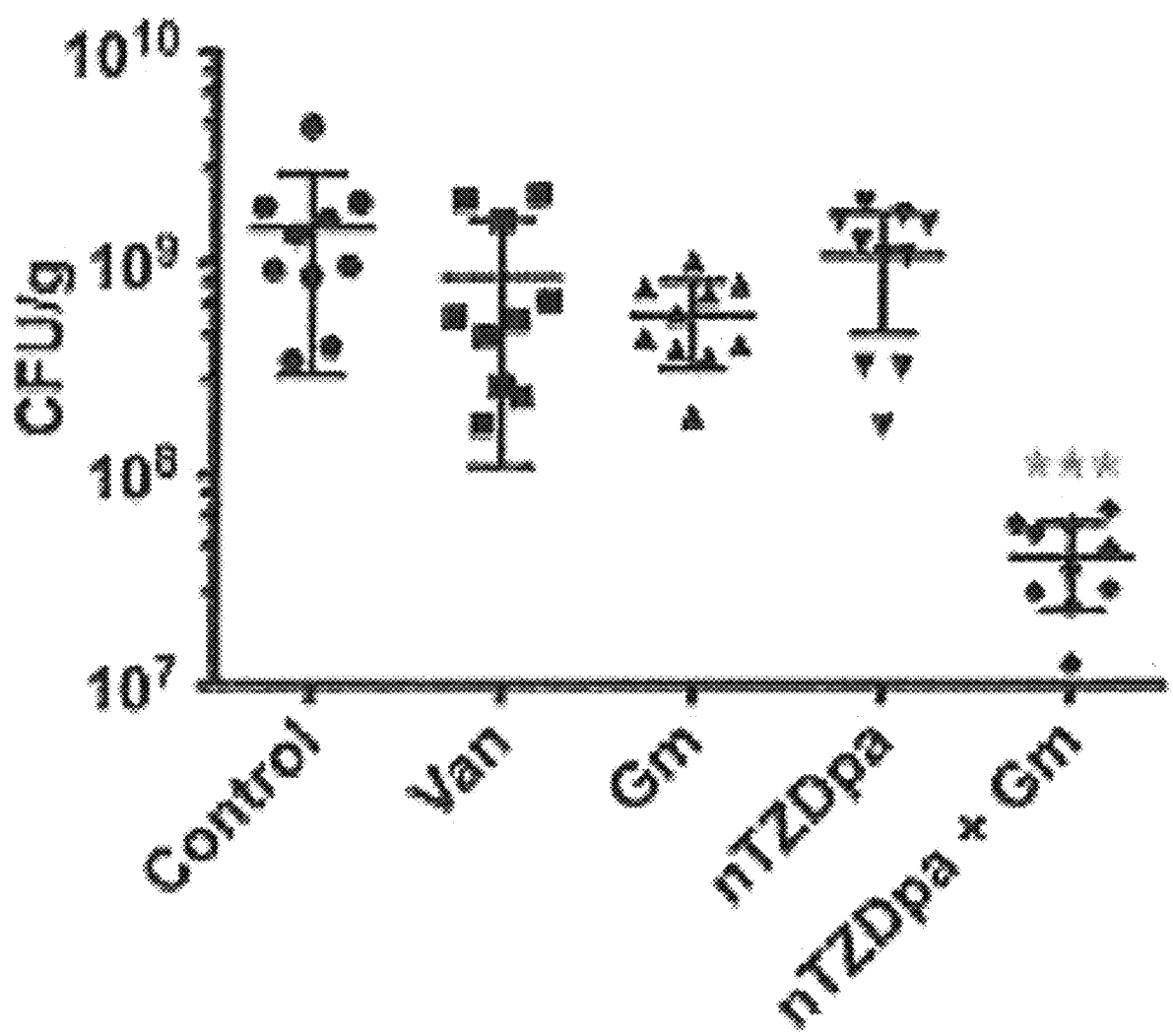
FIG. 27 contains a plot showing results of deep thigh infection study when $5\times10^5$ CPU of MRSA MW2 was injected to the right thigh of each mouse. Ten mice per group infected with MRSA MW2 were treated with control (5% Killophor+5% ethanol, i.p. every 24 h), vancomycin (25 mg/kg, i.p. every 24 h), gentamicin (30 mg/kg, s.c. every 12 h), nTZDpa (50 mg/kg, i.p. every 24 h), or a combination of nTZDpa (50 mg/kg, i.p. every 24 h) and gentamicin (30 mg/kg, s.c. every 12 h) for 5 days at 24 h post-infection. At 12 h after the last treatment, mice were euthanized. Their thighs were excised and homogenized. CPUs from each mouse thigh are plotted as individual points and error bars represent the standard deviation in each experimental group. Statistical differences between control and antibiotic treatment groups were analyzed by one-way ANOVA and post-hoc Tukey test (***$p<0.001$).
Figure 28:
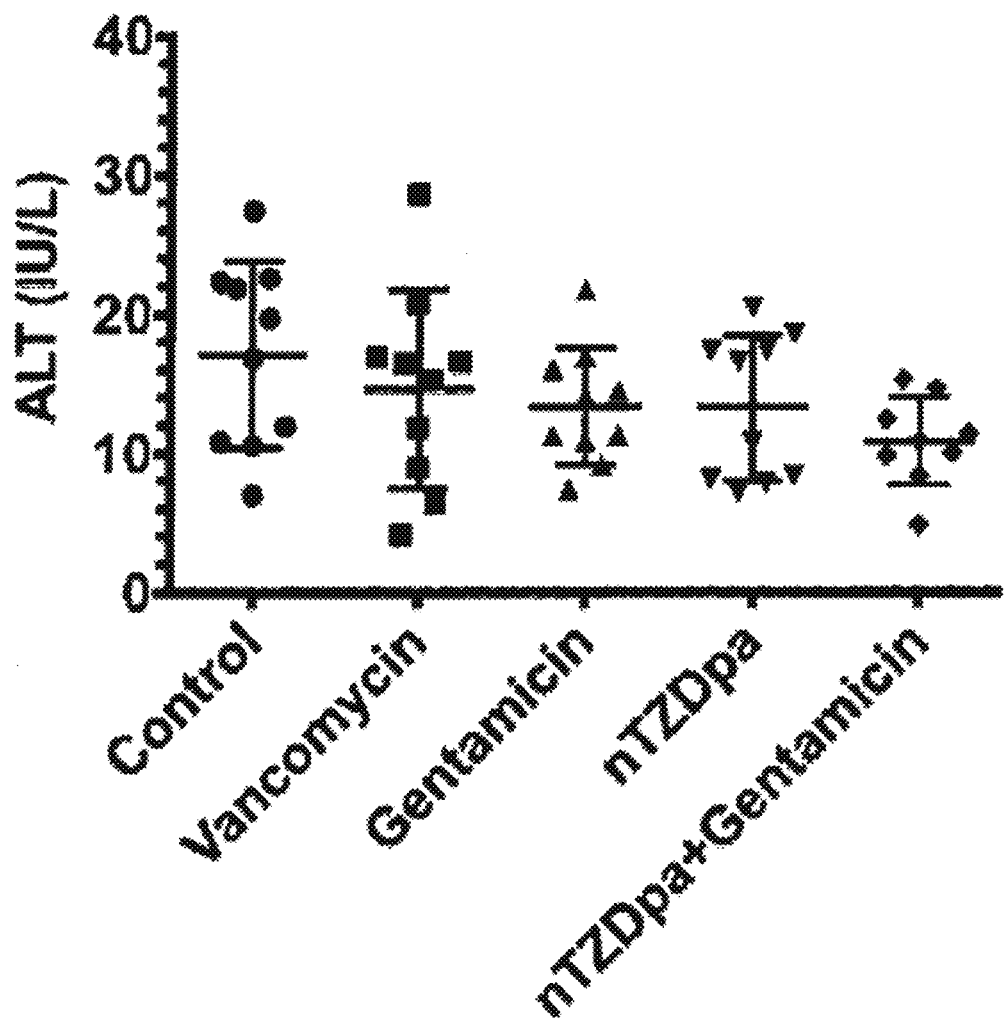
FIG. 28 contains a plot showing in vivo efficacy of nTZDpa in combination with gentamicin in a deep-seated mouse thigh infection model. App. $5\times10^5$ CPU of MRSA MW2 was injected to the right thigh of each mouse. Ten mice per group infected with MRSA MW2 were treated with control (5% Killophor+5% ethanol, i.p. every 24 h), vancomycin (25 mg/kg, i.p. every 24 h), gentamicin (30 mg/kg, s.c. every 12 h), nTZDpa (50 mg/kg, i.p. every 24 h), or a combination of nTZDpa (50 mg/kg, i.p. every 24 h) and gentamicin (30 mg/kg, s.c. every 12 h) for 5 days at 24 h post-infection. At 12 h after the last treatment, mice were euthanized. Before excising thighs to evaluate bacterial loads (FIG. 27), blood was collected and analyzed for ALT. International Units per Liter (IU/L) of alanine aminotransferase (ALT) for each mouse serum are plotted as individual points and error bars represent the deviation in each experiment group. Control and antibiotic treatment were analyzed by one-way ANOVA and the post-hoc Tukey test to confirm a lack of significant difference.
Figure 29:
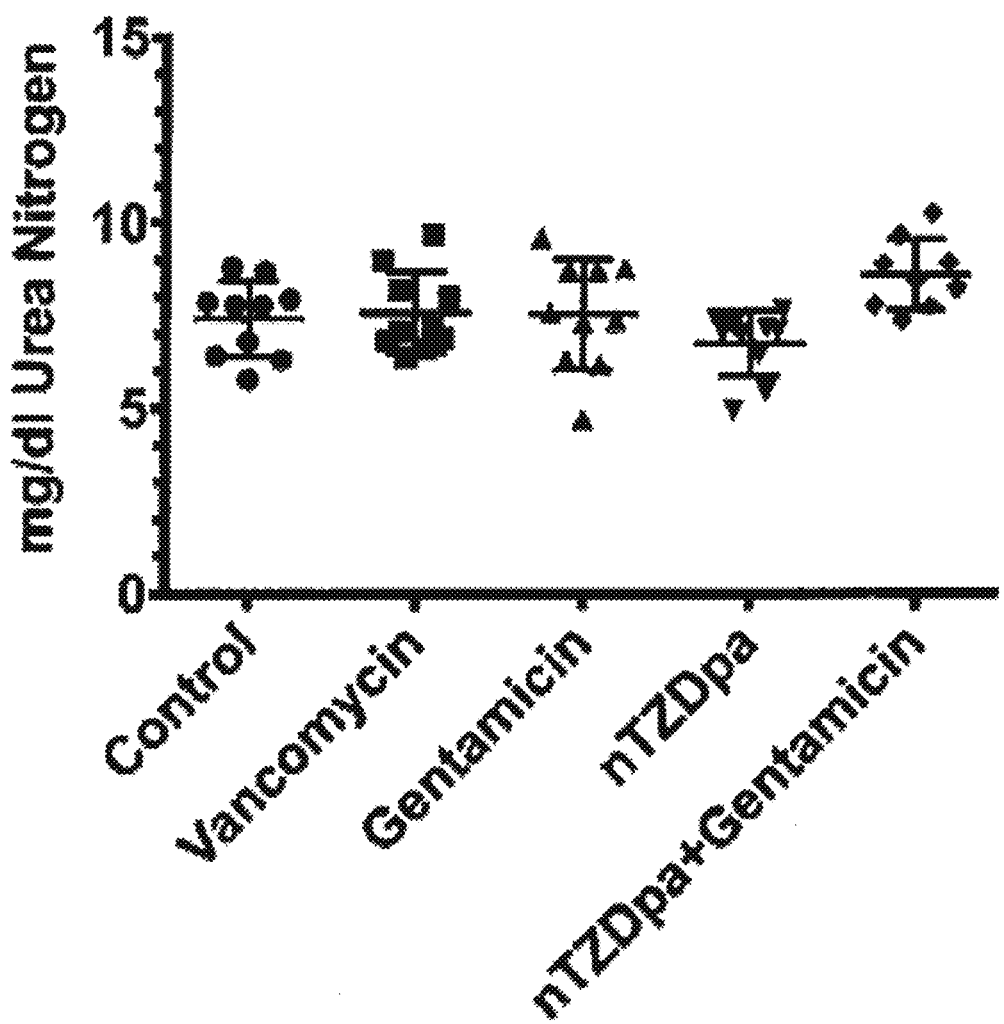
FIG. 29 contains a line plot showing in vivo efficacy of nTZDpa in combination with gentamicin in a deep-seated mouse thigh infection model. App. $5\times10^5$ CPU of MRSA MW2 was injected to the right thigh of each mouse. Ten mice per group infected with MRSA MW2 were treated with control (5% Killophor+5% ethanol, i.p. every 24 h), vancomycin (25 mg/kg, i.p. every 24 h), gentamicin (30 mg/kg, s.c. every 12 h), nTZDpa (50 mg/kg, i.p. every 24 h), or a combination of nTZDpa (50 mg/kg, i.p. every 24 h) and gentamicin (30 mg/kg, s.c. every 12 h) for 5 days at 24 h post-infection. At 12 h after the last treatment, mice were euthanized. Before excising thighs to evaluate bacterial loads (FIG. 27), blood was collected and analyzed for BUN. Absorbance at 430 nm of BUN urea nitrogen are plotted as individual points and error bars represent the deviation in each experiment group. Control and antibiotic treatment were analyzed by one-way ANOVA and the post-hoc Tukey test to confirm a lack of significant difference.
Figure 30:
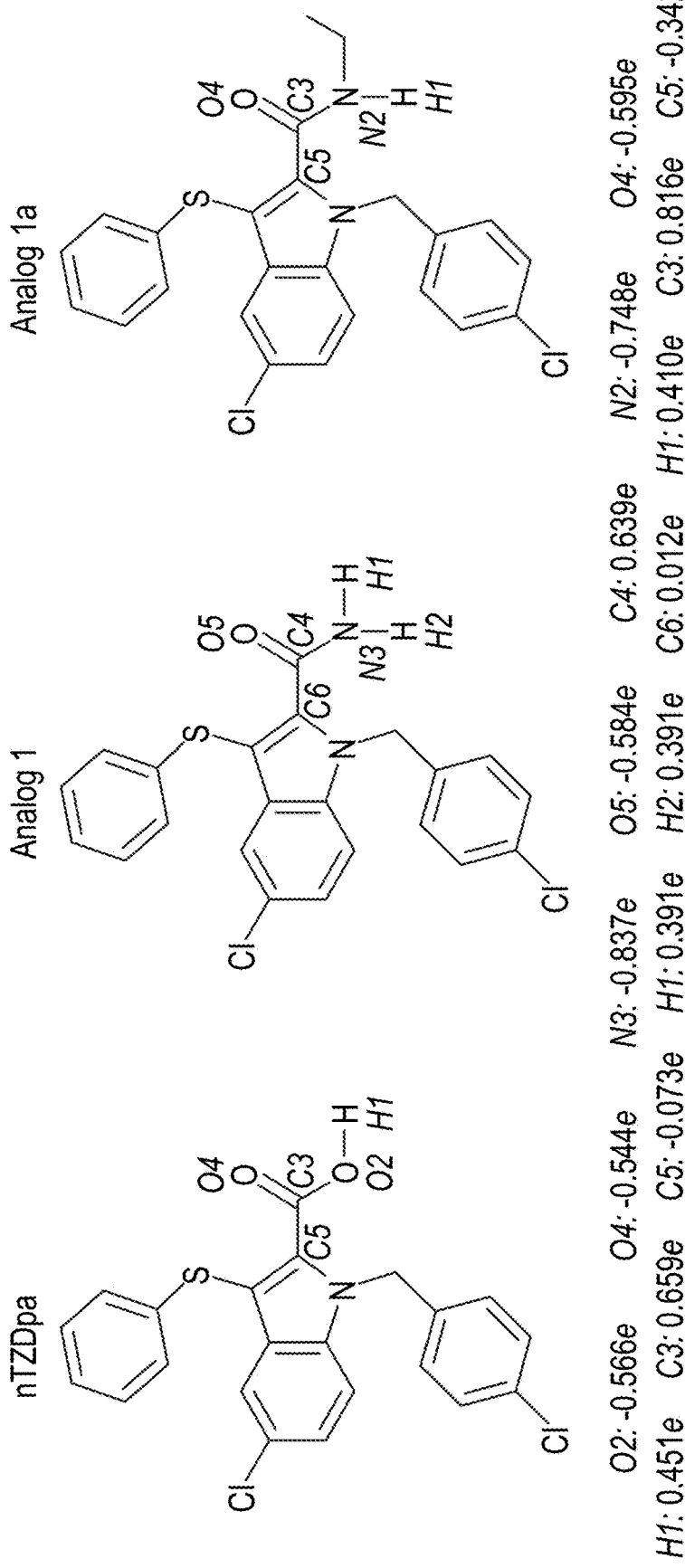
FIG. 30 contains an image showing comparison of partial atomic charges among nTZDpa, Analog 1 (compound S1) and Analog 1a (compound S2).

In vivo evaluation: The efficacy and toxicity of nTZDpa as well as the combination of nTZDpa and gentamicin was also evaluated in a murine, deep-seated thigh infection model, which mimics human deep-seated, chronic infections. A dose of 50 mg/kg nTZDpa was selected to test its in vivo efficacy based on the previous in vivo study that a dose of 50 mg/kg has shown in vivo efficacy in a mouse model of hyperglycemia and insulin resistance without showing observable toxicity. Neutropenic mice was infected with app. $10^7$ stationary phase MRSA cells and 24 hours post infection treated with 50 mg/kg nTZDpa with or without 30 mg/kg gentamicin for 5 days. Hepatic and renal toxicities were evaluated by measuring serum alanine aminotransferase (ALT) and blood urea nitrogen (BUN) levels. Consistent with a previous report, neither vancomycin nor gentamicin reduced MRSA CFUs in the deep-seated model (FIG. 27). Although nTZDpa alone had no effect on the viability of persisters, it did not increase serum levels of ALT or BUN (FIGS. 28 and 29). However, the combination of nTZDpa with gentamicin killed app. 95% persister cells (p<0.001), while not increasing ALT or BUN (FIGS. 27, 28, 29).

Example 5—Antimicrobial Activity of nTZDpa's Analogs

Figure 17:
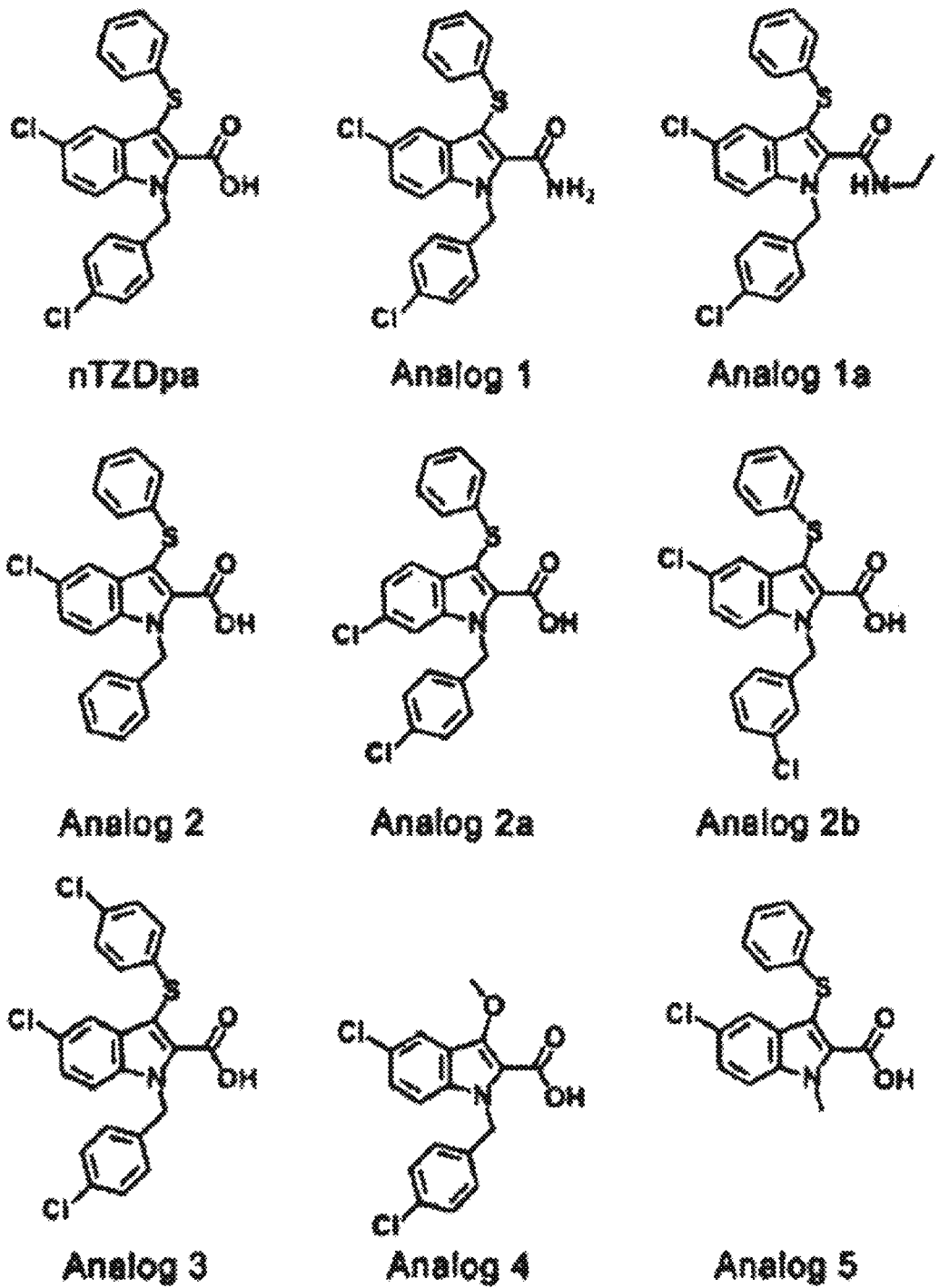
FIG. 17 contains chemical structures of nTZDpa and its analogs 1, 1a, 2, 2a, 2b, 3, 4, and 5.
Figure 18:
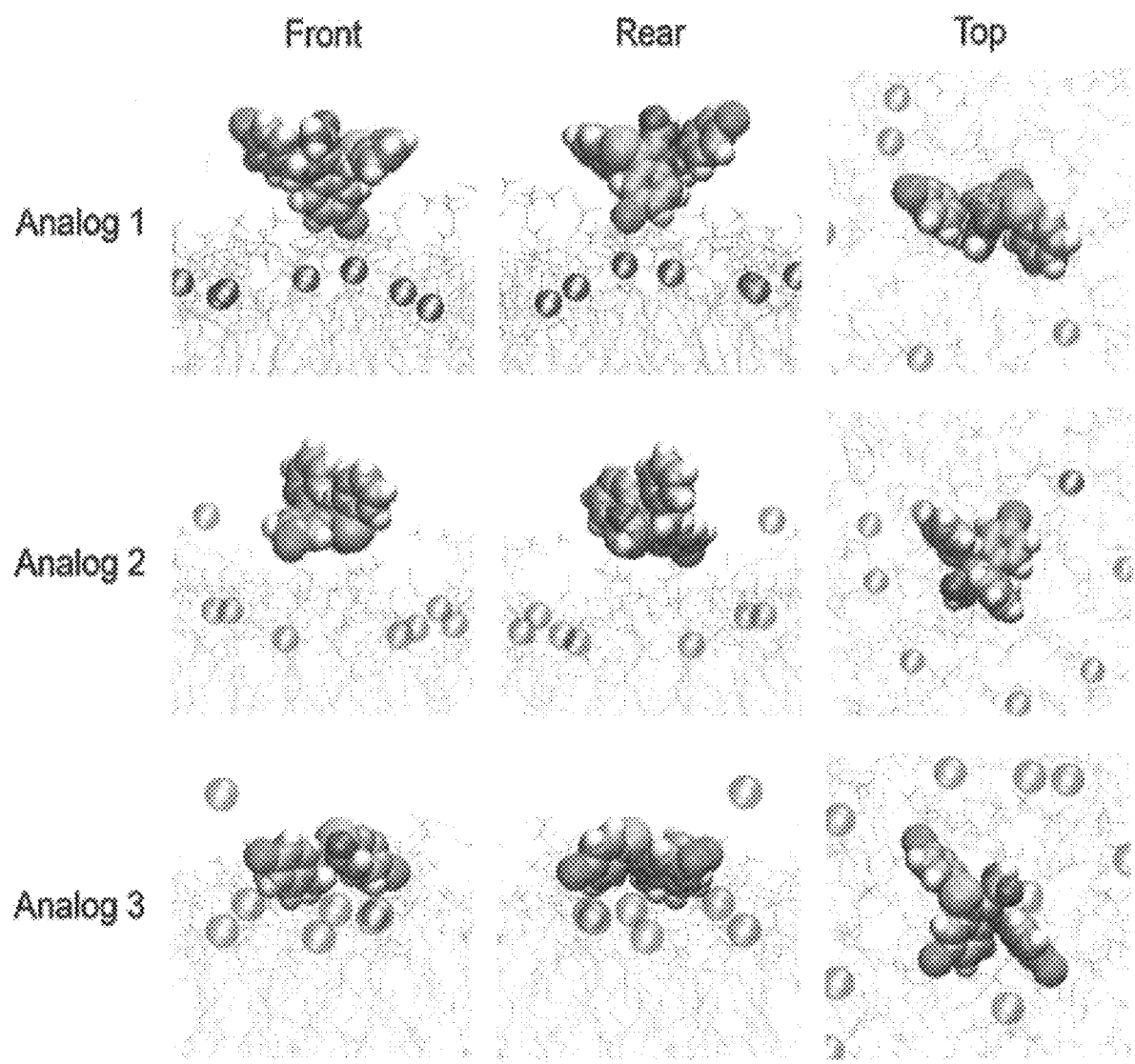
FIG. 18 contains representative configurations of nTZDpa analogs at the point of membrane attachment. The attachment configurations are shown in front, rear and top views, respectively. Analogs and sodium ions are depicted as large spheres, and phospholipids are represented as chains.
Figure 21:
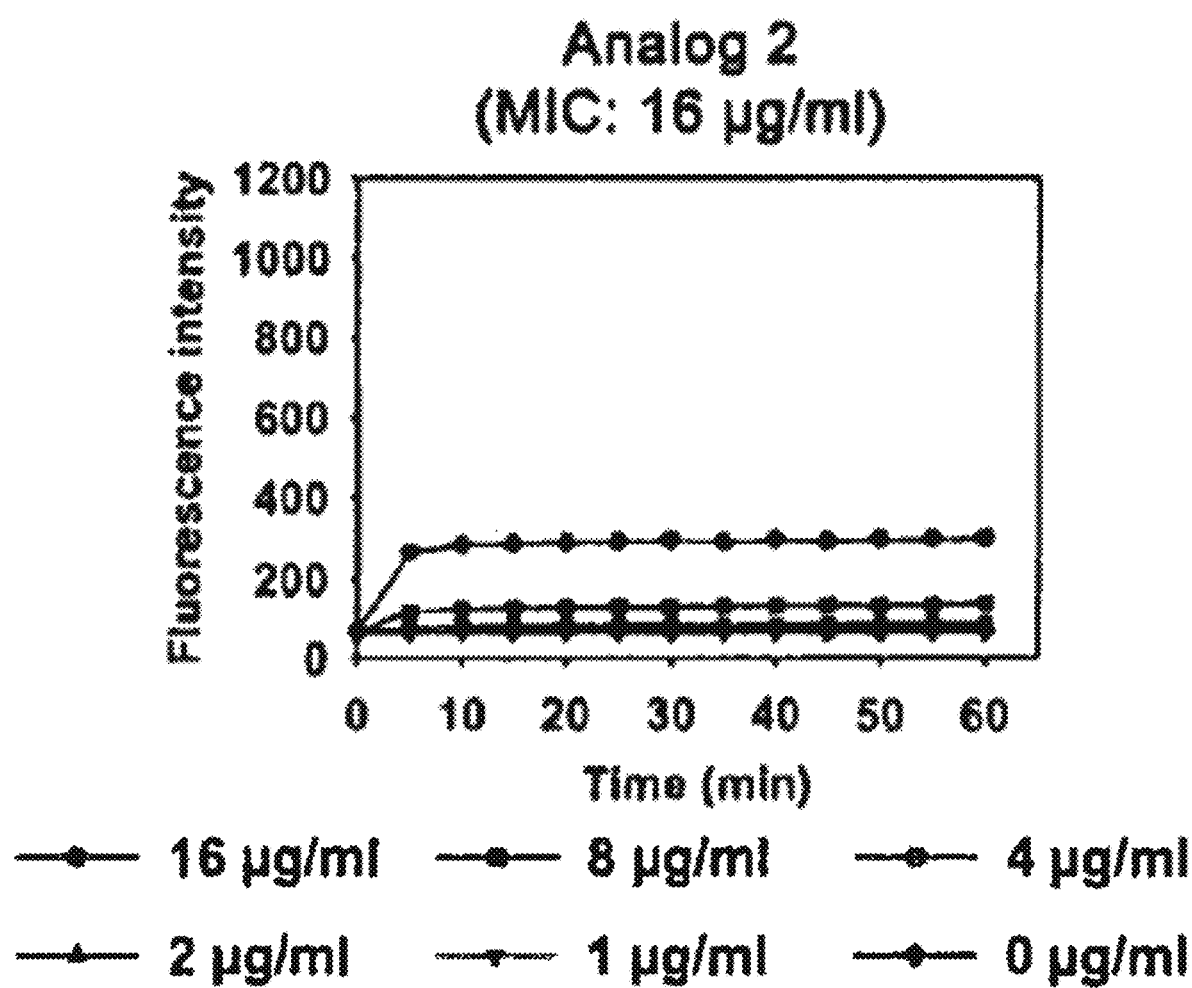
FIG. 21 contains a line plot showing antimicrobial activity and membrane permeability Analog 2 (compound S4). MICs and membrane permeability were measured with MRSA MW2. Membrane permeability was evaluated spectrophotometrically by monitoring the uptake of SYTOX Green (Ex=485 nm, Em=525 nm) over time. Results are shown as mean of triplicates. Error bars (s.d.) are not shown for clarity.
Figure 22:
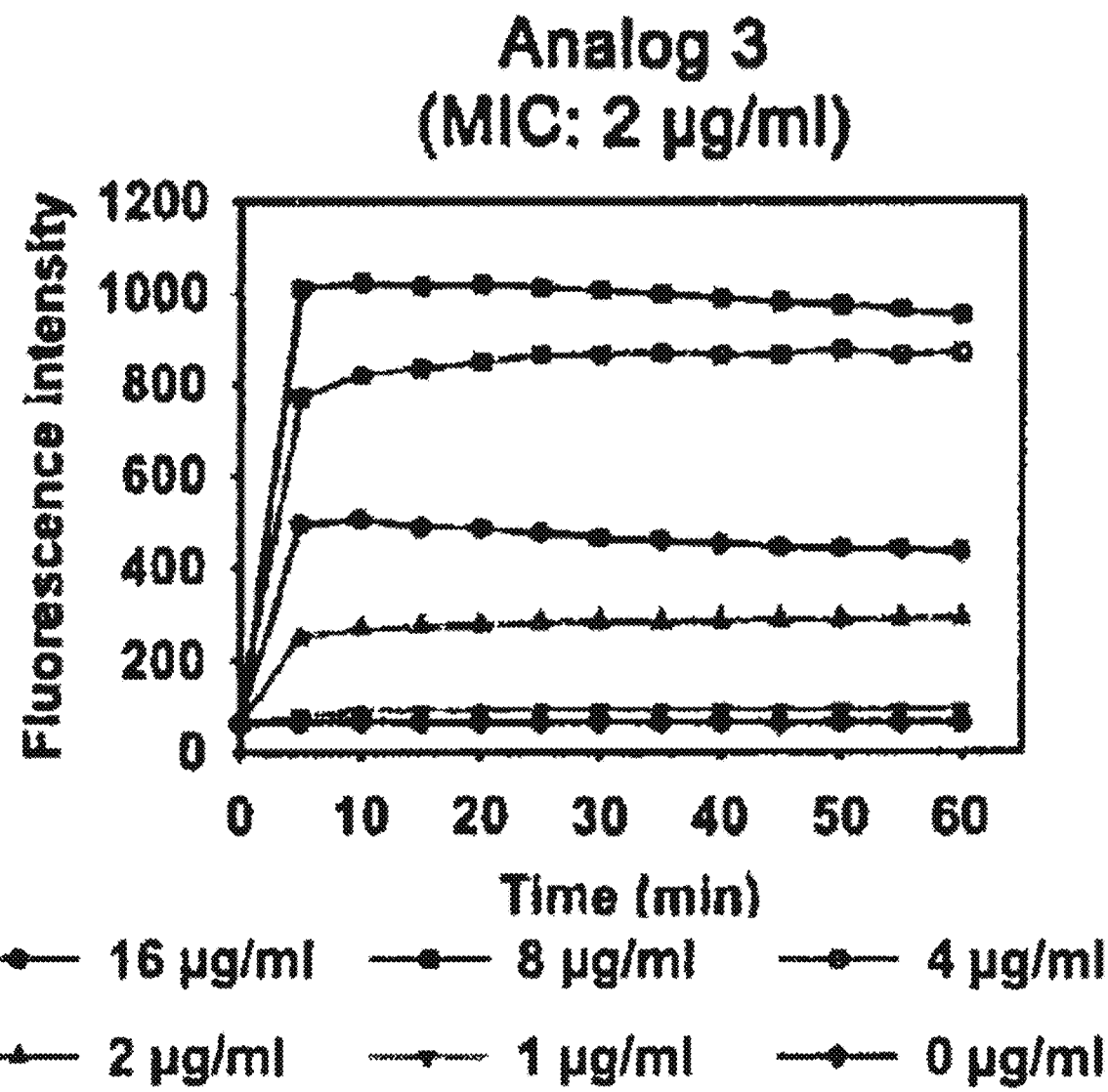
FIG. 22 contains a line plot showing antimicrobial activity and membrane permeability for Analog 3 (compound 4). MICS and membrane permeability were measured with MRSA MW2. Membrane permeability was evaluated spectrophotometrically by monitoring the uptake of SYTOX Green (Ex=485 nm, Em=525 nm) over time. Results are shown as mean of triplicates. Error bars (s.d.) are not shown for clarity.
Figure 23:
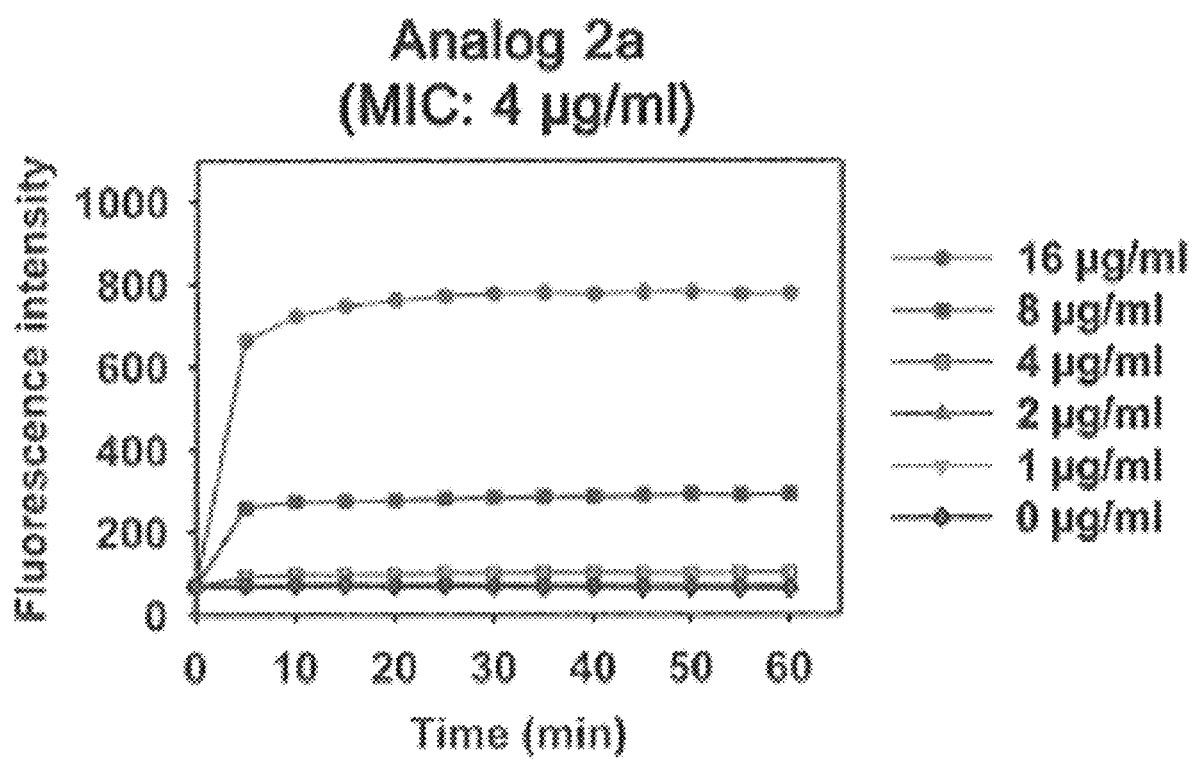
FIG. 23 contains a line plot showing antimicrobial activity and membrane permeability Analog 2a (compound S9). MICs and membrane permeability were measured with MRSA MW2. Membrane permeability was evaluated spectrophotometrically by monitoring the uptake of SYTOX Green (Ex=485 nm, Em=525 nm) over time. Results are shown as mean of triplicates. Error bars (s.d.) are not shown for clarity.
Figure 24:
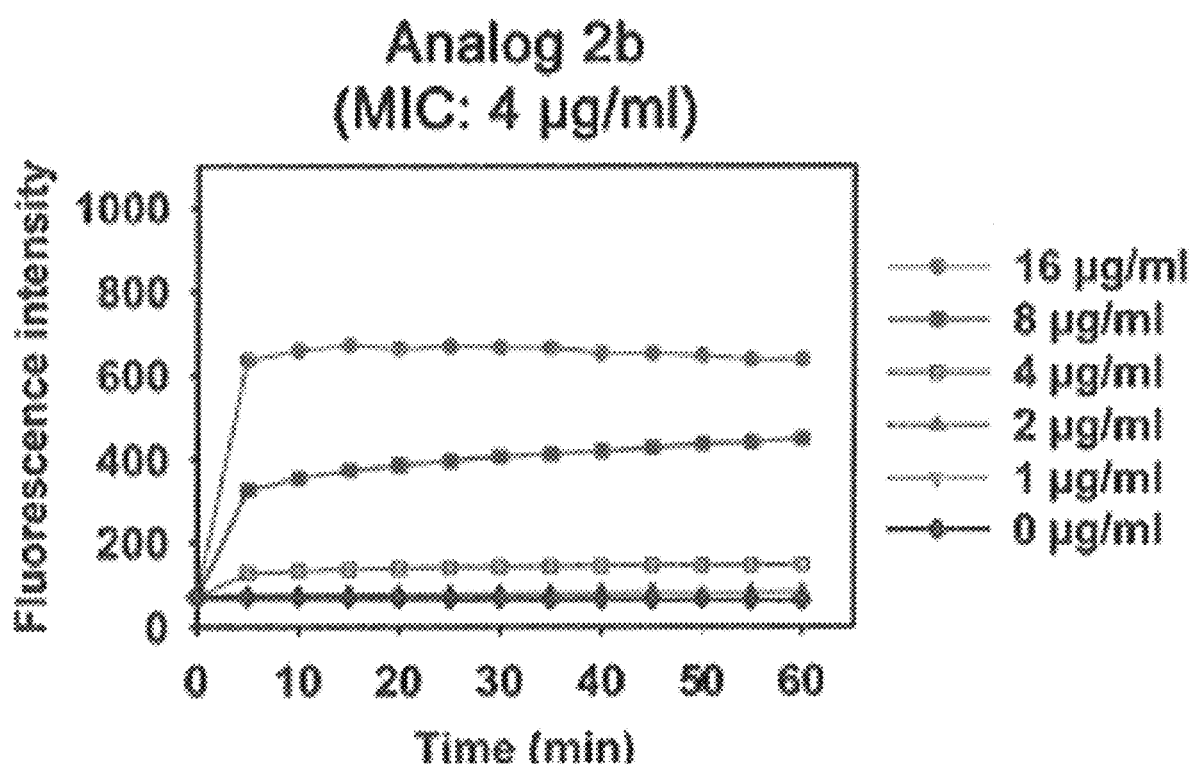
FIG. 24 contains a line plot showing antimicrobial activity and membrane permeability for Analog 2b (compound S5). MICs and membrane permeability were measured with MRSA MW2. Membrane permeability was evaluated spectrophotometrically by monitoring the uptake of SYTOX Green (Ex=485 nm, Em=525 nm) over time. Results are shown as mean of triplicates. Error bars (s.d.) are not shown for clarity.

Structurers of analogs 1-5 are shown in FIG. 17. Analog 2 (compound S4) showed MIC of 16 µg/ml. Analogs 2a (compound S9) and 2b (compound S5) have the same MIC and a similar effect on membrane permeability as nTZDpa. Analog 3 (compound 4) showed MIC of 2 µg/ml and maximum SYTOX Green fluorescence at 8 µg/ml, as compared to nTZDpa's maximum at 16 µg/ml. Analog 4 showed MIC of 32 µg/ml and induced SYTOX Green fluorescence at 64 µg/ml. Analog 5 (compound S3) showed MIC of 64 µg/ml. FIG. 21 shows results of membrane permeability assays for Analogs 2, 2a, and 3.

Figure 20:
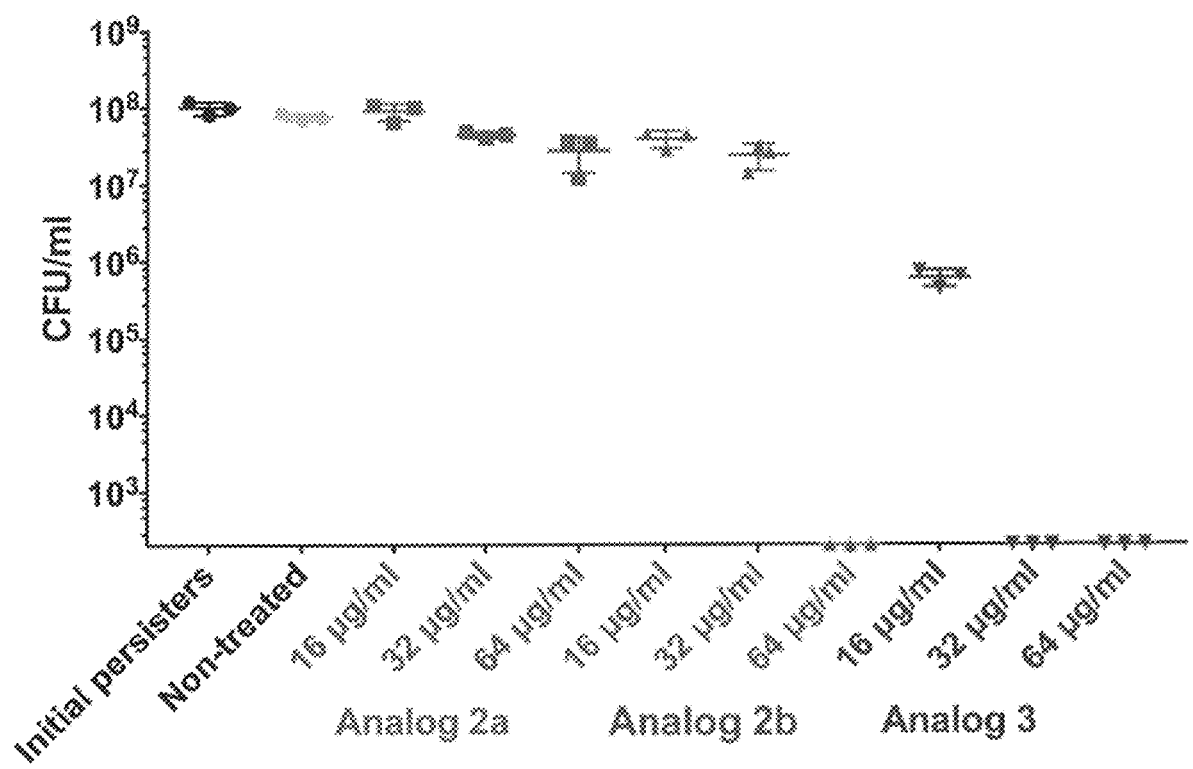
FIG. 20 contains a plot showing anti-persister activity of nTZDpa analogs. MRSA MW2 persister cells were treated with the indicated concentrations of nTZDpa analogs for 4 h. The data points on the x-axis are below the level of detection ($2 \times 10^2$ CFU/ml). Individual data points (n=3 biological replicates) are shown; error bars represent means±s.d.

MRSA persisters: Analog 2b exhibited a similar level of anti-persister activity as nTZDpa (FIG. 20).

MD simulations: For nTZDpa, interaction of the carboxylic acid with the phospholipid polar head occurs at 180 ns, followed by the sulfur atom of the thioether at 200 ns. From there, the phenyl moiety attached to sulfur penetrates the nonpolar interior of the membrane, followed by the rest of the molecule. In contrast to the nTZDpa simulation, Analog 2 shows attachment of the carboxylic acid at 80 ns without involvement of sulfur. Analog 2 exhibited an increased transfer energy of −0.27 kBT and an energy barrier of 17.98 kBT relative to nTZDpa. Therefore, the perceived interaction of the sulfur of nTZDpa with the polar membrane heads may be a result of the thiophenyl moiety entering the interior of the membrane. The simulations with Analog 1 demonstrate the importance of the carboxylic acid moiety for lipid head interaction. With a negatively charged membrane, the sulfur and chlorine atoms make contacts several times with the membrane throughout the simulation, but the compound repeatedly diffuses away. In a second simulation of Analog 1 with a neutral polar membrane composition (DOPC alone instead of 7DOPC:3DOPG), membrane attachment is initiated at 196 ns by the chlorine substituent on the indole ring, and the compound can penetrate fully. The decreased polarity of the membrane likely compensates for the absence of the acid, but still shows the importance of the chlorine polar contacts. The simulation results with Analog 3 further demonstrate the importance of chlorine substituents for initial membrane attachment, as the polar interaction is initiated by the chlorine substituent unique to this analog (159 ns), followed by the carboxylic acid. Analog 3 showed much lower transfer energy of −13.62 kBT, and energy barrier of 0.79 kBT, compared to nTZDpa. Taken in sum, these data suggest that the carboxylic acid is important for strong anchoring of the compound to the polar lipid membrane heads. The chlorine substituents make weaker polar contacts, which may work in concert with the carboxylic acid for stronger initial attachment. The sulfur atom does not appear to be essential for attachment or penetration.

TABLE 2a

Characteristic parameters derived from the energy profile

| Compound | Transfer Energy ($k_BT$) | Energy Barrier ($k_BT$) |
| --- | --- | --- |
| nTZDpa | −0.81 | 6.14 |
| S1 (analog 1) | 101.52 | 98.80 |
| S4 (analog 2) | −0.27 | 17.98 |
| 4 (analog 3) | −13.62 | 0.79 |

Figure 19:
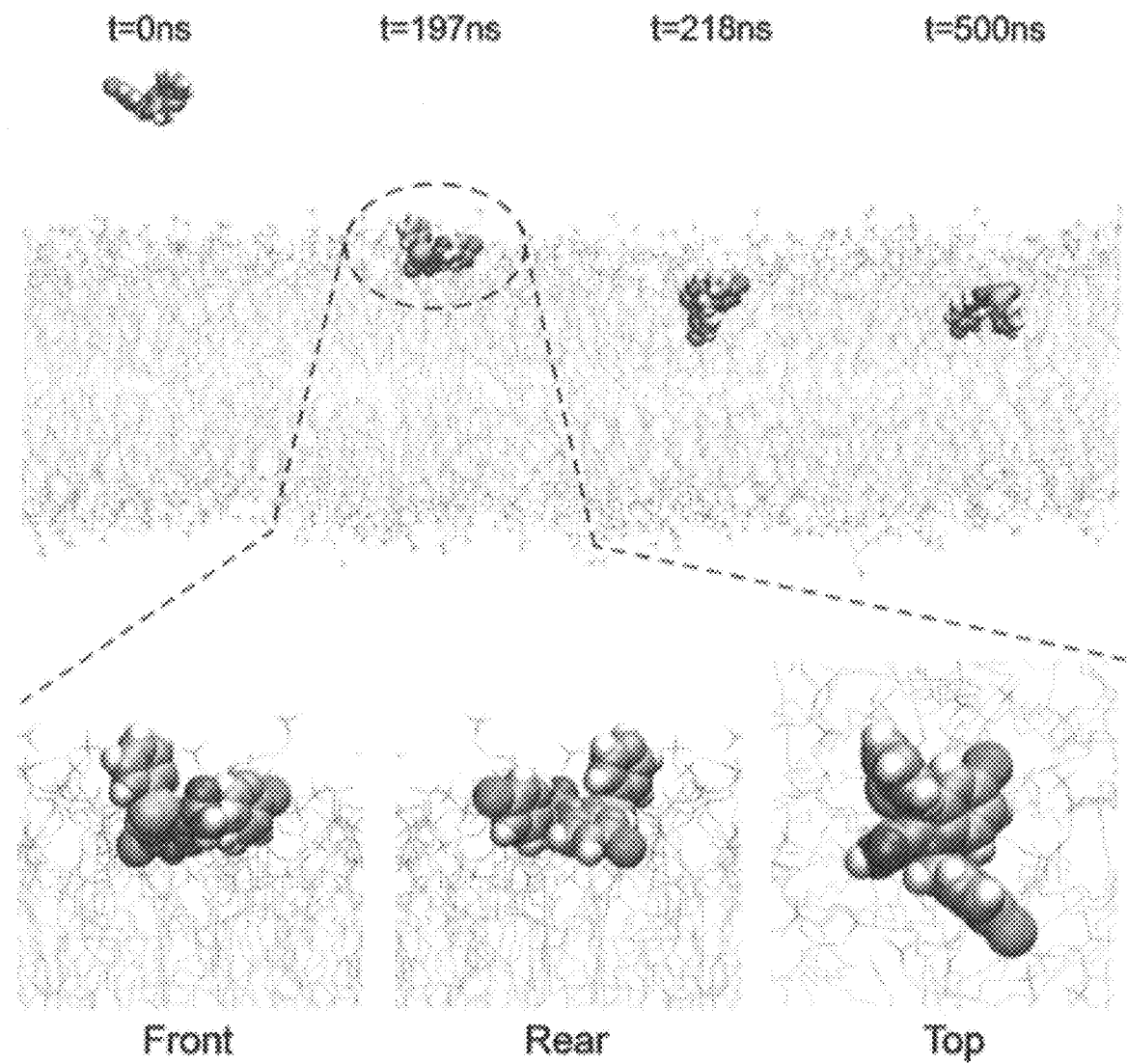
FIG. 19 shows representative configurations of Analog 1 (compound S1) interacting with pure DOPC lipid bilayer at the onset of simulation, membrane attachment, membrane penetration and equilibrium state. The attachment configuration is magnified and shown in front, rear and top views, respectively. Analog 1 (compound S1) and phospholipids are depicted as large spheres and chains, respectively.
Figure 31:
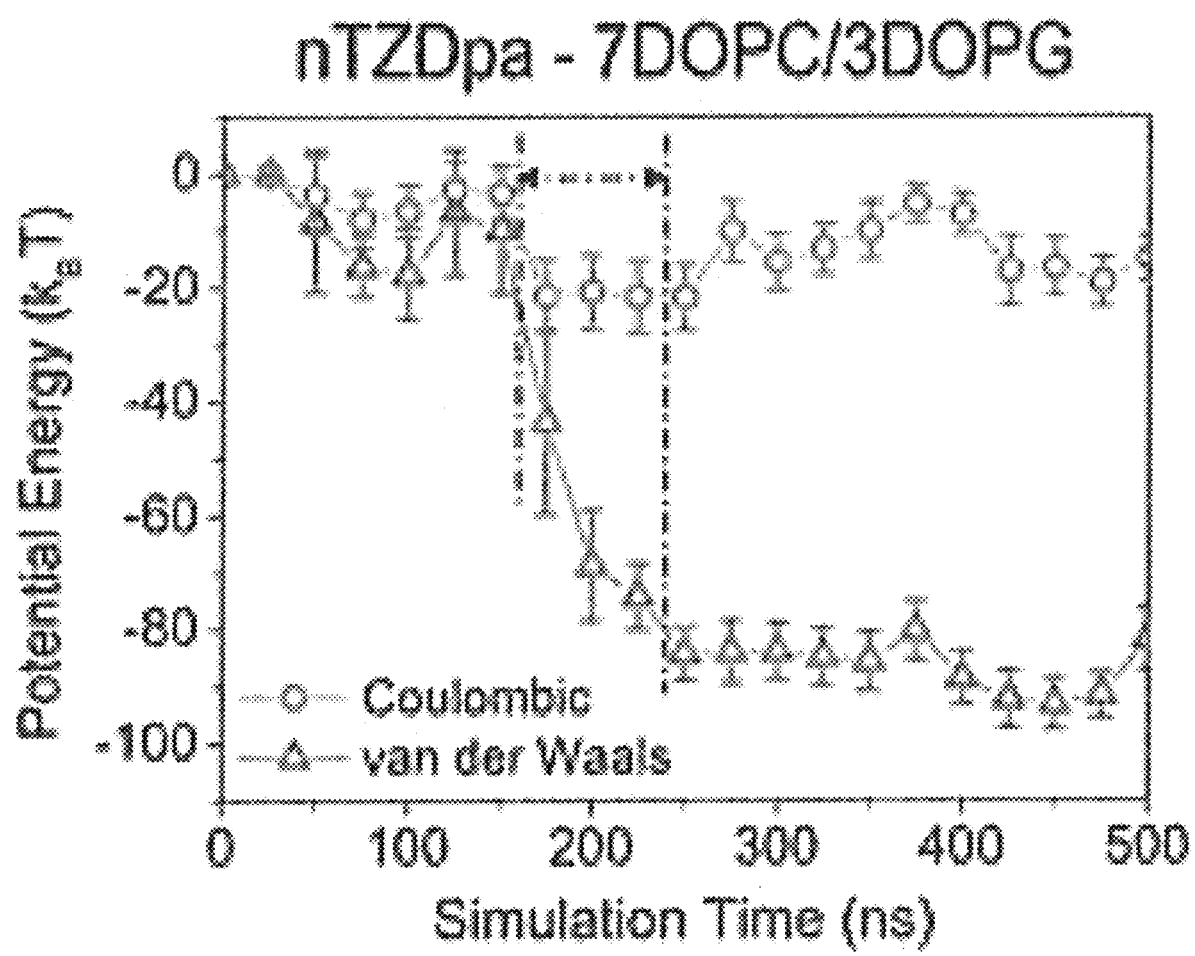
FIG. 31 contains a plot showing potential energies of Coulombic and van der Waals (vdW) interactions for nTZDpa and DOPC/DOPG (7:3) lipids.
Figure 32:
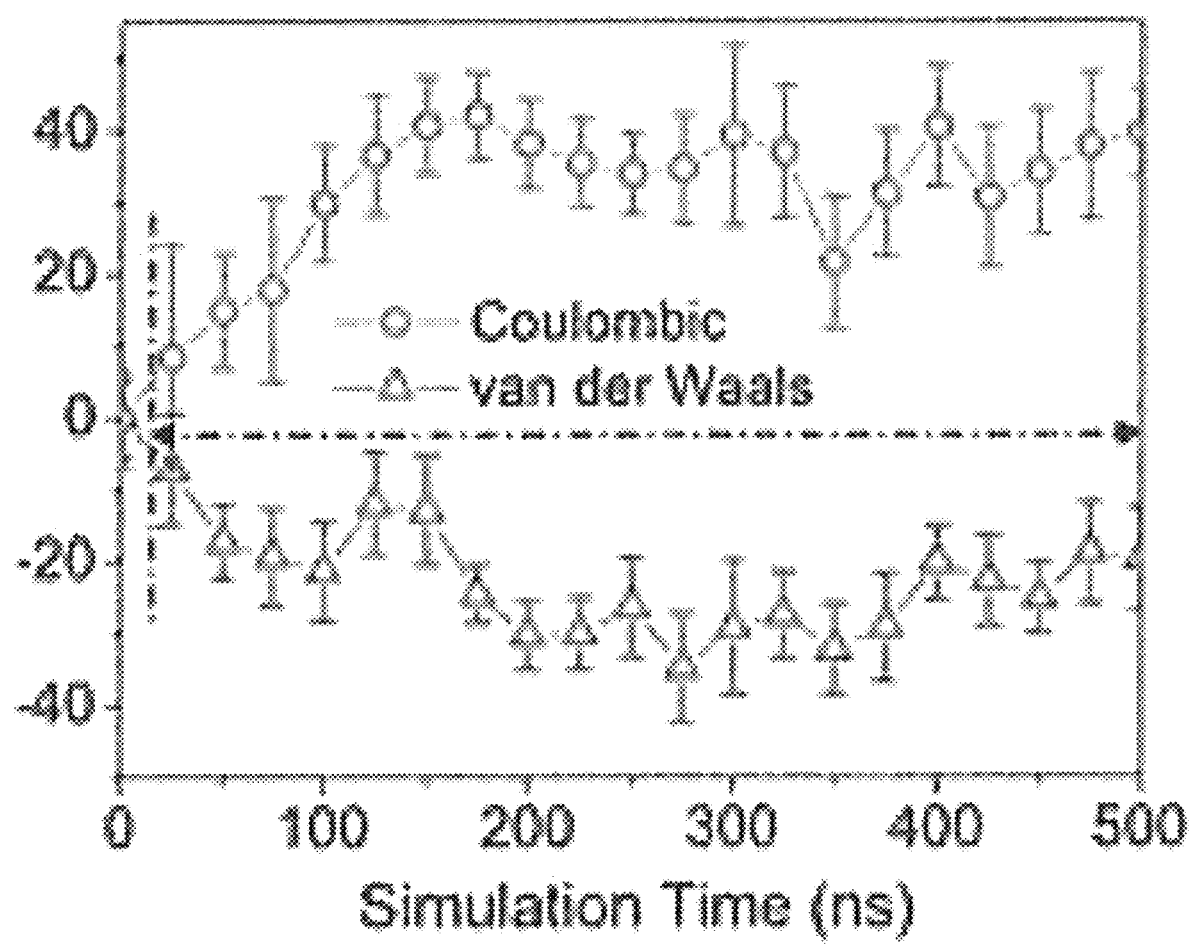
FIG. 32 contains a plot showing potential energies of Coulombic and van der Waals (vdW) interactions for Analog 1 and DOPC/DOPG (7:3) lipids.
Figure 33:
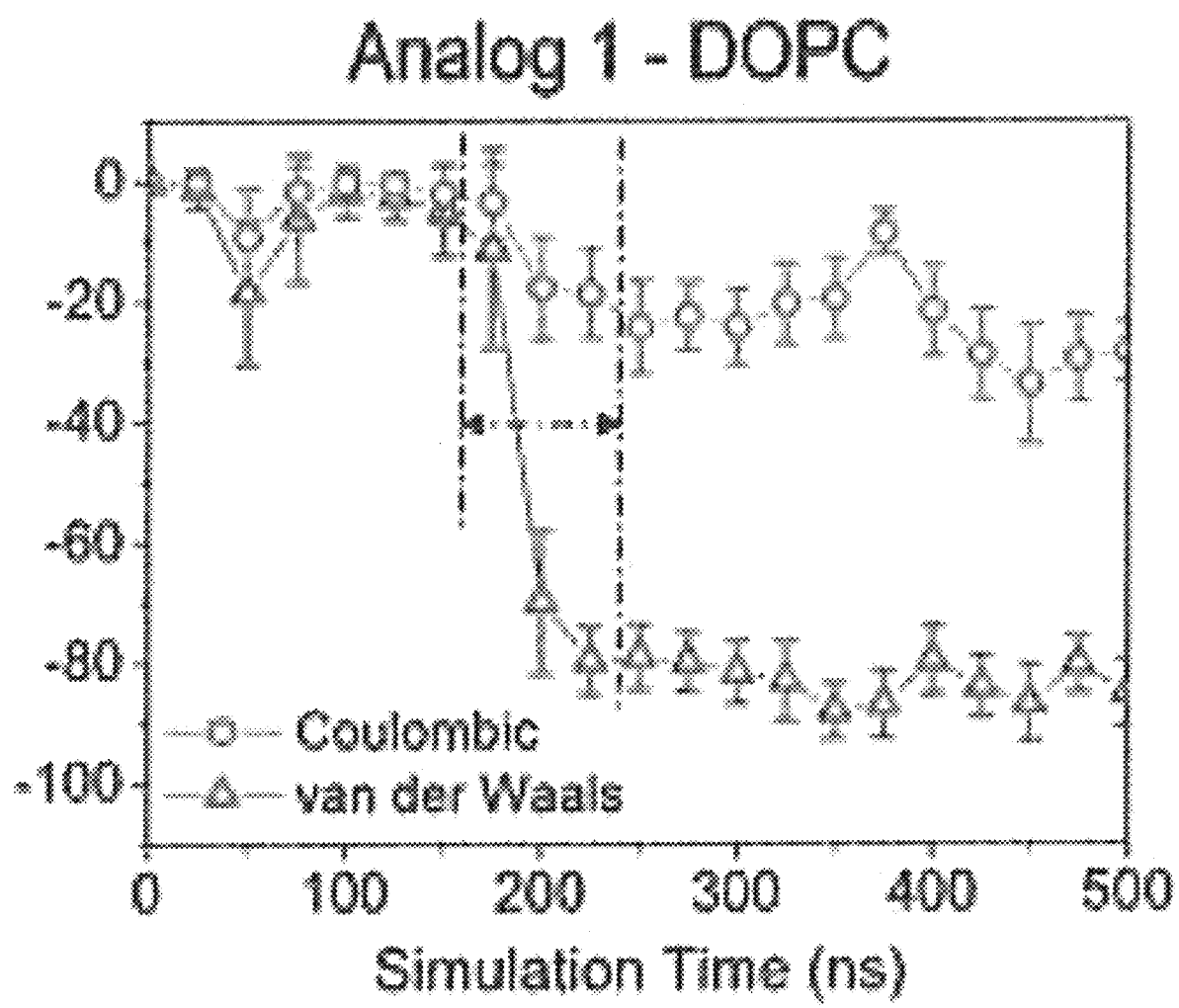
FIG. 33 contains a plot showing potential energies of Coulombic and van der Waals (vdW) interactions for Analog 1 and DOPC lipids.
Figure 34:
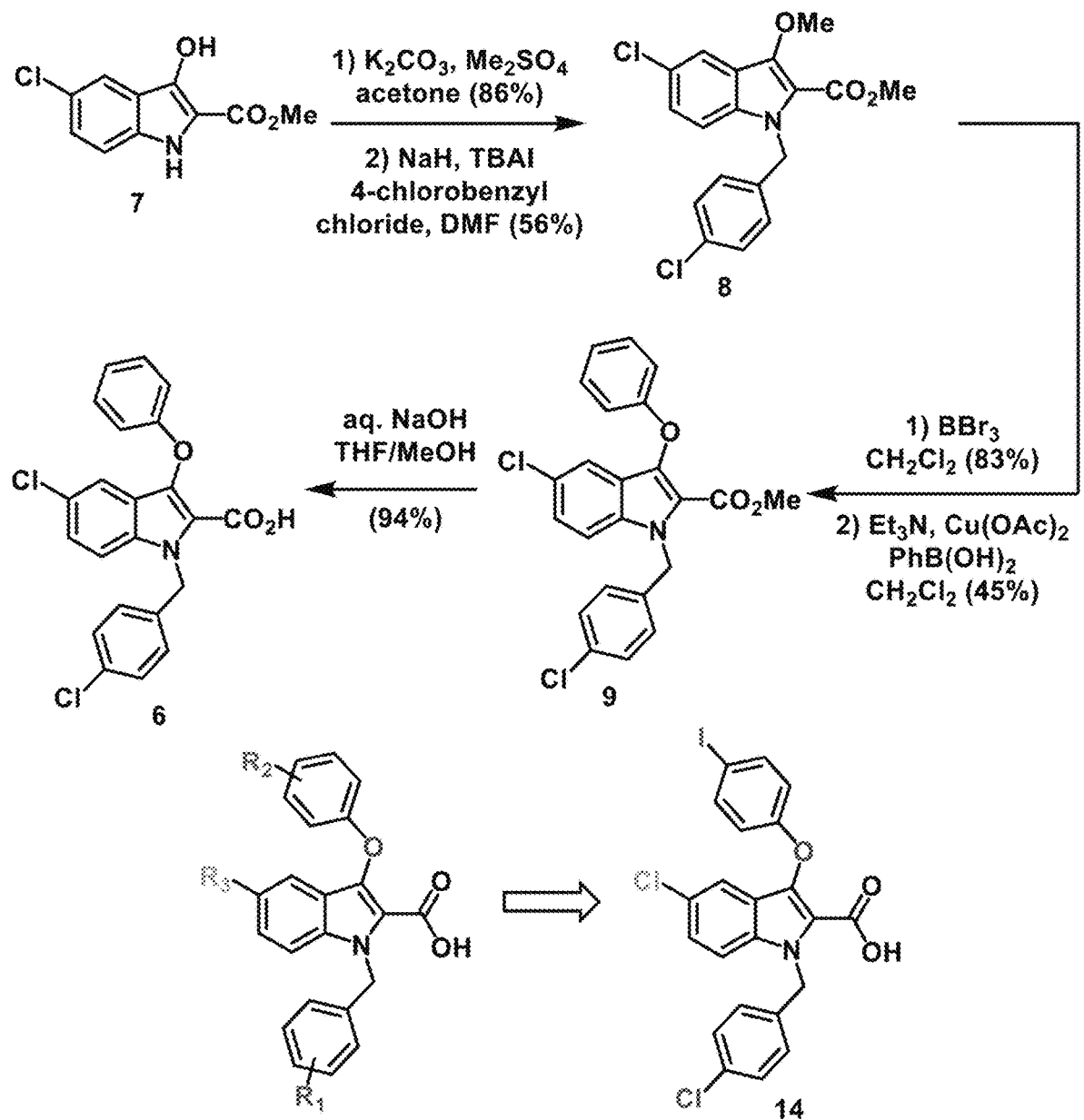
FIG. 34 contains a reaction scheme showing synthesis of compounds 6 and 14.
Figure 37:
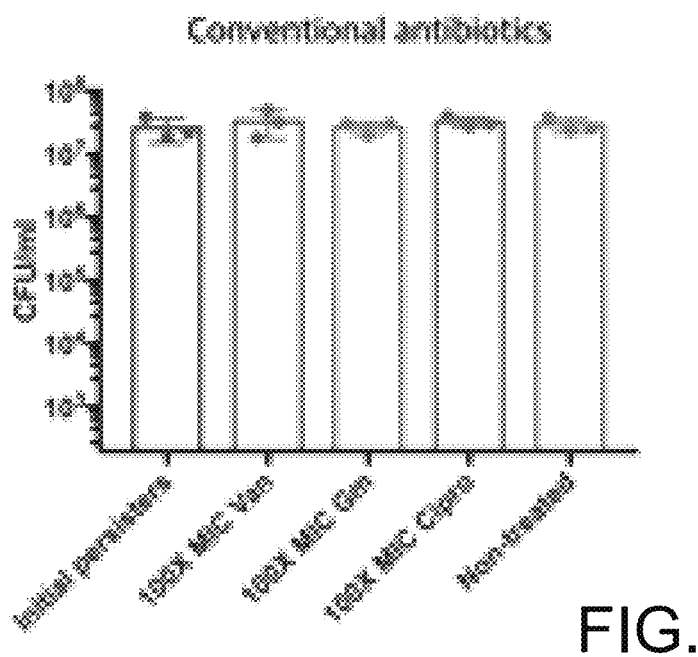
FIG. 37 contains a bar graph showing anti-persister activity of other antibiotics. Stationary-phase *S. aureus* MW2 was treated with 100× MIC other antibiotics (Van: vancomycin, Gm: gentamicin, Cipro: ciprofloxacin) for 4 h. Viability was measured by serial dilution and plating on agar plates. The data points on the x-axis are below the level of detection (2×102 CFU/mL). Individual data points (n=3 biologically independent samples) and mean±s. d. are shown.
Figure 38:
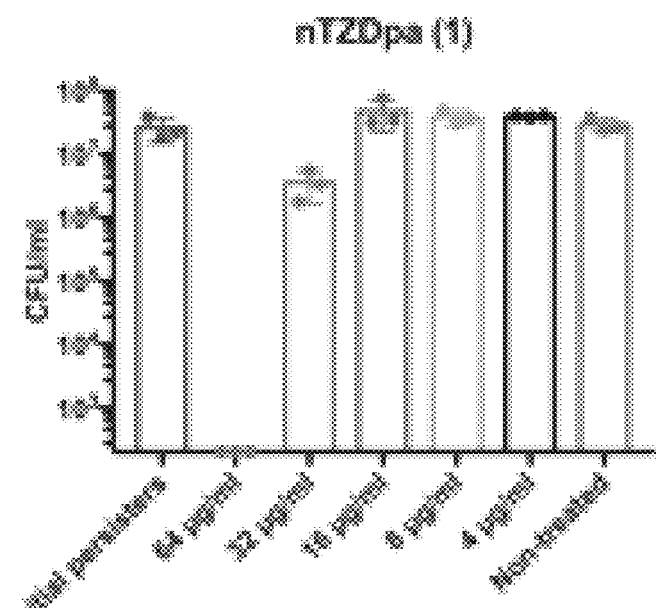
FIG. 38 contains a bar graph showing anti-persister activity of nTZDpa. Stationary-phase *S. aureus* MW2 was treated with 100× MIC other antibiotics (Van: vancomycin, Gm: gentamicin, Cipro: ciprofloxacin) or an indicated range of concentration of nTZDpa for 4 h. Viability was measured by serial dilution and plating on agar plates. The data points on the x-axis are below the level of detection (2×102 CFU/mL). Individual data points (n=3 biologically independent samples) and mean±s.d. are shown.
Figure 39:
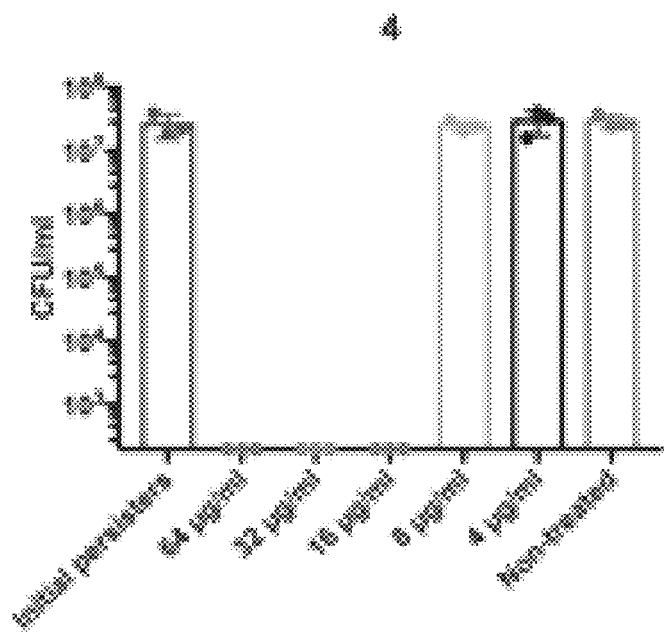
FIG. 39 contains a bar graph showing anti-persister activity of compound 4. Stationary-phase *S. aureus* MW2 was treated with 100× MIC other antibiotics (Van: vancomycin, Gm: gentamicin, Cipro: ciprofloxacin) or an indicated range of concentration of compound 4 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 40:
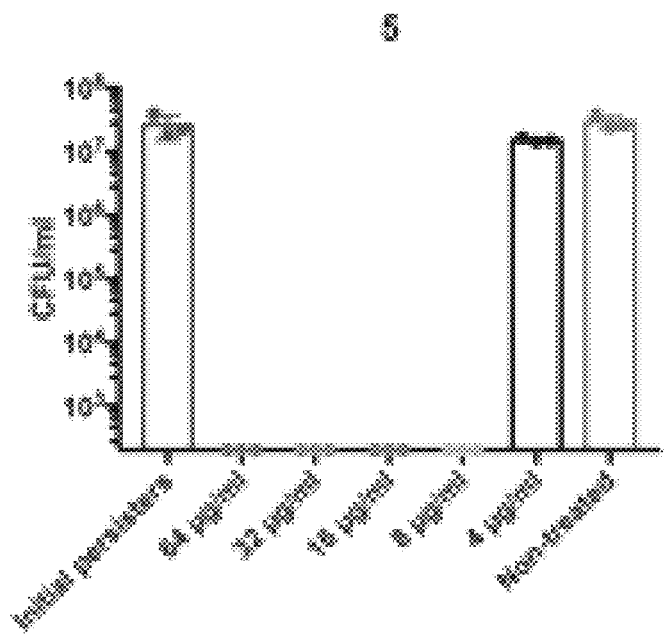
FIG. 40 contains a bar graph showing anti-persister activity of compound 5. Stationary-phase *S. aureus* MW2 was treated with 100× MIC other antibiotics (Van: vancomycin, Gm: gentamicin, Cipro: ciprofloxacin) or an indicated range of concentration of compound 5 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.

Electrostatic repulsion between Analog 1 (compound S1) and negatively-charged membranes: To verify the electrostatic repulsion between Analog 1 and negative-charged membranes, the negatively-charged DOPC/DOPG lipid bilayer was replaced with a neutrally charged, pure DOPC bilayer. In this case, Analog 1's amide group is no longer repelled from the DOPC membrane; instead it binds tightly to lipid heads (FIG. 19). The chlorinated benzene and chlorinated indole groups then attach and lead to the successful penetration of Analog 1 into the neutrally charged membrane (FIG. 19). To further test the hypothesis that electrostatic repulsion prevents Analog 1 from negatively charged membrane attachment and penetration, the non-covalent energy was calculated composed of the Coulombic and van der Waals (vdW) energies at the molecular level. The Coulombic potential energy represents the electrostatic interaction, while both Coulombic and vdW energies contribute to hydrogen bonding. Unlike the simultaneous reduction in both Coulombic and vdW energies for nTZDpa-DOPC/DOPG and Analog 1-DOPC (FIGS. 31, 32, and 33), the potential energy profile of Analog 1 with the DOPC/DOPG lipid bilayer shows a dramatic rise in Coulombic energy at the time of attachment (FIG. 32). Because the increase in Coulombic energy is larger than that of the corresponding vdW energy reduction (FIG. 32), the electrostatic repulsion between the negatively-charged nitrogen atoms and DOPG lipids prevails over the hydrogen bonds between the amide group and lipid heads, thus preventing Analog 1 from membrane attachment and penetration.

A series of compounds (FIG. 35) showed that the chlorine substituent on the benzyl moiety ($R^1$, FIG. 35) is important for activity. Removal resulted in decreased potency against growing MRSA and less toxicity. The position of chlorine on the benzyl moiety did not seem to be important, however, as placement on 4- or 3-position had minimal effects on potency and selectivity.

The addition of either a tert-butyl or chlorine substituent in position $R^2$ resulted in increased potency against both planktonic and persister cells, but increased toxicity (compare 4 and 5, Table 3). Next, substitution of the indole ring ($R^3$) was varied. None of these changes resulted in significantly improved biological activity.

TABLE 3

Antimicrobial activity of compounds 4-6, and 10-14

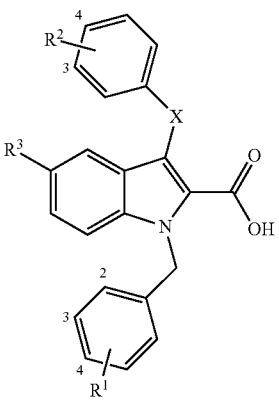

| compound[a] | $R^1$ | $R^2$ | $R^3$ | X | MIC[b] | PKC[b,c] | HC$_{50}$[b,d] |
| --- | --- | --- | --- | --- | --- | --- | --- |
| 1 (nTZDpa) | 4-Cl | H | Cl | S | 4 | 64 | 47 |
| 4 | 4-Cl | 4-Cl | Cl | S | 2 | 16 | 34 |
| 5 | 4-Cl | 4-tBu | Cl | S | 2 | 8 | 26 |
| 6 | 4-Cl | H | Cl | O | 4 | >64 | >64 |
| 10 | 3,4-Cl | H | Cl | O | 2 | 32 | >64 |
| 11 | 4-Cl | 4-Cl | Cl | O | 2 | >64 | >64 |

TABLE 3-continued

Antimicrobial activity of compounds 4-6, and 10-14

| compound[a] | R[1] | R[2] | R[3] | X | MIC[b] | PKC[b,c] | HC$_{50}$[b,d] |
|---|---|---|---|---|---|---|---|
| 12 | 4-Cl | 3,4-Cl | | Cl | O | 1 | 8 | 38 |
| 13 | 4-Cl | 4-Br | | Cl | O | 2 | 32 | >64 |
| 14 | 4-Cl | 4-I | | Cl | O | 1 | 16 | >64 |

[a]see structure above table for definitions of "R" and "X" groups.
[b]values given in μg/mL.
[c]PKC: Persister Killing Concentration to kill 5 × 10[7] CFU/mL MRSA persister below the limit of detection.
[d]HC$_{50}$: median hemolytic concentration.

Figure 41:
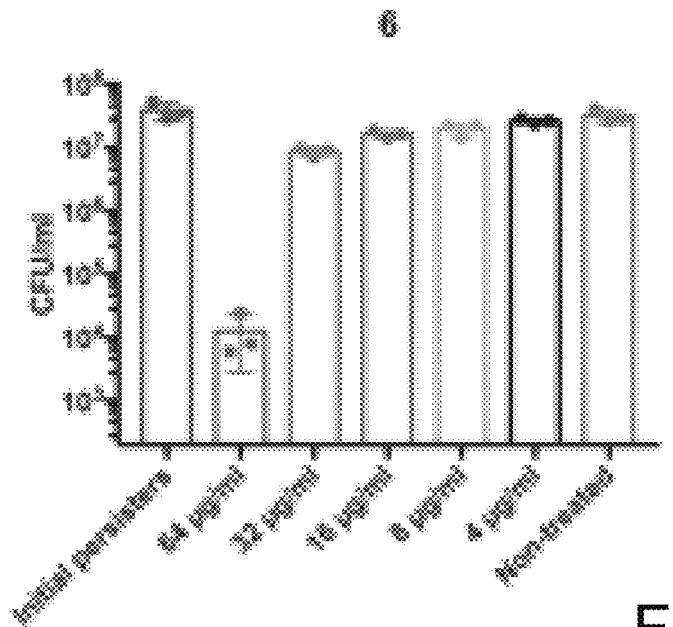
FIG. 41 contains a bar graph showing anti-persister activity of compound 6. Stationary-phase *S. aureus* MW2 was treated with 100× MIC other antibiotics (Van: vancomycin, Gm: gentamicin, Cipro: ciprofloxacin) or an indicated range of concentration of compound 6 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 42:
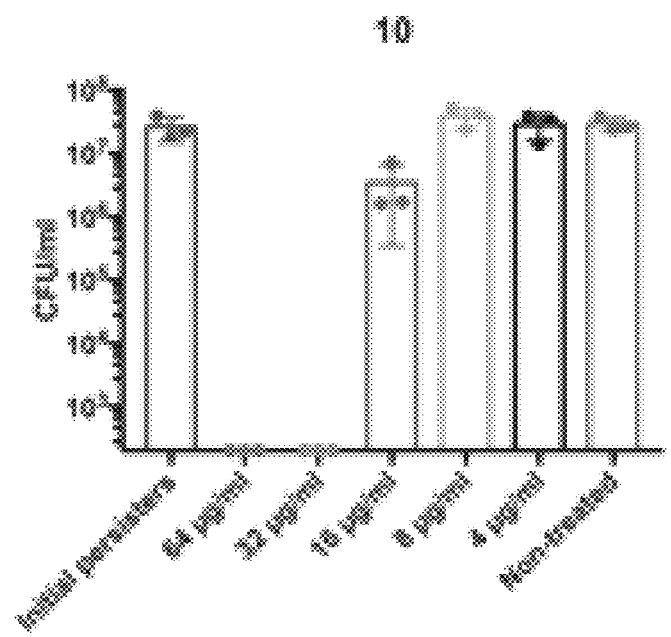
FIG. 42 contains a bar graph showing anti-persister activity of compound 10. Stationary-phase *S. aureus* MW2 was treated with 100× MIC other antibiotics (Van: vancomycin, Gm: gentamicin, Cipro: ciprofloxacin) or an indicated range of concentration of compound 10 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 43:
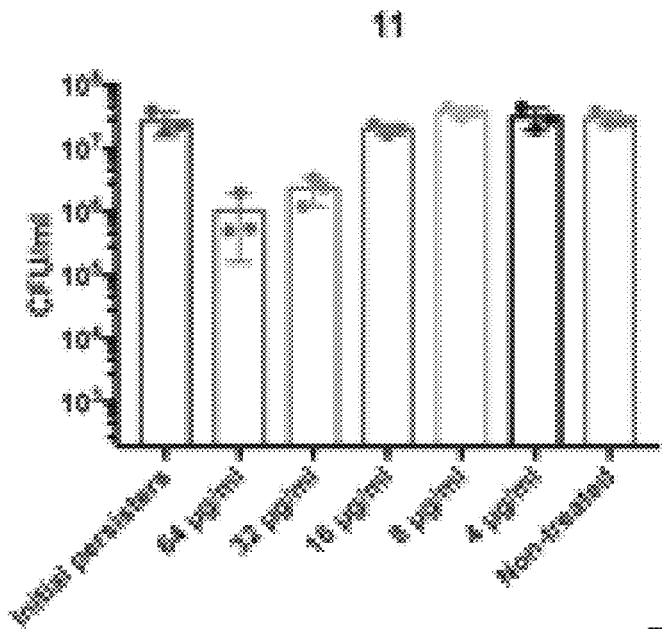
FIG. 43 contains a bar graph showing anti-persister activity of compound 11. Stationary-phase *S. aureus* MW2 was treated with 100× MIC other antibiotics (Van: vancomycin, Gm: gentamicin, Cipro: ciprofloxacin) or an indicated range of concentration of compound 11 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 44:
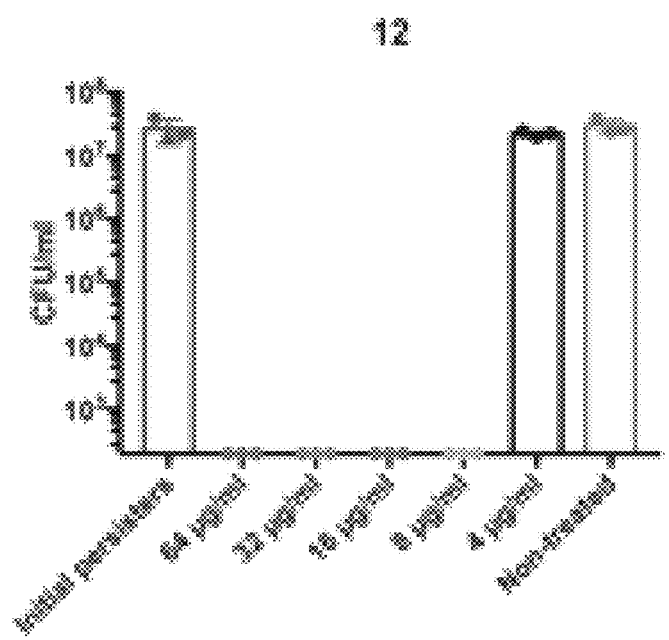
FIG. 44 contains a bar graph showing anti-persister activity of compound 12. Stationary-phase *S. aureus* MW2 was treated with 100× MIC other antibiotics (Van: vancomycin, Gm: gentamicin, Cipro: ciprofloxacin) or an indicated range of concentration of compound 12 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 45:
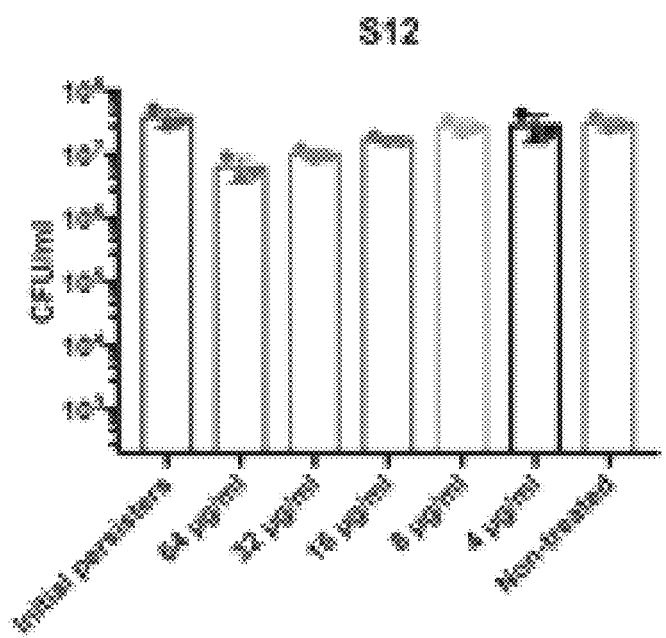
FIG. 45 contains a bar graph showing anti-persister activity of compound S12. Stationary-phase *S. aureus* MW2 was treated with 100× MIC other antibiotics (Van: vancomycin, Gm: gentamicin, Cipro: ciprofloxacin) or an indicated range of concentration of compound S12 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 46:
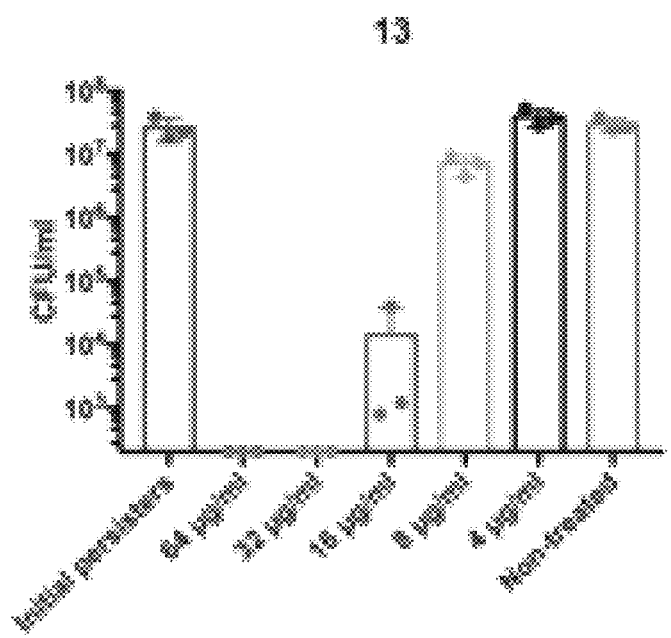
FIG. 46 contains a bar graph showing anti-persister activity of compound 13. Stationary-phase *S. aureus* MW2 was treated with 100× MIC other antibiotics (Van: vancomycin, Gm: gentamicin, Cipro: ciprofloxacin) or an indicated range of concentration of compound 13 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 47:
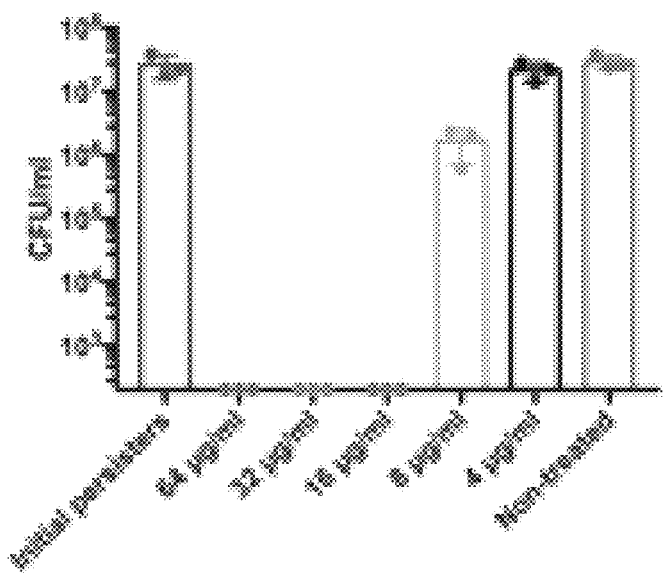
FIG. 47 contains a bar graph showing anti-persister activity of compound 14. Stationary-phase *S. aureus* MW2 was treated with 100× MIC other antibiotics (Van: vancomycin, Gm: gentamicin, Cipro: ciprofloxacin) or an indicated range of concentration of compound 14 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 48:
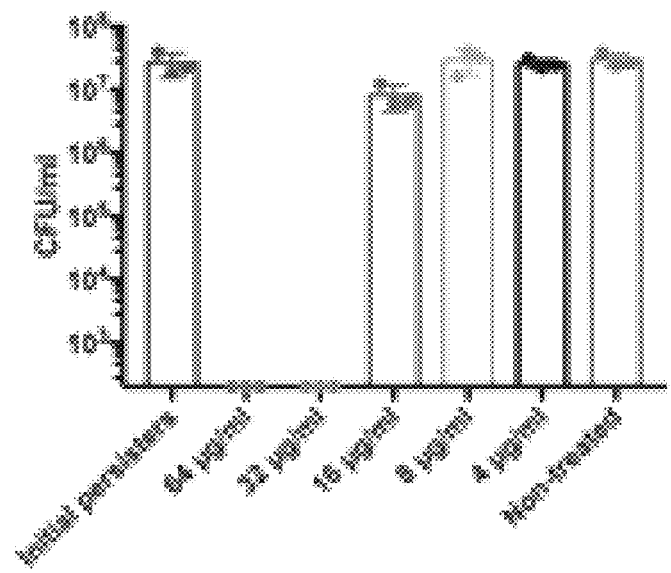
FIG. 48 contains a bar graph showing anti-persister activity of compound S21. Stationary-phase *S. aureus* MW2 was treated with 100× MIC other antibiotics (Van: vancomycin, Gm: gentamicin, Cipro: ciprofloxacin) or an indicated range of concentration of compound S21 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 49:
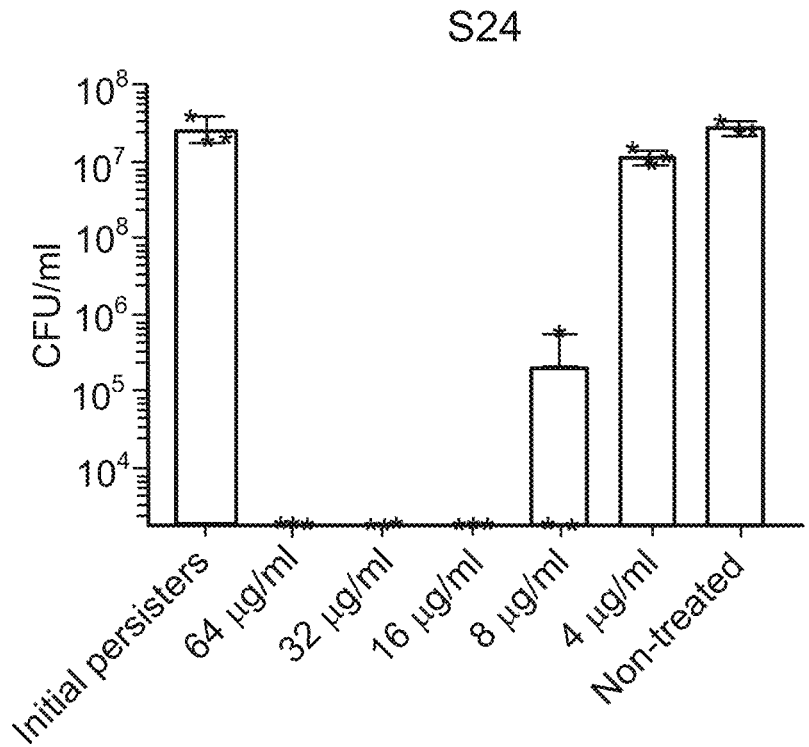
FIG. 49 contains a bar graph showing anti-persister activity of compound S24. Stationary-phase *S. aureus* MW2 was treated with 100× MIC other antibiotics (Van: vancomycin, Gm: gentamicin, Cipro: ciprofloxacin) or an indicated range of concentration of compound S24 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.
Figure 50:
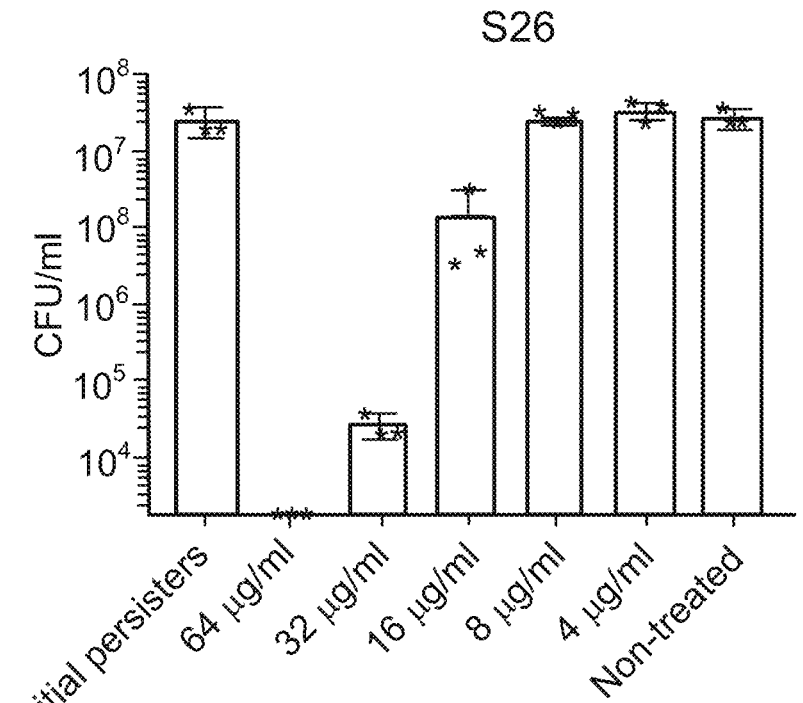
FIG. 50 contains a bar graph showing anti-persister activity of compound S26. Stationary-phase *S. aureus* MW2 was treated with 100× MIC other antibiotics (Van: vancomycin, Gm: gentamicin, Cipro: ciprofloxacin) or an indicated range of concentration of compound S26 for 4 h. Viability was measured by serial dilution and plating on agar plates. The data points on the x-axis are below the level of detection ($2 \times 10^2$ CFU/mL). Individual data points (n=3 biologically independent samples) and mean±s.d. are shown.

As discussed above, the nTZDpa MD simulations showed that the sulfur atom interacts with the membrane early in the attachment phase. Substitution of the sulfur with methylene (compound S12, FIG. 35) resulted in less potency, but replacement with oxygen yielded an analog that was equipotent with nTZDpa for growing *S. aureus* cells, but showed improved membrane selectivity and cytotoxicity profiles (compound 6, Table 3 and FIG. 13A). However, treatment of persisters with 6 only caused a 3-log decrease in viability at 64 μg/mL (FIG. 41).

Compound S13 and compound S14 (analog 4) displayed a reduction of antibiotic activity (FIG. 36) as compared to nTZDpa. Compounds S15-S17 (FIG. 36) were also less active than nTZDpa.

Table 3 summarizes the results of making and testing the compounds. Addition of a chlorine (compound 4) or tert-butyl (compound 5) substituent on the aryl thioether moiety (R[2], Table 3) generated more potent compounds but not more selective for bacterial membranes. Substitution of oxygen for sulfur (compound 6) improved the toxicity profile, but decreased its ability to kill persisters. Additional chlorine atoms on either aryl branch group (compounds 10, 11, and 12) increased potency, but not selectivity. Addition of bromine and especially iodine on the aryl ether moiety enhanced potency (compounds 13, 14) against growing and persister cells relative to compound 6, retaining improved membrane selectivity and cytotoxicity profiles. The MD simulations suggest that larger halogens perturb the membrane more than smaller ones once penetration occurs. In addition, the decreasing polarity of halogens from chlorine to bromine to iodine increases the hydrophobic attraction between the substituent and the lipid tails upon penetration.

Example 6—Synthesis of nTZDpa and its Analogs

Instrumentation and General Notes

NMR spectra were recorded using the following spectrometers: INOVA (600/150 MHz), INOVA (500/125 MHz), Bruker Ascend (600/150 MHz), INOVA (400/100 MHz), VNMR (400/100 MHz), or Mercury (300/75 MHz). Chemical shifts are quoted in ppm relative to tetramethylsilane and with the indicated solvent as an internal reference. The following abbreviations are used to describe signal multiplicities: s (singlet), d (doublet), t (triplet), q (quartet), m (multiplet), br (broad), dd (doublet of doublets), dt (doublet of triplets), etc. Accurate mass spectra were recorded on a Thermo LTQ-FTMS APCI or ESI as indicated. Non-aqueous reactions were performed under an atmosphere of argon, in flame-dried glassware, with HPLC-grade solvents purified on a Pure Process Technology purification system. Amine bases were freshly distilled from CaH$_2$ prior to use. Brine refers to a saturated aqueous solution of sodium chloride. "Column chromatography", unless otherwise indicated, refers to purification on a Biotage Isolera One Automated system in a gradient of ethyl acetate in hexanes, or by standard flash chromatography techniques on small scale (<100 mg). Reactions were monitored via thin-layer chromatography (TLC) using EMD Millipore® TLC silica gel glass plates with KMnO$_4$, p-anisaldehyde, or vanillin stain.

Scheme S1. Synthesis of first generation nTZDpa analogs.

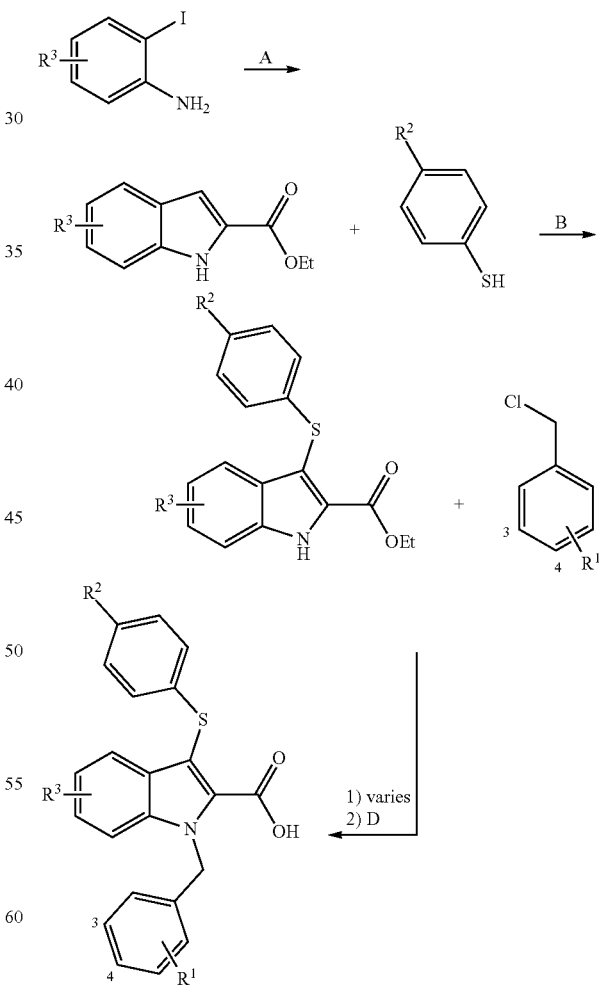

(A) 1) DABCO, pyruvic acid, Pd(OAc)$_2$, DMF, 105° C. 2) SOCl$_2$, EtOH, reflux (B) NCS, CH$_2$Cl$_2$/MeCN, -78° C. to 0° C. (D) aq. NaOH, THF/EtOH General Procedure A: Synthesis of indoles from 2-iodoanilines. To a solution of aniline (1 equiv) in DMF (0.5 M) was added DABCO (3 equiv). After 30 minutes, pyruvic acid (3 equiv) was added over 10 minutes. The reaction flask was purged with argon, then Pd(OAc)$_2$ (5 mol %) was added and the reaction flask was purged with argon again. The reaction was heated to 105° C. for 1 hour then cooled to room temperature. After an hour at this temperature the reaction was acidified to a pH of 3 with 1M HCl. The total volume was doubled with water and the mixture was filtered. The brown solid was washed with two portions of water, and the crude acid was carried directly to the next step. The acid was dissolved in EtOH (0.2 M) and SOCl$_2$ (1.8 equiv) was slowly added. The mixture was heated to reflux overnight, and then concentrated to dryness. The solid was dissolved in acetone then dry-loaded onto silica gel and purified by column chromatography, yielding the product as a tan solid.

General Procedure B: Sulfenylation. To a solution of N-chlorosuccinimide (1.2 equiv) in CH$_2$Cl$_2$ (0.2 M) at −78° C. was added thiophenol (1.2 equiv). The reaction was warmed to 0° C., over which time the reaction turned from clear to bright yellow. After 15 minutes at this temperature, indole-2-carboxylate (1 equiv) was added as a solution in 1:1 CH$_2$Cl$_2$:MeCN (0.2 M). After stirring for 1 hour at 0° C., the reaction was quenched with water and extracted with CH$_2$Cl$_2$ 3×. The combined organic layers were washed with brine, dried over Na$_2$SO$_4$, filtered, concentrated and purified by column chromatography, yielding the product as a white solid.

General Procedure C: Alkylation with sodium hydride as base. To a suspension of sodium hydride (60% in mineral oil, 1.2 equiv) in DMF (0.1 M) at 0° C. was added indole (1 equiv) dissolved in DMF (0.1 M). The reaction was warmed to room temperature and stirred for 30 minutes. 4-chlorobenzyl chloride (1.5 equiv) and TBAI (1 equiv) were added, and the reaction was stirred at room temperature overnight. The reaction was quenched with water and extracted with EtOAc 3×. The combined organic layers were washed with brine, dried over Na$_2$SO$_4$, filtered concentrated and purified by column chromatography, yielding the intermediate mixture of benzyl and ethyl esters.

General Procedure D: Ethyl ester hydrolysis. Ethyl ester (1 equiv) was dissolved in 1:1 THF:EtOH (0.1 M), 1M NaOH (5 equiv) was added, and the reaction was stirred at room temperature until complete by TLC. The reaction was acidified with 1M HCl and extracted with EtOAc 3×. The combined organic layers were washed with brine, dried over Na$_2$SO$_4$, filtered, and concentrated.

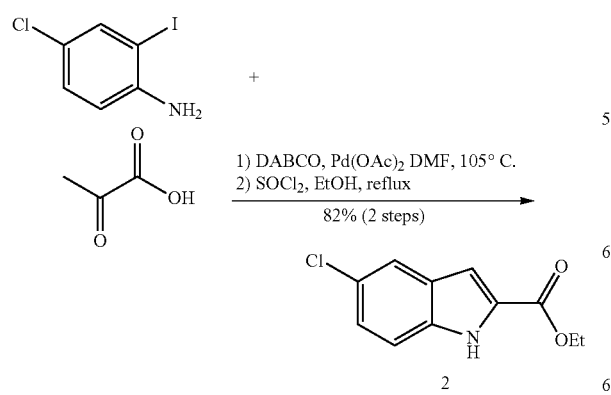

Ethyl 5-chloro-1H-indole-2-carboxylate (2). Using general procedure A, 4-chloro-2-iodoaniline (4.99 g, 19.69 mmol, purified on silica gel prior to use—from Oakwood Products, Inc.) yielded the title compound as a tan solid (3.60 g, 82% yield over two steps) with spectral data matching that previously described.[37]

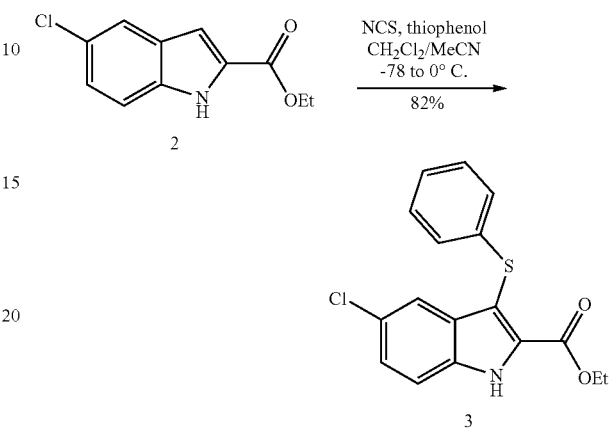

Ethyl 5-chloro-3-(phenylthio)-1H-indole-2-carboxylate (3). Following general procedure B, 2 (414 mg, 1.851 mmol) yielded the title compound as a white solid (449 mg, 82% yield). $^1$H NMR (500 MHz, CDCl$_3$) δ 9.28 (br s, 1H), 7.60 (dd, J=1.3, 0.7 Hz, 1H), 7.38 (dd, J=8.7, 0.5 Hz, 1H), 7.31 (dd, J=8.8, 2.0 Hz, 1H), 7.22-7.08 (m, 5H), 4.39 (q, J=7.1 Hz, 2H), 1.30 (t, J=7.1 Hz, 3H); $^{13}$C NMR (125 MHz, CDCl$_3$) δ 161.10, 137.52, 134.04, 131.39, 130.26, 128.98, 127.63, 127.43, 126.92, 125.71, 121.13, 113.40, 110.19, 61.83, 14.29; HRMS APCI (m/z): [M−H]$^-$ calcd for C$_{17}$H$_{13}$ClNO$_2$S 330.0356, found 330.0362.

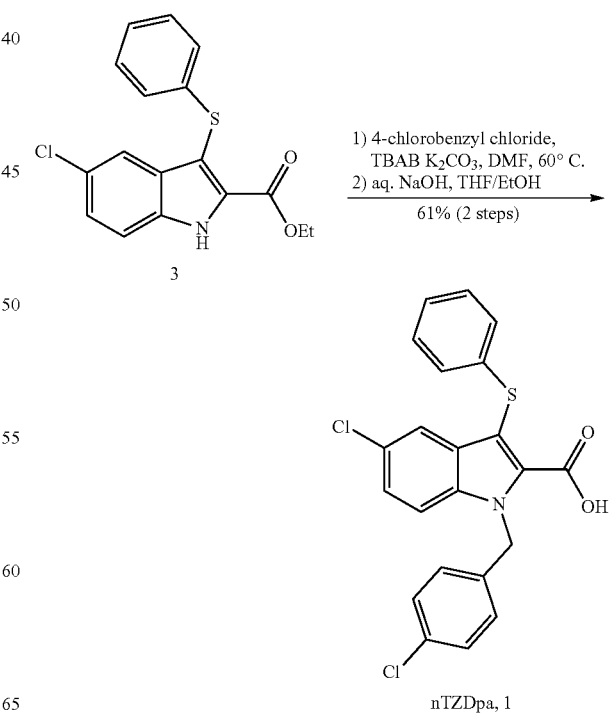

5-chloro-1-(4-chlorobenzyl)-3-(phenylthio)-1H-indole-2-carboxylic acid (nTZDpa, 1). To a solution of indole 3 (90 mg, 0.303 mmol) in DMF (2 mL) was added K$_2$CO$_3$ (84 mg, 0.605 mmol), TBAB (10 mg, 0.030 mmol), and 4-chlorobenzyl chloride (97 mg, 0.605 mmol), and the reaction was stirred at 60° C. overnight. The reaction was quenched with water and extracted with EtOAc 3×. The combined organic layers were washed with brine, dried over Na$_2$SO$_4$, filtered, concentrated, and purified by column chromatography. Using general procedure D, the ethyl ester intermediate was hydrolyzed, and after purification by column chromatography (0→5% MeOH/0.1% AcOH/CH$_2$Cl$_2$), yielded the title compound as a white solid (75 mg, 61% over 2 steps). $^1$H NMR (500 MHz, DMSO) δ 13.89 (br s, 1H), 7.71 (dd, J=8.6, 0.9 Hz, 1H), 7.41-7.33 (m, 4H), 7.29-7.23 (m, 2H), 7.17-7.11 (m, 1H), 7.11-7.05 (m, 4H), 5.83 (s, 2H); $^{13}$C NMR (125 MHz, DMSO) δ 162.00, 137.17, 136.77, 136.11, 134.32, 131.94, 129.14, 129.03, 128.65, 128.22, 126.56, 126.41, 125.59, 125.55, 119.32, 113.88, 107.17, 47.57; HRMS APCI (m/z): [M−H]$^-$ calcd for C$_{22}$H$_{14}$Cl$_2$NO$_2$S 426.0122, found 426.0132.

reaction was diluted with water and extracted with EtOAc 3×. The combined organic layers were washed with brine, dried over Na$_2$SO$_4$, filtered, concentrated, and purified by column chromatography, yielding the title compound as a white solid (14 mg, 93% yield). $^1$H NMR (500 MHz, Acetone) δ 7.72 (br s, 2H), 7.63 (d, J=8.9 Hz, 1H), 7.58 (d, J=2.1 Hz, 1H), 7.35-7.28 (m, 4H), 7.28-7.21 (m, 4H), 7.18-7.11 (m, 3H), 5.94 (s, 2H); $^{13}$C NMR (125 MHz, Acetone) δ 162.89, 138.79, 137.94, 137.77, 136.94, 133.53, 131.04, 130.12, 129.52, 129.46, 128.07, 127.23, 126.73, 125.99, 120.27, 114.11, 103.52, 48.69; HRMS APCI (m/z): [M−H]$^-$ calcd for C$_{22}$H$_{15}$Cl$_2$N$_2$OS 425.0282, found 425.0288.

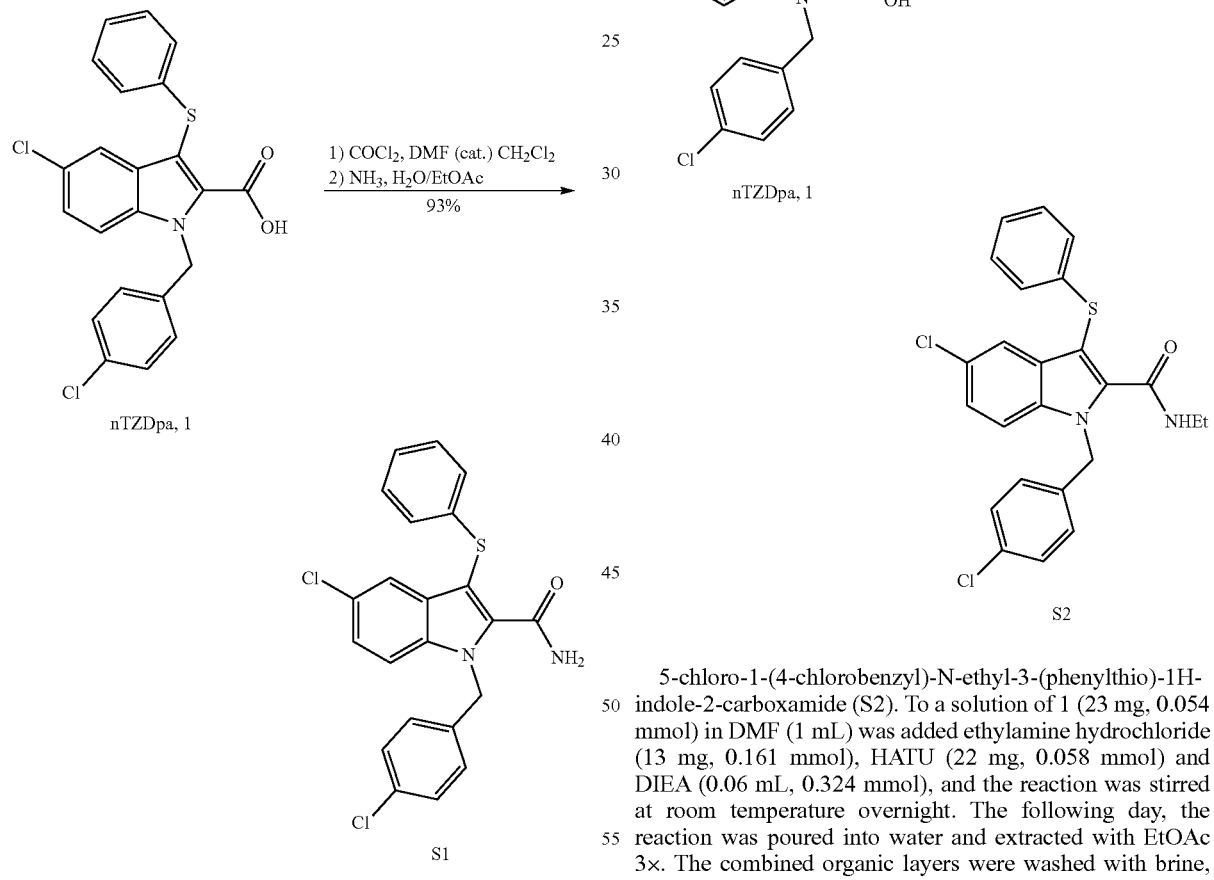

5-chloro-1-(4-chlorobenzyl)-N-ethyl-3-(phenylthio)-1H-indole-2-carboxamide (S2). To a solution of 1 (23 mg, 0.054 mmol) in DMF (1 mL) was added ethylamine hydrochloride (13 mg, 0.161 mmol), HATU (22 mg, 0.058 mmol) and DIEA (0.06 mL, 0.324 mmol), and the reaction was stirred at room temperature overnight. The following day, the reaction was poured into water and extracted with EtOAc 3×. The combined organic layers were washed with brine, dried over Na$_2$SO$_4$, filtered, concentrated, and purified by prep TLC (2:1 hexanes:EtOAc, R$_f$=0.61), yielding the title compound as a white solid (19 mg, 76% yield). $^1$H NMR (500 MHz, CDCl$_3$) δ 7.71 (dd, J=1.9, 0.6 Hz, 1H), 7.62 (br s, 1H), 7.32-7.19 (m, 6H), 7.17-7.12 (m, 1H), 7.08-7.02 (m, 4H), 5.87 (s, 2H), 3.42-3.33 (m, 2H), 1.07 (t, J=7.3 Hz, 3H); $^{13}$C NMR (100 MHz, CDCl$_3$) δ 160.71, 136.55, 136.19, 136.11, 135.91, 133.37, 130.61, 129.50, 129.00, 128.04, 126.23, 125.98, 120.31, 112.30, 102.93, 48.63, 34.72, 14.52; HRMS APCI (m/z): [M+H]$^+$ calcd for C$_{24}$H$_{21}$Cl$_2$N$_2$OS 455.0752, found 455.0753.

5-chloro-1-(4-chlorobenzyl)-3-(phenylthio)-1H-indole-2-carboxamide (S1). To a solution of 1 (15 mg, 0.035 mmol) dissolved in CH$_2$Cl$_2$ (2 mL) was added oxalyl chloride (2M in CH$_2$Cl$_2$, 0.04 mL, 0.08 mmol) and the reaction turned from clear to yellow color. A drop of DMF was then added, and the reaction was stirred at room temperature for 2 hours. The reaction was concentrated under reduced pressure and dried under vacuum for 5 minutes, after which time the crude acid chloride was cooled to 0° C. and 8:1 EtOAc:NH4OH (5 mL) was added. After 30 minutes at 0° C., the

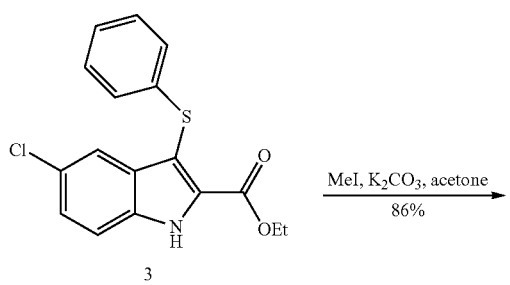

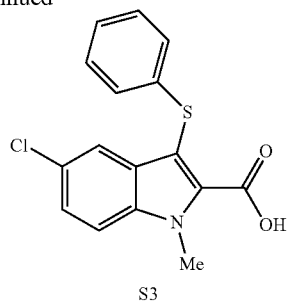

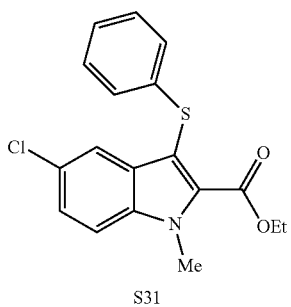

Ethyl 5-chloro-1-methyl-3-(phenylthio)-1H-indole-2-carboxylate (S31). To a solution of indole 3 (42 mg, 0.127 mmol) in acetone (2 mL) was added $K_2CO_3$ (70 mg, 0.506 mmol) and iodomethane (0.016 mL, 0.254 mmol), and the reaction was stirred at room temperature overnight. The following day a large amount of white solids were visible in the reaction flask. The reaction was poured into water and extracted with EtOAc 3×. The combined organic layers were washed with brine, dried over $Na_2SO_4$, filtered, concentrated, and purified by column chromatography, yielding the title compound as a clear oil (38 mg, 86% yield). $^1$H NMR (500 MHz, $CDCl_3$) δ 7.64 (dd, J=1.9, 0.6 Hz, 1H), 7.37-7.30 (m, 2H), 7.20-7.15 (m, 2H), 7.12-7.06 (m, 3H), 4.35 (q, J=7.1 Hz, 2H), 4.05 (s, 3H), 1.26 (t, J=7.1 Hz, 3H); $^{13}$C NMR (125 MHz, $CDCl_3$) δ 161.61, 138.34, 136.88, 132.81, 130.09, 128.87, 127.51, 126.76, 126.19, 125.31, 120.90, 111.79, 108.86, 61.63, 32.77, 14.13; HRMS APCI (m/z): [M+H]$^+$ calcd for $C_{18}H_{17}ClNO_2S$ 346.0669, found 346.0665.

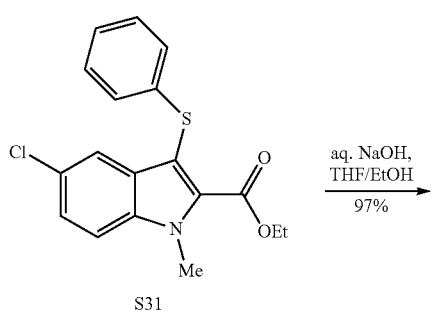

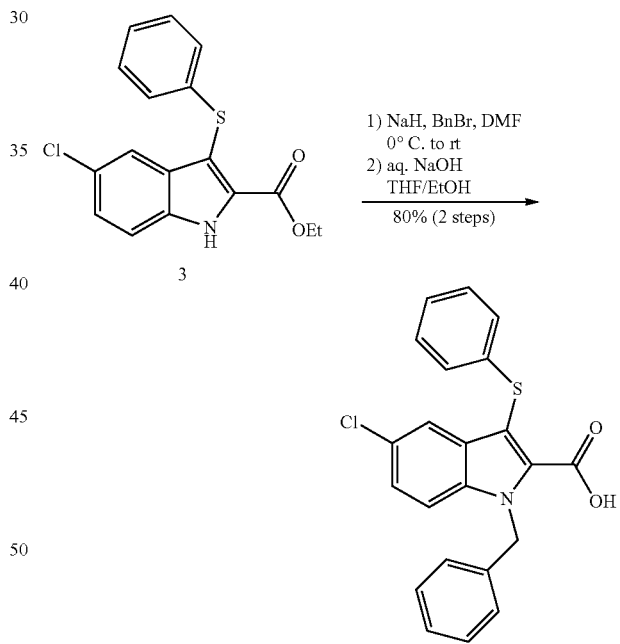

5-chloro-1-methyl-3-(phenylthio)-1H-indole-2-carboxylic acid (S3). Using general procedure D, S31 (38 mg, 0.110 mmol) was hydrolyzed, and after purification by column chromatography (0→5% MeOH/0.1% AcOH/$CH_2Cl_2$), yielded the title compound as a white solid (34 mg, 97% yield). $^1$H NMR (500 MHz, DMSO) δ 7.75 (d, J=8.8 Hz, 1H), 7.41-7.34 (m, 2H), 7.22 (dt, J=20.2, 7.2 Hz, 2H), 7.11 (ddd, J=6.9, 2.3, 1.2 Hz, 1H), 7.08-7.04 (m, 2H), 4.02 (s, 3H); $^{13}$C NMR (125 MHz, MeOD+drop of $CDCl_3$) δ 154.47, 129.76, 128.77, 125.52, 121.25, 120.29, 118.66, 118.57, 117.19, 116.88, 111.56, 103.89, 100.04, 23.57; HRMS APCI (m/z): [M−H]$^-$ calcd for $C_{16}H_{11}ClNO_2S$ 316.0199, found 316.0206.

1-benzyl-5-chloro-3-(phenylthio)-1H-indole-2-carboxylic acid (S4). To a suspension of sodium hydride (60% in mineral oil, 10 mg, 0.250 mmol) in DMF (1 mL) at 0° C. was added a solution of indole 3 (40 mg, 0.121 mmol) in DMF (1 mL). The solution was stirred at 0° C. for 30 minutes, and then held at room temperature for 30 minutes. The reaction was cooled to 0° C. and benzyl bromide (0.03 mL, 0.270 mmol) was added, and the reaction was allowed to warm to room temperature and stirred overnight. The following day, the reaction was poured into water and extracted with EtOAc 3×. The combined organic layers were washed with brine, dried over Na$_2$SO$_4$, filtered, concentrated, and purified by column chromatography (The N-alkylated product was an inseparable mixture of ethyl and chlorobenzyl esters, which was carried to the next step). Using general procedure D, the intermediate was hydrolyzed, yielding the title compound as a white solid (41 mg, 80% yield). $^1$H NMR (500 MHz, DMSO) δ 13.88 (br s, 1H), 7.71 (d, J=8.8 Hz, 1H), 7.38-7.28 (m, 4H), 7.27-7.21 (m, 3H), 7.16-7.11 (m, 1H), 7.10-7.05 (m, 4H), 5.85 (s, 2H); $^{13}$C NMR (125 MHz, DMSO) δ 173.33, 162.07, 137.69, 137.27, 136.15, 134.61, 129.12, 129.04, 128.67, 127.37, 126.50, 126.30, 125.52, 125.45, 119.24, 113.96, 106.82, 48.10; HRMS APCI (m/z): [M–H]$^-$ calcd for C$_{22}$H$_{15}$ClNO$_2$S 392.0512, found 392.0518.

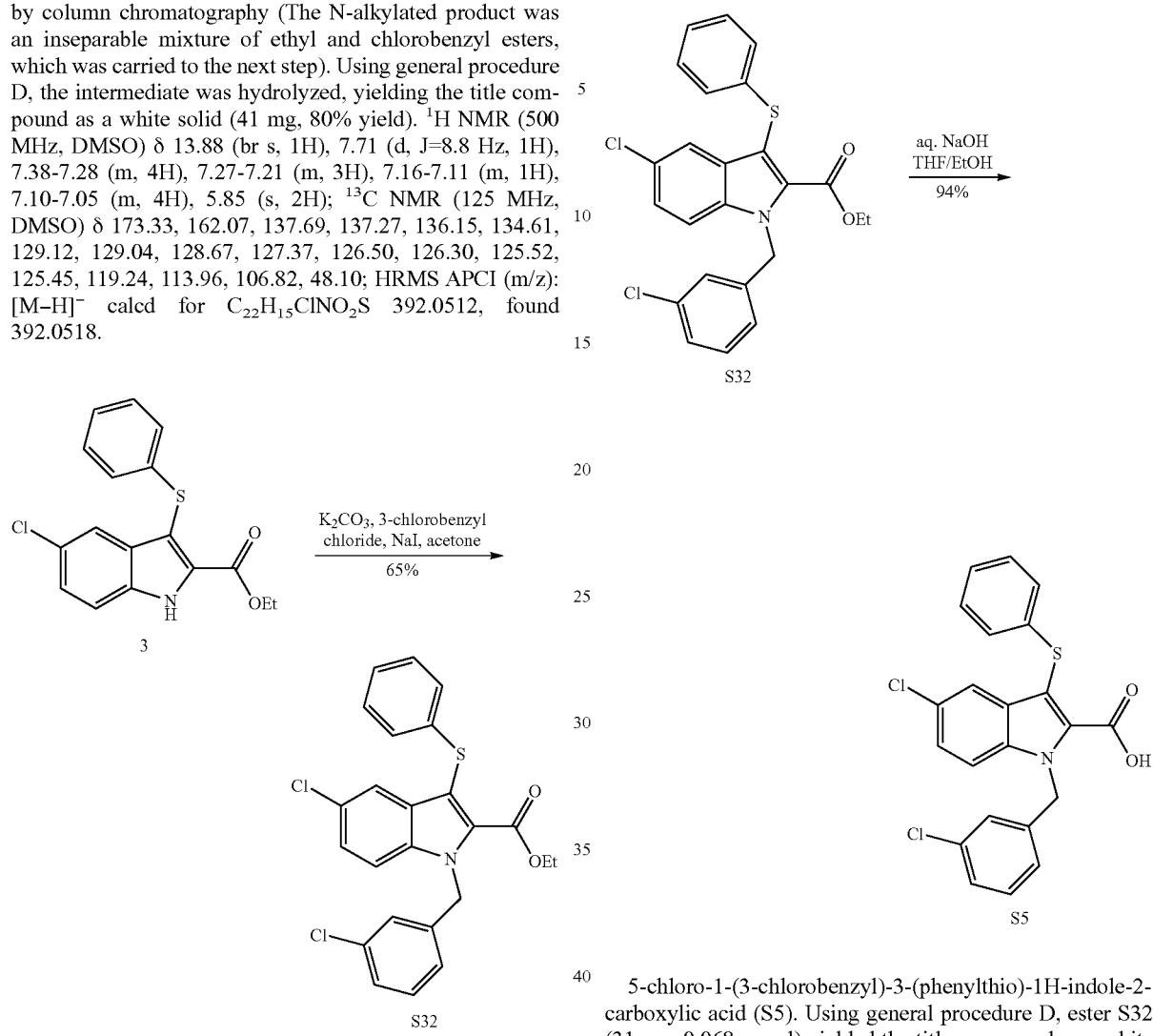

Ethyl 5-chloro-1-(3-chlorobenzyl)-3-(phenylthio)-1H-indole-2-carboxylate (S32). Indole 3 (37 mg, 0.112 mmol) was dissolved in acetone (3 mL) and K$_2$CO$_3$ (62 mg, 0.446 mmol), NaI (29 mg, 0.190 mmol), and 3-chlorobenzyl chloride (0.028 mL, 0.224 mmol) were sequentially added to the solution and the reaction was stirred at room temperature overnight. The following day the reaction was heated to reflux for 2 hours and cooled back to room temperature. The reaction was poured into water and extracted with EtOAc 3×. The combined organic layers were washed with brine, dried over Na$_2$SO$_4$, filtered, concentrated, and purified by column chromatography, yielding the title compound as a clear oil (33 mg, 65% yield). $^1$H NMR (500 MHz, CDCl$_3$) δ 7.64 (dd, J=1.8, 0.8 Hz, 1H), 7.31-7.27 (m, 2H), 7.23-7.17 (m, 4H), 7.14-7.08 (m, 3H), 7.04 (s, 1H), 6.93-6.89 (m, 1H), 5.75 (s, J=6.9 Hz, 2H), 4.28 (q, J=7.1 Hz, 2H), 1.18 (t, J=7.1 Hz, 3H); $^{13}$C NMR (125 MHz, CDCl$_3$) δ 161.40, 139.44, 137.93, 136.67, 130.24, 129.00, 127.99, 126.95, 126.77, 126.51, 125.54, 124.48, 121.27, 112.16, 110.60, 61.81, 48.51, 14.03; HRMS APCI (m/z): [M+H]$^+$ calcd for C$_{24}$H$_{20}$Cl$_2$NO$_2$S 456.0592, found 456.0590.

5-chloro-1-(3-chlorobenzyl)-3-(phenylthio)-1H-indole-2-carboxylic acid (S5). Using general procedure D, ester S32 (31 mg, 0.068 mmol) yielded the title compound as a white solid (29 mg, 94% yield). $^1$H NMR (500 MHz, MeOD) δ 7.50 (d, J=8.9 Hz, 1H), 7.45 (dd, J=2.0, 0.4 Hz, 1H), 7.30 (dd, J=8.9, 2.1 Hz, 1H), 7.27-7.17 (m, 4H), 7.13-7.08 (m, 3H), 7.06 (s, 1H), 6.98 (dt, J=7.3, 1.6 Hz, 1H), 5.84 (s, 2H); $^{13}$C NMR (125 MHz, MeOD) δ 163.88, 141.60, 139.04, 138.05, 135.64, 134.77, 131.28, 131.00, 129.96, 128.62, 128.59, 128.25, 127.50, 127.16, 126.62, 125.82, 121.38, 113.92, 111.15; HRMS APCI (m/z): [M–H]$^-$ calcd for C$_{22}$H$_{14}$Cl$_2$NO$_2$S 426.0122, found 426.0127.

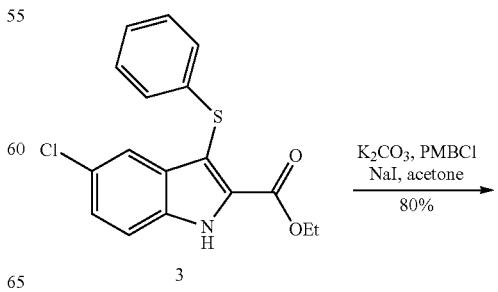

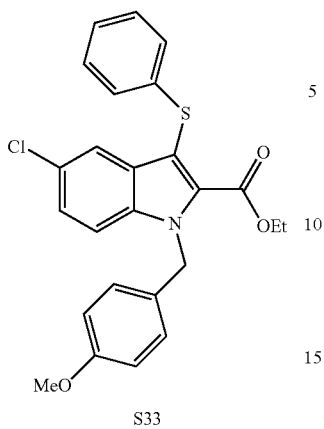

S33

Ethyl 5-chloro-1-(4-methoxybenzyl)-3-(phenylthio)-1H-indole-2-carboxylate (S33). To a solution of indole 3 (54 mg, 0.163 mmol) in acetone (2 mL) was added K$_2$CO$_3$ (90 mg, 0.651 mmol), NaI (42 mg, 0.277 mmol), and PMBCl (0.044 mL, 0.326 mmol). The reaction was stirred at room temperature overnight. The following day, yellow solids were observed in the reaction. Water was added, and the aqueous layer was extracted with EtOAc 3×. The combined organic layers were washed with brine, dried over Na$_2$SO$_4$, filtered, concentrated, and purified by column chromatography, yielding the title compound as a clear oil (59 mg, 80% yield). $^1$H NMR (500 MHz, CDCl$_3$) δ 7.62 (dd, J=2.0, 0.5 Hz, 1H), 7.33 (dd, J=8.9, 0.4 Hz, 1H), 7.26 (dd, J=8.8, 2.0 Hz, 1H), 7.23-7.16 (m, 2H), 7.12-7.08 (m, 3H), 7.03-6.99 (m, 2H), 6.83-6.79 (m, 2H), 5.70 (s, 2H), 4.29 (q, J=7.1 Hz, 2H), 3.76 (s, 3H), 1.19 (t, J=7.1 Hz, 3H); $^{13}$C NMR (125 MHz, CDCl$_3$) δ 161.47, 159.10, 138.09, 136.64, 132.66, 130.20, 129.34, 128.91, 127.75, 127.65, 126.78, 126.36, 125.36, 120.98, 114.23, 112.45, 109.63, 61.70, 55.36, 48.47, 14.05; HRMS APCI (m/z): [M+H]$^+$ calcd for C$_{25}$H$_{23}$ClNO$_3$S 452.1087, found 452.1087.

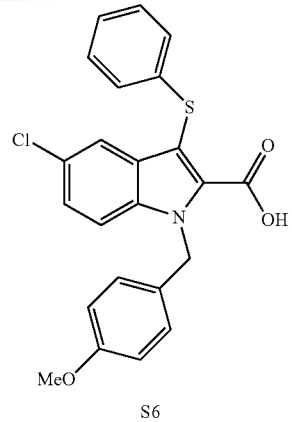

S6

5-chloro-1-(4-methoxybenzyl)-3-(phenylthio)-1H-indole-2-carboxylic acid (S6). Using general procedure D, ester S33 (37 mg, 0.082 mmol) yielded the title compound as a white solid (31 mg, 89% yield). $^1$H NMR (600 MHz, Acetone) δ 7.66 (d, J=8.9 Hz, 1H), 7.50 (d, J=1.8 Hz, 1H), 7.32 (dd, J=8.9, 2.0 Hz, 1H), 7.22 (t, J=7.7 Hz, 2H), 7.17-7.07 (m, 5H), 6.84 (d, J=8.5 Hz, 2H), 5.84 (s, 2H), 3.73 (s, 3H); $^{13}$C NMR (150 MHz, Acetone) δ 160.10, 138.80, 137.59, 130.70, 130.58, 129.81, 128.89, 127.78, 126.49, 126.32, 120.81, 114.84, 114.42, 55.49, 48.81; HRMS APCI (m/z): [M+H]$^+$ calcd for C$_{23}$H$_{17}$ClNO$_3$S 422.0618, found 422.0623.

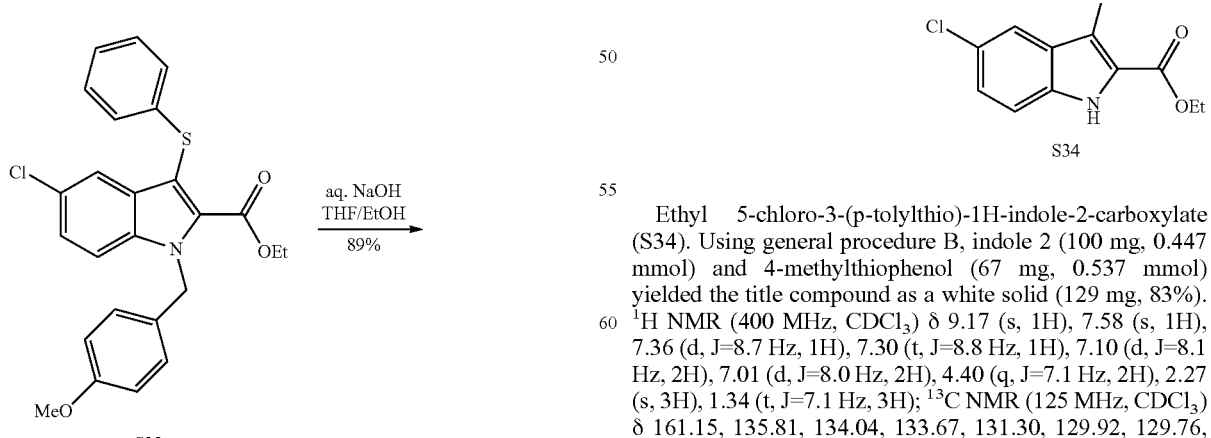

S34

Ethyl 5-chloro-3-(p-tolylthio)-1H-indole-2-carboxylate (S34). Using general procedure B, indole 2 (100 mg, 0.447 mmol) and 4-methylthiophenol (67 mg, 0.537 mmol) yielded the title compound as a white solid (129 mg, 83%). $^1$H NMR (400 MHz, CDCl$_3$) δ 9.17 (s, 1H), 7.58 (s, 1H), 7.36 (d, J=8.7 Hz, 1H), 7.30 (t, J=8.8 Hz, 1H), 7.10 (d, J=8.1 Hz, 2H), 7.01 (d, J=8.0 Hz, 2H), 4.40 (q, J=7.1 Hz, 2H), 2.27 (s, 3H), 1.34 (t, J=7.1 Hz, 3H); $^{13}$C NMR (125 MHz, CDCl$_3$) δ 161.15, 135.81, 134.04, 133.67, 131.30, 129.92, 129.76, 128.12, 127.47, 126.83, 121.20, 113.34, 111.15, 61.79, 21.10, 14.35; HRMS APCI (m/z): [M−H]$^−$ calcd for C$_{18}$H$_{15}$ClNO$_2$S 344.0512, found 344.0517.

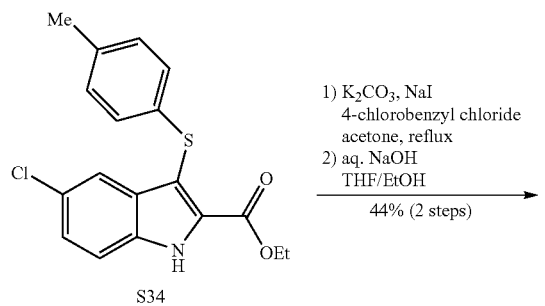

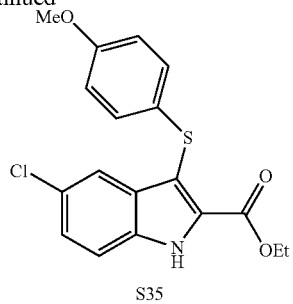

Ethyl 5-chloro-3-((4-methoxyphenyl)thio)-1H-indole-2-carboxylate (S35). Using general procedure B, indole 2 (207 mg, 0.926 mmol) and 4-methoxythiophenol (0.14 mL, 1.111 mmol) yielded the title compound as a white solid (308 mg, 92% yield). $^1$H NMR (500 MHz, CDCl$_3$) δ 9.12 (s, 1H), 7.55 (dd, J=1.3, 0.7 Hz, 1H), 7.34 (dd, J=8.7, 0.6 Hz, 1H), 7.28 (dd, J=8.7, 2.0 Hz, 1H), 7.26-7.22 (m, 2H), 6.80-6.75 (m, 2H), 4.42 (q, J=7.1 Hz, 2H), 3.76 (s, 3H), 1.38 (t, J=7.1 Hz, 3H); $^{13}$C NMR (125 MHz, CDCl$_3$) δ 161.42, 158.45, 134.20, 130.89, 130.59, 129.27, 127.72, 127.08, 126.50, 120.92, 114.63, 113.44, 111.94, 61.66, 55.42, 14.30; HRMS APCI (m/z): [M−H]$^-$ calcd for C$_{18}$H$_{15}$ClNO$_3$S 360.0461, found 360.0458.

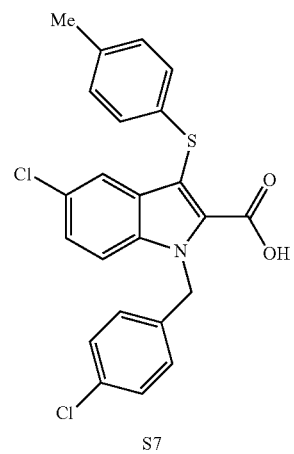

5-chloro-1-(4-chlorobenzyl)-3-(p-tolylthio)-1H-indole-2-carboxylic acid (S7). To a solution of indole S34 (110 mg, 0.318 mmol) in acetone (5 mL) was added K$_2$CO$_3$ (176 mg, 1.272 mmol), NaI (81 mg, 0.541 mmol), and 4-chlorobenzyl chloride (102 mg, 0.636 mmol). The reaction was stirred overnight at room temperature, then refluxed for 2 hours. Water was added, and the aqueous layer was extracted with EtOAc 3×. The combined organic layers were washed with brine, dried over Na$_2$SO$_4$, filtered, concentrated, and purified by column chromatography. Following general procedure D, the intermediate was hydrolyzed, yielding the title compound as a white solid (45 mg, 44% yield over two steps). $^1$H NMR (500 MHz, Acetone) δ 7.65-7.58 (m, 1H), 7.52 (dd, J=2.1, 0.4 Hz, 1H), 7.35-7.30 (m, 3H), 7.15 (d, J=8.6 Hz, 2H), 7.13-7.09 (m, 2H), 7.06 (d, J=8.1 Hz, 2H), 5.91 (s, 2H), 2.24 (s, 3H); $^{13}$C NMR (125 MHz, Acetone) δ 162.55, 137.75, 137.62, 136.39, 134.85, 133.54, 130.59, 130.54, 129.52, 129.12, 128.48, 127.87, 126.75, 121.06, 114.12, 110.92, 48.73, 29.84, 20.87; HRMS APCI (m/z): [M−H]$^-$ calcd for C$_{23}$H$_{16}$Cl$_2$NO$_2$S 440.0279, found 440.0284.

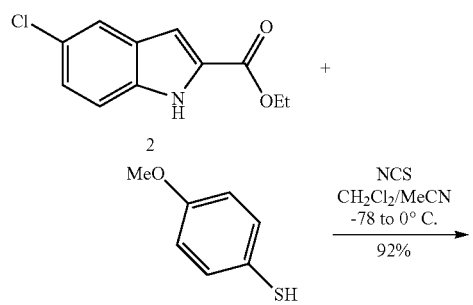

5-chloro-1-(4-chlorobenzyl)-3-((4-methoxyphenyl)thio)-1H-indole-2-carboxylic acid (S8). To a suspension of sodium hydride (60% in mineral oil, 13 mg, 0.331 mmol) in DMF (2 mL) at 0° C. was added indole S35 (100 mg, 0.276 mmol) dissolved in DMF (2 mL). The reaction was warmed to room temperature and stirred for 30 minutes. 4-chlorobenzyl chloride (67 mg, 0.414 mmol) and TBAI (102 mg, 0.276 mmol) were added, and the reaction was stirred at room temperature overnight. The reaction was quenched with water and extracted with EtOAc 3×. The combined organic layers were washed with brine, dried over Na$_2$SO$_4$, filtered concentrated and purified by column chromatography, yielding the intermediate mixture of benzyl and ethyl esters. Using general procedure D, the intermediate was hydrolyzed, yielding the title compound as a white solid (67 mg, 53% yield over two steps). $^1$H NMR (500 MHz, DMSO) δ 7.65 (d, J=8.7 Hz, 1H), 7.39-7.35 (m, 2H), 7.34-7.29 (m, 2H), 7.20-7.16 (m, 2H), 7.06 (d, J=8.5 Hz, 2H), 6.89-6.85 (m, 2H), 5.79 (s, 2H), 3.70 (s, 3H); $^{13}$C NMR (125 MHz, DMSO) δ 162.18, 158.08, 136.85, 135.99, 135.79, 131.91, 130.07, 128.80, 128.63, 128.23, 126.07, 119.43, 114.87, 113.70, 55.20, 47.43; HRMS APCI (m/z): [M–H]$^-$ calcd for C$_{23}$H$_{16}$Cl$_2$NO$_3$S 456.0228, found 456.0233.

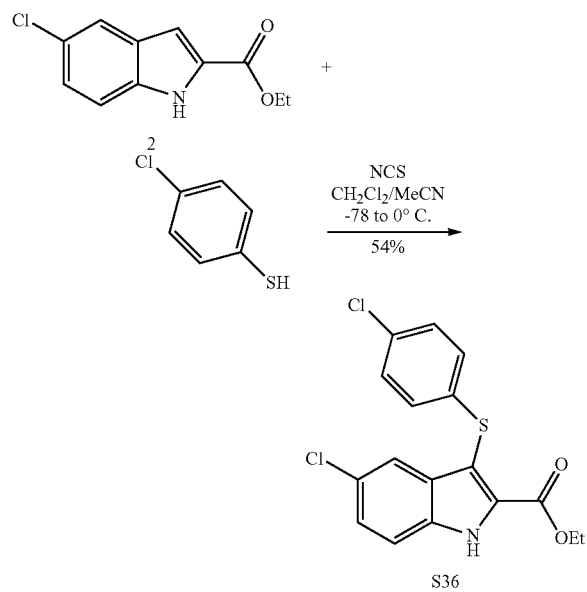

Ethyl 5-chloro-3-((4-chlorophenyl)thio)-1H-indole-2-carboxylate (S36). Using general procedure B, indole 2 (100 mg, 0.449 mmol) and 4-chlorothiophenol (78 mg, 0.539 mmol) yielded the title compound as a white solid (88 mg, 54% yield). $^1$H NMR (500 MHz, CDCl$_3$) δ 9.23 (s, 1H), 7.61 (dd, J=1.3, 0.7 Hz, 1H), 7.39 (dd, J=8.8, 0.5 Hz, 1H), 7.33 (dd, J=8.8, 2.0 Hz, 1H), 7.18-7.13 (m, 2H), 7.10-7.04 (m, 2H), 4.39 (q, J=7.1 Hz, 2H), 1.32 (t, J=7.1 Hz, 3H); $^{13}$C NMR (125 MHz, CDCl$_3$) δ 161.17, 136.53, 134.31, 131.14, 130.99, 130.47, 128.89, 128.16, 127.46, 126.63, 120.46, 113.73, 108.57, 61.69, 14.11; HRMS APCI (m/z): [M–H]$^-$ calcd for C$_{17}$H$_{12}$Cl$_2$NO$_2$S 363.9966, found 363.9976.

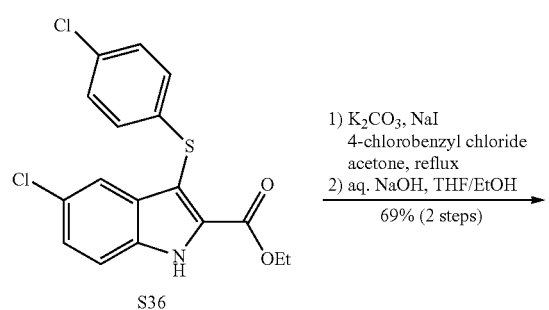

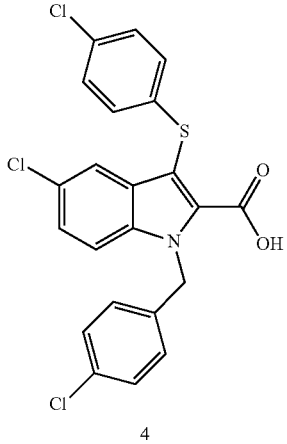

5-chloro-1-(4-chlorobenzyl)-3-((4-chlorophenyl)thio)-1H-indole-2-carboxylic acid (4). To a solution of indole S36 (75 mg, 0.205 mmol) in acetone (4 mL) was added K$_2$CO$_3$ (113 mg, 0.819 mmol), NaI (52 mg, 0.349 mmol), and 4-chlorobenzyl chloride (66 mg, 0.410 mmol). The reaction was refluxed for 6 hours then stirred at room temperature overnight. The reaction was poured into water and extracted with EtOAc 3×. The combined organic layers were washed with brine, dried over Na$_2$SO$_4$, filtered, concentrated, and purified by column chromatography. Using general procedure D, the intermediate was hydrolyzed, yielding the title compound as a white solid (65 mg, 69% yield over 2 steps). $^1$H NMR (500 MHz, Acetone) δ 7.65 (d, J=8.9 Hz, 1H), 7.56 (dd, J=2.0, 0.4 Hz, 1H), 7.38-7.30 (m, 3H), 7.30-7.23 (m, 2H), 7.20-7.13 (m, 4H), 5.94 (s, 2H); $^{13}$C NMR (125 MHz, Acetone) δ 162.35, 137.87, 137.62, 134.58, 133.57, 131.59, 130.59, 129.80, 129.55, 129.17, 129.12, 128.24, 126.94, 120.77, 114.30, 109.13, 48.85; HRMS APCI (m/z): [M–H]$^-$ calcd for C$_{22}$H$_{13}$Cl$_3$NO$_2$S 459.9733, found 459.9740.

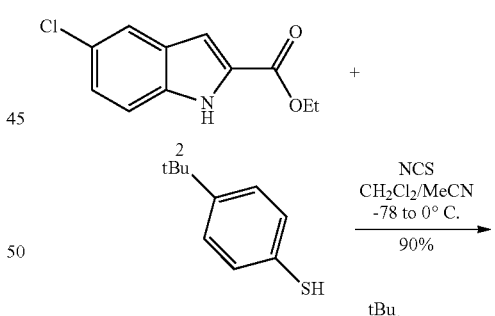

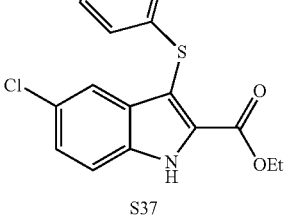

Ethyl 3-((4-(tert-butyl)phenyl)thio)-5-chloro-1H-indole-2-carboxylate (S37). Using general procedure B, indole 2 (218 mg, 0.975) and 4-tert-butylbenzenethiol (0.20 mL, 1.170 mmol) yielded the title compound as a white solid (341 mg, 90% yield). $^1$H NMR (500 MHz, Acetone) δ 11.52 (s, 1H), 7.61 (d, J=8.8 Hz, 1H), 7.49 (s, J=0.6 Hz, 1H), 7.34-7.30 (m, 1H), 7.28 (d, J=8.0 Hz, 2H), 7.14 (d, J=8.2 Hz, 2H), 4.35 (q, J=7.1 Hz, 2H), 1.28 (t, J=7.1 Hz, 3H), 1.25 (s, 9H); $^{13}$C NMR (125 MHz, Acetone) δ 161.12, 149.63, 135.69, 135.01, 131.77, 131.62, 128.34, 127.37, 126.75, 120.78, 115.41, 109.98, 61.79, 34.90, 31.52, 14.48; HRMS APCI (m/z): [M−H]$^-$ calcd for $C_{21}H_{21}ClNO_2S$ 386.0988, found 386.0988.

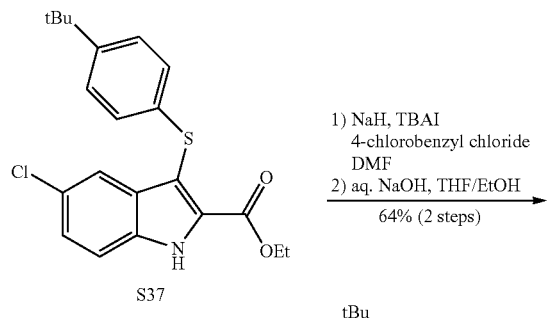

3-((4-(tert-butyl)phenyl)thio)-5-chloro-1-(4-chlorobenzyl)-1H-indole-2-carboxylic acid (5). Using general procedure C, followed by general procedure D, indole S37 (100 mg, 0.258 mmol) yielded the title compound as a white solid (80 mg, 64% yield over two steps). $^1$H NMR (500 MHz, DMSO) δ 13.87 (s, 1H), 7.69 (d, J=9.5 Hz, 1H), 7.40-7.37 (m, 2H), 7.35 (td, J=4.7, 2.1 Hz, 2H), 7.30-7.27 (m, 2H), 7.09-7.06 (m, 2H), 7.05-7.02 (m, 2H), 5.83 (s, 2H), 1.22 (s, 9H); $^{13}$C NMR (125 MHz, DMSO) δ 162.07, 148.37, 136.80, 136.10, 134.04, 133.58, 131.94, 129.08, 128.67, 128.59, 128.20, 128.11, 126.72, 126.35, 126.08, 125.57, 119.41, 113.82, 107.82, 47.54, 39.52, 34.14, 31.02; HRMS APCI (m/z): [M−H]$^-$ calcd for $C_{26}H_{22}Cl_2NO_2S$ 482.0748, found 482.0756.

Ethyl 6-chloro-1H-indole-2-carboxylate (S38). Using general procedure A, 5-chloro-2-iodoaniline (874 mg, 3.45 mmol) yielded the title compound as a tan solid (394 mg, 51% yield over two steps). $^1$H NMR (400 MHz, CDCl$_3$) δ 8.86 (br s, 1H), 7.60 (d, J=8.6 Hz, 1H), 7.42 (s, 1H), 7.19 (s, 1H), 7.12 (d, J=8.6 Hz, 1H), 4.41 (q, J=7.1 Hz, 1H), 1.42 (t, J=7.1 Hz, 2H); $^{13}$C NMR (100 MHz, CDCl$_3$) δ 161.92, 137.14, 131.42, 123.67, 122.01, 111.83, 108.75, 61.38, 14.52; HRMS APCI (m/z): [M−H]$^-$ calcd for $C_{11}H_9ClNO_2$ 222.0327, found 222.0328.

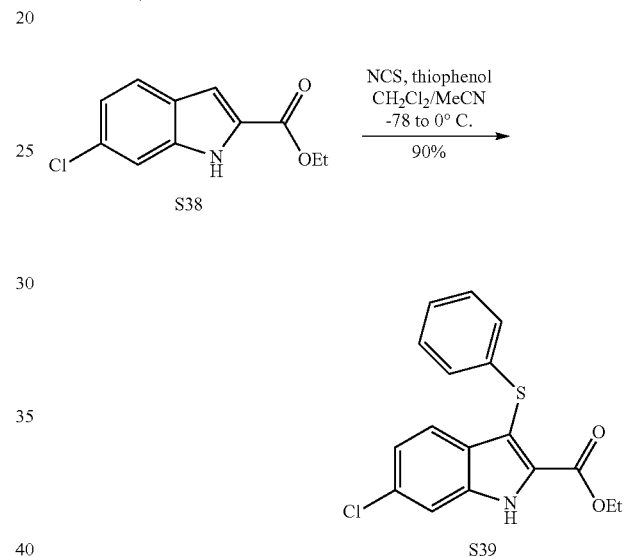

Ethyl 6-chloro-3-(phenylthio)-1H-indole-2-carboxylate (S39). Using general procedure B, indole S38 (108 mg, 0.483 mmol) yielded the title compound as a white solid (137 mg, 90% yield). $^1$H NMR (500 MHz, CDCl$_3$) δ 9.18 (s, 1H), 7.48 (d, J=8.6 Hz, 1H), 7.46-7.44 (m, 1H), 7.21-7.14 (m, 4H), 7.13-7.08 (m, 2H), 4.39 (q, J=7.1 Hz, 2H), 1.32 (t, J=7.1 Hz, 3H); $^{13}$C NMR (100 MHz, CDCl$_3$) δ 161.21, 137.46, 136.04, 132.29, 128.95, 127.62, 125.74, 122.96, 122.68, 112.04, 99.77, 61.80, 14.32; HRMS APCI (m/z): [M−H]$^-$ calcd for $C_{17}H_{13}ClNO_2S$ 330.0356, found 330.0361. 4-chlorobenzyl chloride

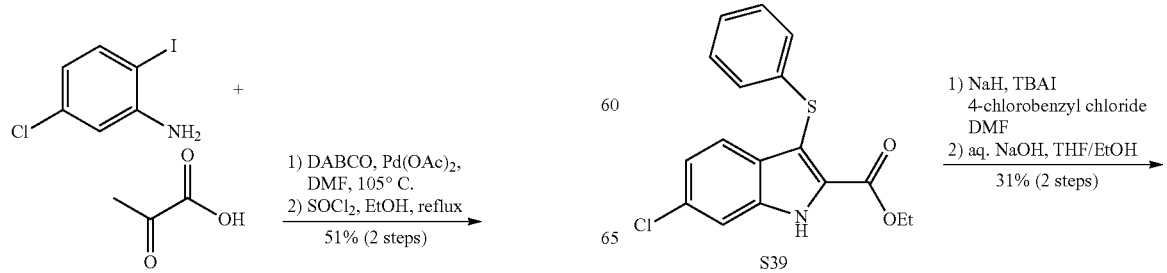

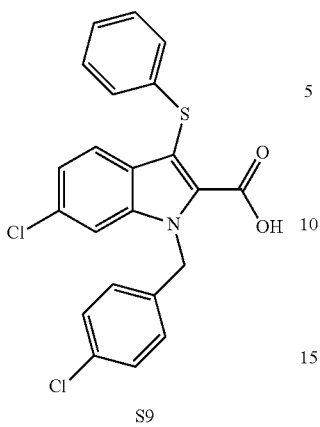

6-chloro-1-(4-chlorobenzyl)-3-(phenylthio)-1H-indole-2-carboxylic acid (S9). Using general procedure C, followed by general procedure D, indole S39 (115 mg, 0.365 mmol) yielded the title compound as a yellow solid (49 mg, 31% yield over two steps). $^1$H NMR (500 MHz, DMSO) δ 13.85 (br s, 1H), 7.84 (dd, J=6.9, 1.6 Hz, 1H), 7.40 (dd, J=14.5, 8.5 Hz, 3H), 7.27-7.19 (m, 2H), 7.17-7.05 (m, 6H), 5.89-5.80 (s, 2H); $^{13}$C NMR (125 MHz, DMSO) δ 162.06, 138.05, 137.32, 136.82, 133.79, 131.95, 130.31, 129.07, 128.65, 128.22, 126.63, 126.54, 125.46, 122.27, 122.08, 111.62, 108.24, 47.45; HRMS APCI (m/z): [M+H]$^+$ calcd for $C_{22}H_{16}Cl_2NO_2S$ 428.0279, found 428.0275.

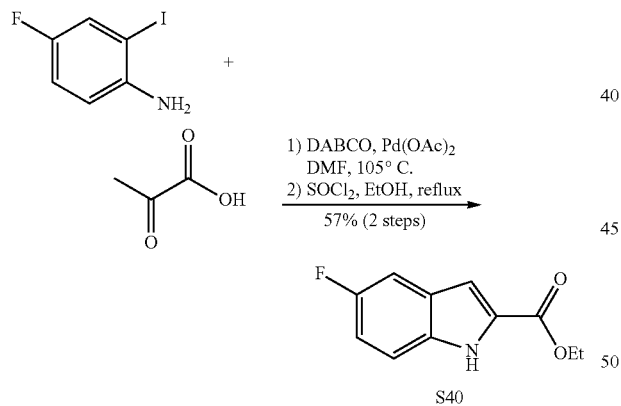

Ethyl 5-chloro-1H-indole-2-carboxylate (S40). Using general procedure A, aniline 4-fluoro-2-iodoaniline (445 mg, 1.877 mmol) yielded the title compound as a brown solid (222 mg, 57% yield over two steps). Spectral data matched that previously described.[38]

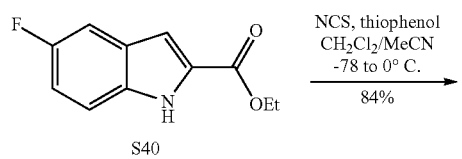

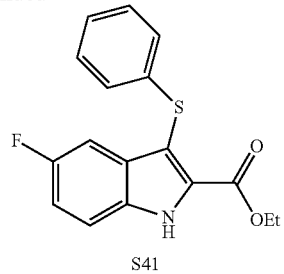

Ethyl 5-fluoro-3-(phenylthio)-1H-indole-2-carboxylate (S41). Using general procedure B, indole S40 (101 mg, 0.487 mmol) yielded the title compound as a white solid (129 mg, 84% yield). $^1$H NMR (500 MHz, CDCl$_3$) δ 9.24 (s, 1H), 7.41-7.37 (m, 1H), 7.23 (dd, J=7.7, 5.2 Hz, 1H), 7.21-7.08 (m, 6H), 4.39 (q, J=7.1 Hz, 2H), 1.31 (t, J=7.1 Hz, 3H); $^{13}$C NMR (125 MHz, CDCl$_3$) δ 161.14, 157.77, 137.54, 132.29, 130.91 (d, J=10 Hz), 130.53, 128.95, 127.46, 125.67, 115.54 (d, J=27.2 Hz), 113.32 (d, J=9.5 Hz), 110.53 (d, J=5.9 Hz), 106.36 (d, J=24.4 Hz), 61.76, 14.30; HRMS APCI (m/z): [M-H]$^-$ calcd for $C_{17}H_{13}FNO_2S$ 314.0651, found 314.0660.

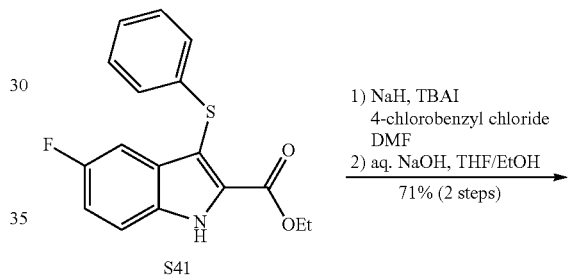

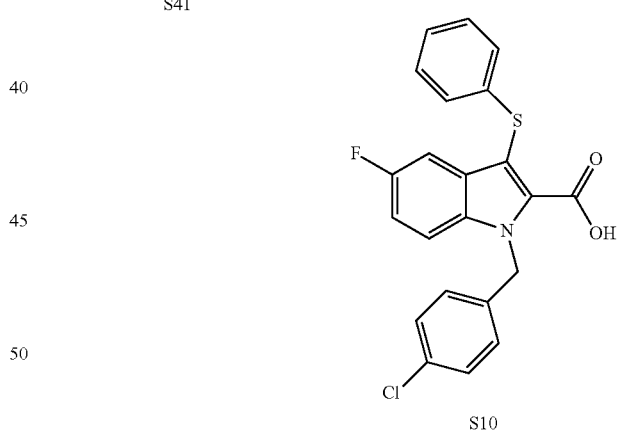

1-(4-chlorobenzyl)-5-fluoro-3-(phenylthio)-1H-indole-2-carboxylic acid (S10). Using general procedure C, followed by general procedure D, indole S41 (58 mg, 0.184 mmol) yielded the title compound as a white solid (54 mg, 71% yield over two steps). $^1$H NMR (500 MHz, DMSO) δ 13.84 (s, 1H), 7.70 (dd, J=9.2, 4.2 Hz, 1H), 7.40-7.36 (m, 2H), 7.27-7.20 (m, 3H), 7.15-7.06 (m, 6H), 5.84 (s, 2H); $^{13}$C NMR (100 MHz, DMSO) 162.10, 159.32, 156.97, 137.10 (d, J=36.5 Hz), 134.34 (d, J=8.1 Hz), 131.95, 129.13, 128.68, 128.52, 128.25, 126.57, 125.52, 114.35 (d, J=26.5 Hz), 113.75 (d, J=9.1 Hz), 107.56, 104.79 (d, J=24.0 Hz), 47.62; HRMS APCI (m/z): [M-H]$^-$ calcd for $C_{22}H_{14}ClFNO_2S$ 410.0418, found 410.0424.

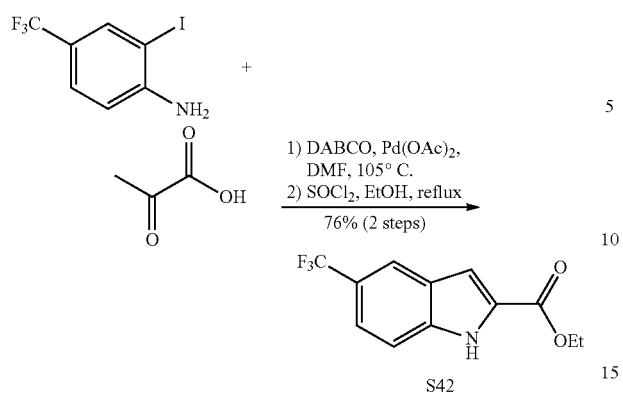

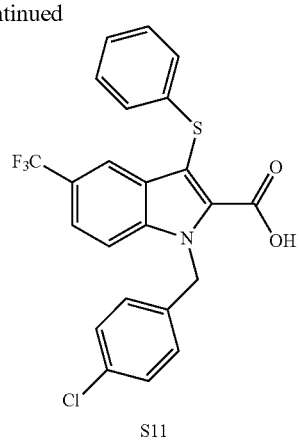

Ethyl 5-(trifluoromethyl)-1H-indole-2-carboxylate (S42). Using general procedure A, 2-iodo-4-(trifluoromethyl)aniline (2.30 g, 8.03 mmol) yielded the title compound as a white solid (1.57 g, 76% over two steps) with spectral data matching that previously described.[39]

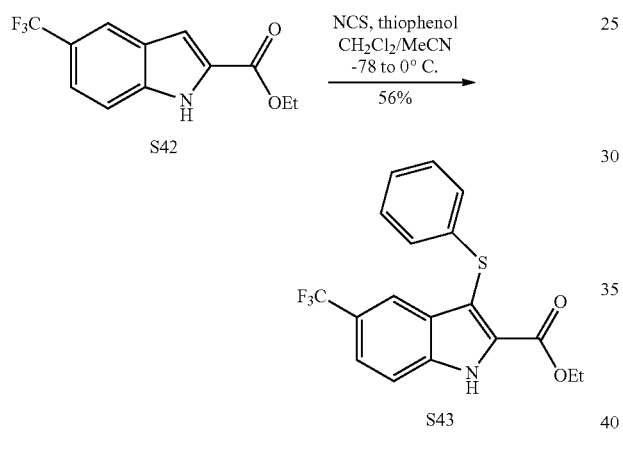

Ethyl 3-(phenylthio)-5-(trifluoromethyl)-1H-indole-2-carboxylate (S43). Using general procedure B, indole S42 (75 mg, 0.292 mmol) yielded the title compound as a white solid (60 mg, 56% yield) $^1$H NMR (500 MHz, CDCl$_3$) δ 9.65 (br s, 1H), 7.91 (d, J=0.8 Hz, 1H), 7.59-7.52 (m, 2H), 7.23-7.17 (m, 4H), 7.15-7.11 (m, 1H), 4.42 (q, J=7.1 Hz, 2H), 1.32 (t, J=7.1 Hz, 3H); $^{13}$C NMR (125 MHz, CDCl$_3$) δ 161.47, 137.20, 137.15, 130.49, 129.03, 127.75, 125.97, 124.80 (q, J=271.7 Hz), 124.10 (q, J=32.2 Hz), 122.73 (d, J=3.0 Hz), 119.83 (d, J=4.2 Hz), 112.94, 112.18, 62.08, 14.21; HRMS APCI (m/z): [M–H]$^-$ calcd for C$_{18}$H$_{13}$F$_3$NO$_2$S 364.0619, found 364.0625.

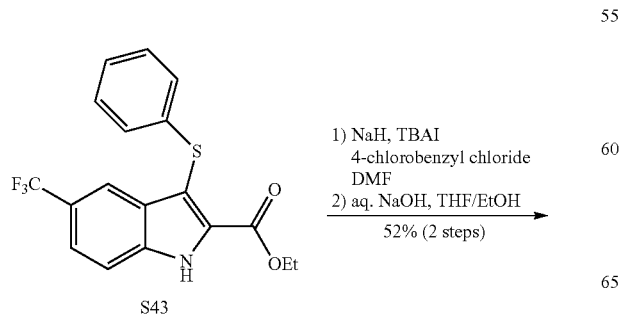

1-(4-chlorobenzyl)-5-fluoro-3-(phenylthio)-1H-indole-2-carboxylic acid (S11). Using general procedure C, followed by general procedure D, indole S43 (45 mg, 0.123 mmol) yielded the title compound as a white solid (35 mg, 52% yield over two steps). $^1$H NMR (500 MHz, MeOD) δ 7.73 (s, 1H), 7.68 (d, J=8.8 Hz, 1H), 7.55 (dd, J=8.8, 1.6 Hz, 1H), 7.31-7.28 (m, 2H), 7.24-7.19 (m, 2H), 7.18-7.11 (m, 3H), 7.08 (d, J=8.5 Hz, 2H), 5.87 (s, 2H); $^{13}$C NMR (100 MHz, Acetone) δ 162.37, 140.55, 138.25, 137.54, 133.62, 129.89, 129.57, 129.16, 128.86, 128.17, 126.62, 124.27 (q, J=31.8 Hz) 122.73, 119.62 (d, J=4.1 Hz), 113.62, 111.99, 48.89, 29.84. HRMS APCI (m/z): [M–H]$^-$ calcd for C$_{23}$H$_{14}$ClF$_3$NO$_2$S 460.0386, found 460.0393.

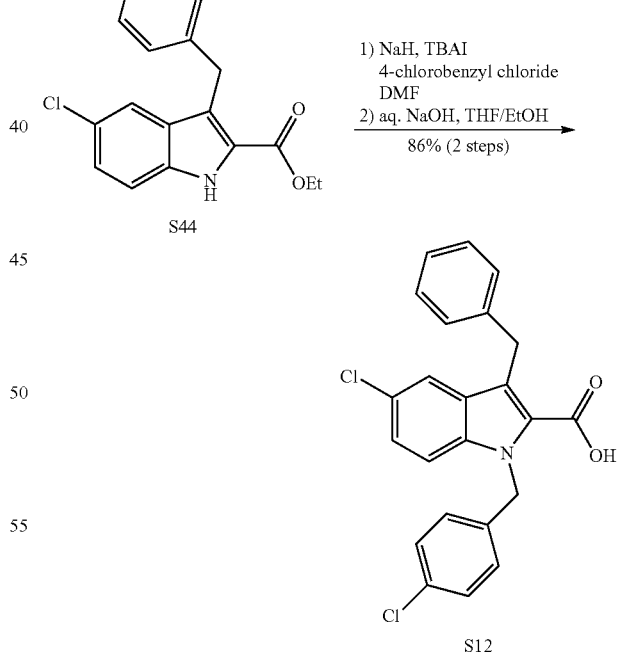

3-benzyl-5-chloro-1-(4-chlorobenzyl)-1H-indole-2-carboxylic acid (S12). Using general procedure C, followed by general procedure D, indole S44 (prepared as previously described: Mahmoud, M. M.; Ali, H. I.; Ahn, K. H.; Damaraju, A.; Samala, S.; Pulipati, V. K.; Kolluru, S.; Kendall, D. A.; Lu, D. *J. Med. Chem.* 2013, 56, 7975.) (78 mg, 0.249 mmol) yielded the title compound as a white solid (88 mg, 86% yield over two steps). $^1$H NMR (500 MHz, DMSO) δ 13.49 (s, 1H), 7.69 (d, J=2.0 Hz, 1H), 7.58 (d, J=8.9 Hz, 1H), 7.37-7.31 (m, 2H), 7.28 (dd, J=8.9, 2.1 Hz, 1H), 7.26-7.21 (m, 4H), 7.15-7.11 (m, 1H), 6.99 (d, J=8.6 Hz, 2H), 5.82 (s, 2H), 4.45 (s, 2H); $^{13}$C NMR (125 MHz, DMSO) δ 163.16, 140.93, 137.65, 136.42, 131.61, 128.51, 128.30, 128.11, 128.03, 127.41, 125.79, 125.29, 124.92, 122.19, 119.97, 113.00, 46.99, 30.10; HRMS APCI (m/z): [M−H]$^−$ calcd for $C_{23}H_{16}Cl_2NO_2$ 408.0558, found 408.0565.

(2 equiv) was added to a flame dried flask in an ice bath, and MeOH (1M) was added slowly. The flask was removed from the ice bath and the solution stirred until complete dissolution occurred. Intermediate from the previous step dissolved in THF (0.3M) was added to the NaOMe solution, and the reaction was refluxed for 1 hour. The reaction was cooled to room temperature, acidified with 1M HCl (pH ~7) and extracted with EtOAc 3×. The combined organic layers were washed with water and brine, dried over $Na_2SO_4$, and purified by column chromatography, yielding the title compound as a tan solid.

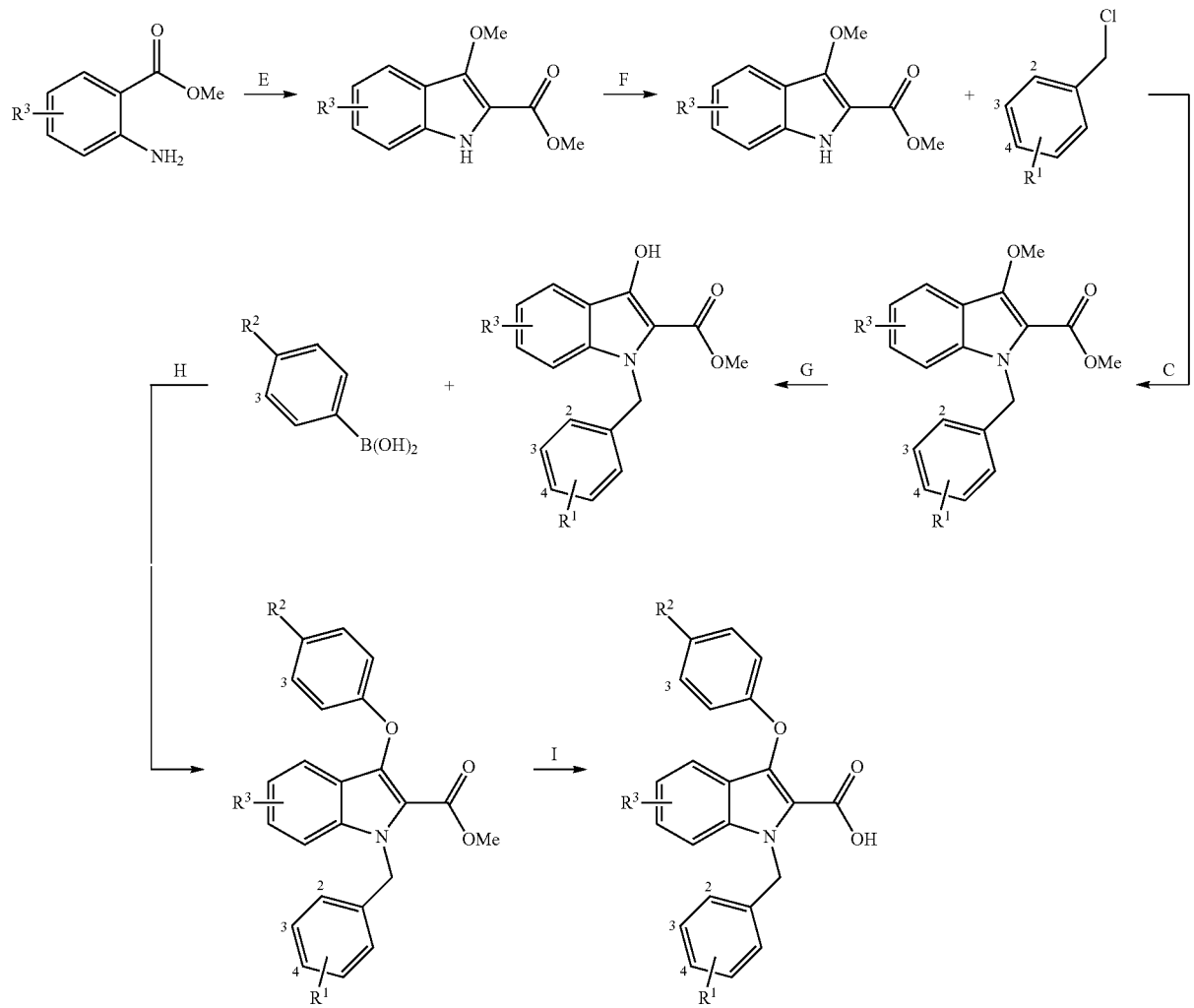

Scheme S2. Synthesis of second-generation nTZDpa analogs.

(E) 1) $Na_2CO_3$, methyl bromoacetate, DMF, 80° C. 2) NaOMe, THF/MeOH (F) $K_2CO_3$, $Me_2SO_4$, acetone (C) NaH, TBAI, DMF (G) $BBr_3$, $CH_2Cl_2$, -30° C. (H) $Cu(OAc)_2$, $Et_3N$, 4 Å mol sieves, $CH_2Cl_2$, air (I) aq. NaOH, THF/MeOH.

General Procedure E: Alkylation and indole formation. $Na_2CO_3$ (1.5 equiv) was dried under vacuum for 30 minutes at 105° C., and cooled to room temperature. Methyl 2-aminobenzoate starting material (1 equiv) was added followed by DMF (1M), then methyl bromoacetate (1.2 equiv), and the reaction was heated to 80° C. and stirred at this temperature overnight. The following day, the reaction was filtered and the filtrate was concentrated, diluted with EtOAc, and washed with water followed by brine, dried over $Na_2SO_4$, filtered, concentrated, and then triturated with $Et_2O$, yielding the intermediate as a tan solid. Sodium metal General Procedure F: Hydroxyindole methylation. To a solution of hydroxyindole (1 equiv) dissolved in acetone (0.5M) was added $K_2CO_3$ (1.1 equiv) and dimethyl sulfate (1.2 equiv). The reaction was stirred at room temperature overnight. The following day the reaction was poured into water and extracted with EtOAc 3×. The combined organic layers were washed with brine, dried over $Na_2SO_4$, filtered, concentrated, and purified by column chromatography, yielding the title compound as a green solid.

General Procedure G: Demethylation. To a solution of methyl ether starting material (1 equiv) in $CH_2Cl_2$ (0.1M) at -30° C. was added BBr₃ (1M in CH₂Cl₂, 1.01 equiv), and the reaction was stirred at this temperature for 30 minutes. The reaction was quenched with sat. NaHCO₃ and extracted with CH₂Cl₂ 3×. The combined organic layers were washed with brine, dried over Na₂SO₄, filtered, concentrated, and purified by column chromatography, yielding the title compound as a green solid.

General Procedure H: Chan-Lam coupling. 4 Å molecular sieves were flame dried, and to the activated molecular sieves was added hydroxyindole (1 equiv), CH₂Cl₂ (0.1M), boronic acid (2 equiv), Et₃N (5 equiv), and Cu(OAc)₂ (1 equiv). The reaction was stirred exposed to air overnight, filtered over Celite, concentrated, and purified by column chromatography, yielding the title compound as a yellow oil.

General Procedure I: Methyl ester hydrolysis. Methyl ester (1 equiv) was dissolved in 1:1 THF:MeOH (0.1 M) was added 1M NaOH (5 equiv) and the reaction was stirred at room temperature until complete by TLC. The reaction was acidified with 1M HCl and extracted with EtOAc 3×. The combined organic layers were washed with brine, dried over Na₂SO₄, filtered, and concentrated.

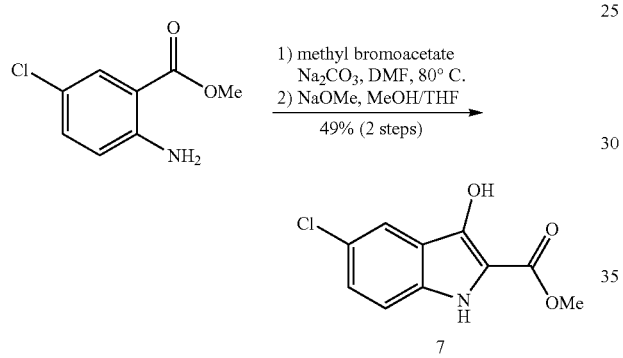

Methyl 5-chloro-3-hydroxy-1H-indole-2-carboxylate (7). Using general procedure E, methyl 2-amino-5-chlorobenzoate (4.96 g, 26.94 mmol) yielded the title compound as a tan solid (2.95 g, 49% yield over two steps). Spectroscopic data was identical with that previously described.[40]

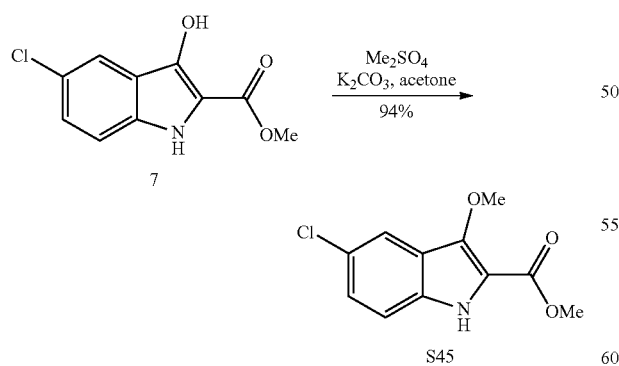

Methyl 5-chloro-3-methoxy-1H-indole-2-carboxylate (S45). Using general procedure F, hydroxyindole 7 (2.95 g, 13.09 mmol) yielded the title compound as a green solid (2.94 g, 94% yield). Spectroscopic data was identical with that previously described.[40]

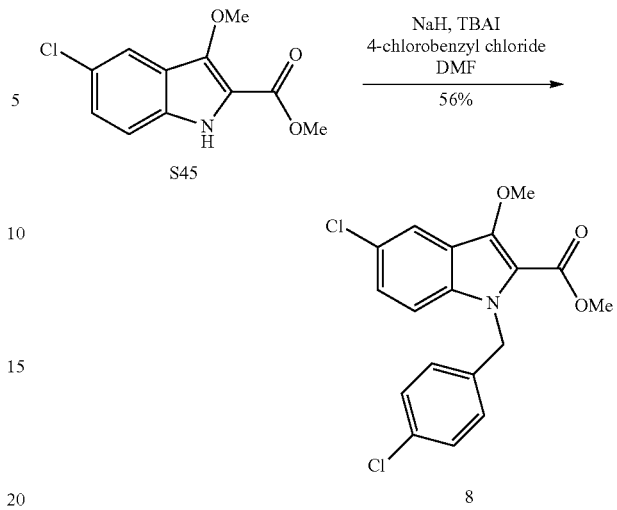

Ethyl 5-chloro-1-(4-chlorobenzyl)-3-methoxy-1H-indole-2-carboxylate (8). Using general procedure C, indole S45 (406 mg, 1.694 mmol) yielded the title compound as a white solid (344 mg, 56% yield). $^1$H NMR (500 MHz, CDCl₃) δ 7.76 (dd, J=2.0, 0.5 Hz, 1H), 7.26-7.16 (m, 4H), 6.95-6.90 (m, 2H), 5.65 (s, 2H), 4.05 (s, 3H), 3.90 (s, 3H); $^{13}$C NMR (125 MHz, CDCl₃) δ 161.84, 145.69, 136.55, 135.01, 133.14, 128.88, 127.64, 126.85, 126.16, 120.62, 119.54, 117.10, 111.92, 62.90, 51.93, 47.51; HRMS APCI (m/z): [M+H]⁺ calcd for $C_{18}H_{16}Cl_2NO_3$ 364.0507, found 364.0501.

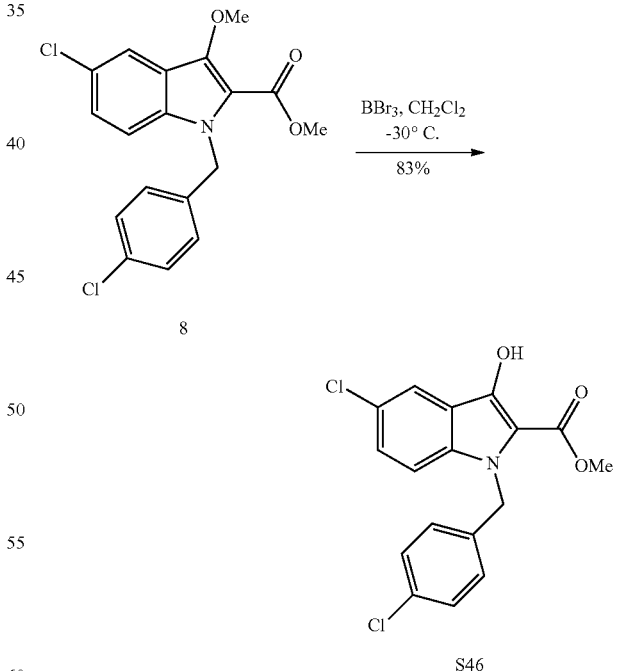

Methyl 5-chloro-1-(4-chlorobenzyl)-3-hydroxy-1H-indole-2-carboxylate (S46). Using general procedure G, methyl ether 8 (216 mg, 0.593 mmol) yielded the title compound as a yellow foam (172 mg, 83% yield). $^1$H NMR (500 MHz, CDCl₃) δ 8.46 (s, 1H), 7.76 (d, J=1.9 Hz, 1H), 7.28 (dt, J=7.1, 3.6 Hz, 1H), 7.24-7.20 (m, 2H), 7.14 (d, J=9.0 Hz, 1H), 6.90 (d, J=8.4 Hz, 2H), 5.52 (s, 2H), 3.90 (s, 3H); $^{13}$C NMR (125 MHz, CDCl$_3$) δ 163.90, 148.13, 136.65, 135.91, 133.30, 128.98, 128.31, 127.53, 125.51, 119.93, 117.80, 111.55, 109.87, 51.89, 47.72; HRMS APCI (m/z): [M−H]$^−$ calcd for C$_{17}$H$_{12}$Cl$_2$NO$_3$ 348.0194, found 348.0199.

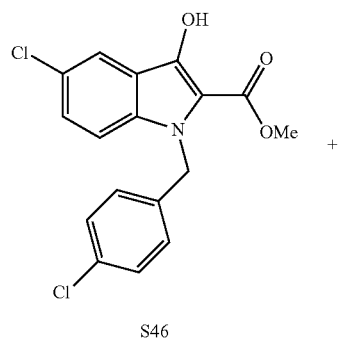

S46

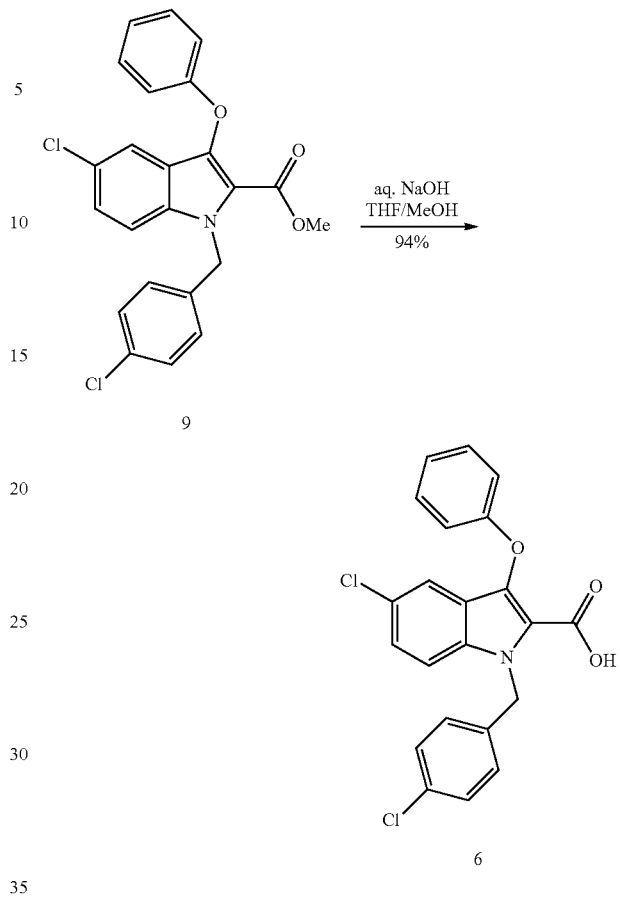

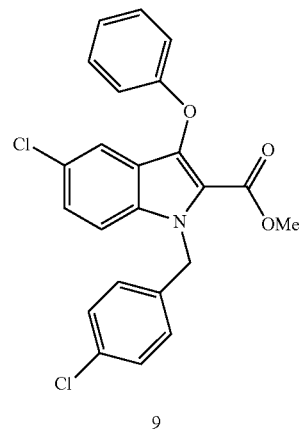

9

Methyl 5-chloro-1-(4-chlorobenzyl)-3-phenoxy-1H-indole-2-carboxylate (9). Using general procedure H, hydroxyindole S46 (80 mg, 0.228 mmol) yielded the title compound as a tan solid (45 mg, 45% yield). $^1$H NMR (500 MHz, CDCl$_3$) δ 7.42 (t, J=1.1 Hz, 1H), 7.32-7.23 (m, 7H), 7.05 (t, J=7.4 Hz, 1H), 7.00-6.93 (m, 4H), 5.76 (s, 2H), 3.71 (s, 3H); $^{13}$C NMR (125 MHz, CDCl$_3$) δ 161.58, 158.89, 139.05, 136.34, 135.16, 133.41, 129.73, 129.07, 127.70, 127.22, 126.86, 122.55, 120.95, 119.63, 118.56, 115.69, 112.10, 52.03, 47.66; HRMS APCI (m/z): [M−H]$^−$ calcd for C$_{23}$H$_{16}$Cl$_2$NO$_3$ 424.0507, found 424.0511.

5-chloro-1-(4-chlorobenzyl)-3-phenoxy-1H-indole-2-carboxylic acid (6). Using general procedure I, methyl ester 9 (28 mg, 0.066 mmol) yielded the title compound as a white solid (25 mg, 94% yield). $^1$H NMR (500 MHz, Acetone) δ 7.64 (dd, J=8.6, 1.0 Hz, 1H), 7.36-7.28 (m, 6H), 7.17 (d, J=8.6 Hz, 2H), 7.07-7.02 (m, 1H), 7.00 (dt, J=9.1, 2.2 Hz, 2H), 5.94 (s, 2H); $^{13}$C NMR (125 MHz, Acetone) δ 162.16, 159.85, 139.19, 138.29, 135.99, 133.36, 130.45, 129.48, 129.08, 127.25, 126.92, 123.13, 121.53, 119.46, 116.48, 114.00, 47.88; HRMS APCI (m/z): [M−H]$^−$ calcd for C$_{22}$H$_{14}$Cl$_2$NO$_3$ 410.0351, found 410.0357.

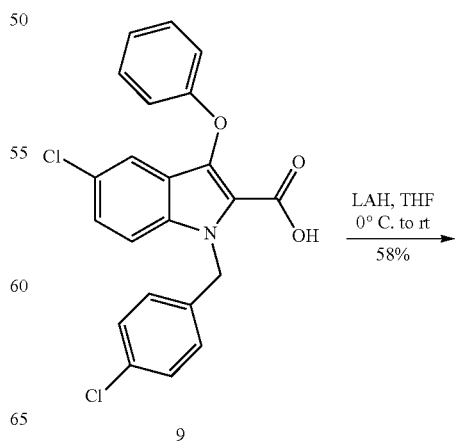

9

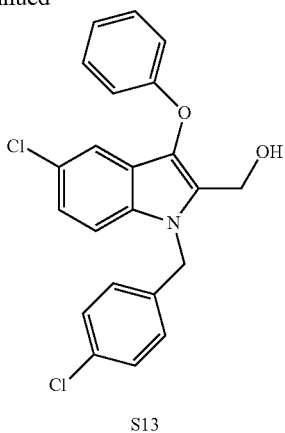

S13

(5-chloro-1-(4-chlorobenzyl)-3-phenoxy-1H-indol-2-yl)methanol (S13). To a solution of compound 9 (68 mg, 0.160 mmol) in THF (3 mL) at 0° C. was added LAH (6 mg, 0.167 mmol). The reaction was warmed to room temperature and stirred for 30 minutes. The reaction was cooled to 0° C., quenched with 1M NaOH, and warmed room temperature. After stirring for 10 minutes, the aqueous layer was extracted with EtOAc 3×. The combined organic layers were washed with water and brine, dried over $Na_2SO_4$, filtered, concentrated, and purified by column chromatography, yielding the title compound as a white solid. (37 mg, 58% yield). $^1$H NMR (300 MHz, Acetone) δ 7.44-7.28 (m, 5H), 7.24-6.96 (m, 7H), 5.64 (s, 2H), 4.74 (d, J=3.7 Hz, 2H), 4.53 (br s, 1H); $^{13}$C NMR (75 MHz, Acetone) δ 160.14, 138.06, 133.90, 133.35, 131.82, 130.87, 130.45, 129.47, 129.03, 125.70, 123.45, 122.93, 122.11, 117.82, 116.24, 112.78, 52.91, 47.21; HRMS APCI (m/z): [M+H]$^+$ calcd for $C_{22}H_{18}Cl_2NO_2$ 398.0715, found 398.0718.

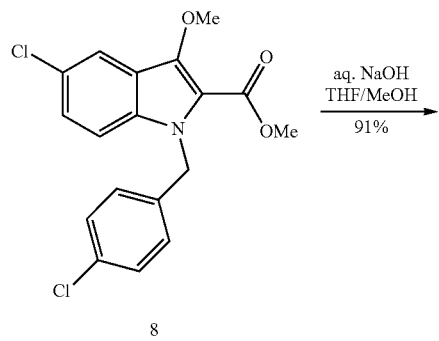

5-chloro-1-(4-chlorobenzyl)-3-methoxy-1H-indole-2-carboxylic acid (S14). Using general procedure I, methyl ester 8 (34 mg, 0.093 mmol) yielded the title compound as a white solid (30 mg, 91% yield). $^1$H NMR (500 MHz, MeOD) δ 7.73 (d, J=1.6 Hz, 1H), 7.39 (d, J=8.9 Hz, 1H), 7.26 (dd, J=9.0, 2.1 Hz, 1H), 7.24-7.21 (m, 2H), 6.98 (d, J=8.6 Hz, 2H), 5.74 (s, 2H), 4.04 (s, 3H); $^{13}$C NMR (125 MHz, MeOD) δ 163.79, 146.80, 138.64, 136.25, 133.95, 129.60, 129.01, 127.49, 127.10, 121.81, 119.94, 118.94, 113.54, 63.22, 48.08; HRMS APCI (m/z): [M−H]$^−$ calcd for $C_{17}H_{12}Cl_2NO_3$ 348.0194, found 348.0201.

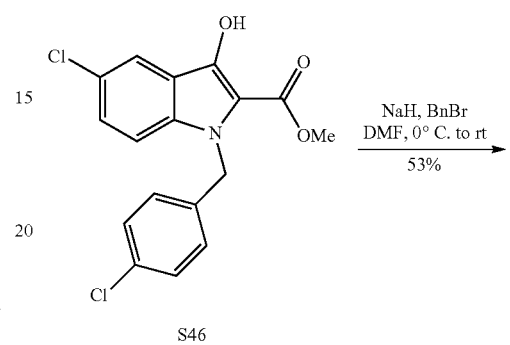

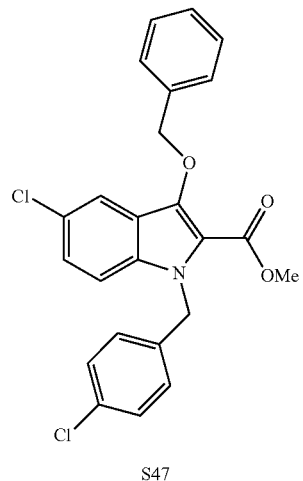

S47

Methyl 3-(benzyloxy)-5-chloro-1-(4-chlorobenzyl)-1H-indole-2-carboxylate (S47). To a suspension of NaH (40 mg, 0.984 mmol) in DMF (5 mL) at 0° C. was added hydroxyindole S46 (265 mg, 0.757 mmol) dissolved in DMF (3 mL). The reaction mixture was stirred at room temperature for 30 minutes. Benzyl bromide (0.13 mL, 1.136 mmol) was added and the reaction was stirred for 2 hours at room temperature. The reaction was quenched with water, and the aqueous layer was extracted with EtOAc 3×. The combined organic layers were washed with water and brine, dried over $Na_2SO_4$, filtered, concentrated, and purified by column chromatography, yielding the title compound as a yellow solid (178 mg, 53% yield). $^1$H NMR (600 MHz, $CDCl_3$) δ 7.63 (dd, J=2.0, 0.5 Hz, 1H), 7.47-7.42 (m, 2H), 7.41-7.35 (m, 3H), 7.25 (dd, J=8.9, 2.0 Hz, 1H), 7.23-7.18 (m, 3H), 6.93-6.88 (m, 2H), 5.67 (s, 2H), 5.19 (s, 2H), 3.84 (s, 3H); $^{13}$C NMR (150 MHz, $CDCl_3$) δ 161.81, 144.09, 137.03, 136.57, 135.01, 133.21, 128.95, 128.60, 128.52, 128.48, 127.62, 126.94, 126.36, 121.37, 119.56, 118.13, 111.93, 77.70, 51.90, 47.58; HRMS ESI (m/z): [M+H]$^+$ calcd for $C_{24}H_{20}Cl_2NO_3$ 440.0820, found 440.0814.

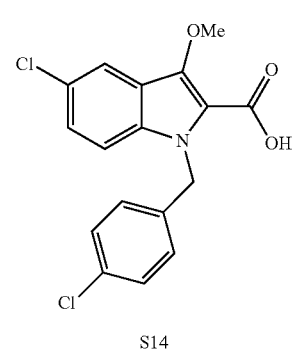

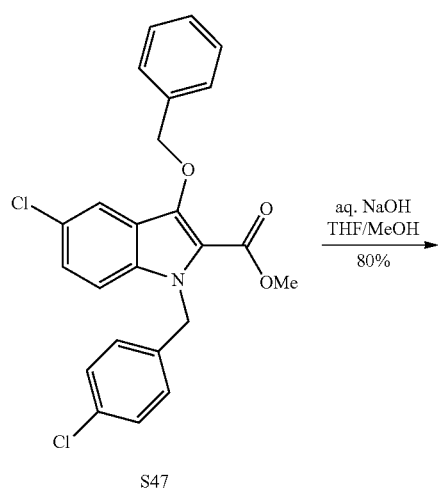

S47

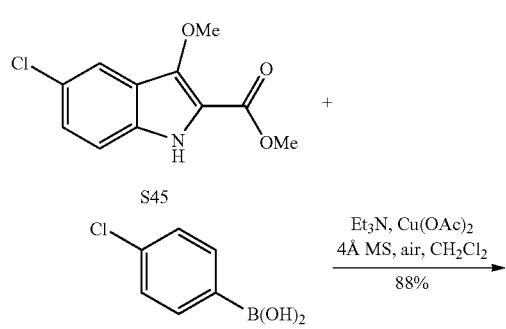

S15

3-(benzyloxy)-5-chloro-1-(4-chlorobenzyl)-1H-indole-2-carboxylic acid (S15). Using general procedure I, methyl ester S47 (65.1 mg, 0.148 mmol) yielded the title compound as a pale yellow solid (50 mg, 80% yield). $^1$H NMR (400 MHz, Acetone) δ 7.69 (d, J=1.7 Hz, 1H), 7.61-7.50 (m, 3H), 7.43-7.33 (m, 3H), 7.33-7.26 (m, 3H), 7.09-7.02 (m, 2H), 5.86 (s, 2H), 5.35 (s, 2H); $^{13}$C NMR (150 MHz, Acetone) δ 161.29, 143.80, 137.56, 137.36, 134.87, 132.34, 128.56, 128.47, 128.29, 128.16, 128.10, 126.22, 125.57, 121.10, 119.10, 118.11, 112.69, 76.98, 46.80; HRMS ESI (m/z): [M+Na]$^+$ calcd for $C_{23}H_{17}Cl_2NO_3Na$ 448.0483, found 448.0482.

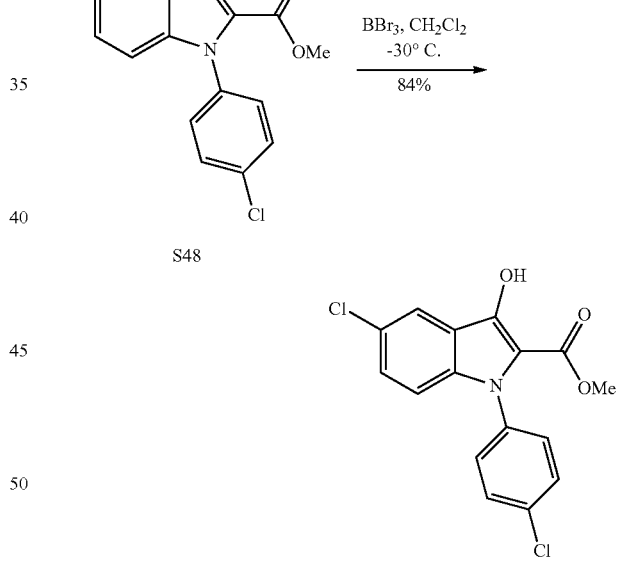

S48

Methyl 5-chloro-1-(4-chlorophenyl)-3-methoxy-1H-indole-2-carboxylate (S48). Using general procedure H, indole S45 (50 mg, 0.209 mmol) yielded the title compound as a white-yellow solid (65 mg, 88% yield). $^1$H NMR (500 MHz, CDCl$_3$) δ 7.78 (d, J=1.9 Hz, 1H), 7.50-7.43 (m, 2H), 7.26-7.16 (m, 3H), 6.96 (d, J=9.0 Hz, 1H), 4.12 (s, 3H), 3.79 (s, 3H); $^{13}$C NMR (125 MHz, CDCl$_3$) δ 161.14, 146.43, 136.88, 136.05, 134.11, 129.50, 129.28, 127.13, 126.72, 120.92, 119.43, 118.42, 112.71, 62.89, 51.91; HRMS APCI (m/z): [M+H]$^+$ calcd for $C_{16}H_{10}Cl_2NO_3$ 350.0351, found 350.0349.

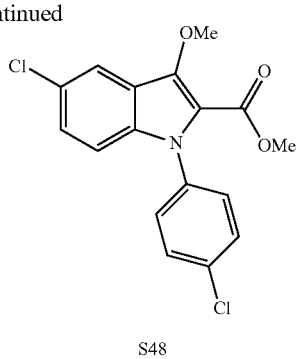

S49

Methyl 5-chloro-1-(4-chlorophenyl)-3-hydroxy-1H-indole-2-carboxylate (S49). Using general procedure G, methyl ether S48 (65 mg, 0.184 mmol) yielded the title compound as a green solid (52 mg, 84% yield). $^1$H NMR (500 MHz, CDCl$_3$) δ 8.66 (s, 1H), 7.78 (d, J=2.0 Hz, 1H), 7.52-7.39 (m, 2H), 7.28-7.19 (m, 3H), 6.95 (d, J=9.0 Hz, 1H), 3.74 (s, 3H); $^{13}$C NMR (150 MHz, Acetone) δ 163.54, 148.26, 138.00, 137.48, 133.86, 130.46, 129.97, 128.69, 126.39, 119.77, 119.55, 113.63, 112.37, 51.86; HRMS APCI (m/z): [M−H]$^−$ calcd for $C_{16}H_{10}Cl_2NO_3$ 334.0038, found 334.0045.

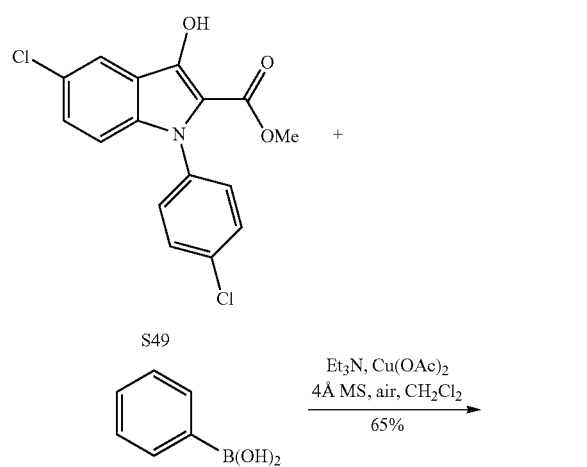

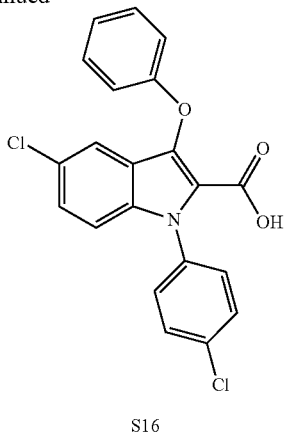

5-chloro-1-(4-chlorophenyl)-3-phenoxy-1H-indole-2-carboxylic acid (S16). Using general procedure I, methyl ester S50 (41 mg, 0.099 mmol) yielded the title compound as a white solid (26 mg, 65% yield). $^1$H NMR (500 MHz, MeOD) δ 7.58-7.51 (m, 2H), 7.42-7.36 (m, 2H), 7.36-7.27 (m, 2H), 7.29-7.21 (m, 2H), 7.10 (d, J=9.5 Hz, 1H), 7.08-7.04 (m, 1H), 7.04-7.00 (m, 2H); $^{13}$C NMR (125 MHz, Acetone) δ 161.11, 159.71, 139.71, 137.91, 136.83, 134.24, 130.61, 130.46, 130.09, 127.49, 127.33, 123.28, 122.27, 121.89, 119.40, 116.69, 114.13; HRMS APCI (m/z): [M+H]$^+$ calcd for $C_{21}H_{14}Cl_2NO_3$ 398.0351, found 398.0349.

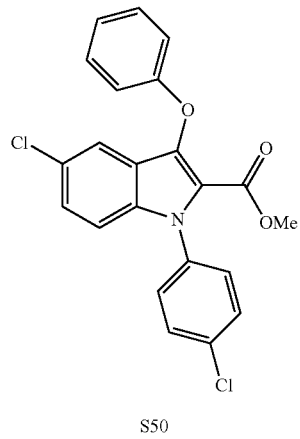

Methyl 5-chloro-1-(4-chlorophenyl)-3-phenoxy-1H-indole-2-carboxylate (S50). Using general procedure H, hydroxyindole S49 (52 mg, 0.154 mmol) yielded the title compound as a yellow solid (41 mg, 65% yield). $^1$H NMR (500 MHz, CDCl$_3$) δ 7.57-7.47 (m, 2H), 7.45-7.40 (m, 1H), 7.37-7.27 (m, 4H), 7.24 (dd, J=8.9, 2.0 Hz, 1H), 7.12-7.00 (m, 4H), 3.65 (s, 3H); $^{13}$C NMR (125 MHz, CDCl$_3$) δ 160.76, 158.69, 139.83, 136.45, 136.18, 134.47, 129.76, 129.63, 129.36, 127.39, 122.75, 121.69, 121.05, 119.86, 119.46, 115.90, 112.82, 51.99; HRMS APCI (m/z): [M+H]$^+$ calcd for $C_{22}H_{16}Cl_2NO_3$ 412.0507, found 412.0507.

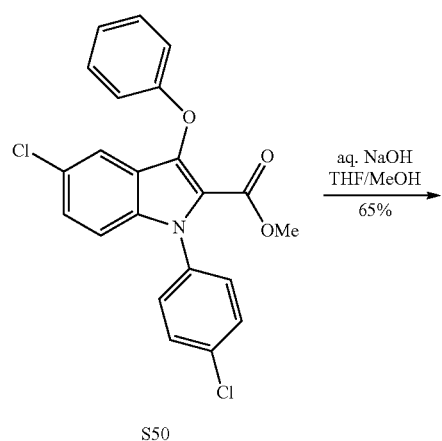

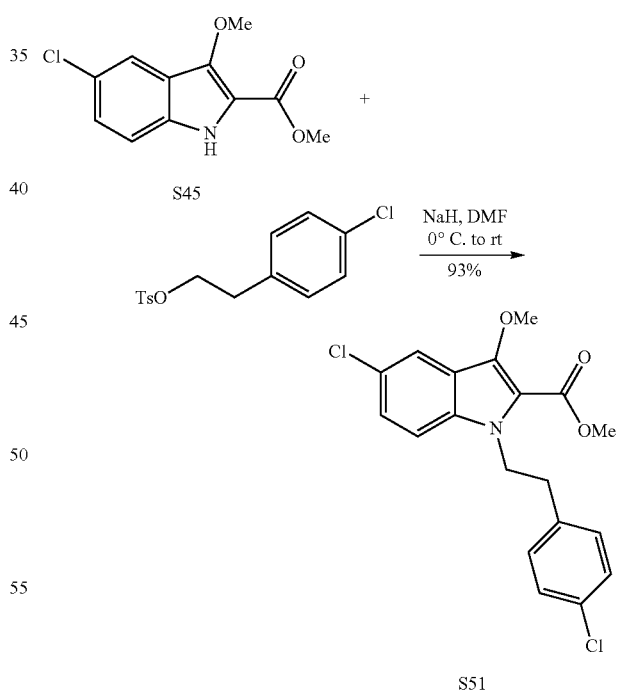

Methyl 5-chloro-1-(4-chlorophenethyl)-3-methoxy-1H-indole-2-carboxylate (S51). Indole S45 (200 mg, 0.835 mmol) dissolved in DMF (2 mL) was added to a suspension of NaH (60% in mineral oil, 43 mg, 1.086 mmol) in DMF (3 mL) at 0° C. The reaction was stirred for 30 minutes, then 4-chlorophenethyl-4-methylbenzenesulfonate (Cheng, K. et al, *Org. Biomol. Chem.* 2007, 5, 1177. 389 mg, 1.253 mmol)

was added. The ice bath was removed, and the reaction was stirred for 72 hours. The reaction was poured into EtOAc and water, and the aqueous layer was extracted with EtOAc 3×. The combined organic layers were washed with water and brine, dried over $Na_2SO_4$, filtered, concentrated, and purified by column chromatography, yielding the title compound as a yellow solid (293 mg, 93%). $^1$H NMR (400 MHz, $CDCl_3$) δ 7.71 (dd, J=2.0, 0.5 Hz, 1H), 7.25-7.21 (m, 2H), 7.21-7.19 (m, 1H), 7.17-7.13 (m, 1H), 7.05-7.01 (m, 2H), 4.67-4.60 (m, 2H), 4.00 (s, 3H), 3.93 (s, 3H), 3.02-2.92 (m, 2H); $^{13}$C NMR (100 MHz, $CDCl_3$) δ 161.95, 145.14, 136.87, 134.32, 132.55, 130.38, 128.70, 126.44, 125.79, 120.38, 119.39, 117.10, 111.52, 62.94, 51.91, 46.22, 36.32; HRMS ESI (m/z): $[M+Na]^+$ calcd for $C_{19}H_{17}Cl_2NO_3Na$ 400.0483, found 400.0481.

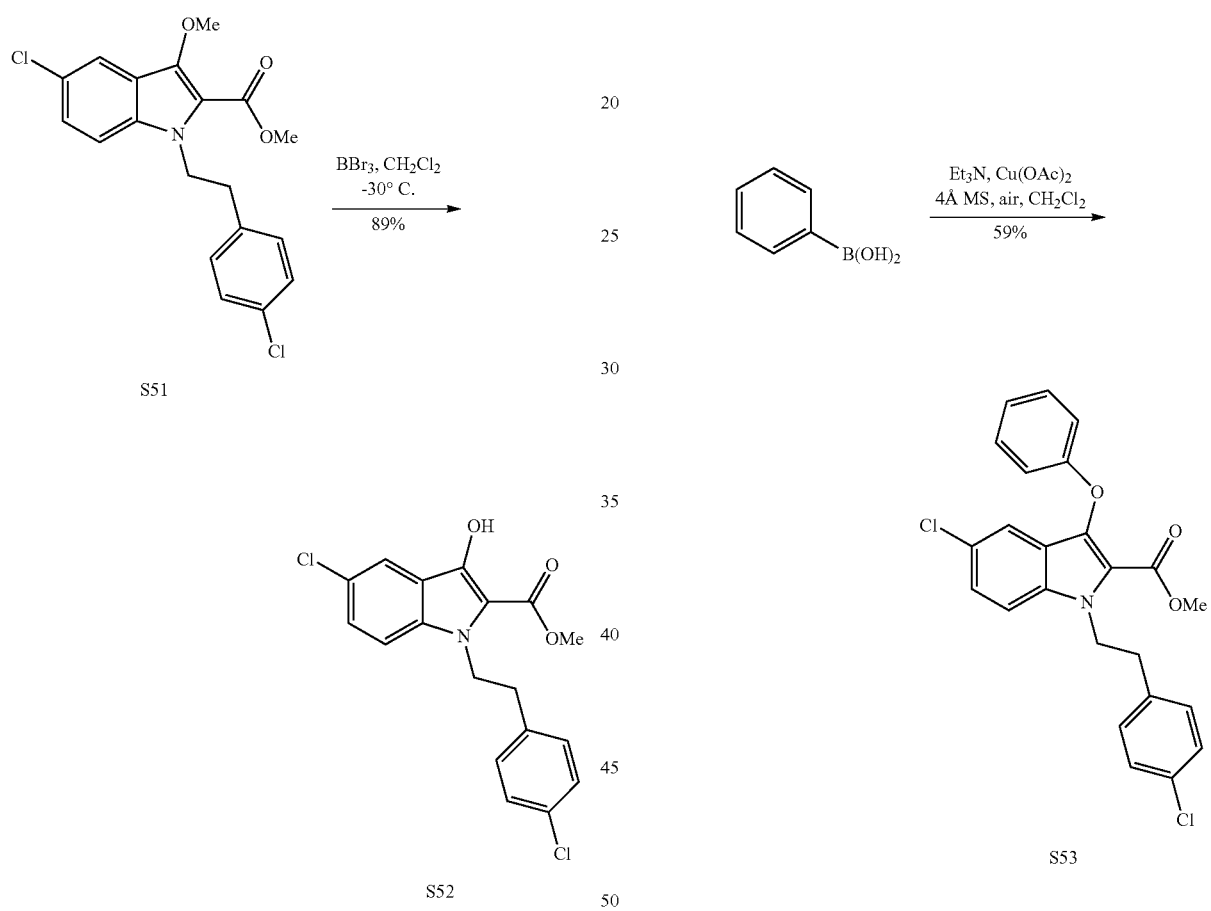

Methyl 5-chloro-1-(4-chlorophenethyl)-3-hydroxy-1H-indole-2-carboxylate (S52). Using general procedure G, methyl ether S51 (243.1 mg, 0.643 mmol) yielded the title compound as a yellow solid (208.4 mg, 89% yield). $^1$H NMR (400 MHz, $CDCl_3$) δ 8.39 (br s, 1H), 7.71 (d, J=2.1 Hz, 1H), 7.25-7.18 (m, 3H), 7.04-6.95 (m, 3H), 4.53-4.45 (m, 2H), 3.97 (s, 3H), 2.96-2.89 (m, 2H); $^{13}$C NMR (150 MHz, Acetone) δ 163.13, 146.15, 137.64, 135.18, 131.73, 130.68, 128.24, 126.84, 124.19, 118.70, 117.56, 112.16, 109.96, 51.12, 45.87, 35.79; HRMS ESI (m/z): $[M+Na]^+$ calcd for $C_{24}H_{19}Cl_2NO_3Na$ 462.0640, found 462.0634.

Methyl 5-chloro-1-(4-chlorophenethyl)-3-phenoxy-1H-indole-2-carboxylate (S53). Using general procedure H, hydroxyindole S52 (243 mg, 0.643 mmol) yielded the title compound as a yellow solid (208 mg, 89% yield). $^1$H NMR (400 MHz, Acetone) δ 7.65-7.59 (m, 1H), 7.43-7.23 (m, 6H), 7.20-7.15 (m, 2H), 7.08-7.01 (m, 1H), 6.94-6.88 (m, 2H), 4.94-4.82 (m, 2H), 3.68 (s, 3H), 3.17-3.05 (m, 2H); $^{13}$C NMR (150 MHz, Acetone) δ 160.99, 159.11, 137.77, 137.35, 134.41, 131.85, 130.77, 129.51, 128.28, 125.97, 125.72, 122.18, 120.37, 118.95, 118.29, 115.54, 112.92, 51.07, 45.69, 35.69; HRMS ESI (m/z): $[M+H]^+$ calcd for $C_{23}H_{20}O_3NCl_2$ 440.0815, found 440.0822.

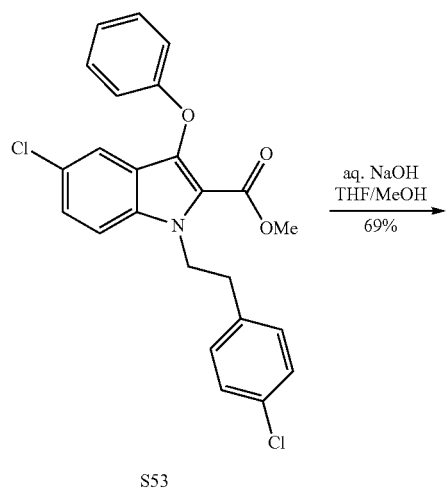

S53

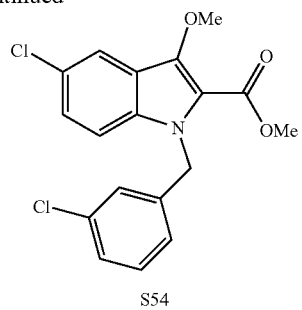

S54

Methyl 5-chloro-1-(3-chlorobenzyl)-3-methoxy-1H-indole-2-carboxylate (S54). Using general procedure C, indole S45 (214 mg, 0.892 mmol) yielded the title compound as an orange oil (286 mg, 88% yield). $^1$H NMR (400 MHz, CDCl$_3$) δ 7.77 (dd, J=2.0, 0.5 Hz, 1H), 7.26 (dd, J=8.9, 2.0 Hz, 1H), 7.21 (s, 1H), 7.20-7.17 (m, 2H), 7.00 (dd, J=1.8, 0.8 Hz, 1H), 6.90-6.83 (m, 1H), 5.68 (s, 2H), 4.07 (s, 3H), 3.91 (s, 3H); $^{13}$C NMR (125 MHz, CDCl$_3$) δ 161.50, 145.43, 140.00, 134.70, 134.30, 129.76, 127.30, 126.53, 126.15, 125.85, 124.18, 120.34, 119.24, 116.79, 111.67, 62.51, 51.60, 47.27; HRMS APCI (m/z): [M+H]$^+$ calcd for C$_{18}$H$_{16}$Cl$_2$NO$_3$ 364.0507, found 364.0506.

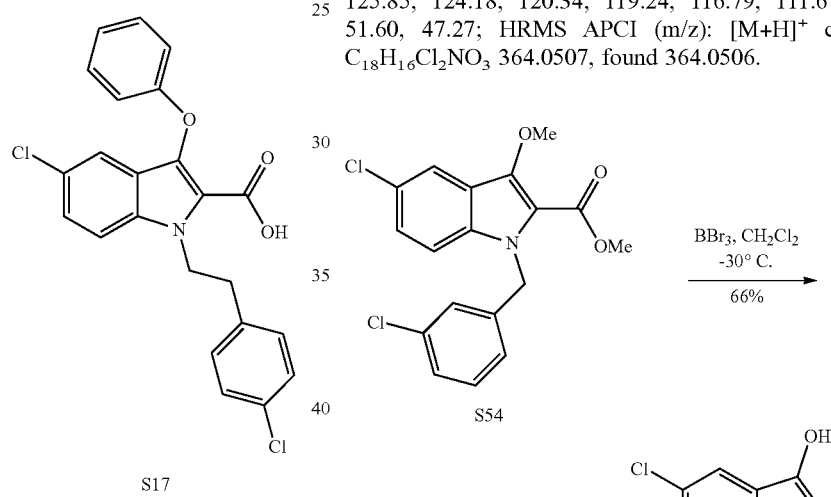

S17

5-chloro-1-(4-chlorophenethyl)-3-phenoxy-1H-indole-2-carboxylic acid (S17). Using general procedure I, methyl ester S53 (46 mg, 0.132 mmol) yielded the title compound as a white solid (34 mg, 53% yield). $^1$H NMR (400 MHz, Acetone) δ 7.65-7.54 (m, 1H), 7.39-7.10 (m, 8H), 7.02 (tt, J=7.2, 1.1 Hz, 1H), 6.92 (dt, J=7.9, 1.0 Hz, 2H), 4.88 (t, J=7.3 Hz, 2H), 3.12 (t, J=7.3 Hz, 2H); $^{13}$C NMR (150 MHz, Acetone) δ 161.23, 159.06, 137.79, 137.44, 134.57, 131.80, 130.73, 129.48, 128.29, 125.86, 125.58, 122.07, 120.24, 119.21, 118.27, 115.51, 112.89, 45.69, 35.77; HRMS ESI (m/z): [M+H]$^+$ calcd for C$_{23}$H$_{18}$O$_3$NCl$_2$ 426.0658, found 426.0666.

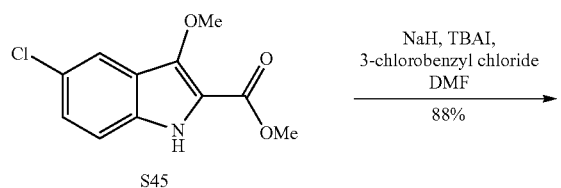

S45

S55

Methyl 5-chloro-1-(3-chlorobenzyl)-3-hydroxy-1H-indole-2-carboxylate (S55). Using general procedure G, methyl ether S54 (286 mg, 0.785 mmol) yielded the title compound as a green solid (182 mg, 66% yield). $^1$H NMR (500 MHz, CDCl$_3$) δ 8.48 (s, 1H), 7.76 (dd, J=2.1, 0.6 Hz, 1H), 7.28 (dd, J=9.0, 2.1 Hz, 1H), 7.23-7.14 (m, 2H), 7.13 (dd, J=9.0, 0.6 Hz, 1H), 6.99 (td, J=1.8, 0.9 Hz, 1H), 6.86-6.79 (m, 1H), 5.52 (s, 2H), 3.91 (s, 3H); $^{13}$C NMR (125 MHz, CDCl$_3$) δ 163.88, 148.12, 140.24, 135.86, 134.75, 130.12, 128.32, 127.74, 126.32, 125.52, 124.25, 119.91, 117.79, 111.50, 109.86, 51.90, 47.79; HRMS APCI (m/z): [M−H]$^−$ calcd for C$_{17}$H$_{12}$Cl$_2$NO$_3$ 348.0194, found 348.0202.

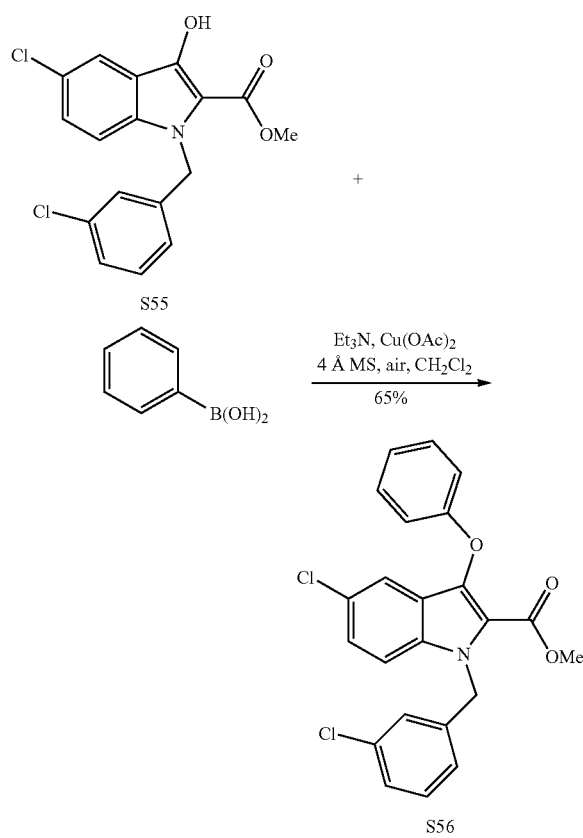

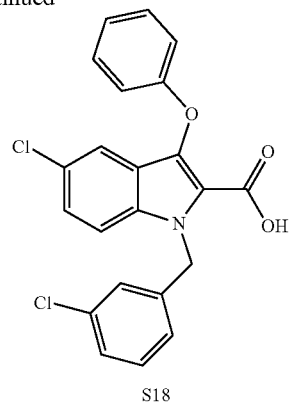

5-chloro-1-(3-chlorobenzyl)-3-phenoxy-1H-indole-2-carboxylic acid (S18). Using general procedure I, methyl ester S56 (39 mg, 0.090 mmol) yielded the title compound as a white solid (26 mg, 76% yield). $^1$H NMR (400 MHz, Acetone) δ 7.66 (d, J=9.1 Hz, 1H), 7.39-7.24 (m, 6H), 7.18 (s, 1H), 7.10-6.98 (m, 4H), 5.96 (s, 2H); $^{13}$C NMR (75 MHz, Acetone) δ 162.19, 159.79, 141.84, 139.22, 135.98, 134.77, 131.16, 130.42, 128.10, 127.30, 127.22, 126.93, 125.72, 123.10, 121.49, 120.38, 119.46, 116.44, 113.93, 47.95; HRMS APCI (m/z): [M−H]$^-$ calcd for $C_{22}H_{14}Cl_2NO_3$ 410.0351, found 410.0361.

Methyl 5-chloro-1-(3-chlorobenzyl)-3-phenoxy-1H-indole-2-carboxylate (S56). Using general procedure H, hydroxyindole S55 (98 mg, 0.280 mmol) yielded the title compound as a tan solid (77 mg, 65% yield). $^1$H NMR (400 MHz, CDCl$_3$) δ 7.45 (t, J=1.2 Hz, 1H), 7.35-7.28 (m, 2H), 7.28 (d, J=1.2 Hz, 2H), 7.24-7.20 (m, 2H), 7.10-7.03 (m, 2H), 7.01-6.95 (m, 2H), 6.92 (ddd, J=6.1, 3.2, 1.6 Hz, 1H), 5.78 (s, 2H), 3.73 (s, 3H); $^{13}$C NMR (125 MHz, CDCl$_3$) δ 161.51, 158.87, 139.91, 139.06, 135.14, 134.81, 130.17, 129.71, 127.81, 127.24, 126.87, 126.40, 124.36, 122.53, 120.94, 119.60, 118.54, 115.67, 112.07, 52.01, 47.70; HRMS APCI (m/z): [M+H]$^+$ calcd for $C_{23}H_{18}Cl_2NO_3$ 426.0664, found 426.0664.

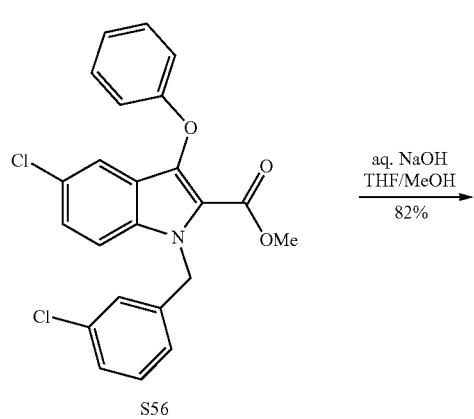

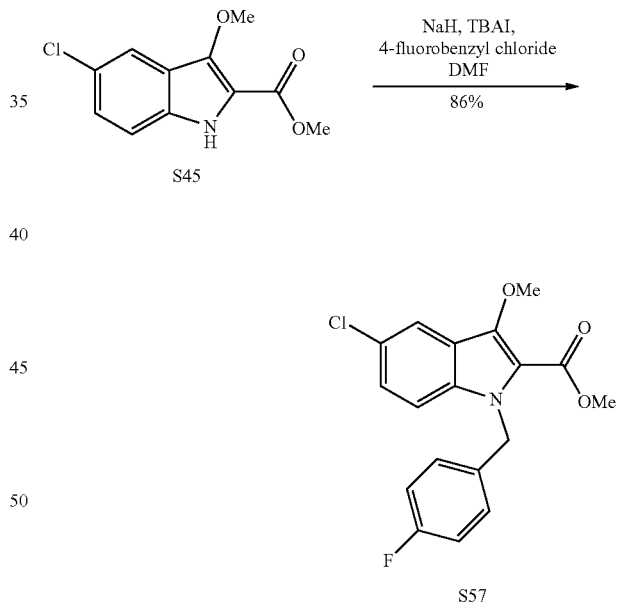

Methyl 5-chloro-1-(4-fluorobenzyl)-3-methoxy-1H-indole-2-carboxylate (S57). Using general procedure C, indole S45 (150 mg, 0.626 mmol) yielded the title compound as a white solid (187 mg, 86% yield). $^1$H NMR (600 MHz, CDCl$_3$) δ 7.81 (d, J=1.8 Hz, 1H), 7.32-7.27 (m, 2H), 7.06-7.01 (m, 2H), 7.01-6.95 (m, 2H), 5.71 (s, 2H), 4.10 (s, 3H), 3.96 (s, 3H); $^{13}$C NMR (150 MHz, CDCl$_3$) δ 162.08 (d, J=245.5 Hz), 161.89, 145.67, 135.01, 133.74 (d, J=3.0 Hz), 127.95 (d, J=7.8 Hz), 126.80, 126.10, 120.62, 119.52, 117.14, 115.60 (d, J=21.1 Hz), 112.00, 62.90, 51.94, 47.45; HRMS APCI (m/z): [M+H]$^+$ calcd for $C_{18}H_{16}ClFNO_3$ 348.0803, found 348.0803.

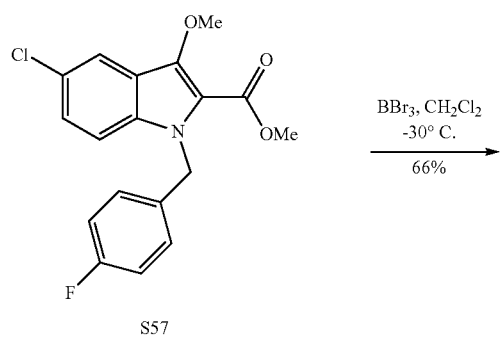

S57

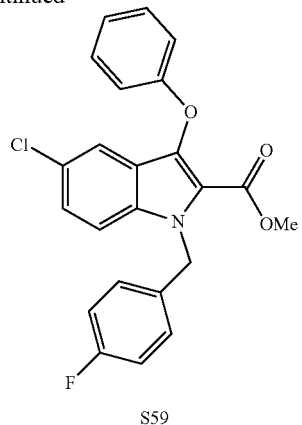

S59

Methyl 5-chloro-1-(4-fluorobenzyl)-3-phenoxy-1H-indole-2-carboxylate (S59). Using general procedure H, hydroxyindole S58 (47 mg, 0.141 mmol) yielded the title compound as a yellow oil (32 mg, 55% yield). $^1$H NMR (400 MHz, Acetone) δ 7.67 (dd, J=8.8, 0.7 Hz, 1H), 7.39-7.28 (m, 4H), 7.25-7.15 (m, 2H), 7.12-7.01 (m, 3H), 7.02-6.95 (m, 2H), 5.90 (s, 2H), 3.69 (s, 3H); $^{13}$C NMR (150 MHz, Acetone) δ 162.85 (d, J=243.3 Hz), 161.89, 159.89, 139.38, 135.94, 135.21 (d, J=3.3 Hz), 130.48, 129.31 (d, J=8.6 Hz), 127.37, 126.98, 123.22, 121.55, 119.75, 119.44, 116.48, 116.13 (d, J=21.4 Hz), 114.04, 52.05, 47.92; HRMS APCI (m/z): [M+H]$^+$ calcd for C$_{23}$H$_{18}$ClFNO$_3$ 410.0959, found 410.0962.

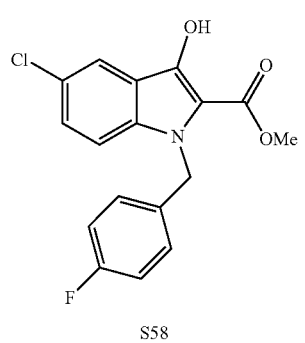

S58

Methyl 5-chloro-1-(4-fluorobenzyl)-3-hydroxy-1H-indole-2-carboxylate (S58). Using general procedure G, methyl ether S57 (75 mg, 0.215 mmol) yielded the title compound as a yellow solid (47 mg, 66% yield). $^1$H NMR (600 MHz, Acetone) δ 8.67 (s, 1H), 7.68 (dd, J=2.1, 0.5 Hz, 1H), 7.53 (d, J=9.0 Hz, 1H), 7.33 (dd, J=9.0, 2.1 Hz, 1H), 7.20-7.09 (m, 2H), 7.09-6.96 (m, 2H), 5.70 (s, 2H), 3.92 (s, 3H); $^{13}$C NMR (150 MHz, Acetone) δ 163.89, 162.80 (d, J=243.2 Hz), 147.27, 136.61, 135.58 (d, J=3.3 Hz), 129.26 (d, J=7.8 Hz), 128.19, 125.53, 119.81, 118.97, 116.02 (d, J=22.1 Hz), 113.38, 111.04, 51.98, 47.74; HRMS APCI (m/z): [M+H]$^+$ calcd for C$_{17}$H$_{14}$ClFNO$_3$ 334.0646, found 334.0644.

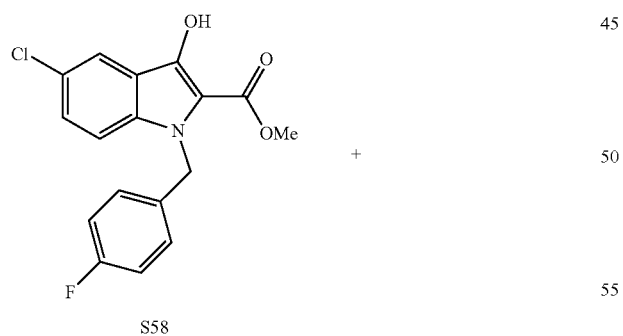

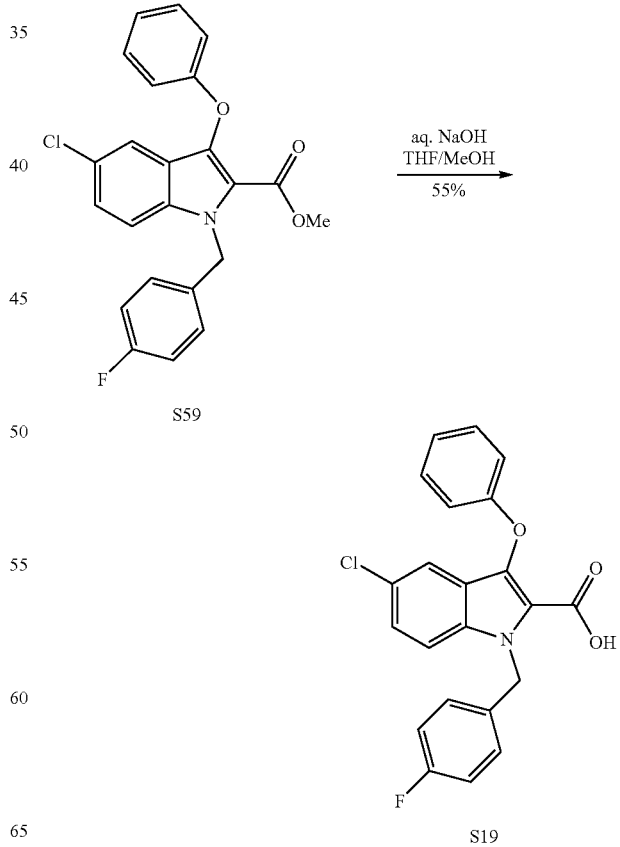

5-chloro-1-(4-fluorobenzyl)-3-phenoxy-1H-indole-2-carboxylic acid (S19). Using general procedure I, methyl ester S59 (32 mg, 0.078 mmol) yielded the title compound as a white solid (17 mg, 55% yield). $^1$H NMR (400 MHz, Acetone) δ 7.66 (d, J=9.5 Hz, 1H), 7.38-7.26 (m, 4H), 7.26-7.16 (m, 2H), 7.12-7.00 (m, 3H), 7.01-6.93 (m, 2H), 5.93 (s, 2H); $^{13}$C NMR (150 MHz, Acetone) δ 162.85 (d, J=244.2 Hz), 162.51, 159.86, 139.09, 135.91, 135.41 (d, J=3.1 Hz), 130.44, 129.39 (d, J=8.0 Hz), 127.13, 126.83, 123.10, 121.53, 120.55, 119.40, 116.50, 116.10 (d, J=22.0 Hz), 114.05, 47.78; HRMS APCI (m/z): [M−H]$^-$ calcd for C$_{22}$H$_{14}$ClFNO$_3$ 394.0646, found 394.0657.

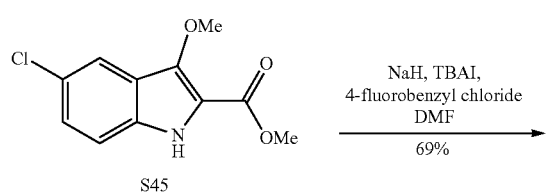

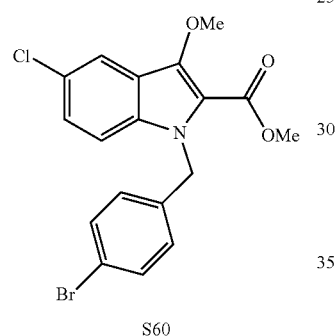

Methyl 1-(4-bromobenzyl)-5-chloro-3-methoxy-1H-indole-2-carboxylate (S60). Using general procedure C, indole S45 (150 mg, 0.626 mmol) yielded the title compound as a white solid (176 mg, 69% yield). $^1$H NMR (400 MHz, CDCl$_3$) δ 7.85 (d, J=2.6 Hz, 1H), 7.47-7.42 (m, 2H), 7.36-7.27 (m, 2H), 6.96 (d, J=8.8 Hz, 2H), 5.72 (s, 2H), 4.14 (s, 3H), 3.99 (s, 3H); $^{13}$C NMR (125 MHz, Acetone) δ 162.26, 146.33, 138.81, 135.74, 132.35, 129.31, 127.13, 126.41, 121.59, 121.33, 119.79, 118.26, 113.55, 63.08, 52.01, 47.88; HRMS APCI (m/z): [M+H]$^+$ calcd for C$_{18}$H$_{16}$BrClNO$_3$ 408.0002 and 409.9982, found 408.0004 and 409.9981.

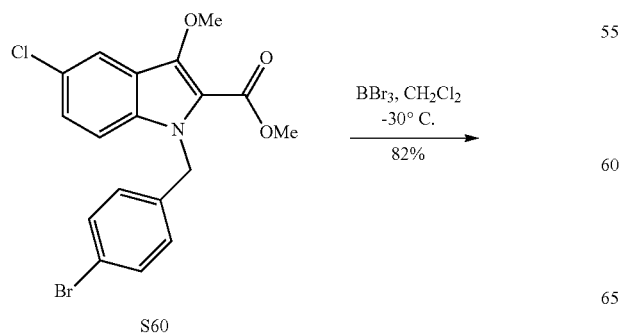

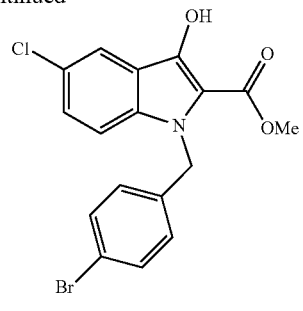

Methyl 1-(4-bromobenzyl)-5-chloro-3-hydroxy-1H-indole-2-carboxylate (S61). Using general procedure G, methyl ether S60 (176 mg, 0.430 mmol) yielded the title compound as a yellow solid (139 mg, 82% yield). $^1$H NMR (500 MHz, Acetone) δ 8.67 (s, 1H), 7.68 (dd, J=2.1, 0.6 Hz, 1H), 7.48 (dd, J=9.0, 0.6 Hz, 1H), 7.46-7.38 (m, 2H), 7.32 (dd, J=9.0, 2.1 Hz, 1H), 7.06-6.95 (m, 2H), 5.68 (s, 2H), 3.91 (s, 3H); $^{13}$C NMR (125 MHz, Acetone) δ 163.80, 147.24, 138.92, 136.57, 132.34, 129.28, 128.21, 125.56, 121.33, 119.81, 118.92, 113.23, 111.00, 51.98, 47.86; HRMS APCI (m/z): [M+H]$^+$ calcd for C$_{17}$H$_{14}$BrClNO$_3$ 393.9846 and 395.9825, found 393.9849 and 395.9827.

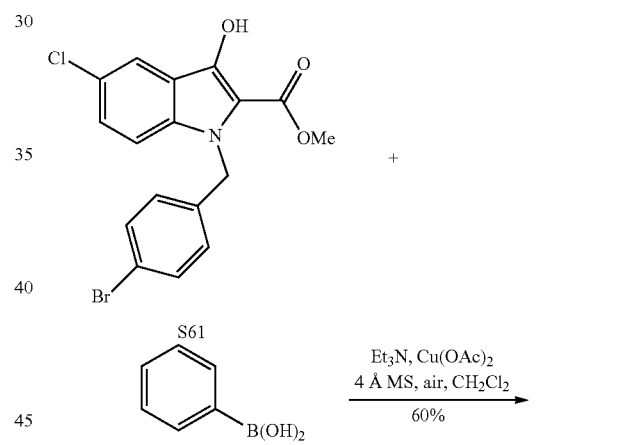

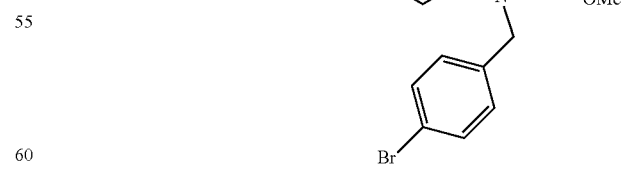

Methyl 1-(4-bromobenzyl)-5-chloro-3-phenoxy-1H-indole-2-carboxylate (S62). Using general procedure H, hydroxyindole S61 (75 mg, 0.190 mmol) yielded the title compound as a tan solid (54 mg, 60% yield). $^1$H NMR (400

MHz, Acetone) δ 7.65 (dd, J=8.9, 0.7 Hz, 1H), 7.54-7.45 (m, 2H), 7.41-7.28 (m, 4H), 7.15-7.03 (m, 3H), 7.03-6.95 (m, 2H), 5.89 (s, 2H), 3.68 (s, 3H); $^{13}$C NMR (150 MHz, Acetone) δ 161.85, 159.88, 139.42, 138.62, 135.97, 132.48, 130.49, 129.35, 127.44, 127.03, 123.23, 121.55, 121.47, 119.74, 119.48, 116.49, 113.99, 52.06, 48.07; HRMS APCI (m/z): [M+H]$^+$ calcd for $C_{23}H_{18}BrClNO_3$ 470.0159 and 472.0138, found 470.0160 and 472.0139.

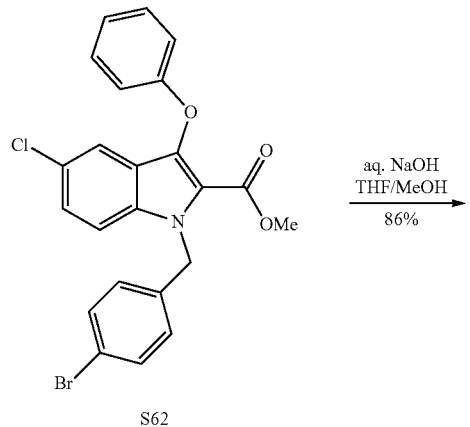

S62

1-(4-bromobenzyl)-5-chloro-3-phenoxy-1H-indole-2-carboxylic acid (S20). Using general procedure I, methyl ester S62 (32 mg, 0.069 mmol) yielded the title compound as a white solid (27 mg, 86% yield). $^1$H NMR (400 MHz, Acetone) δ 7.71-7.62 (m, 1H), 7.53-7.46 (m, 2H), 7.38-7.28 (m, 4H), 7.14-7.02 (m, 3H), 7.02-6.95 (m, 2H), 5.93 (s, 2H); $^{13}$C NMR (150 MHz, Acetone) δ 162.09, 159.86, 139.29, 138.79, 136.06, 132.49, 130.47, 129.42, 127.32, 126.96, 123.15, 121.55, 121.44, 120.24, 119.49, 116.49, 114.02, 47.97; HRMS APCI (m/z): [M–H]$^-$ calcd for $C_{22}H_{14}BrClNO_3$ 453.9846 and 455.9825, found 453.9847 and 455.9823.

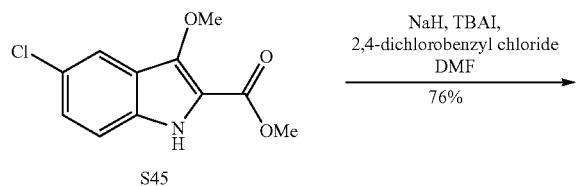

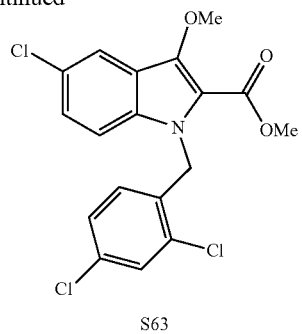

S63

Methyl 5-chloro-1-(2,4-dichlorobenzyl)-3-methoxy-1H-indole-2-carboxylate (S63). Using general procedure C indole S45 (150 mg, 0.626 mmol) yielded the title compound as a yellow-pink solid (190 mg, 76% yield). $^1$H NMR (300 MHz, Acetone) δ 7.82 (dd, J=2.0, 0.6 Hz, 1H), 7.54 (d, J=2.1 Hz, 1H), 7.46 (dd, J=9.0, 0.6 Hz, 1H), 7.31 (dd, J=9.0, 2.1 Hz, 1H), 7.17 (dd, J=8.4, 2.2 Hz, 1H), 6.27 (dt, J=8.4, 0.9 Hz, 1H), 5.82 (s, 2H), 4.07 (s, 3H), 3.83 (s, 3H); $^{13}$C NMR (150 MHz, Acetone) δ 162.07, 146.47, 136.12, 135.85, 133.74, 133.15, 129.73, 128.64, 128.38, 127.42, 126.66, 121.61, 119.95, 118.22, 113.29, 63.12, 52.02, 46.34; HRMS APCI (m/z): [M+H]$^+$ calcd for $C_{18}H_{15}Cl_3NO_3$ 398.0118, found 398.0119.

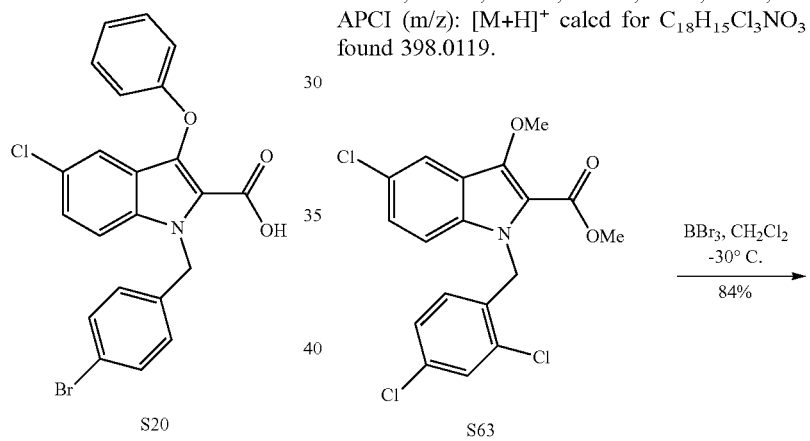

Methyl 5-chloro-1-(2,4-dichlorobenzyl)-3-hydroxy-1H-indole-2-carboxylate (S64). Using general procedure G, methyl ether S63 (190 mg, 0.477 mmol) yielded the title compound as a pink-white solid (154 mg, 84% yield). $^1$H NMR (400 MHz, Acetone) δ 8.70 (s, 1H), 7.73 (dd, J=2.1, 0.7 Hz, 1H), 7.55 (d, J=2.1 Hz, 1H), 7.45 (d, J=9.0 Hz, 1H), 7.35 (dd, J=9.0, 2.1 Hz, 1H), 7.19 (dd, J=8.4, 2.2 Hz, 1H), 6.30 (dd, J=8.4, 1.0 Hz, 1H), 5.77 (s, 2H), 3.85 (s, 3H); $^{13}$C NMR (150 MHz, Acetone) δ 163.62, 147.19, 136.70, 136.27, 133.77, 133.15, 129.77, 128.68, 128.49, 128.45, 125.86, 119.95, 119.02, 113.04, 111.09, 52.04, 46.16; HRMS APCI (m/z): [M−H]⁻ calcd for $C_{17}H_{11}Cl_3NO_3$ 381.9805, found 381.9816.

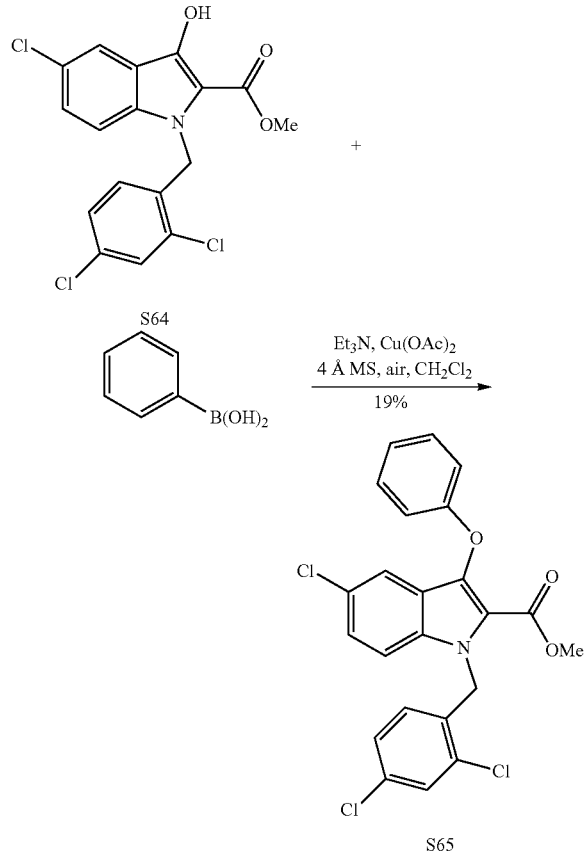

S64

Et₃N, Cu(OAc)₂
4 Å MS, air, CH₂Cl₂
19%

S65

Methyl 5-chloro-1-(2,4-dichlorobenzyl)-3-phenoxy-1H-indole-2-carboxylate (S65). Using general procedure H, hydroxyindole S64 (137 mg, 0.357 mmol) yielded the title compound as a tan-white solid (31 mg, 19% yield). ¹H NMR (600 MHz, Acetone) δ 7.62-7.55 (m, 2H), 7.41 (d, J=2.0 Hz, 1H), 7.39-7.31 (m, 3H), 7.23 (dd, J=8.4, 2.2 Hz, 1H), 7.08 (td, J=7.4, 0.9 Hz, 1H), 7.06-7.00 (m, 2H), 6.45 (dd, J=8.3, 0.9 Hz, 1H), 5.94 (s, 2H), 3.65 (s, 3H); ¹³C NMR (150 MHz, Acetone) δ 161.67, 159.87, 139.56, 136.11, 135.92, 133.89, 133.26, 130.53, 129.84, 128.71, 128.54, 127.70, 127.26, 123.32, 121.60, 119.78, 119.62, 116.57, 113.77, 52.08, 46.56; HRMS APCI (m/z): [M+H]⁺ calcd for $C_{23}H_{17}Cl_3NO_3$ 460.0274, found 460.0277.

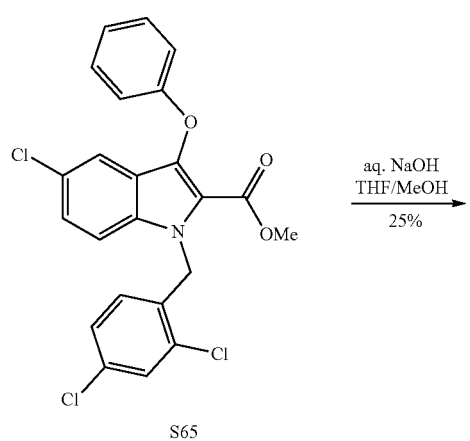

S65 aq. NaOH
THF/MeOH
25%

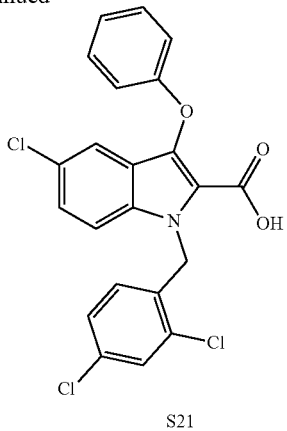

S21

5-chloro-1-(2,4-dichlorobenzyl)-3-phenoxy-1H-indole-2-carboxylic acid (S21). Using general procedure I, methyl ester S65 (31 mg, 0.067 mmol) yielded the title compound as a white solid (7 mg, 25% yield). ¹H NMR (400 MHz, Acetone) δ 7.63-7.55 (m, 2H), 7.41-7.30 (m, 4H), 7.29-7.21 (m, 1H), 7.11-7.00 (m, 3H), 6.45 (dt, J=8.4, 0.8 Hz, 1H), 5.98 (s, 2H); ¹³C NMR (150 MHz, Acetone) δ 161.86, 159.83, 139.44, 136.16, 136.06, 133.87, 133.30, 130.50, 129.83, 128.75, 128.54, 127.58, 127.19, 123.22, 121.58, 120.27, 119.63, 116.56, 113.76, 46.47; HRMS APCI (m/z): [M−H]⁻ calcd for $C_{22}H_{13}Cl_3NO_3$ 443.9961, found 443.9974.

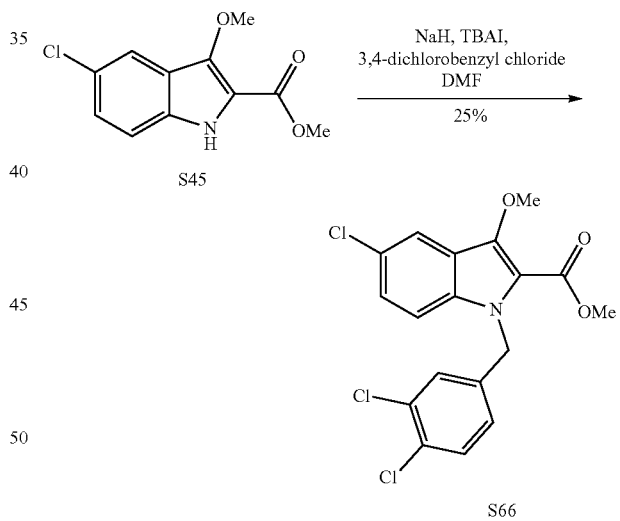

S45

NaH, TBAI,
3,4-dichlorobenzyl chloride
DMF
25%

S66

Methyl 5-chloro-1-(3,4-dichlorobenzyl)-3-methoxy-1H-indole-2-carboxylate (S66). Using general procedure C, indole S45 (150 mg, 0.625 mmol) yielded the title compound as a white solid (83 mg, 33% yield). ¹H NMR (400 MHz, Acetone) δ 7.79 (d, J=2.0 Hz, 1H), 7.55 (d, J=9.0 Hz, 1H), 7.45 (d, J=8.3 Hz, 1H), 7.31 (dd, J=9.3, 2.0 Hz, 2H), 6.99 (dd, J=8.3, 2.0 Hz, 1H), 5.80 (s, 2H), 4.04 (s, 3H), 3.88 (s, 3H); ¹³C NMR (100 MHz, Acetone) δ 162.25, 146.38, 140.49, 135.70, 132.68, 131.49, 131.27, 129.31, 127.28, 127.26, 126.52, 121.59, 119.89, 118.09, 113.41, 63.05, 52.05, 47.47; HRMS APCI (m/z): [M+H]⁺ calcd for $C_{18}H_{15}Cl_3NO_3$ 398.0118, found 398.0120.

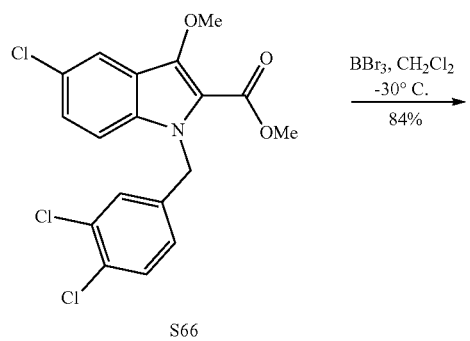

S66

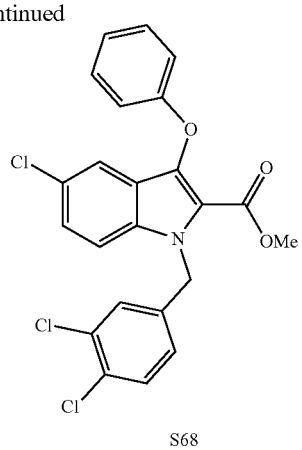

S68

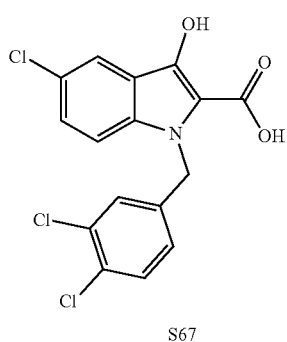

S67

Methyl 5-chloro-1-(3,4-dichlorobenzyl)-3-hydroxy-1H-indole-2-carboxylate (S67). Using general procedure G, methyl ether S66 (83 mg, 0.209 mmol) yielded the title compound as a green solid (68 mg, 84% yield). $^1$H NMR (300 MHz, Acetone) δ 8.68 (s, 1H), 7.69 (d, J=2.1 Hz, 1H), 7.52 (d, J=9.0 Hz, 1H), 7.45 (d, J=8.3 Hz, 1H), 7.34 (dd, J=9.0, 2.0 Hz, 1H), 7.29 (d, J=1.7 Hz, 1H), 6.99 (dd, J=8.3, 1.6 Hz, 1H), 5.73 (s, 2H), 3.91 (s, 3H); $^{13}$C NMR (150 MHz, Acetone) δ 163.70, 147.18, 140.68, 136.56, 132.71, 131.55, 131.30, 129.31, 128.36, 127.29, 125.74, 119.91, 119.06, 113.17, 110.99, 52.02, 47.43; HRMS APCI (m/z): [M−H]$^−$ calcd for C$_{17}$H$_{11}$Cl$_3$NO$_3$ 381.9805, found 381.9815.

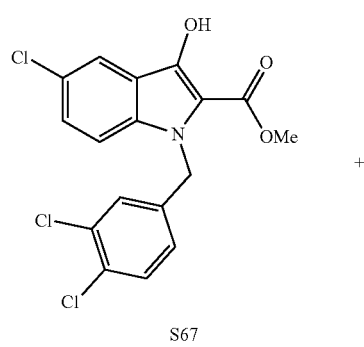

S67

+

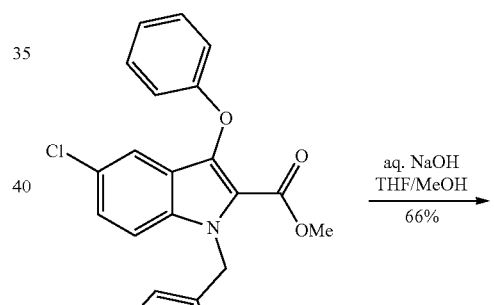

Methyl 5-chloro-1-(3,4-dichlorobenzyl)-3-phenoxy-1H-indole-2-carboxylate (S68). Using general procedure H, hydroxyindole S67 (68 mg, 0.176 mmol) yielded the title compound as a tan solid (40 mg, 50% yield). $^1$H NMR (400 MHz, Acetone) δ 7.68 (dd, J=8.7, 0.9 Hz, 1H), 7.50 (d, J=8.3 Hz, 1H), 7.39-7.35 (m, 2H), 7.35 (d, J=2.3 Hz, 1H), 7.33 (d, J=1.2 Hz, 1H), 7.32-7.30 (m, 1H), 7.10-7.07 (m, 1H), 7.07-7.04 (m, 1H), 7.00 (dd, J=8.8, 1.0 Hz, 2H), 5.92 (s, 2H), 3.69 (s, 3H); $^{13}$C NMR (150 MHz, Acetone) δ 161.86, 159.86, 140.33, 139.57, 135.99, 132.82, 131.65, 131.44, 130.50, 129.40, 127.61, 127.33, 127.18, 123.29, 121.63, 119.70, 119.57, 116.53, 113.91, 52.12, 47.69; HRMS APCI (m/z): [M+H]$^+$ calcd for C$_{23}$H$_{17}$Cl$_3$NO$_3$ 460.0274, found 460.0277.

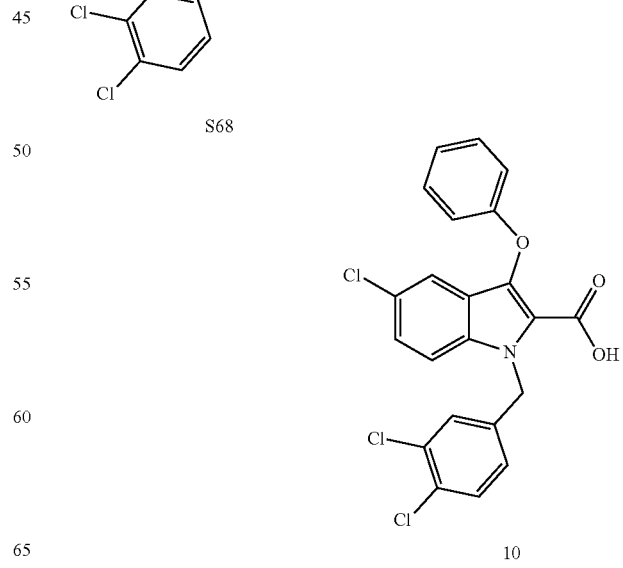

5-chloro-1-(3,4-dichlorobenzyl)-3-phenoxy-1H-indole-2-carboxylic acid (10). Using general procedure I, methyl ester S68 (20 mg, 0.044 mmol) yielded the title compound as a white solid (13 mg, 66% yield). $^1$H NMR (400 MHz, Acetone) δ 7.69 (d, J=9.5 Hz, 1H), 7.51 (d, J=8.3 Hz, 1H), 7.40-7.38 (m, 1H), 7.36 (td, J=4.7, 2.1 Hz, 2H), 7.35-7.30 (m, 2H), 7.11-7.03 (m, 2H), 7.03-6.98 (m, 2H), 5.96 (s, 2H); $^{13}$C NMR (150 MHz, Acetone) δ 162.16, 159.82, 140.50, 139.38, 136.02, 132.79, 131.65, 131.40, 130.47, 129.47, 127.46, 127.40, 127.07, 123.18, 121.60, 120.25, 119.55, 116.49, 113.91, 47.56; HRMS APCI (m/z): [M−H]⁻ calcd for $C_{22}H_{13}Cl_3NO_3$ 443.9961, found 443.9963.

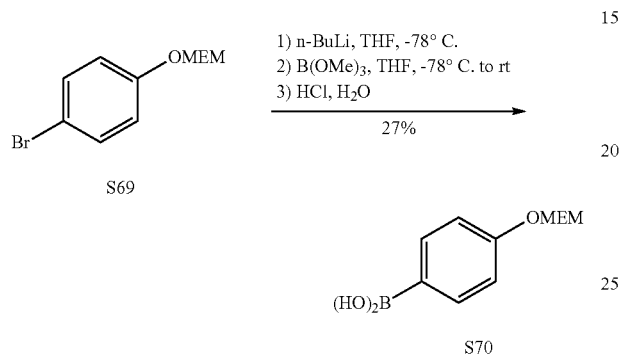

(4-((2-methoxyethoxy)methoxy)phenyl)boronic acid (S70). To a solution of compound S69 (1.85 g, 7.08 mmol, Chuang, C-L.; Santos, O.; Xu, X.; Canary, J. W. *Inorg. Chem.* 1997, 36, 1967-1972.) at −78° C. in THF (10 mL) was added n-BuLi (2.5M in hexanes, 3.40 mL, 8.50 mmol). The reaction was stirred for 30 minutes at −78° C. B(OMe)₃ (1.58 mL, 14.16 mmol) was added slowly and the solution turned from dark brown to yellow. This was warmed to room temperature and reacted overnight. The next day another portion of B(OMe)₃ (0.40 mL, 3.54 mL) was added. After 3 hours the reaction was quenched with HCl and stirred for 3 hours. The aqueous layer was extracted with EtOAc 3×. The combined organic layers were washed with brine, dried over Na₂SO₄, filtered, concentrated, and purified by column chromatography, yielding the title compound as a clear oil (423 mg, 27% yield). $^1$H NMR (500 MHz, CDCl₃) δ 8.10 (d, J=8.5 Hz, 2H), 7.12 (d, J=8.5 Hz, 2H), 5.30 (s, 2H), 3.87-3.81 (m, 2H), 3.59-3.52 (m, 2H), 3.37 (s, 3H); $^{13}$C NMR (125 MHz, CDCl₃) δ 160.73, 137.38, 123.34, 115.46, 92.89, 71.54, 67.74, 58.96; HRMS APCI (m/z): [M+H]⁺ calcd for $C_{10}H_{16}BO_5$ 227.1091, found 227.1072.

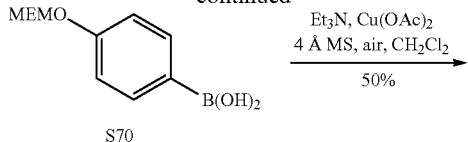

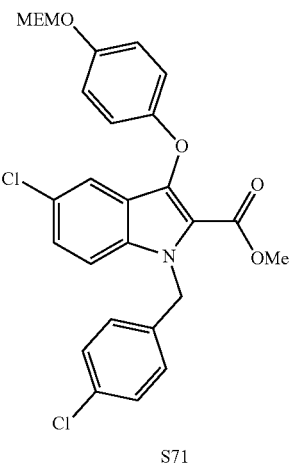

Methyl 5-chloro-1-(4-chlorobenzyl)-3-(4-((2-methoxyethoxy)methoxy)phenoxy)-1H-indole-2-carboxylate (S71). Using general procedure H, hydroxyindole S46 (60 mg, 0.171 mmol) yielded the title compound as a yellow oil (47 mg, 51% yield). $^1$H NMR (400 MHz, CDCl₃) δ 7.40 (t, J=1.3 Hz, 1H), 7.28-7.26 (m, 3H), 7.26-7.23 (m, 1H), 7.03-6.96 (m, 4H), 6.92-6.86 (m, 2H), 5.75 (s, 2H), 5.23 (s, 2H), 3.87-3.82 (m, 2H), 3.75 (s, 3H), 3.60-3.55 (m, 2H), 3.39 (s, 3H); $^{13}$C NMR (125 MHz, CDCl₃) δ 161.60, 153.77, 152.73, 139.62, 136.35, 135.16, 133.36, 129.03, 127.68, 127.12, 126.71, 120.81, 119.67, 118.45, 117.59, 116.62, 112.07, 94.27, 71.75, 67.71, 59.15, 52.01, 47.62; HRMS APCI (m/z): [M+H]⁺ calcd for $C_{27}H_{26}Cl_2NO_6$ 530.1137, found 530.1139.

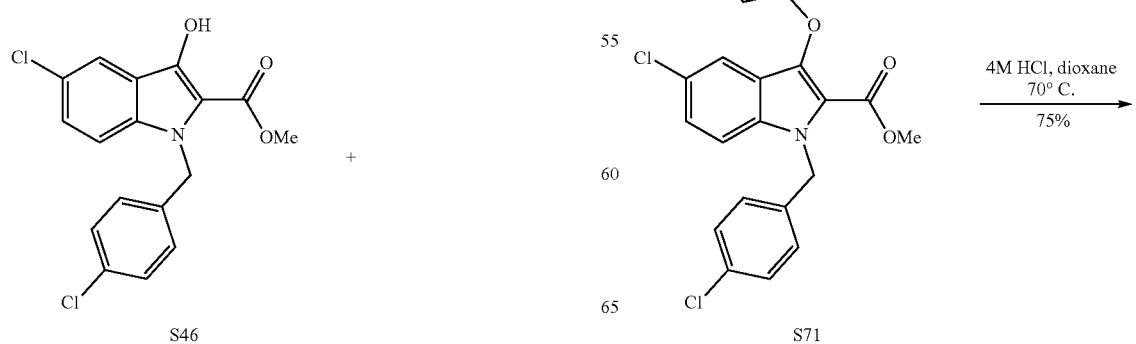

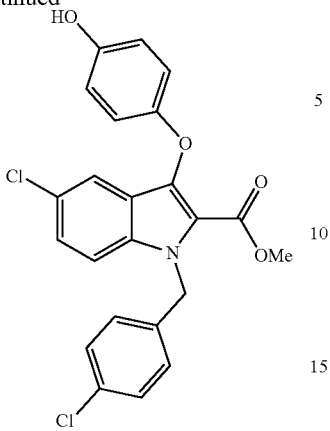

S72

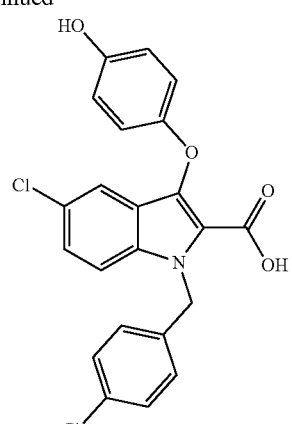

S22

Methyl 5-chloro-1-(4-chlorobenzyl)-3-(4-hydroxyphenoxy)-1H-indole carboxylate (S72). Compound S71 (12 mg, 0.022 mmol) was stirred in 4M HCl in dioxane (3 mL) at 70° C. overnight. The reaction was quenched with sat. NaHCO$_3$, and the aqueous layer was extracted with EtOAc 3×. The combined organic layers were washed with brine, dried over Na$_2$SO$_4$, filtered, and concentrated, yielding the title compound as a reddish oil (26 mg, 75% yield). $^1$H NMR (500 MHz, CDCl$_3$) δ 7.39 (t, J=1.3 Hz, 1H), 7.29-7.26 (m, 3H), 7.26-7.23 (m, 1H), 6.99 (d, J=8.6 Hz, 2H), 6.88-6.84 (m, 2H), 6.79-6.74 (m, 2H), 5.75 (s, 2H), 3.77 (s, 3H); $^{13}$C NMR (125 MHz, CDCl$_3$) δ 161.72, 152.84, 151.04, 139.94, 136.36, 135.21, 133.39, 129.05, 127.69, 127.16, 126.70, 120.77, 119.75, 118.33, 116.97, 116.25, 112.07, 52.06, 47.66; HRMS APCI (m/z): [M+H]$^+$ calcd for C$_{23}$H$_{18}$Cl$_2$NO$_4$ 442.0613, found 442.0616.

5-chloro-1-(4-chlorobenzyl)-3-(4-hydroxyphenoxy)-1H-indole-2-carboxylic acid (S22). Using general procedure I, methyl ester S72 (26 mg, 0.060 mmol) yielded the title compound as a white solid (14 mg, 53% yield). $^1$H NMR (500 MHz, Acetone) δ 7.61 (d, J=8.8 Hz, 1H), 7.37-7.25 (m, 4H), 7.19-7.12 (m, 2H), 6.92-6.86 (m, 2H), 6.84-6.74 (m, 2H), 5.92 (s, 2H); $^{13}$C NMR (150 MHz, Acetone) δ 162.28, 153.69, 152.78, 140.57, 138.36, 136.08, 133.35, 129.47, 129.08, 127.15, 126.64, 126.19, 121.36, 119.82, 117.88, 116.71, 113.91, 47.83; HRMS APCI (m/z): [M−H]$^-$ calcd for C$_{22}$H$_{14}$Cl$_2$NO$_4$ 426.0300, found 426.0314.

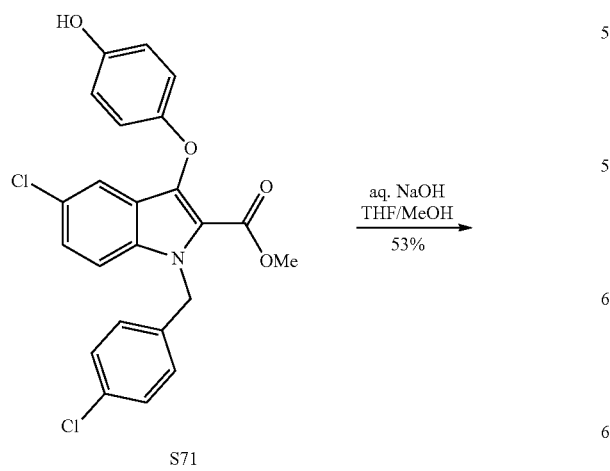

S71

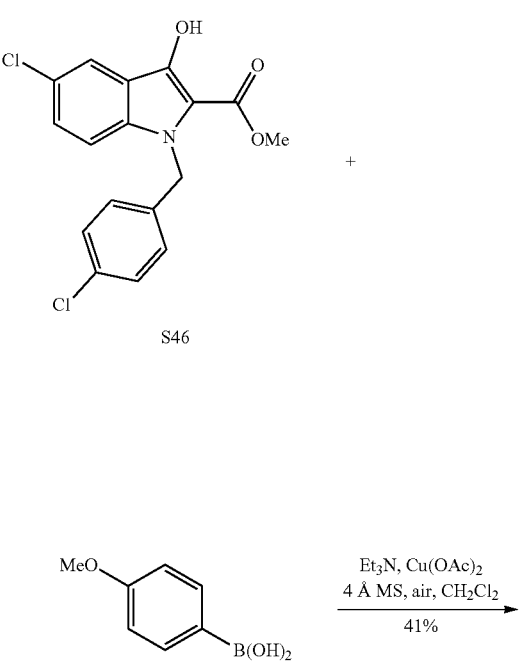

S46

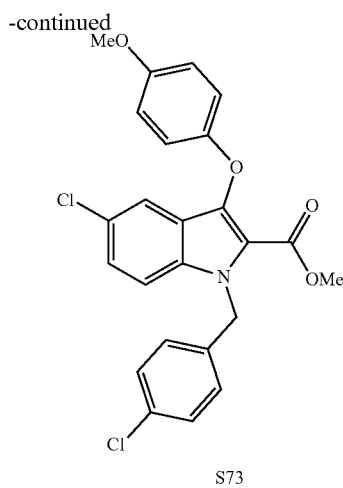

S73

Methyl 5-chloro-1-(4-chlorobenzyl)-3-(4-methoxyphenoxy)-1H-indole carboxylate (S73). Using general procedure H, hydroxyindole S46 (50 mg, 0.143 mmol) yielded the title compound as a white solid (27 mg, 41% yield). $^1$H NMR (500 MHz, CDCl$_3$) δ 7.39 (t, J=1.4 Hz, 1H), 7.27 (d, J=1.6 Hz, 3H), 7.27-7.22 (m, 1H), 7.03-6.95 (m, 2H), 6.94-6.88 (m, 2H), 6.86-6.81 (m, 2H), 5.75 (s, 2H), 3.79 (s, 3H), 3.76 (s, 3H); $^{13}$C NMR (125 MHz, CDCl$_3$) δ 161.67, 155.10, 152.83, 139.85, 136.38, 135.18, 133.36, 129.03, 127.68, 127.12, 126.68, 120.80, 119.73, 118.37, 116.74, 114.76, 112.05, 55.82, 52.04, 47.62; HRMS APCI (m/z): [M+H]$^+$ calcd for C$_{24}$H$_{20}$Cl$_2$NO$_4$ 456.0769, found 456.0772.

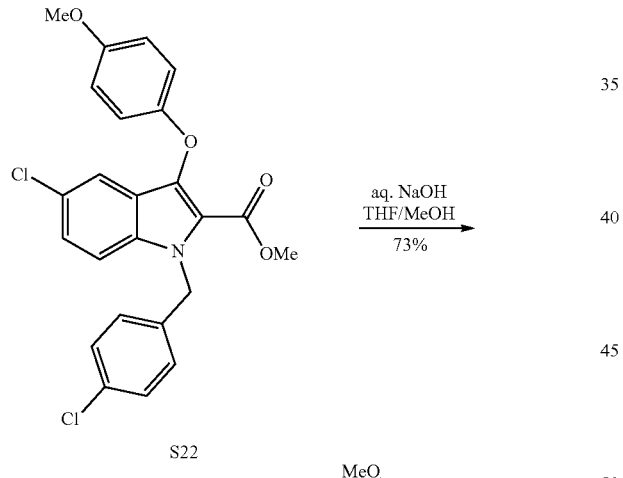

S22

S23

5-chloro-1-(4-chlorobenzyl)-3-(4-methoxyphenoxy)-1H-indole-2-carboxylic acid (S23). Using general procedure I, methyl ester S73 (9 mg, 0.019 mmol) yielded the title compound as a white solid (6 mg, 73% yield). $^1$H NMR (500 MHz, Acetone) δ 7.62 (dd, J=8.6, 1.1 Hz, 1H), 7.39-7.25 (m, 4H), 7.15 (d, J=8.3 Hz, 2H), 7.03-6.90 (m, 2H), 6.91-6.80 (m, 2H), 5.93 (s, 2H), 3.75 (s, 3H); $^{13}$C NMR (150 MHz, Acetone) δ 162.20, 156.13, 153.66, 140.22, 138.34, 136.08, 133.37, 129.48, 129.08, 127.22, 126.77, 121.43, 120.00, 119.67, 117.61, 115.46, 113.96, 55.88, 47.85; HRMS APCI (m/z): [M−H]$^-$ calcd for C$_{23}$H$_{16}$Cl$_2$NO$_4$ 440.0456, found 440.0460.

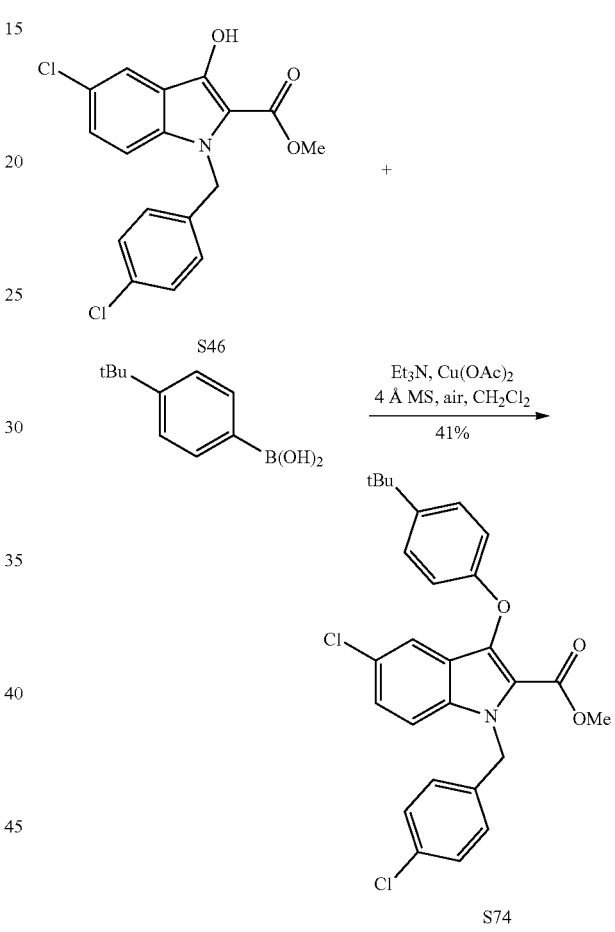

Methyl 3-(4-(tert-butyl)phenoxy)-5-chloro-1-(4-chlorobenzyl)-1H-indole-2-carboxylate (S74). Using general procedure H, hydroxyindole S46 (60 mg, 0.171 mmol) yielded the title compound as a yellow oil (37 mg, 45% yield). $^1$H NMR (400 MHz, CDCl$_3$) δ 7.44-7.37 (m, 1H), 7.35-7.20 (m, 6H), 7.00 (dd, J=12.1, 8.7 Hz, 2H), 6.92-6.86 (m, 2H), 5.76 (s, 2H), 3.73 (s, 3H), 1.32 (s, 9H); $^{13}$C NMR (100 MHz, CDCl$_3$) δ 161.63, 156.57, 145.30, 139.42, 136.38, 135.13, 133.33, 129.03, 127.65, 127.11, 126.70, 126.48, 120.97, 119.74, 118.49, 115.14, 112.03, 52.02, 47.62, 34.35, 31.64; HRMS APCI (m/z): [M+H]$^+$ calcd for C$_{27}$H$_{26}$Cl$_2$NO$_3$ 482.1290, found 482.1288.

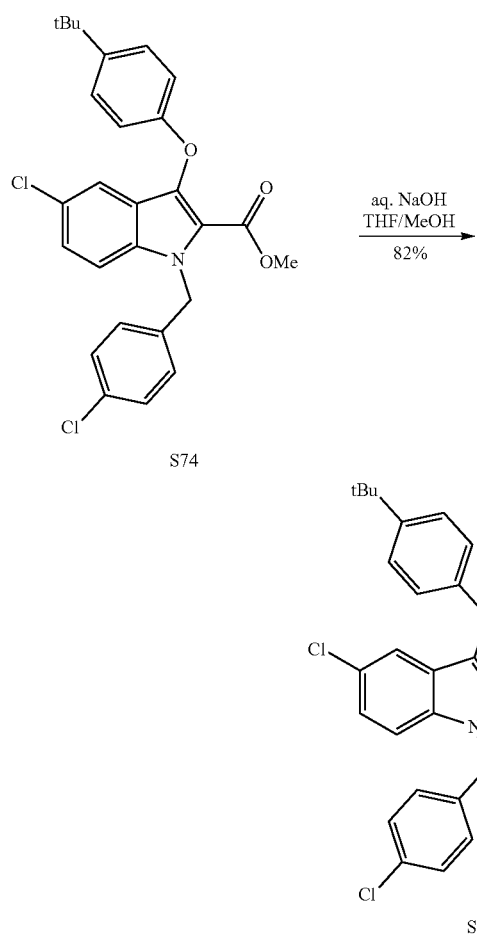

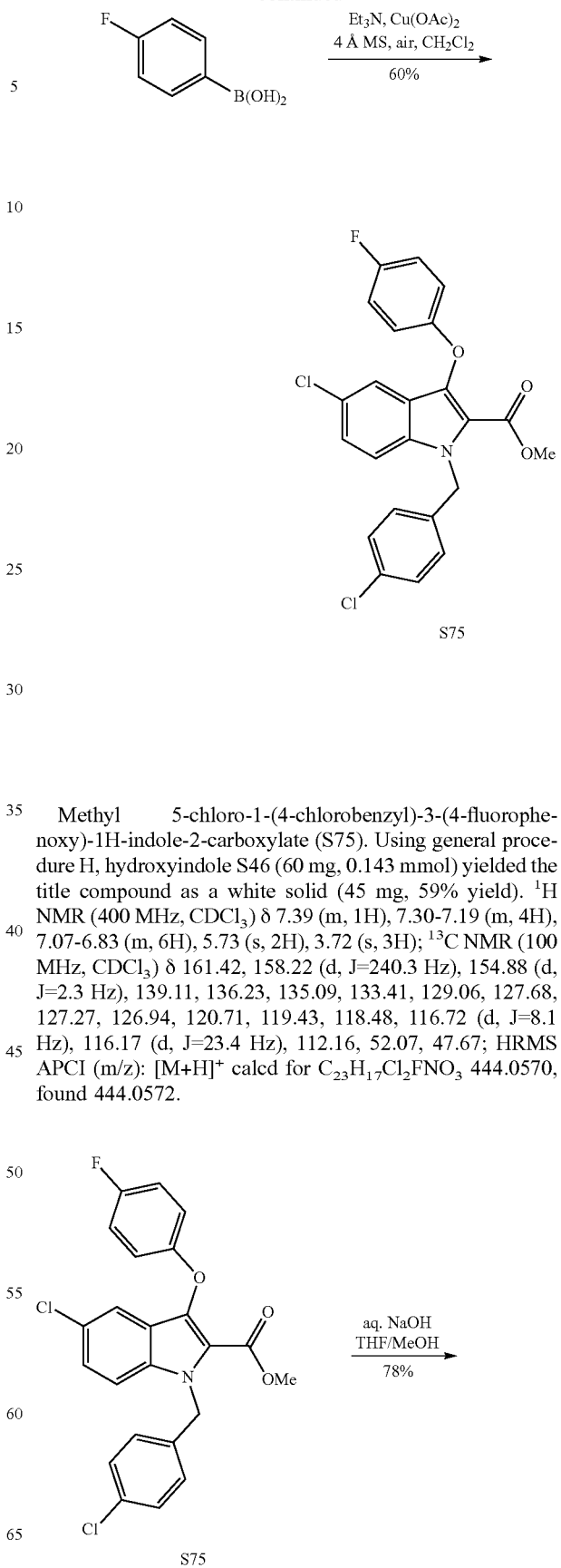

3-(4-(tert-butyl)phenoxy)-5-chloro-1-(4-chlorobenzyl)-1H-indole-2-carboxylic acid (S24). Using general procedure I, methyl ester S74 (24 mg, 0.038 mmol) yielded the title compound as a white solid (19 mg, 82% yield). $^1$H NMR (300 MHz, Acetone) δ 7.65 (dd, J=8.8, 0.8 Hz, 1H), 7.40-7.30 (m, 6H), 7.20-7.12 (m, 2H), 6.96-6.87 (m, 2H), 5.94 (s, 2H), 1.29 (s, 9H); $^{13}$C NMR (75 MHz, Acetone) δ 162.13, 157.60, 145.66, 139.51, 138.28, 135.98, 133.32, 129.45, 129.02, 127.24, 127.18, 126.84, 121.60, 120.18, 119.51, 115.85, 113.95, 47.83, 34.70, 31.77; HRMS APCI (m/z): [M+H]$^+$ calcd for $C_{26}H_{24}Cl_2NO_3$ 468.1133, found 468.1136.

Methyl 5-chloro-1-(4-chlorobenzyl)-3-(4-fluorophenoxy)-1H-indole-2-carboxylate (S75). Using general procedure H, hydroxyindole S46 (60 mg, 0.143 mmol) yielded the title compound as a white solid (45 mg, 59% yield). $^1$H NMR (400 MHz, CDCl$_3$) δ 7.39 (m, 1H), 7.30-7.19 (m, 4H), 7.07-6.83 (m, 6H), 5.73 (s, 2H), 3.72 (s, 3H); $^{13}$C NMR (100 MHz, CDCl$_3$) δ 161.42, 158.22 (d, J=240.3 Hz), 154.88 (d, J=2.3 Hz), 139.11, 136.23, 135.09, 133.41, 129.06, 127.68, 127.27, 126.94, 120.71, 119.43, 118.48, 116.72 (d, J=8.1 Hz), 116.17 (d, J=23.4 Hz), 112.16, 52.07, 47.67; HRMS APCI (m/z): [M+H]$^+$ calcd for $C_{23}H_{17}Cl_2FNO_3$ 444.0570, found 444.0572.

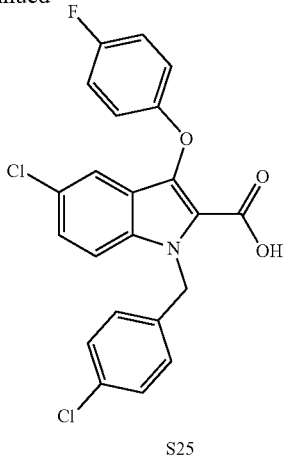

5-chloro-1-(4-chlorobenzyl)-3-(4-fluorophenoxy)-1H-indole-2-carboxylic acid (S25). Using general procedure I, methyl ester S75 (26 mg, 0.058 mmol) yielded the title compound as a white-yellow solid (20 mg, 78% yield). $^1$H NMR (300 MHz, Acetone) δ 7.66 (dd, J=8.9, 0.7 Hz, 1H), 7.39 (dd, J=2.1, 0.7 Hz, 1H), 7.37-7.27 (m, 3H), 7.21-6.96 (m, 6H), 5.94 (s, 2H); $^{13}$C NMR (100 MHz, Acetone) δ 162.00, 158.88 (d, J=238.1 Hz), 156.03 (d, J=2.0 Hz), 139.34, 138.21, 135.96, 133.35, 129.46, 129.05, 127.34, 127.03, 121.38, 120.21, 119.35, 117.78 (d, J=8.4 Hz), 116.73 (d, J=23.7 Hz), 114.02, 47.89; HRMS APCI (m/z): [M–H]$^-$ calcd for C$_{22}$H$_{13}$Cl$_2$FNO$_3$ 428.0257, found 428.0264.

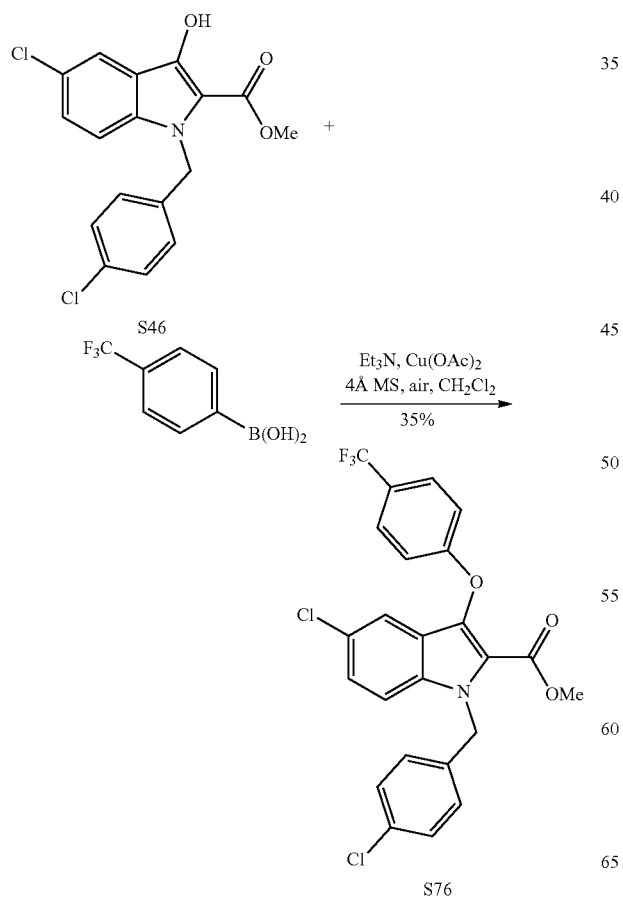

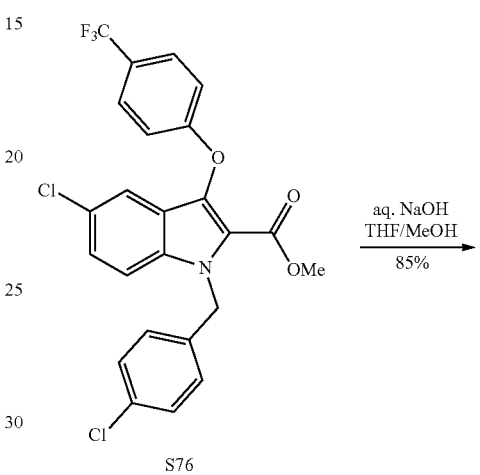

Methyl 5-chloro-1-(4-chlorobenzyl)-3-(4-(trifluoromethyl)phenoxy)-1H-indole-2-carboxylate (S76). Using general procedure H, hydroxyindole S46 (100 mg, 0.286 mmol) yielded the title compound as a white solid (50 mg, 35% yield). $^1$H NMR (400 MHz, Acetone) δ 7.79-7.60 (m, 3H), 7.50 (dd, J=2.1, 0.6 Hz, 1H), 7.44-7.27 (m, 2H), 7.24-7.10 (m, 3H), 5.94 (s, 2H), 3.68 (s, 3H); $^{13}$C NMR (150 MHz, Acetone) δ 160.76, 159.18, 138.50, 137.83, 137.15, 135.03, 132.55, 128.62, 128.15, 126.69, 126.43, 120.54, 118.99, 118.37, 118.06, 113.21, 84.21, 51.27, 47.19; HRMS ESI (m/z): [M+H]$^+$ calcd for C$_{24}$H$_{17}$O$_3$NCl$_2$F$_3$ 494.0532, found 494.0536.

5-chloro-1-(4-chlorobenzyl)-3-(4-(trifluoromethyl)phenoxy)-1H-indole-2-carboxylic acid (S26). Using general procedure I, methyl ester S76 (25 mg, 0.051 mmol) yielded the title compound as a white solid (21 mg, 85% yield). $^1$H NMR (600 MHz, Acetone) δ 7.68 (dd, J=8.8, 6.2 Hz, 3H), 7.48 (d, J=2.1 Hz, 1H), 7.42-7.27 (m, 3H), 7.17 (dd, J=8.5, 4.4 Hz, 4H), 5.96 (s, 2H); $^{13}$C NMR (150 MHz, Acetone) δ 161.79, 160.91, 137.24, 135.04, 132.53, 128.61, 128.19, 127.08 (q, J=3.8 Hz), 125.59, 124.56 (q, J=270.6 Hz), 123.67 (q, J=32.5 Hz), 120.51, 119.55, 118.22, 115.83, 113.24, 47.10; HRMS ESI (m/z): [M+Na]$^+$ calcd for C$_{23}$H$_{14}$O$_3$NCl$_2$F$_3$Na 502.0201, found 502.0198.

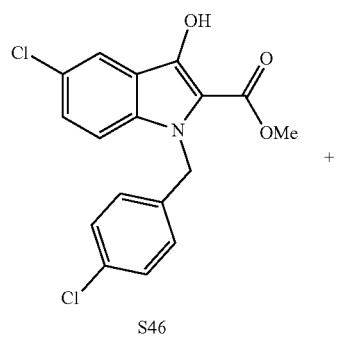
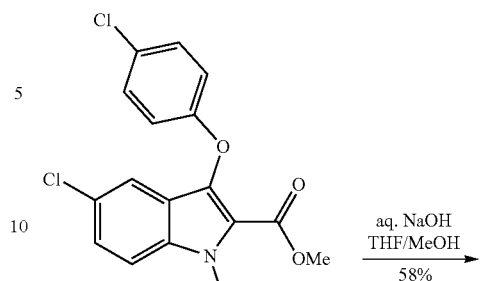
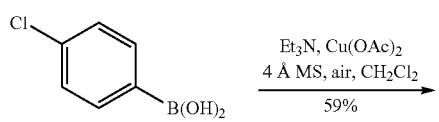
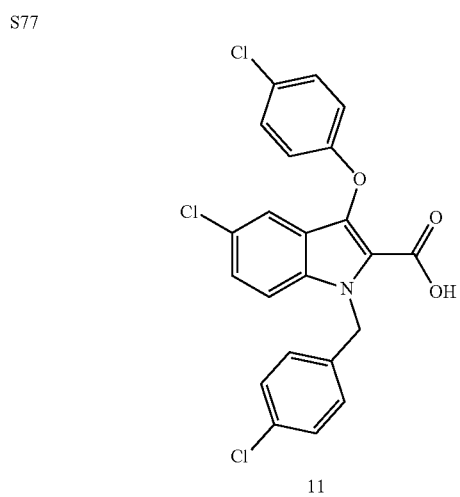
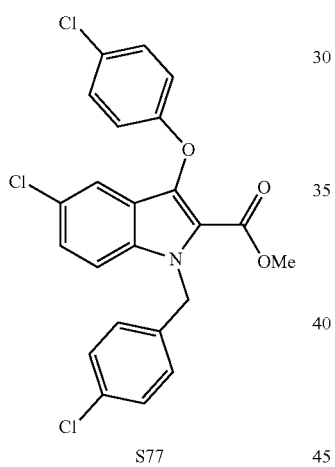

Methyl 5-chloro-1-(4-chlorobenzyl)-3-(4-chlorophenoxy)-1H-indole-2-carboxylate (S77). Using general procedure H, hydroxyindole S46 (50 mg, 0.143 mmol) yielded the title compound as a white-yellow solid (39 mg, 59% yield). $^1$H NMR (500 MHz, CDCl$_3$) δ 7.42 (t, J=1.4 Hz, 1H), 7.28 (d, J=1.4 Hz, 2H), 7.27-7.20 (m, 4H), 7.01-6.95 (m, 2H), 6.91-6.84 (m, 2H), 5.75 (s, 2H), 3.72 (s, 3H); $^{13}$C NMR (125 MHz, CDCl$_3$) δ 161.32, 157.54, 138.54, 136.19, 135.07, 133.46, 129.65, 129.07, 127.70, 127.43, 127.34, 127.09, 120.71, 119.31, 118.57, 116.87, 112.20, 52.07, 47.69; HRMS APCI (m/z): [M+H]$^+$ calcd for C$_{23}$H$_{17}$Cl$_3$NO$_3$ 460.0274, found 460.0275.

5-chloro-1-(4-chlorobenzyl)-3-(4-chlorophenoxy)-1H-indole-2-carboxylic acid (11). Using general procedure I, methyl ester S77 (39 mg, 0.084 mmol) yielded the title compound as a white solid (22 mg, 58% yield). $^1$H NMR (400 MHz, Acetone) δ 7.66 (dt, J=9.0, 1.0 Hz, 1H), 7.40 (ddd, J=23.3, 2.1, 0.9 Hz, 2H), 7.37-7.28 (m, 4H), 7.20-7.12 (m, 2H), 7.05-6.96 (m, 2H), 5.94 (s, 2H); $^{13}$C NMR (100 MHz, Acetone) δ 161.90, 158.72, 138.71, 138.16, 135.92, 133.35, 130.29, 129.46, 129.04, 127.42, 127.40, 127.16, 121.36, 120.27, 119.24, 117.96, 114.06, 47.90; HRMS APCI (m/z): [M−H]$^-$ calcd for C$_{22}$H$_{13}$Cl$_3$NO$_3$ 443.9961, found 443.9934.

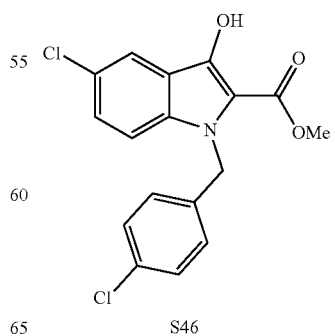

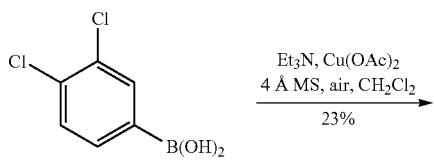

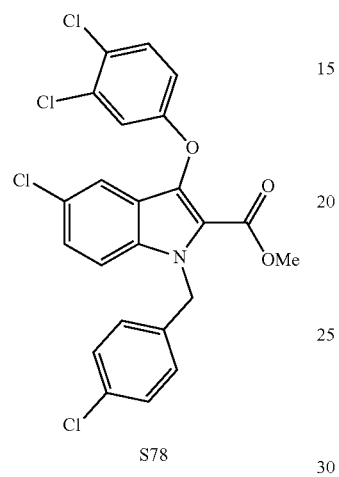

Methyl 5-chloro-1-(4-chlorobenzyl)-3-(3,4-dichlorophenoxy)-1H-indole-2-carboxylate (S78). Using general procedure H, hydroxyindole S46 (150 mg, 0.428 mmol) yielded the title compound as a tan solid (49 mg, 23% yield). $^1$H NMR (600 MHz, Acetone) δ 7.75-7.62 (m, 1H), 7.53-7.51 (m, 1H), 7.50 (d, J=8.9 Hz, 1H), 7.38 (dd, J=9.0, 2.1 Hz, 1H), 7.35-7.32 (m, 2H), 7.20 (d, J=2.9 Hz, 1H), 7.18-7.15 (m, 2H), 6.98 (dd, J=8.9, 2.9 Hz, 1H), 5.92 (s, 2H), 3.72 (s, 3H); $^{13}$C NMR (150 MHz, Acetone) δ 161.50, 159.27, 138.23, 138.00, 135.94, 133.49, 133.32, 132.04, 129.52, 129.09, 127.72, 127.56, 125.85, 121.28, 120.01, 119.15, 118.50, 116.67, 114.18, 52.27, 48.19; HRMS APCI (m/z): [M+Cl]$^-$ calcd for C$_{23}$H$_{15}$Cl$_5$NO$_3$ 527.9495, found 527.9511.

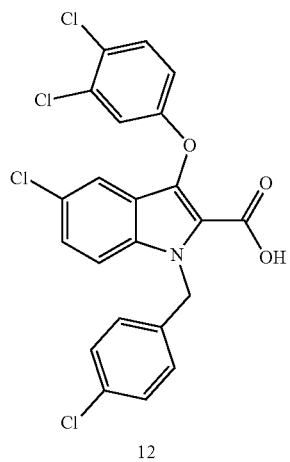

5-chloro-1-(4-chlorobenzyl)-3-(3,4-dichlorophenoxy)-1H-indole-2-carboxylic acid (12). Using general procedure I, methyl ester S78 (21 mg, 0.043 mmol) yielded the title compound as a white solid (14 mg, 67% yield). $^1$H NMR (600 MHz, Acetone) δ 7.67 (d, J=9.0 Hz, 1H), 7.53-7.49 (m, 1H), 7.49 (d, J=8.9 Hz, 1H), 7.37 (dd, J=9.0, 2.0 Hz, 1H), 7.35-7.31 (m, 2H), 7.20 (d, J=2.9 Hz, 1H), 7.19-7.15 (m, 2H), 6.98 (dd, J=8.9, 2.9 Hz, 1H), 5.95 (s, 2H); $^{13}$C NMR (150 MHz, Acetone) δ 161.87, 159.34, 138.17, 137.98, 135.88, 133.43, 133.26, 132.00, 129.49, 129.14, 127.49, 127.42, 125.66, 121.34, 120.73, 119.09, 118.48, 116.63, 114.15, 48.02; HRMS APCI (m/z): [M−H]$^-$ calcd for C$_{22}$H$_{12}$Cl$_4$NO$_3$ 477.9571, found 477.9584.

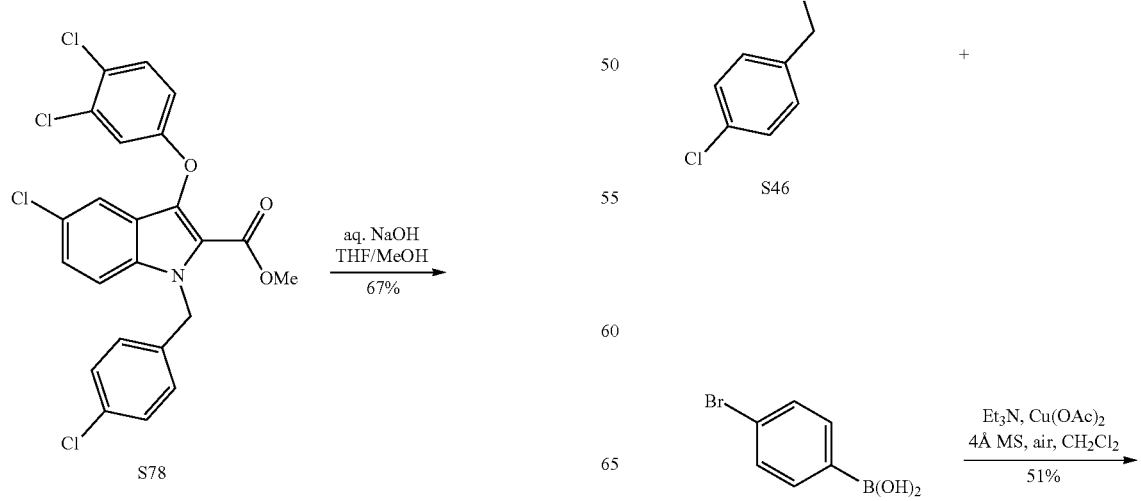

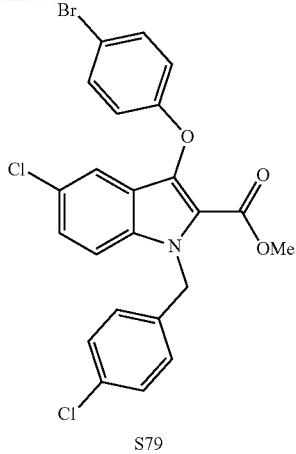

S79

Methyl 3-(4-bromophenoxy)-5-chloro-1-(4-chlorobenzyl)-1H-indole-2-carboxylate (S79). Using general procedure H, hydroxyindole S46 (100 mg, 0.286 mmol) yielded the title compound as a white solid (29 mg, 20% yield). $^1$H NMR (400 MHz, Acetone) δ 7.68 (dd, J=9.0, 0.7 Hz, 1H), 7.51-7.46 (m, 2H), 7.44 (dd, J=2.1, 0.6 Hz, 1H), 7.38 (d, J=2.1 Hz, 1H), 7.35-7.32 (m, 2H), 7.18-7.12 (m, 2H), 6.98-6.92 (m, 2H), 5.92 (s, 2H), 3.70 (s, 3H); $^{13}$C NMR (150 MHz, Acetone) δ 160.77, 158.40, 137.93, 137.15, 135.03, 132.55, 132.45, 128.62, 128.15, 126.70, 126.43, 120.53, 118.96, 118.39, 117.62, 114.07, 113.21, 51.30, 47.19; HRMS ESI (m/z): [M+H]$^+$ calcd for $C_{23}H_{17}BrCl_2NO_3$ 503.9769, found 503.9764.

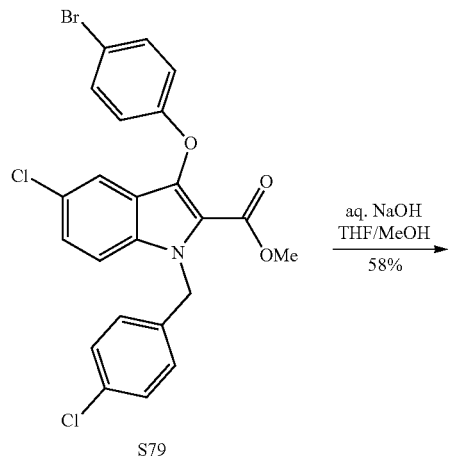

S79 aq. NaOH
THF/MeOH
→
58%

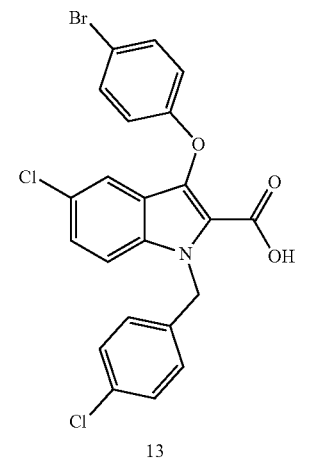

13

3-(4-bromophenoxy)-5-chloro-1-(4-chlorobenzyl)-1H-indole-2-carboxylic acid (13). Using general procedure I, methyl ester S79 (25 mg, 0.050 mmol) yielded the title compound as a white solid (14 mg, 58% yield). $^1$H NMR (400 MHz, Acetone) δ 7.67 (d, J=9.0 Hz, 1H), 7.51-7.41 (m, 3H), 7.38-7.31 (m, 3H), 7.20-7.13 (m, 2H), 6.99-6.94 (m, 2H), 5.95 (s, 2H); $^{13}$C NMR (150 MHz, Acetone) δ 161.08, 158.38, 137.68, 137.31, 135.00, 132.49, 132.38, 128.58, 128.20, 126.46, 126.29, 120.54, 119.63, 118.33, 117.59, 113.90, 113.17, 47.04; HRMS ESI (m/z): [M+H]$^+$ calcd for $C_{22}H_{15}O_3NBrCl_2$ 489.9607 and 491.9607, found 489.9611 and 491.9582.

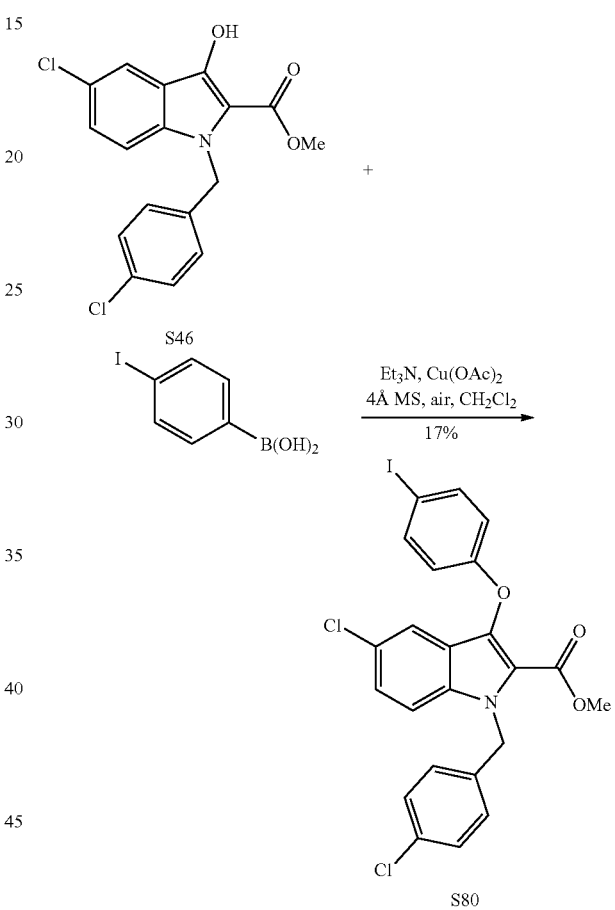

Methyl 5-chloro-1-(4-chlorobenzyl)-3-(4-iodophenoxy)-1H-indole-2-carboxylate (S80). Using general procedure H, hydroxyindole S46 (100 mg, 0.286 mmol) yielded the title compound as a white solid (27 mg, 17% yield). $^1$H NMR (400 MHz, Acetone) δ 7.70-7.61 (m, 3H), 7.44 (dd, J=2.1, 0.6 Hz, 1H), 7.36 (dd, J=9.0, 2.1 Hz, 1H), 7.35-7.30 (m, 2H), 7.17-7.12 (m, 2H), 6.86-6.81 (m, 2H), 5.91 (s, 2H), 3.70 (s, 3H); $^{13}$C NMR (100 MHz, Acetone) δ 161.63, 160.04, 139.37, 138.69, 138.02, 135.90, 133.42, 129.49, 129.02, 127.57, 127.30, 121.40, 119.84, 119.26, 118.93, 114.08, 85.11, 52.18, 48.06; HRMS ESI (m/z): [M+H]$^+$ calcd for $C_{23}H_{17}O_3NCl_2I$ 551.9625, found 551.9628.

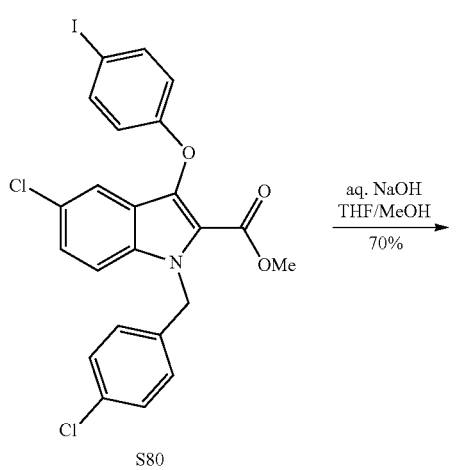

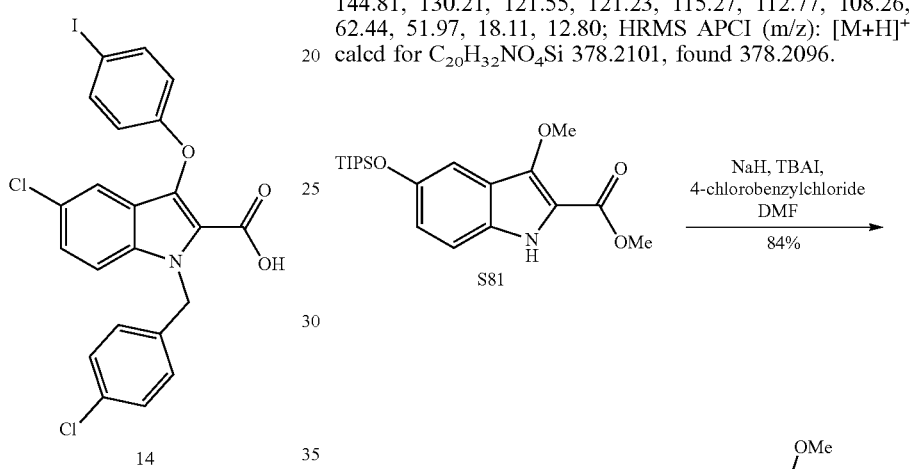

hydroxybenzoate (1.34 g, 8.75 mmol) in DMF (10 mL) was added imidazole (2.38 g, 35.00 mmol) and TIPSCl (3.42 mL, 15.97 mmol). The reaction was stirred at room temperature overnight. The following day, the reaction was poured into water and EtOAc. The aqueous layer was extracted with EtOAc 3×. The combined organic layers were washed with water and brine, dried over MgSO₄, filtered, concentrated, and purified by column chromatography. The product (3.52 g, yellow oil) was contaminated with side-products from the silyl reagent, and carried to the next step. Using general procedure E, the aniline methyl ester yielded the corresponding hydroxyindole as a tan solid (491 mg). Then, using general procedure F, the hydroxyindole yielded the title compound as a white solid (422 mg, 13% yield over 4 steps). $^1$H NMR (600 MHz, CDCl₃) δ 8.21 (br s, 1H), 7.16 (dd, J=5.6, 2.9 Hz, 2H), 6.95 (dd, J=9.0, 2.2 Hz, 1H), 4.08 (s, 3H), 3.95 (s, 3H), 1.32-1.24 (m, 3H), 1.12 (d, J=7.4 Hz, 18H); $^{13}$C NMR (150 MHz, CDCl₃) δ 161.86, 149.95, 144.81, 130.21, 121.55, 121.23, 115.27, 112.77, 108.26, 62.44, 51.97, 18.11, 12.80; HRMS APCI (m/z): [M+H]⁺ calcd for C₂₀H₃₂NO₄Si 378.2101, found 378.2096.

5-chloro-1-(4-chlorobenzyl)-3-(4-iodophenoxy)-1H-indole-2-carboxylic acid (14). Using general procedure I, methyl ester S80 (27 mg, 0.049 mmol) yielded the title compound as a white solid (18 mg, 70% yield). $^1$H NMR (600 MHz, Acetone) δ 7.73-7.60 (m, 3H), 7.44 (d, J=2.1 Hz, 1H), 7.39-7.31 (m, 3H), 7.20-7.13 (m, 2H), 6.91-6.82 (m, 2H), 5.96 (s, 2H); $^{13}$C NMR (150 MHz, Acetone) δ 161.01, 159.16, 138.45, 137.65, 137.29, 135.04, 132.49, 128.59, 128.17, 126.52, 126.31, 120.52, 119.47, 118.35, 118.03, 113.18, 84.02, 47.04; HRMS ESI (m/z): [M+H]⁺ calcd for C₂₂H₁₅O₃NCl₂I 537.9474, found 537.9471.

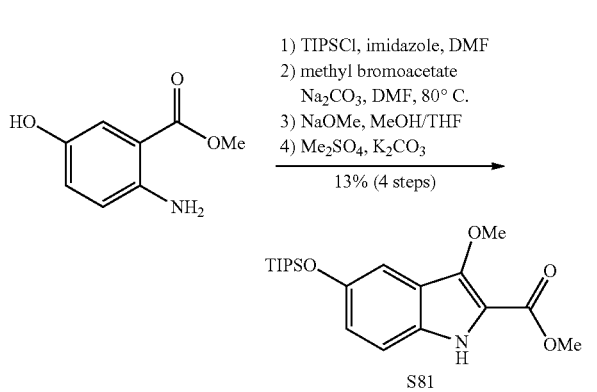

Methyl 3-methoxy-5-((triisopropylsilyl)oxy)-1H-indole-2-carboxylate (S81). To a solution of methyl 2-amino-5-

Methyl 1-(4-chlorobenzyl)-3-methoxy-5-((triisopropylsilyl)oxy)-1H-indole carboxylate (S82). Using general procedure C, indole S81 (200 mg, 0.530 mmol) yielded the title compound as a yellow oil (222 mg, 84% yield). $^1$H NMR (500 MHz, CDCl₃) δ 7.23 (d, J=2.4 Hz, 1H), 7.23-7.20 (m, 2H), 7.14 (d, J=9.0 Hz, 1H), 7.00-6.95 (m, 3H), 5.64 (s, 2H), 4.06 (s, 3H), 3.90 (s, 3H), 1.32 (hept, J=7.3 Hz, 3H), 1.15 (d, J=7.4 Hz, 18H); $^{13}$C NMR (125 MHz, CDCl₃) δ 162.04, 150.08, 145.96, 137.14, 132.83, 132.74, 128.69, 127.67, 121.43, 120.14, 116.48, 111.25, 108.04, 62.59, 51.60, 47.38, 18.02, 12.71; HRMS APCI (m/z): [M+H]⁺ calcd for C₂₇H₃₇ClNO₄Si 502.2180, found 502.2179.

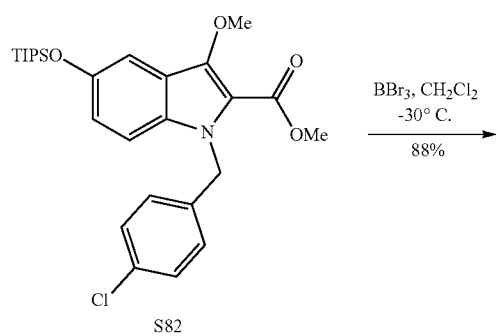

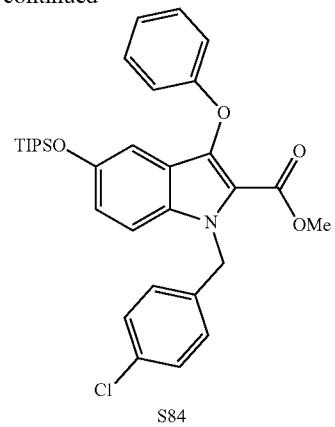

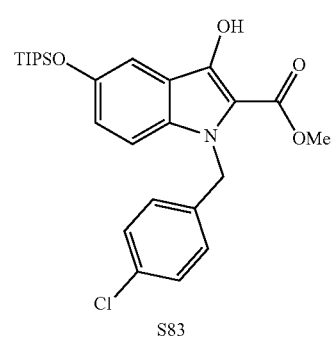

Methyl 1-(4-chlorobenzyl)-3-hydroxy-5-((triisopropylsilyl)oxy)-1H-indole-2-carboxylate (S83). Using general procedure G, methyl ether S82 (222 mg, 0.442 mmol) yielded the title compound as a green-yellow oil (189 mg, 88% yield). $^1$H NMR (500 MHz, CDCl$_3$) δ 8.53 (s, 1H), 7.24-7.18 (m, 3H), 7.07 (dd, J=9.1, 0.7 Hz, 1H), 7.00 (dd, J=9.0, 2.4 Hz, 1H), 6.96-6.88 (m, 2H), 5.47 (s, 2H), 3.88 (s, 3H), 1.30 (hept, J=7.5 Hz, 3H), 1.13 (d, J=7.4 Hz, 18H); $^{13}$C NMR (125 MHz, CDCl$_3$) δ 164.19, 149.66, 148.59, 137.28, 133.79, 132.98, 128.79, 127.59, 123.09, 117.25, 110.96, 109.44, 108.21, 51.58, 47.64, 18.08, 12.74; HRMS APCI (m/z): [M+H]$^+$ calcd for C$_{26}$H$_{35}$ClNO$_4$Si 488.2024, found 488.2023.

Methyl 1-(4-chlorobenzyl)-3-phenoxy-5-((triisopropylsilyl)oxy)-1H-indole carboxylate (S84). Using general procedure H, hydroxyindole S83 (189 mg, 0.387 mmol) yielded the title compound as a yellow solid (149 mg, 68% yield). $^1$H NMR (500 MHz, CDCl$_3$) δ 7.20-7.14 (m, 2H), 7.14-7.10 (m, 2H), 7.07 (d, J=9.1 Hz, 1H), 6.95-6.87 (m, 5H), 6.85 (dd, J=9.0, 2.4 Hz, 1H), 6.66 (d, J=2.3 Hz, 1H), 5.61 (s, 2H), 3.62 (s, 3H), 1.04 (hept, J=7.1 Hz, 3H), 0.91 (d, J=7.4 Hz, 18H); $^{13}$C NMR (125 MHz, CDCl$_3$) δ 161.94, 158.92, 150.39, 139.69, 136.99, 133.08, 132.78, 129.53, 128.90, 127.74, 122.37, 121.78, 120.10, 117.44, 116.27, 111.45, 108.29, 51.78, 47.53, 17.99, 12.61; HRMS APCI (m/z): [M−H+Na$_2$]$^+$ calcd for C$_{32}$H$_{37}$ClNO$_4$Na$_2$Si 608.1976, found 608.1885.

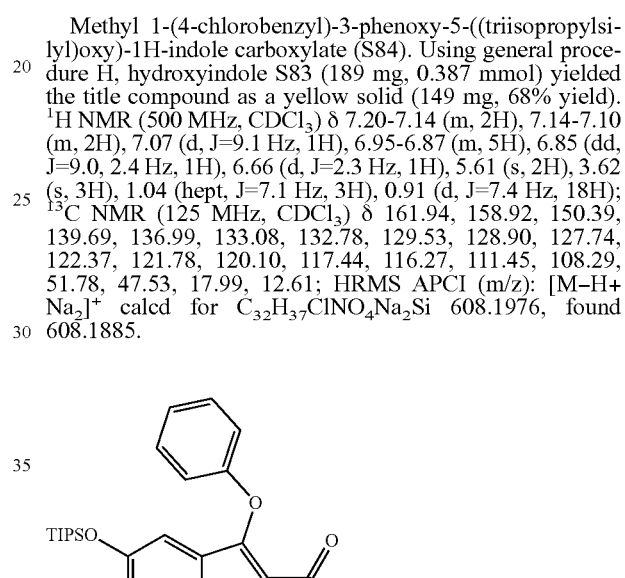

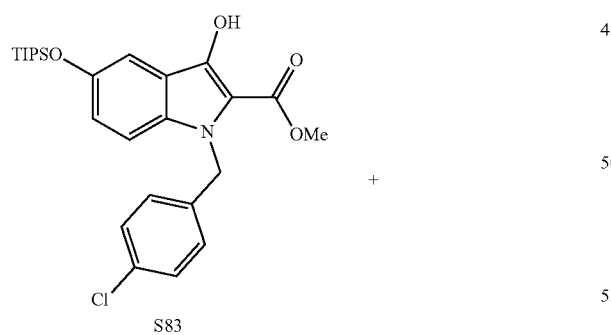

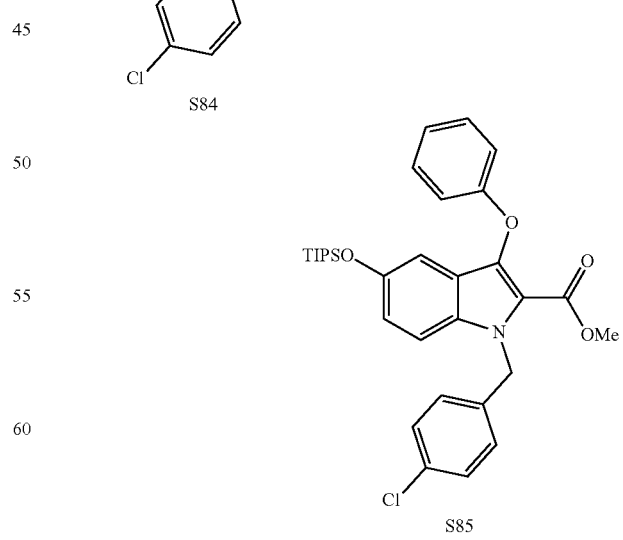

Methyl 1-(4-chlorobenzyl)-5-hydroxy-3-phenoxy-1H-indole-2-carboxylate (S85). Silyl ether S84 (75 mg, 0.132 mmol) was dissolved in THF (2 mL) and TBAF (1M in THF, 0.26 mL, 0.26 mmol) was added. After stirring for an hour at room temperature, sat. NH₄Cl was added and the aqueous layer was extracted with Et₂O 3×. The combined organic layers were washed with brine, dried over Mg₂SO₄, filtered, concentrated, and purified by column chromatography, yielding the title compound as a tan oil (40 mg, 75% yield). $^1$H NMR (400 MHz, Acetone) δ 8.16 (s, 1H), 7.49-7.37 (m, 1H), 7.36-7.23 (m, 4H), 7.19-7.07 (m, 2H), 7.08-6.92 (m, 4H), 6.73 (dd, J=2.4, 0.7 Hz, 1H), 5.84 (s, 2H), 3.66 (s, 3H); $^{13}$C NMR (125 MHz, CDCl₃) δ 161.87, 158.94, 150.29, 139.07, 136.84, 133.17, 132.66, 129.63, 128.96, 127.71, 122.28, 120.40, 118.04, 117.62, 115.76, 112.01, 103.52, 51.89, 47.58; HRMS APCI (m/z): [M+H]⁺ calcd for C₂₃H₁₉ClNO₄ 408.1003, found 408.1001.

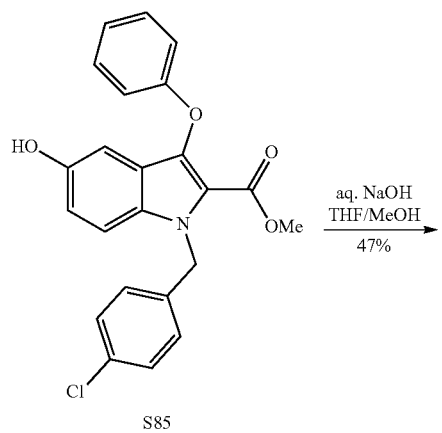

1-(4-chlorobenzyl)-5-hydroxy-3-phenoxy-1H-indole-2-carboxylic acid (S27). Using general procedure I, methyl ester S85 (20 mg, 0.050 mmol) yielded the title compound as a white-tan solid (9 mg, 47% yield). $^1$H NMR (500 MHz, Acetone) δ 7.44 (d, J=9.1 Hz, 1H), 7.35-7.26 (m, 4H), 7.15 (dd, J=8.7, 2.3 Hz, 2H), 7.05-6.98 (m, 1H), 7.00-6.92 (m, 3H), 6.68 (d, J=2.3 Hz, 1H), 5.88 (s, 2H); $^{13}$C NMR (125 MHz, Acetone) δ 162.61, 159.97, 152.78, 139.21, 138.95, 133.15, 132.93, 130.31, 129.37, 129.09, 122.71, 121.19, 119.26, 118.36, 116.44, 113.11, 102.99, 47.65; HRMS APCI (m/z): [M−H]⁻ calcd for C₂₂H₁₅ClNO₄ 392.0690, found 392.0697.

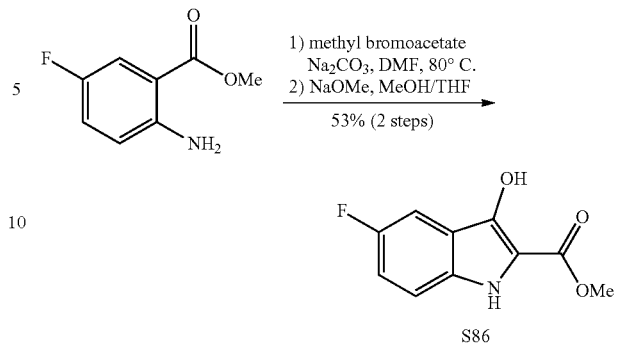

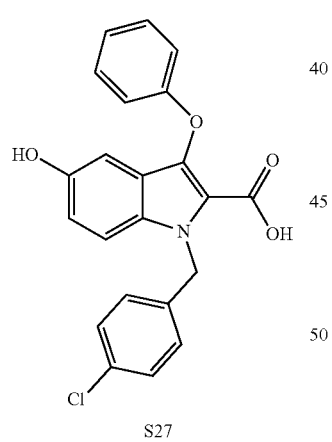

Methyl 5-fluoro-3-hydroxy-1H-indole-2-carboxylate (S86). Using general procedure E, methyl 2-amino-5-fluorobenzoate (5.00 g, 29.6 mmol) yielded the title compound as a yellow solid (3.31 g, 53% yield over two steps). $^1$H NMR (400 MHz, Acetone) δ 10.13 (s, 1H), 8.23 (s, 1H), 7.41 (ddd, J=9.0, 4.3, 0.6 Hz, 1H), 7.32 (dd, J=9.1, 2.6 Hz, 1H), 7.13 (td, J=9.2, 2.6 Hz, 1H), 3.91 (s, 3H); $^{13}$C NMR (150 MHz, Acetone) δ 163.82, 157.89 (d, J=233.5 Hz), 145.79 (d, J=5.6 Hz), 133.20, 118.43 (d, J=9.9 Hz), 116.27 (d, J=27.5 Hz), 114.78 (d, J=9.8 Hz), 111.18, 104.34 (d, J=24.2 Hz), 51.76; HRMS APCI (m/z): [M+H]⁺ calcd for C₁₀H₉FNO₃ 210.0566, found 210.0563.

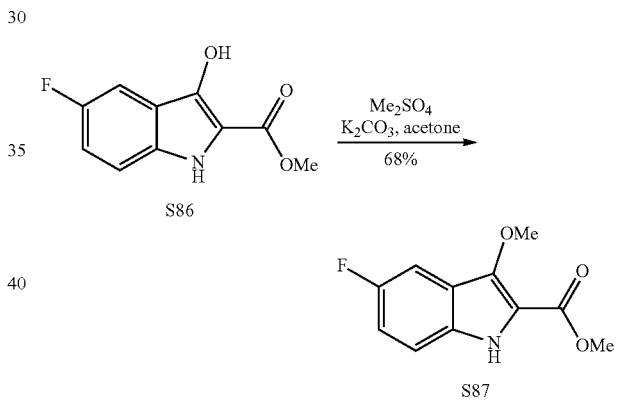

Methyl 5-fluoro-3-methoxy-1H-indole-2-carboxylate (S87). Using general procedure F, hydroxyindole S86 (3.31 g, 15.83 mmol) yielded the title compound as a green-brown solid (2.41 g, 68% yield). $^1$H NMR (400 MHz, Acetone) δ 10.44 (s, 1H), 7.47 (dd, J=9.0, 4.4 Hz, 1H), 7.39 (dd, J=9.3, 2.5 Hz, 1H), 7.11 (td, J=9.2, 2.5 Hz, 1H), 4.04 (s, 3H), 3.89 (s, 3H); $^{13}$C NMR (150 MHz, Acetone) δ 161.73, 158.31 (d, J=234.7 Hz), 145.52 (d, J=5.5 Hz), 132.16, 121.29 (d, J=9.9 Hz), 117.39, 115.51 (d, J=27.5 Hz), 114.95 (d, J=9.0 Hz), 104.45 (d, J=24.3 Hz), 62.56, 51.85; HRMS APCI (m/z): [M+H]⁺ calcd for C₁₁H₁₁FNO₃ 224.0723, found 224.0720.

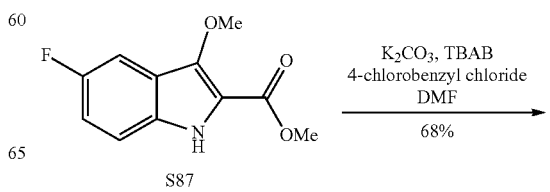

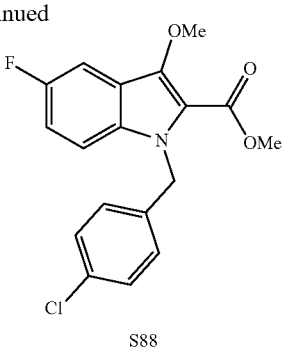

S88

Methyl 1-(4-chlorobenzyl)-5-fluoro-3-methoxy-1H-indole-2-carboxylate (S88). Indole S87 (1.00 g, 4.48 mmol), K$_2$CO$_3$ (1.24 g, 8.96 mmol), 4-chlorobenzyl chloride (1.44 g, 8.96 mmol) and TBAB (145 mg, 0.448 mmol) in DMF (20 mL) was stirred at 80° C. overnight. The reaction was quenched with water and extracted with EtOAc 3×. The combined organic layers were washed with brine, dried over Na$_2$SO$_4$, filtered concentrated and purified by column chromatography, yielding the title compound as a white-yellow solid (1.06 g, 68% yield). $^1$H NMR (400 MHz, CDCl$_3$) δ 7.41 (dd, J=8.7, 2.5 Hz, 1H), 7.35-7.29 (m, 1H), 7.23-7.20 (m, 2H), 7.07 (td, J=9.0, 2.5 Hz, 1H), 6.97-6.91 (m, 2H), 5.67 (s, 2H), 4.04 (s, 3H), 3.91 (s, 3H); $^{13}$C NMR (150 MHz, Acetone) δ 162.39, 158.60 (d, J=236.5 Hz), 146.92 (d, J=5.5 Hz), 138.53, 134.21, 133.26, 129.39, 129.02, 120.75 (d, J=9.8 Hz), 118.63, 115.85 (d, J=26.6 Hz), 113.51 (d, J=9.8 Hz), 104.86 (d, J=24.3 Hz), 62.93, 51.96, 47.86; HRMS APCI (m/z): [M+H]$^+$ calcd for C$_{18}$H$_{16}$ClFNO$_3$ 348.0803, found 348.0803.

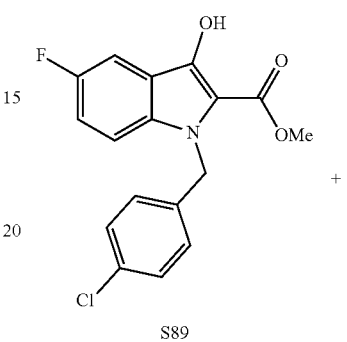

S88

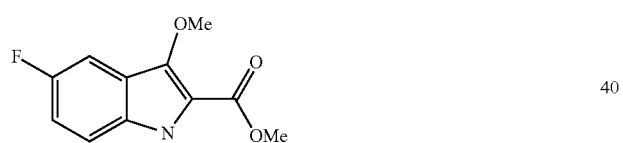

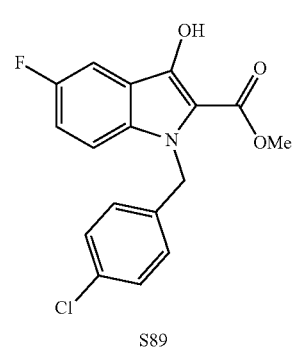

S89

Methyl 1-(4-chlorobenzyl)-5-fluoro-3-hydroxy-1H-indole-2-carboxylate (S89). Using general procedure G, methyl ether S88 (500 mg, 1.44 mmol) yielded the title compound as a grey solid (242 mg, 50% yield). $^1$H NMR (400 MHz, Acetone) δ 8.64 (s, 1H), 7.48 (dd, J=9.2, 4.1 Hz, 1H), 7.38 (dd, J=8.8, 2.6 Hz, 1H), 7.32-7.21 (m, 2H), 7.18 (td, J=9.2, 2.6 Hz, 1H), 7.13-7.03 (m, 2H), 5.69 (s, 2H), 3.91 (s, 3H); $^{13}$C NMR (100 MHz, Acetone) δ 163.90, 158.00 (d, J=235.7 Hz), 147.80 (d, J=5.5 Hz), 138.59, 135.06, 133.19, 129.32, 128.93, 117.83 (d, J=9.9 Hz), 116.95 (d, J=27.1 Hz), 113.13 (d, J=9.2 Hz), 111.27, 104.82 (d, J=24.0 Hz), 51.92, 47.80; HRMS APCI (m/z): [M+H]$^+$ calcd for C$_{17}$H$_{14}$ClFNO$_3$ 334.0646, found 334.0645.

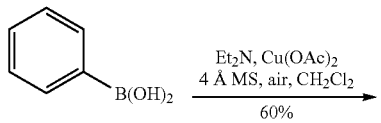

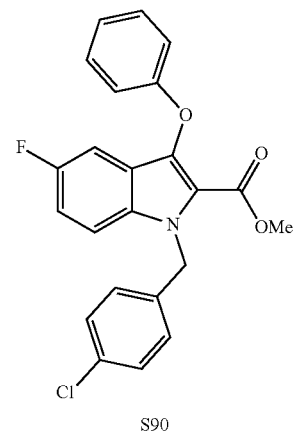

S90

Methyl 1-(4-chlorobenzyl)-5-fluoro-3-phenoxy-1H-indole-2-carboxylate (S90). Using general procedure H, hydroxyindole S89 (100 mg, 0.300 mmol) yielded the title compound as a tan solid (74 mg, 60% yield). $^1$H NMR (300 MHz, CDCl$_3$) δ 7.32-7.20 (m, 5H), 7.13-6.99 (m, 3H), 7.03-6.90 (m, 4H), 5.74 (s, 2H), 3.70 (s, 3H); $^{13}$C NMR (150 MHz, Acetone) δ 161.94, 159.92, 158.82 (d, J=237.5 Hz), 140.05 (d, J=5.5 Hz), 138.28, 134.34, 133.39, 130.46, 129.49, 129.04, 123.15, 120.78 (d, J=10.0 Hz), 119.97, 116.50, 116.18 (d, J=27.2 Hz), 113.98 (d, J=9.6 Hz), 104.61 (d, J=24.4 Hz), 52.00, 48.04; HRMS APCI (m/z): [M+H]$^+$ calcd for C$_{23}$H$_{18}$ClFNO$_3$ 410.0959, found 410.0958.

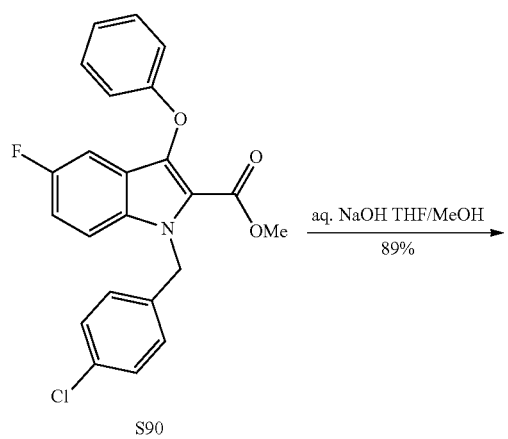

S90 aq. NaOH THF/MeOH
89%

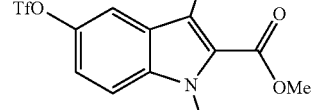
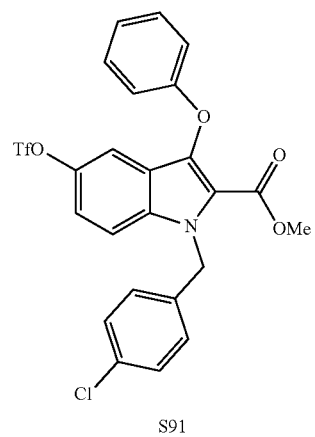

S91

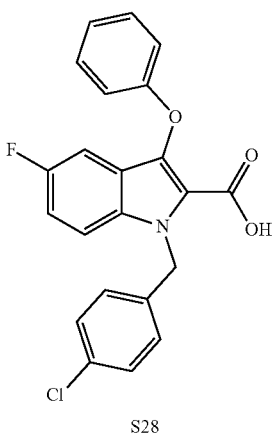

S28

1-(4-chlorobenzyl)-5-fluoro-3-phenoxy-1H-indole-2-carboxylic acid (S28). Using general procedure I, methyl ester S90 (37 mg, 0.090 mmol) yielded the title compound as a white solid (32 mg, 89% yield). $^1$H NMR (400 MHz, Acetone) δ 7.64 (dd, J=9.2, 4.2 Hz, 1H), 7.37-7.27 (m, 4H), 7.23-7.13 (m, 3H), 7.08-6.96 (m, 4H), 5.94 (s, 2H); $^{13}$C NMR (100 MHz, Acetone) δ 162.18, 159.80, 158.73 (d, J=237.2 Hz), 139.82 (d, J=5.6 Hz), 138.39, 134.34, 133.31, 130.40, 129.44, 129.05, 123.03, 120.67 (d, J=10.0 Hz), 120.42, 116.45, 116.00 (d, J=27.1 Hz), 113.94 (d, J=9.3 Hz), 104.58 (d, J=24.4 Hz), 47.88; HRMS APCI (m/z): [M+H]$^+$ calcd for $C_{22}H_{16}ClFNO_3$ 396.0803, found 396.0804.

Methyl 1-(4-chlorobenzyl)-3-phenoxy-5-((((trifluoromethyl)sulfonyl)oxy)-1H-indole-2-carboxylate (S91). To a solution of hydroxyindole S85 (24 mg, 0.060 mmol) in pyridine at 0° C. was added Tf$_2$O (12 μL, 0.072 mmol). The reaction was warmed to room temperature and after 15 minutes was diluted with Et$_2$O. The solution was quenched with 1M HCl, and the layers were separated. The organic layer was washed with sat. NaHCO$_3$. The combined aqueous layers were extracted with Et$_2$O 2×, and the combined organic layers were dried with MgSO$_4$, filtered, concentrated, and purified by column chromatography, yielding the title compound as a yellow-brown oil (29 mg, 90% yield). $^1$H NMR (300 MHz, CDCl$_3$) δ 7.38 (d, J=9.1 Hz, 1H), 7.34-7.24 (m, 5H), 7.21 (dd, J=9.1, 2.5 Hz, 1H), 7.07 (tt, J=7.4, 1.0 Hz, 1H), 7.03-6.91 (m, 4H), 5.77 (s, 2H), 3.72 (s, 3H); $^{13}$C NMR (150 MHz, Acetone) δ 161.71, 159.79, 147.45, 144.89, 141.58, 140.33, 137.90, 136.08, 133.54, 130.52, 129.56, 129.11, 123.43, 120.60, 119.66 (q, J=319.9 Hz), 116.60, 114.33, 113.01, 52.19, 48.26; HRMS APCI (m/z): [M+H]$^+$ calcd for $C_{24}H_{18}ClF_3NO_6S$ 540.0495, found 540.0492.

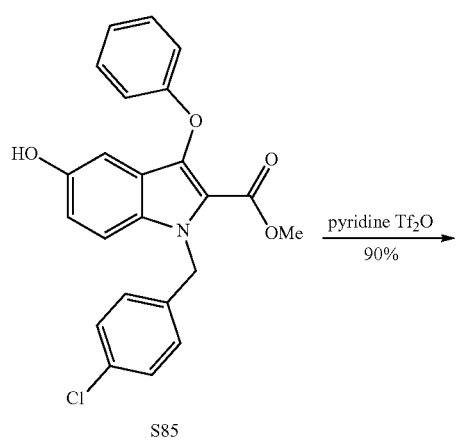

S85 pyridine Tf$_2$O
90%

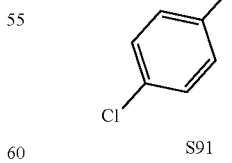

S91

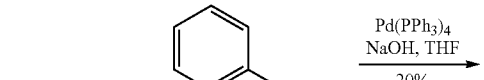

B(OH)$_2$

Pd(PPh$_3$)$_4$
NaOH, THF
20%

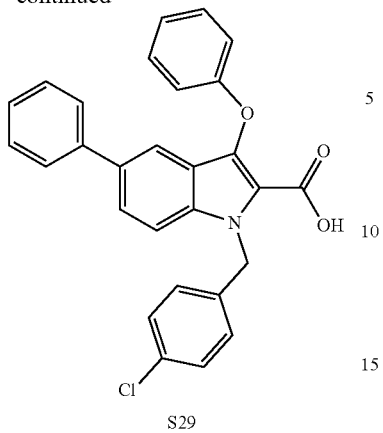

S29

1-(4-chlorobenzyl)-3-phenoxy-5-phenyl-1H-indole-2-carboxylic acid (S29). To a solution of triflate S91 (39 mg, 0.072 mmol) in THF (3 mL) was added to phenylboronic acid (11 mg, 0.086 mmol), Pd(PPh$_3$)$_4$ (2 mg, 0.001 mmol), and NaOH (12 mg, 0.288 mmol). The reaction was stirred overnight at room temperature. The following day, additional NaOH (14 mg, 0.360 mmol), phenylboronic acid (5 mg, 0.043 mmol), and Pd(PPh$_3$)$_4$ (2 mg, 0.001 mmol) were added, and the reaction was heated to 45° C. for 4 hours. The reaction was filtered over Celite, washed with 1M HCl and water, and the aqueous washes were extracted with EtOAc 2×. The combined organic layers were washed with brine, dried over Na$_2$SO$_4$, filtered, concentrated and purified by column chromatography, yielding the title compound as a white solid (7 mg, 20% yield). $^1$H NMR (400 MHz, Acetone) δ 7.77-7.63 (m, 2H), 7.63-7.49 (m, 3H), 7.47-7.26 (m, 7H), 7.21 (dd, J=8.5, 2.5 Hz, 2H), 7.10-6.98 (m, 3H), 5.98 (s, 2H); $^{13}$C NMR (100 MHz, Acetone) δ 162.49, 160.08, 141.95, 140.33, 138.67, 137.20, 134.98, 133.25, 130.37, 129.68, 129.44, 129.13, 127.79, 127.73, 126.76, 122.90, 121.19, 119.58, 118.28, 116.51, 112.70, 47.80; HRMS APCI (m/z): [M−H]$^-$ calcd for C$_{28}$H$_{21}$ClNO$_3$ 454.1210, found 454.1210.

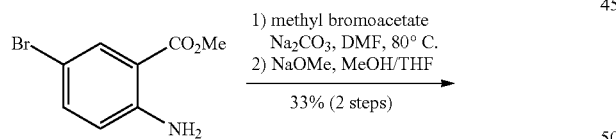

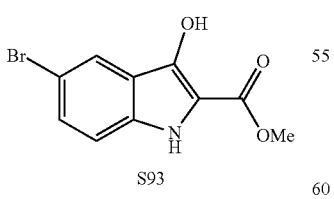

S93

Methyl 5-bromo-3-hydroxy-1H-indole-2-carboxylate (S93). Using general procedure E, methyl 2-amino-5-bromobenzoate (2.00 g, 6.62 mmol) yielded the title compound as a tan solid (789 mg, 33% yield over two steps), with spectroscopic data identical to that previously described (Böttcher, S.; Thiem, J. *Eur. J. Org. Chem.* 2014, 564).

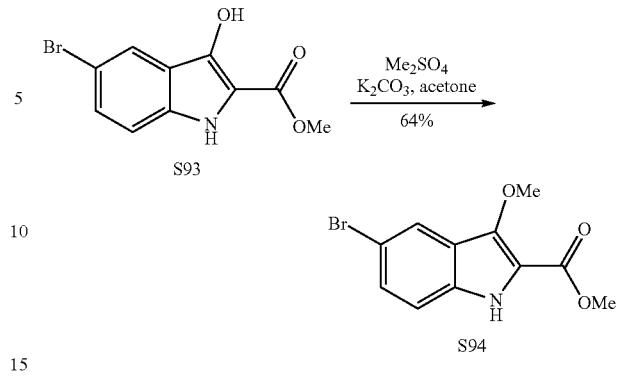

Methyl 5-bromo-3-methoxy-1H-indole-2-carboxylate (S94). Using general procedure F, hydroxyindole S93 (789 mg, 2.92 mmol) yielded the title compound as a yellow solid (531 mg, 64% yield). $^1$H NMR (400 MHz, CDCl$_3$) δ 8.37 (s, 1H), 7.91 (dd, J=1.8, 0.7 Hz, 1H), 7.39 (ddd, J=8.8, 1.9, 0.8 Hz, 1H), 7.21 (dd, J=8.8, 0.6 Hz, 1H), 4.11 (s, 3H), 3.97 (s, 3H); $^{13}$C NMR (150 MHz, CDCl$_3$) δ 167.19, 161.06, 154.58, 138.66, 137.67, 133.95, 122.29, 117.97, 116.98, 54.27, 53.15; HRMS APCI (m/z): [M+H]$^+$ calcd for C$_{11}$H$_{11}$BrNO$_3$ 283.9923 and 285.9902, found 283.9921 and 285.9901.

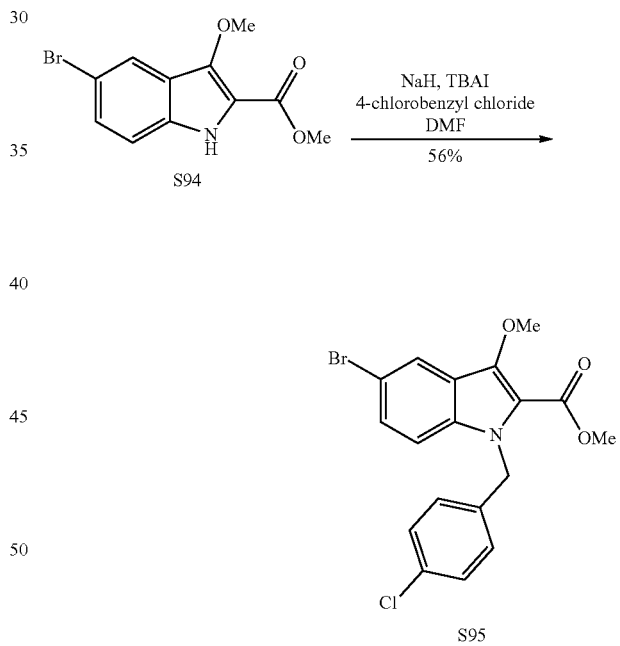

Methyl 5-bromo-1-(4-chlorobenzyl)-3-methoxy-1H-indole-2-carboxylate (S95). Using general procedure C, indole S94 (270 mg, 0.951 mmol) yielded the title compound as a white solid (218 mg, 56% yield). $^1$H NMR (400 MHz, Acetone) δ 7.93 (d, J=1.9 Hz, 1H), 7.47 (d, J=8.9 Hz, 1H), 7.41 (dd, J=8.9, 1.9 Hz, 1H), 7.28 (d, J=8.6 Hz, 2H), 7.06 (d, J=8.7 Hz, 2H), 5.78 (s, 2H), 4.03 (s, 3H), 3.87 (s, 3H); $^{13}$C NMR (100 MHz, Acetone) δ 162.20, 146.13, 138.24, 135.91, 133.24, 130.78, 129.62, 129.33, 128.94, 122.94, 122.23, 118.00, 113.83, 63.09, 52.00, 47.77; HRMS APCI (m/z): [M+H]$^+$ calcd for C$_{18}$H$_{16}$BrClNO$_3$ 408.0002 and 409.9982, found 408.0003 and 409.9982.

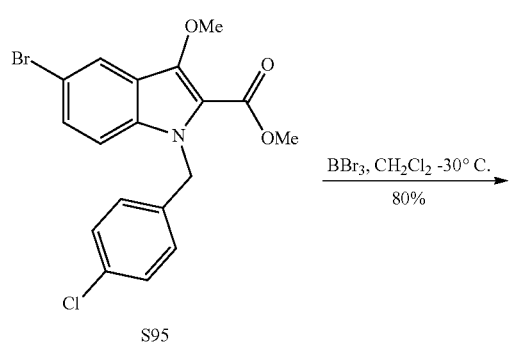

S95

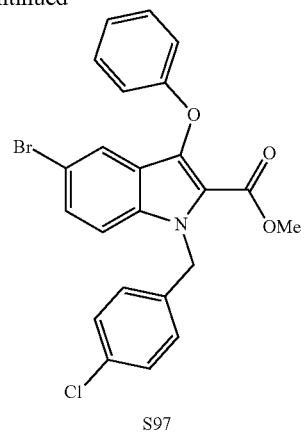

S97

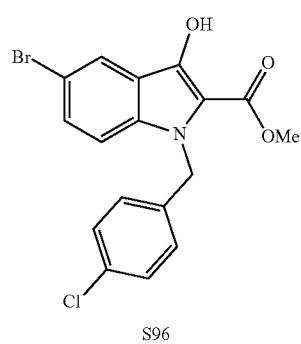

S96

Methyl 5-bromo-1-(4-chlorobenzyl)-3-hydroxy-1H-indole-2-carboxylate (S96). Using general procedure G, methyl ether S95 (218 mg, 0.533 mmol) yielded the title compound as a yellow-green solid (167 mg, 80% yield). $^1$H NMR (400 MHz, CDCl$_3$) δ 8.45 (s, 1H), 7.93 (d, J=1.9 Hz, 1H), 7.41 (dd, J=9.0, 1.9 Hz, 1H), 7.24-7.18 (m, 2H), 7.10 (d, J=9.0 Hz, 1H), 6.93-6.86 (m, 2H), 5.52 (s, 2H), 3.90 (s, 3H); $^{13}$C NMR (150 MHz, Acetone) δ 163.81, 147.09, 138.45, 136.84, 133.29, 130.73, 129.39, 128.99, 123.04, 119.68, 113.64, 112.86, 110.89, 51.99, 47.81; HRMS APCI (m/z): [M+H]$^+$ calcd for C$_{17}$H$_{13}$BrClNO$_3$ 392.9767 and 394.9747, found 392.9767 and 394.9746.

Methyl 5-bromo-1-(4-chlorobenzyl)-3-phenoxy-1H-indole-2-carboxylate (S97). Using general procedure H, hydroxyindole S96 (167 mg, 0.422 mmol) yielded the title compound as a white-yellow solid (93 mg, 47% yield). $^1$H NMR (400 MHz, Acetone) δ 7.60 (d, J=9.0 Hz, 1H), 7.53 (dd, J=1.9, 0.5 Hz, 1H), 7.47 (dd, J=9.0, 1.9 Hz, 1H), 7.37-7.27 (m, 4H), 7.15 (d, J=8.7 Hz, 2H), 7.10-7.01 (m, 1H), 7.02-6.95 (m, 2H), 5.91 (s, 2H), 3.68 (s, 3H); $^{13}$C NMR (150 MHz, Acetone) δ 161.83, 159.90, 139.26, 138.11, 136.21, 133.43, 130.50, 129.95, 129.50, 129.04, 123.25, 122.67, 122.26, 119.59, 116.49, 114.46, 114.31, 52.07, 48.01; HRMS APCI (m/z): [M+H]$^+$ calcd for C$_{23}$H$_{17}$BrClNO$_3$ 469.0081 and 471.0060, found 469.0083 and 471.0062.

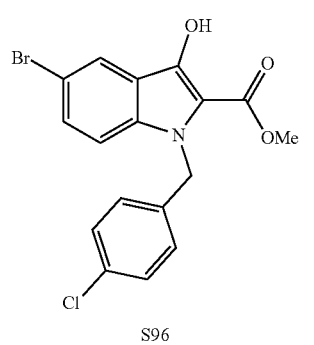

S96

+

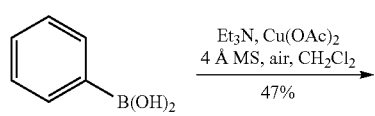

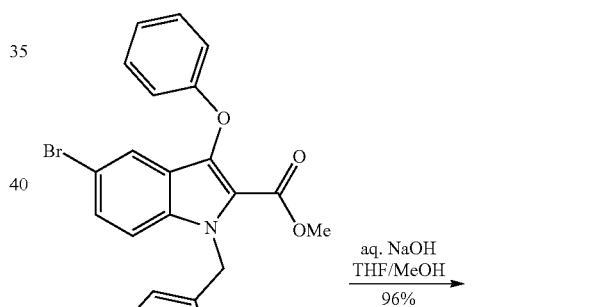

S96

S30

5-bromo-1-(4-chlorobenzyl)-3-phenoxy-1H-indole-2-carboxylic acid (S30). Using general procedure I, methyl ester S96 (93 mg, 0.197 mmol) yielded the title compound as a white solid (87 mg, 94% yield). $^1$H NMR (400 MHz, Acetone) δ 7.61 (dd, J=9.0, 0.6 Hz, 1H), 7.51 (dd, J=1.9, 0.6 Hz, 1H), 7.46 (dd, J=8.9, 1.9 Hz, 1H), 7.37-7.28 (m, 4H), 7.19-7.13 (m, 2H), 7.08-7.02 (m, 1H), 7.02-6.97 (m, 2H), 5.94 (s, 2H); $^{13}$C NMR (150 MHz, Acetone) δ 161.94, 159.83, 139.09, 138.24, 136.26, 133.37, 130.46, 129.82, 129.48, 129.06, 123.14, 122.65, 122.19, 120.08, 116.45, 114.34, 114.33, 47.87; HRMS APCI (m/z): [M+Na]$^+$ calcd for $C_{22}H_{15}BrClNO_3Na$ 477.9822 and 479.9801, found 477.9826 and 479.9804.

REFERENCES

1. Tong S Y C, Davis J S, Eichenberger E, Holland T L, Fowler V G. Staphylococcus aureus infections: epidemiology, pathophysiology, clinical manifestations, and management. *Clin. Microbiol. Rev.* 2015; 28(3): 603-661.
2. Chambers H F, DeLeo F R. Waves of resistance: Staphylococcus aureus in the antibiotic era. *Nat. Rev. Microbial.* 2009; 7(9): 629-641.
3. Keren I, Kaldalu N, Spoering A, Wang Y, Lewis K. Persister cells and tolerance to antimicrobials. *EMS Microbial. Lett.* 2004; 230(1): 13-18.
4. Allison K R, Brynildsen M P, Collins J J. Metabolite-enabled eradication of bacterial persisters by aminoglycosides. *Nature* 2011; 473(7346): 216-220.
5. Conlon B P et al. Activated ClpP kills persisters and eradicates a chronic biofilm infection. *Nature* 2013; 503 (7476): 365-370.
6. Lehar S M et al. Novel antibody-antibiotic conjugate eliminates intracellular *S. aureus*. *Nature* 2015; 527 (7578): 323-328.
7. Lewis K. Persister cells. *Annu. Rev. Microbial.* 2010; 64(1): 357-372.
8. Helaine S, Kugelberg E. Bacterial persisters: formation, eradication, and experimental systems. *Trends Micro biol.* 2014; 22(7): 417-424.
9. Beloin C, Renard S, Ghigo J-M, Lebeaux D. Novel approaches to combat bacterial biofilms. *Curr Opin Pharmacol* 2014; 18: 61-68.
10. Lewis K. Platforms for antibiotic discovery. *Nat. Rev. Drug Discov.* 2013; 12(5): 371-387.
11. Moy T I et al. Identification of novel antimicrobials using a live-animal infection model. *Proc. Natl. Acad. Sci. U.S.A.* 2006; 103(27): 10414-10419.
12. Moy T I et al. High-throughput screen for novel antimicrobials using a whole animal infection model. *ACS Chem. Biol.* 2009; 4(7): 527-533.
13. Conery A L, Larkins-Ford J, Ausubel F M, Kirienko N V. High-throughput screening for novel anti-infectives using a *C. elegans* pathogenesis model. *Curr Protoc. Chem. Biol.* 2014; 6(1): 25-37.
14. Rajamuthiah R et al. Whole animal automated platform for drug discovery against multi-drug resistant *Staphylococcus aureus*. *PLoS ONE* 2014; 9(2): e89189.
15. Kim W, Hendricks G L, Lee K, Mylonakis E. An update on the use of *C. elegans* for preclinical drug discovery: screening and identifying anti-infective drugs. *Expert Opin Drug Discov* 2017; 12(6): 625-633.
16. Kim W et al. A new class of synthetic retinoid antibiotics effective against bacterial persisters. *Nature* 2018, 556, 103-107.
17. Kim W et al. Identification of an antimicrobial agent effective against methicillin-resistant *Staphylococcus aureus* persisters using a fluorescence-based screening strategy. *PLoS ONE* 2015; 10(6): e0127640.
18. Roth B L, Poot M, Yue S T, Millard P J. Bacterial viability and antibiotic susceptibility testing with SYTOX green nucleic acid stain. *Appl. Environ. Microbial.* 1997; 63(6): 2421-2431.
19. Berger J P et al. Distinct properties and advantages of a novel peroxisome proliferator-activated protein [gamma] selective modulator. *Mol. Endocrinol.* 2003; 17(4): 662-676.
20. Hurdle J G, O'Neill A J, Chopra I, Lee R E. Targeting bacterial membrane function: an underexploited mechanism for treating persistent infections. *Nat. Rev. Microbial.* 2011; 9(1): 62-75.
21. Van Bambeke F, Mingeot-Leclercq M P, Struelens M J, Tulkens P M. The bacterial envelope as a target for novel anti-MRSA antibiotics. *Trends Pharmacol. Sci.* 2008; 29(3): 124-134.
22. Shimoda M, Ohki K, Shimamoto Y, Kohashi O. Morphology of defensin-treated *Staphylococcus aureus*. *Infect Immun* 1995; 63(8): 2886-2891.
23. Friedrich C L, Moyles D, Beveridge T J, Hancock R E. Antibacterial action of structurally diverse cationic peptides on Gram-positive bacteria. *Antimicrob. Agents Chemother.* 2000; 44(8): 2086-2092.
24. Friedrich C L, Rozek A, Patrzykat A, Hancock R E. Structure and mechanism of action of an indolicidin peptide derivative with improved activity against gram-positive bacteria. *Biol. Chem.* 2001; 276(26): 24015-24022.
25. Dimova R et al. A practical guide to giant vesicles. Probing the membrane nanoregime via optical microscopy. *J Phys Condens Matter* 2006; 18(28): 81151-76.
26. Sudbrack T P, Archilha N L, Itri R, Riske K A. Observing the solubilization of lipid bilayers by detergents with optical microscopy of GUV s. *J. Phys. Chem. B* 2011; 115(2): 269-277.
27. Tamba Y, Yamazaki M. Single giant unilamellar vesicle method reveals effect of antimicrobial peptide magainin 2 on membrane permeability. *Biochemistry* 2005; 44(48): 15823-15833.
28. Ambroggio E E, Separovic F, Bowie J H, Fidelio G D, Bagatolli L A. Direct visualization of membrane leakage induced by the antibiotic peptides: maculatin, citropin, and aurein. *Biophys. J.* 2005; 89(3): 1874-1881.
29. Chen Y-F, Sun T-L, Sun Y, Huang H W. Interaction of daptomycin with lipid bilayers: lipid extracting effect. *Biochemistry* 2014; 53(33): 5384-5392.
30. Lee C-C, Sun Y, Qian S, Huang H W. Transmembrane pores formed by human antimicrobial peptide LL-37. *Biophys. J.* 2011; 100(7): 1688-1696.
31. Wang Y et al. Direct visualization of bactericidal action of cationic conjugated polyelectrolytes and oligomers. *Langmuir* 2012; 28(1): 65-70.
32. Lee M-T, Sun T-L, Hung W-C, Huang H W. Process of inducing pores in membranes by melittin. *Proc. Natl. Acad. Sci. U.S.A.* 2013; 110(35): 14243-14248.
33. Ganewatta M S et al. Bio-inspired resin acid-derived materials as anti-bacterial resistance agents with unexpected activities. *Chem. Sci.* 2014; 5(5): 2011-2016.
34. Joshi S, Dewangan R P, Yar MS , Rawat D S, Pasha S. N-terminal aromatic tag induced self-assembly of tryptophan-arginine rich ultra short sequences and their potent antibacterial activity. *RSC Advances* 2015; 5(84): 68610-68620.

35. Kim W et al. NH125 kills methicillin-resistant *Staphylococcus aureus* persisters by lipid bilayer disruption. *Future Med. Chem.* 2016; 8(3): 257-269.
36. Li Y et al. Graphene microsheets enter cells through spontaneous membrane penetration at edge asperities and corner sites. *Proc. Natl. Acad. Sci. U.S.A.* 2013; 110(30): 12295-12300.
37. Wang J, Wei Y, Shi X, Gao H. Cellular entry of graphene nanosheets: the role of shickness, oxidation and surface adsorption. *RSC Advances* 2013; 3(36): 15776-15782.
38. Kemnitz C R, Loewen M l "Amide Resonance" correlates with a breadth of C-N rotation barriers. *J Am Chem Soc* 2007; 129(9): 2521-2528.
39. Milner-White E J. The partial charge of the nitrogen atom in peptide bonds. *Protein Sci.* 1997; 6(11): 2477-2482.
40. la Cour Jansen T, Dijkstra A G, Watson T M, Hirst J D, Knoester J. Modeling the amide I bands of small peptides. *J Chem Phys* 2006; 125(4): 044312.
41. Cieplak P, Caldwell J, Kollman P. Molecular mechanical models for organic and biological systems going beyond the atom centered two body additive approximation: aqueous solution free energies of methanol and N-methyl acetamide, nucleic acid base, and amide hydrogen bonding and chloroform/water partition coefficients of the nucleic acid bases. *J. Comput. Chem.* 2001; 22(10): 1048-1057.
42. Rizzo R C, Jorgensen W L. OPLS all-atom model for amines: resolution of the amine hydration problem. *J. Am. Chem. Soc.* 1999; 121(20): 4827-4836.
43. Oostenbrink C, Villa A, Mark A E, van Gunsteren W F. A biomolecular force field based on the free enthalpy of hydration and salvation: The GROMOS force-field parameter sets 53A5 and 53A6. *J. Comput. Chem.* 2004; 25(13): 1656-1676.
44. Wang J, Wolf R M, Caldwell J W, Kollman P A, Case D A. Development and testing of a general amber force field. *J. Comput. Chem.* 2004; 25(9): 1157-1174.
45. Vanommeslaeghe K et al. CHAR.MM general force field: A force field for drug-like molecules compatible with the CHARMM all-atom additive biological force fields. *J. Comput. Chem.* 2010; 31(4): 671-690.
46. Liu C et al. Clinical practice guidelines by the Infectious Diseases Society of America or the treatment of methicillin-resistant *Staphylococcus aureus* infections in adults and children. *Clin. Infect. Dis.* 2011; 52(3): e18-e55.
47. Cosgrove S E et al. Initial low-dose gentamicin for *Staphylococcus aureus* bacteremia and endocarditis is nephrotoxic. *Clin. Infect. Dis.* 2009; 48(6): 713-721.
48. Buchholtz K, Larsen C T, Hassager C, Bruun N E. Severity of gentamicin's nephrotoxic effect on patients with infective endocarditis: a prospective observational cohort study of 373 patients. *Clin. Infect. Dis.* 2009; 48(1): 65-71.
49. Khatib R et al. Persistent *Staphylococcus aureus* bacteremia: incidence and outcome trends over time. *Scand. J. Infect. Dis.* 2009; 41(1): 4-9.
50. Chong Y P et al. Persistent *Staphylococcus aureus* bacteremia: a prospective analysis of risk factors, outcomes, and microbiologic and genotypic characteristics of isolates. *Medicine* (Baltimore) 2013; 92(2): 98-108.
51. Lew D P, Waldvogel F A. Osteomyelitis. *The Lancet* 2004; 364(9431): 369-379.
52. Werdan K et al. Mechanisms of infective endocarditis: pathogen-host interaction and risk states. *Nat. Rev. Cardiol.* 2014; 11(1): 35-50.
53. Elgharably H, Hussain S T, Shrestha N K, Blackstone E H, Pettersson G B. Current hypotheses in cardiac surgery: biofilm in infective endocarditis. *Semin. Thoracic Surg.* 2016; 28(1): 56-59.
54. Sharma V, Kumar P, Pathak D. Biological importance of the indole nucleus in recent years: A comprehensive review. *J. Heterocyclic Chem.* 2010; 47(3): 491-502.
55. Kaushik N et al. Biomedical Importance of indoles. *Molecules* 2013; 18(6): 6620-6662.
56. Zhang M-Z, Chen Q, Yang G-F. A review on recent developments of indole-containing antiviral agents. *Eur. J. Med. Chem.* 2015; 89: 421-441.
57. Baba T et al. Genome and virulence determinants of high virulence community-acquired MRSA. *Lancet* 2002; 359 (9320): 1819-1827.
58. Fey P D et al. A genetic resource for rapid and comprehensive phenotype screening of nonessential *Staphylococcus aureus* genes. *MBio* 2013; 4(1): e00537-12-e00537-12.
59. Baba T, Bae T, Schneewind O, Takeuchi F, Hiramatsu K. Genome sequence of *Staphylococcus aureus* strain Newman and comparative analysis of *Staphylococcal* genomes: polymorphism and evolution of two major pathogenicity islands. *J Bacterial.* 2008; 190(1): 300-310.
60. Garsin D A et al. A simple model host for identifying Gram-positive virulence factors. *Proc. Natl. Acad. Sci. U.S.A.* 2001; 98(19): 10892-10897.
61. Rice L B et al. *Enterococcus faecium* low-affinity pbp5 is a transferable determinant. *Antimicrob. Agents Chemother.* 2005; 49(12): 5007-5012.
62. Carias L L, Rudin S D, Donskey C J, Rice L B. Genetic linkage and cotransfer of a novel, vanB-containing transposon (Tn5382) and a low-affinity penicillin-binding protein 5 gene in a clinical vancomycin-resistant *Enterococcus faecium* isolate. *J Bacterial.* 1998; 180(17): 4426-4434.
63. Garcia-Solache M, Rice L B. Genome sequence of the multiantibiotic-resistant *Enterococcus faecium* Strain C68 and insights on the pLRM23 colonization plasmid. *Genome Announc.* 2016; 4(3): e01719-15.
64. Thorisdottir A S et al. IS6770, an enterococcal insertion-like sequence useful for determining the clonal relationship of clinical enterococcal isolates. *J Infect. Dis.* 1994; 170(6): 1539-1548.
65. Smith M G et al. New insights into *Acinetobacter baumannii* pathogenesis revealed by high-density pyrosequencing and transposon mutagenesis. *Genes Dev.* 2007; 21(5): 601-614.
66. Rahme L G et al. Common virulence factors for bacterial pathogenicity in plants and animals. *Science* 1995; 268 (5219): 1899-1902.
67. Clinical and Laboratory Standards Institute. Methods for dilution antimicrobial susceptibility tests for bacteria that grow aerobically; approved standard-ninth edition. *CLSI document M07-A9.* Wayne, Pa.: 2012.
68. Friedman L, Alder J D, Silverman J A. Genetic changes that correlate with reduced susceptibility to daptomycin in *Staphylococcus aureus. Antimicrob. Agents Chemother.* 2006; 50(6): 2137-2145.
69. Hess B, Kutzner C, van der Spoel D, Lindahl E. GROMACS 4: algorithms for highly efficient, load-balanced, and scalable molecular simulation. *J Chem. Theory Comput.* 2008; 4(3): 435-447.
70. Schmid N et al. Definition and testing of the GROMOS force-field versions 54A7 and 54B7. *Eur. Biophys. J* 2011; 40(7): 843-856.

71. Malde A K et al. An automated force field topology builder (ATB) and repository: version 1.0. *J. Chem. Theory Comput.* 2011; 7(12): 4026-4037.
72. Berger O, Edholm O, Jahnig F. Molecular dynamics simulations of a fluid bilayer of dipalmitoylphosphatidyl-choline at full hydration, constant pressure, and constant temperature. *Biophys. J.* 1997; 72(5): 2002-2013.
73. Celine Anezo, Alex H de Vries, Hans-Dieter Holtje, D Peter Tieleman A, Siewert-Jan Marrink. Methodological issues in lipid bilayer simulations. *J. Phys. Chem. B* 2003; 107(35): 9424-9433.
74. Tu Y et al. Destructive extraction of phospholipids from *Escherichia coli* membranes by graphene nanosheets. *Nat. Nanotechnol.* 2013; 8(8): 594-601.
75. Zhu W et al. Nanomechanical mechanism for lipid bilayer damage induced by carbon nanotubes confined in intracellular vesicles. *Proc. Natl. Acad. Sci. U.S.A.* 2016; 113(44): 12374-12379.
76. Creighton M A et al. Three-dimensional graphene-based microbarriers for controlling release and reactivity in colloidal liquid phases. *ACS Nano* 2016; 10(2): 2268-2276.
77. Isralewitz B, Gao M, Schulten K. Steered molecular dynamics and mechanical functions of proteins. *Curr. Opin. Struct. Biol.* 2001; 11(2): 224-230.
78. Kumar S, Rosenberg J M, Bouzida D, Swendsen R H, Kollman P A. The weighted histogram analysis method for free-energy calculations on biomolecules. I. The method. *J. Comput. Chem.* 1992; 13(8): 1011-1021.
79. Hub J S, de Groot B L, van der Spoel D. g_wham-a free weighted histogram analysis implementation including robust error and autocorrelation estimates. *J. Chem. Theory Comput.* 2010; 6(12): 3713-3720.
80. Racusen LC et al. Cell lines with extended in vitro growth potential from human renal proximal tubule: characterization, response to inducers, and comparison with established cell lines. *J. Lab. Clin. Med.* 1997; 129(3): 318-329.
81. Rajamuthiah R et al. A defensin from the model beetle Tribolium castaneum acts synergistically with telavancin and daptomycin against multidrug resistant *Staphylococcus Aureus*. *PLoS ONE* 2015; 10(6): e0128576.
82. Odds F C. Synergy, antagonism, and what the chequerboard puts between them. *J. Antimicrob. Chemother* 2003; 52(1): 1-1.
83. Conlon B P et al. Persister formation in *Staphylococcus aureus* is associated with ATP depletion. *Nat. Microbiol.* 2016; 1(5): 16051.
84. Cassat J E, Lee C Y, Smeltzer M S. Investigation of biofilm formation in clinical isolates of *Staphylococcus aureus*. *Methods Mol. Biol.* 2007; 391 (Chapter 10): 127-144.
85. Koenig, S. G.; Dankwardt, J. W.; Liu, Y; Zhao, H.; Singh, S. P. *Tetrahedron Lett.* 2010, 51 (50), 6549.
86. Sudhakara, A.; Jayadevappa, H.; Mahadevan, K. M.; Hulikal, V. *Synth. Commun.* 2009, 39 (14), 2506.
87. Temple, K. J.; Duvernay, M. T.; Young, S. E.; Wen, W.; Wu, W.; Maeng, J. G.; Blobaum, A. L.; Stauffer, S. R.; Hamm, H. E.; Lindsley, C. W. *J. Med. Chem.* 2016, 59 (16), 7690.
88. Ngernmeesri, P.; Soonkit, S.; Konkhum, A.; Kongkathip, B. *Tetrahedron Lett.* 2014, 55 (9), 1621.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of treating a bacterial infection, the method comprising administering to a subject in need thereof a therapeutically effective amount of a compound of Formula (I):

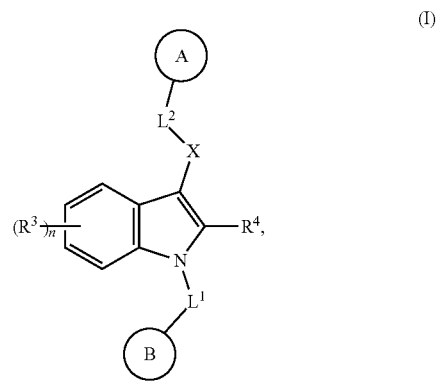

or a pharmaceutically acceptable salt thereof, wherein:

X is selected from S, O, and $C(R^5)_2$; wherein each $R^5$ is independently selected from H, $C_{1-3}$ alkyl, and $C_{1-3}$ haloalkyl;

$L^1$ is selected from a bond, $C(=O)$, $S(=O)$, $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

$L^2$ is selected from a bond, $C(=O)$, $S(=O)$, $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $C_{6-10}$ aryl, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, and $C_{6-10}$ aryl are each optionally substituted with 1, 2 or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

n is an integer selected from 1, 2, 3, and 4;

ring A is adamantyl of formula:

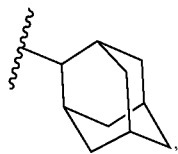 [SMILES: *C1C2CC3CC(C2)CC1C3]

which is optionally substituted with 1, 2, or 3 substituents independently selected from $R^2$;

ring B is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^1$;

each $R^1$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

each $R^2$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

$R^4$ is selected from $C(O)OR^{a3}$ and $C_{1-3}$ alkylene-$OR^{a3}$;

$R^{a1}$, $R^{b1}$, $R^{a2}$, $R^{b2}$, and $R^{a3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, $C(O)OR^{b7}$, $C(O)$ $NR^{c7}R^{d7}$, $C(O)OR^{a7}$, $NR^{c7}R^{d7}$, $S(O)R^{b7}$, $S(O)$ $NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

each $R^{a7}$, $R^{b7}$, $R^{c7}$, and $R^{d7}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO-$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of claim 1, wherein ring B is selected from $C_{6-10}$ aryl and $C_{3-10}$ cycloalkyl.

3. The method of claim 1, wherein:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
ring B is selected from $C_{6-10}$ aryl and $C_{3-10}$ cycloalkyl;
each $R^1$ is independently selected from halo and $OR^{a2}$; and
each $R^2$ is independently selected from halo, $C_{1-6}$ alkyl, $C_{1-6}$ haloalkyl, $OR^{a2}$, and $C(O)OR^{a2}$.

4. The method of claim 1, wherein:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;

n is 1 or 2; and at least one $R^3$ is selected from halo and $C_{1-6}$ haloalkyl;

ring B is selected from phenyl and adamantyl;

each $R^1$ is independently selected from halo, OH, and $C_{1-6}$ alkoxy; and each $R^2$ is independently selected from halo, $C_{1-6}$ alkyl, $C_{1-6}$ haloalkyl, $C_{1-6}$ alkoxy, and C(O)OH.

5. A method of treating a bacterial infection, the method comprising administering to a subject in need thereof a therapeutically effective amount of a compound selected from any one of the following compounds:

| Structure | Compound No. |
|---|---|
| 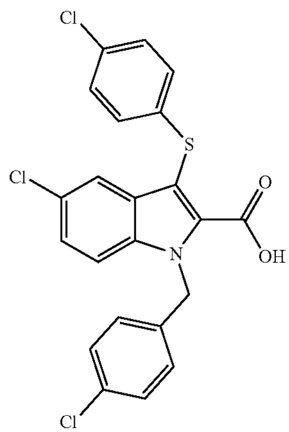 | 4 (analog 3) |
| 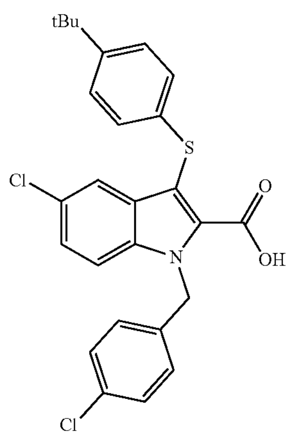 | 5 |
| 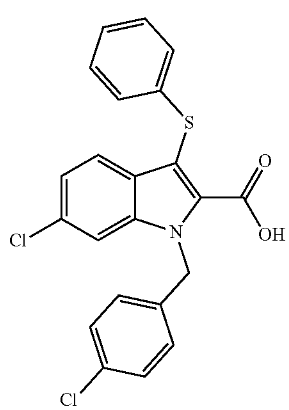 [SMILES: O=C(O)c1c(Sc2ccccc2)c2ccc(Cl)cc2n1Cc1ccc(Cl)cc1] | S9 (analog 2a) |
| | 6 |
| | S13 |
| | S15 |

| Structure | Compound No. |
|---|---|
| 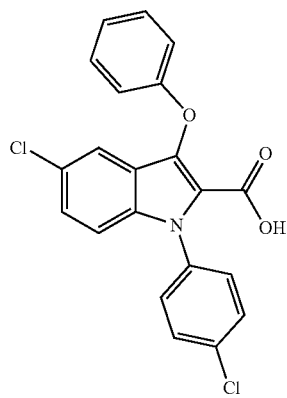 [SMILES: O=C(O)c1c(Oc2ccccc2)c2cc(Cl)ccc2n1-c1ccc(Cl)cc1] | S16 |
| 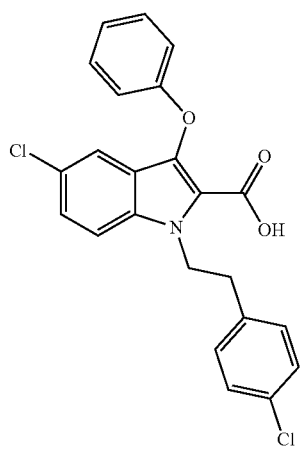 [SMILES: O=C(O)c1c(Oc2ccccc2)c2cc(Cl)ccc2n1CCc1ccc(Cl)cc1] | S17 |
| 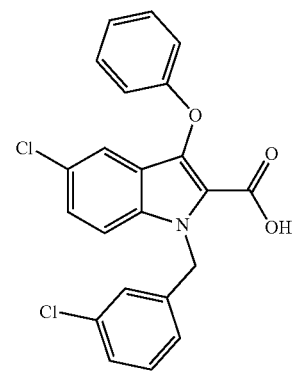 [SMILES: O=C(O)c1c(Oc2ccccc2)c2cc(Cl)ccc2n1Cc1cccc(Cl)c1] | S18 |
| 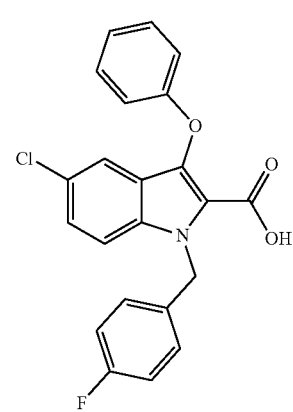 | S19 |
| Structure | Compound No. |
|---|---|
| 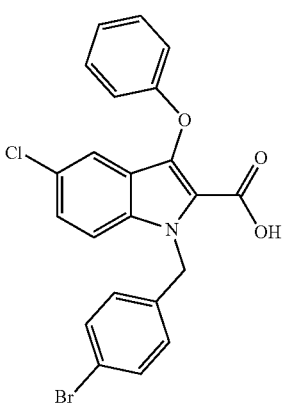 | S20 |
| 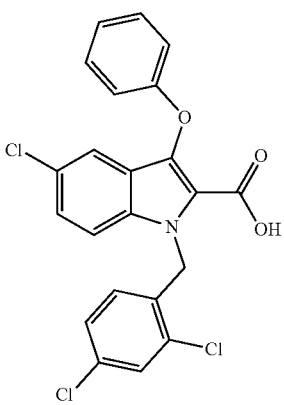 [SMILES: O=C(O)c1c(Oc2ccccc2)c2cc(Cl)ccc2n1Cc1ccc(Cl)cc1Cl] | S21 |
| 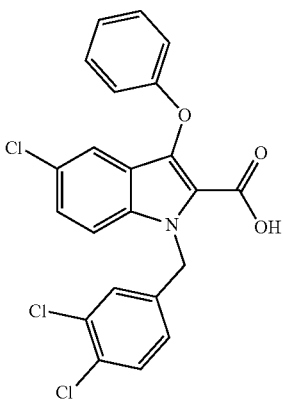 [SMILES: O=C(O)c1c(Oc2ccccc2)c2cc(Cl)ccc2n1Cc1ccc(Cl)c(Cl)c1] | |

161
-continued
| Structure | Compound No. |
|---|---|
| 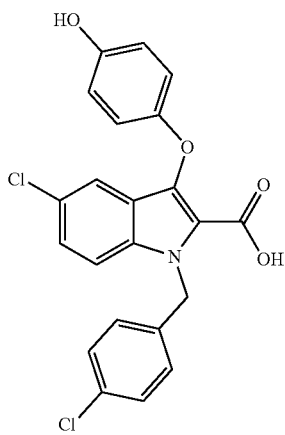 | S22 |
| 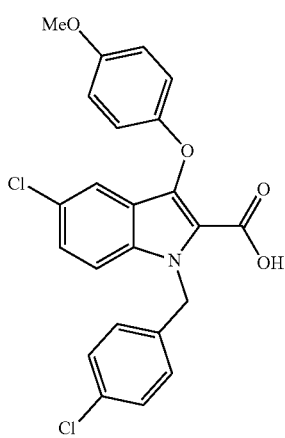 | S23 |
| 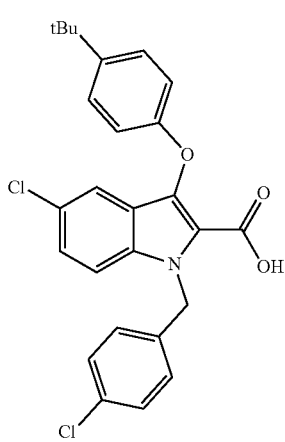 | S24 |
162
-continued
| Structure | Compound No. |
|---|---|
| 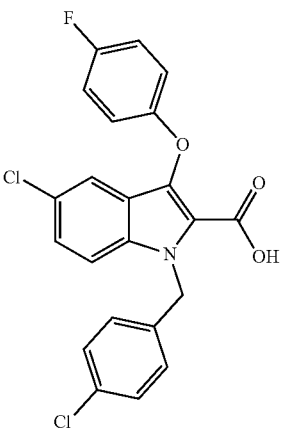 | S25 |
| 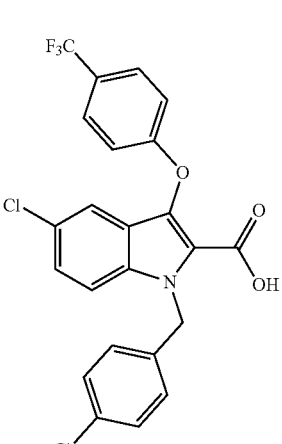 | S26 |
| 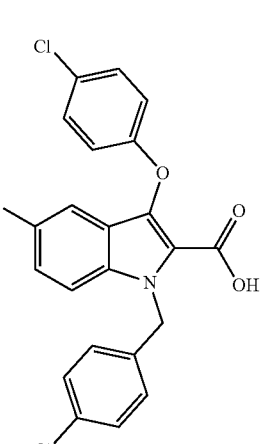 | 11 |

-continued
| Structure | Compound No. |
|---|---|
| 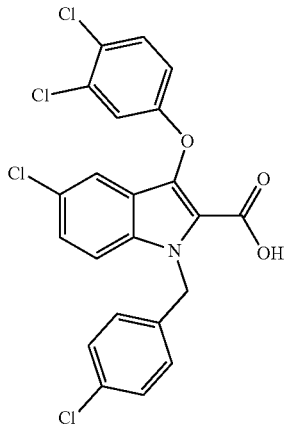 [SMILES: O=C(O)c1c(Oc2ccc(Cl)c(Cl)c2)c2cc(Cl)ccc2n1Cc1ccc(Cl)cc1] | 12 |
| 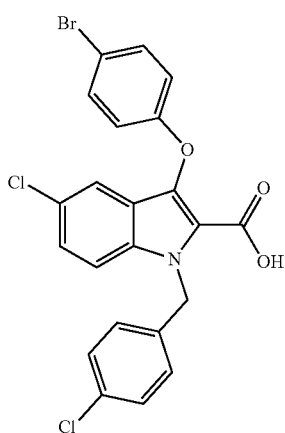 | 13 |
| 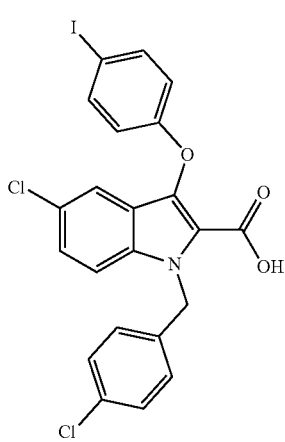 | 14 |
-continued
| Structure | Compound No. |
|---|---|
| 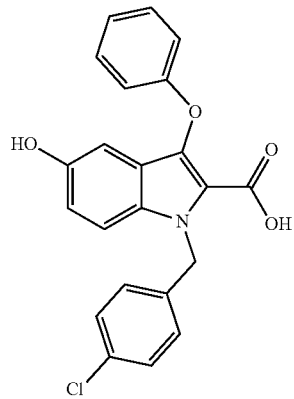 [SMILES: O=C(O)c1c(Oc2ccccc2)c2cc(O)ccc2n1Cc1ccc(Cl)cc1] | S27 |
| 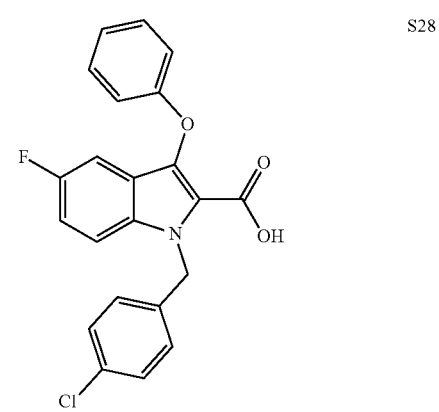 | S28 |
| 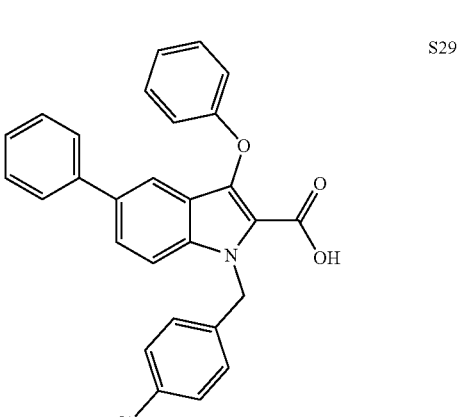 | S29 |

| Structure | Compound No. |
|---|---|
| 5-bromo-3-phenoxy-1-(4-chlorobenzyl)-1H-indole-2-carboxylic acid | S30 | or a pharmaceutically acceptable salt thereof.

6. A method of treating a bacterial infection, the method comprising administering to a subject in need thereof a therapeutically effective amount of a compound selected from any one of the following compounds:

| Structure |
|---|
| 5-methyl-3-phenoxy-1-(4-chlorobenzyl)-1H-indole-2-carboxylic acid |
| 5-chloro-3-(3,4,5-trichlorophenoxy)-1-(4-chlorobenzyl)-1H-indole-2-carboxylic acid |

| Structure |
|---|
| 5-chloro-3-(4-carboxyphenoxy)-1-(4-chlorobenzyl)-1H-indole-2-carboxylic acid |
| 5-chloro-3-phenoxy-1-(4-hydroxybenzyl)-1H-indole-2-carboxylic acid |
| 5-chloro-3-phenoxy-1-(4-iodobenzyl)-1H-indole-2-carboxylic acid |

| 167 -continued | 168 -continued |
|---|---|
| Structure | Structure |
| 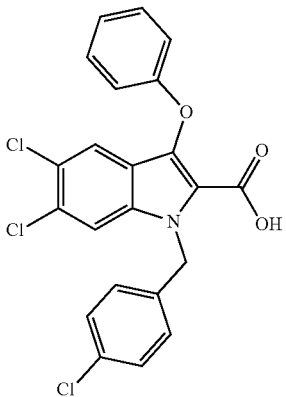 [SMILES: O=C(O)c1c(Oc2ccccc2)c2cc(Cl)c(Cl)cc2n1Cc1ccc(Cl)cc1]<br><br>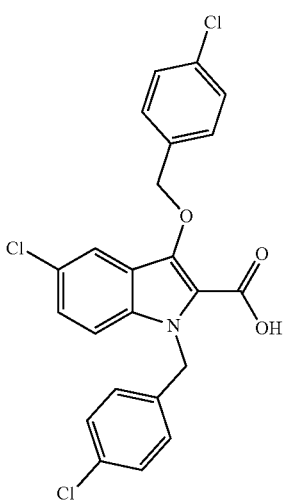<br><br>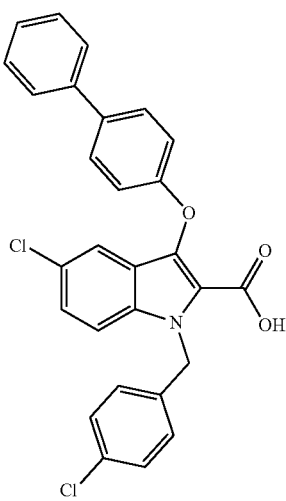 [SMILES: O=C(O)c1c(Oc2ccc(-c3ccccc3)cc2)c2cc(Cl)ccc2n1Cc1ccc(Cl)cc1] | 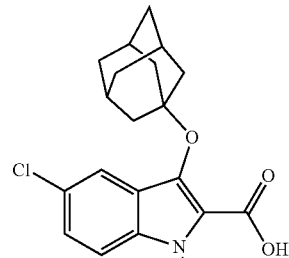<br><br>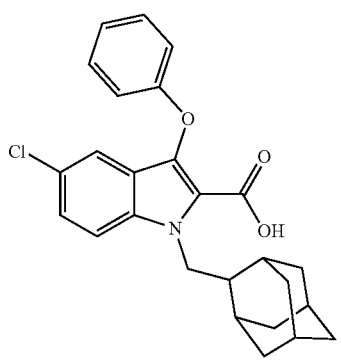 [SMILES: O=C(O)c1c(Oc2ccccc2)c2cc(Cl)ccc2n1CC1C2CC3CC(C2)CC1C3] | or a pharmaceutically acceptable salt thereof.

7. The method of claim 1, wherein the bacterial infection is caused by a Gram-negative bacteria, wherein the Gram-negative bacteria is a member of a genus selected from: *Acinetobacter, Barkholderia, Kilebsiella, Pseudomonas*, and *Escherichia*.

8. The method of claim 1, wherein the bacterial infection is caused by a Gram-positive bacteria, wherein the Gram-positive bacteria is a member of a genus selected from: *Staphylococcus* (including coagulase negative and coagulase positive), *Streptococcus, Propionibacterium, Peptococcus, Enterococcus*, and *Bacillus*, wherein the Gram-positive bacteria is a member of a species selected from: *S. aureus, S. pyogenes, S. pneumoniae, S. salivarius, S. milleri, S. mutans, P. acnes, E. faecalis, E. faecium, B. subtilis*, and *B. anthracis*.

9. The method of claim 1, wherein the bacterial infection is resistant to treatment with one or more other antibiotic agents, wherein the conventional antibiotic agent is selected from methicillin, vancomycin, rifampicin, gentamicin and ciprofloxacim.

10. The method of claim 7, wherein the bacteria is a persister.

11. The method of claim 8, wherein the bacteria is persister.

12. The method of claim 1, wherein the bacterial infection is selected from: acne, septic arthritis, atopic dermatitis, sinusitis, food poisoning, abscess, pneumonia, meningitis, osteomyelitis, endocarditis, bacteremia, sepsis, and urinary tract infection.

13. The method of claim 12, wherein the method further comprises administering to the subject a therapeutically effective amount of at least one additional therapeutic agent, or a pharmaceutically acceptable salt thereof.

14. The method of claim 13, wherein the additional therapeutic agent is an antibiotic.

15. The method of claim 14, wherein the antibiotic is selected from: a quinolone, β-lactam, a cephalosporin, a penicillin, a carbapenem, a lipopeptide, an aminoglycoside, a glycopeptide, a macrolide, an ansamycin, a sulfonamide, a monobactam, oxazolidinone, lipopeptide, macrolide, and a cationic antimicrobial peptide (CAMP).

16. The method of claim 15, wherein the antibiotic is an aminoglycoside, wherein the aminogylcoside is selected from: gentamicin, tobramycin, neomycin, kanamycin, and streptomycin, or a pharmaceutically acceptable salt thereof.

17. The method of claim 16, wherein the antibiotic, is gentamicin, or a pharmaceutically acceptable salt thereof.

18. The method of claim 1, wherein the compound of Formula (I), or a pharmaceutically acceptable salt thereof, and the additional therapeutic agent, or a pharmaceutically acceptable salt thereof, are administered to the subject consecutively.

19. The method of claim 1, wherein the compound of Formula (I), or a pharmaceutically acceptable salt thereof, and the additional therapeutic agent, or a pharmaceutically acceptable salt thereof, are administered to the subject simultaneously.

20. A method of killing or inhibiting growth of bacteria, the method comprising contacting the bacteria with an effective amount of a compound of Formula (I):

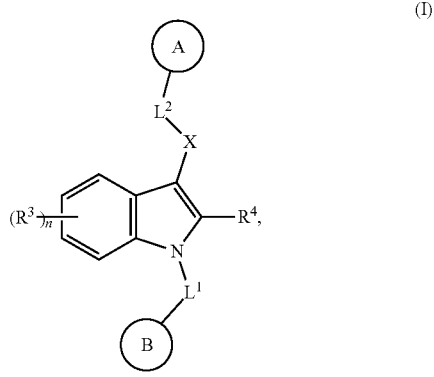

or a pharmaceutically acceptable salt thereof, wherein:

X is selected from S, O, and $C(R^5)_2$; wherein each $R^3$ is independently selected from H, $C_{1-3}$ alkyl, and $C_{1-3}$ haloalkyl;

$L^1$ is selected from a bond, C(=O), S(=O), $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

$L^2$ is selected from a bond, C(=O), S(=O), $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $C_{6-10}$ aryl, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$;

wherein said $C_{1-6}$ alkyl, $_{2-6}$ alkenyl, $C_{2-6}$ alkynyl, and $C_{6-10}$ aryl are each optionally substituted with 1, 2 or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

n is an integer selected from 1, 2, 3, and 4;

ring A is adamantyl of formula:

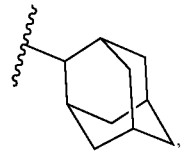 [SMILES: *C1C2CC3CC(C2)CC1C3]

which is optionally substituted with 1, 2, or 3 substituents independently selected from $R^2$;

ring B is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^1$;

each $R^1$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

each $R^2$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $R^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

$R^4$ is selected from $C(O)OR^{a3}$, and $C_{1-3}$ alkylene-$OR^{a3}$;

$R^{a1}$, $R^{b1}$, $R^{a2}$, $R^{b2}$, and $R^{a3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-

$C_{1-4}$ alkylene are optionally substituted with 1, 2, 3, 4, or 5 substituents independently selected from $R^g$;

each $R^{c1}$, $R^{d1}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, $C(O)OR^{b7}$, $C(O)NR^{c7}R^{d7}$, $C(O)OR^{a7}$, $NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

each $R^{a7}$, $R^{b7}$, $R^{c7}$, and $R^{d7}$ is in dependently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO-$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

21. A pharmaceutical composition comprising:
(i) a compound of Formula (I):

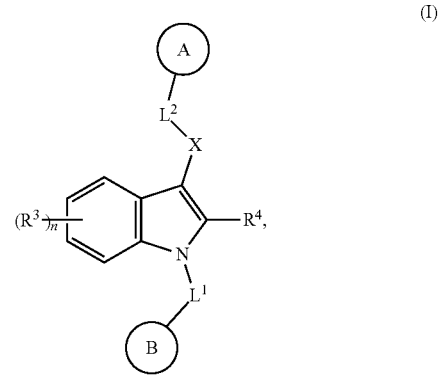

or a pharmaceutically acceptable salt thereof, wherein:

X is selected from S, O, and $C(R^5)_2$; wherein each $R^3$ is independently selected from H, $C_{1-3}$ alkyl, and $C_{1-3}$ haloalkyl;

$L^1$ is selected from a bond, $C(=O)$, $S(=O)$, $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

$L^2$ is selected from a bond, $C(=O)$, $S(=O)$, $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $C_{6-10}$ aryl, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $_{2-6}$ alkenyl, $C_{2-6}$ alkynyl, and $C_{6-10}$ aryl are each optionally substituted with 1, 2 or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

n is an integer selected from 1, 2, 3, and 4;

ring A is adamantyl of formula:

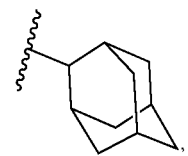 [SMILES: *C1C2CC3CC(C2)CC1C3]

which is optionally substituted with 1, 2, or 3 substituents independently selected from $R^2$;

ring B is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^1$;

each $R^1$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

each $R^2$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

$R^4$ is selected from $C(O)OR^{a3}$ and $C_{1-3}$ alkylene-$OR^{a3}$;

$R^{a1}$, $R^{b1}$, $R^{a2}$, $R^{b2}$, and $R^{a3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, $C(O)OR^{b7}$, $C(O)NR^{c7}R^{d7}$, $C(O)OR^{a7}$, $NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

each $R^{a7}$, $R^{b7}$, $R^{c7}$, and $R^{d7}$ is in dependently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO-$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and (ii) at least one additional antibiotic, or a pharmaceutically acceptable salt thereof; and (iii) a pharmaceutically acceptable carrier.

22. A compound of Formula (I):

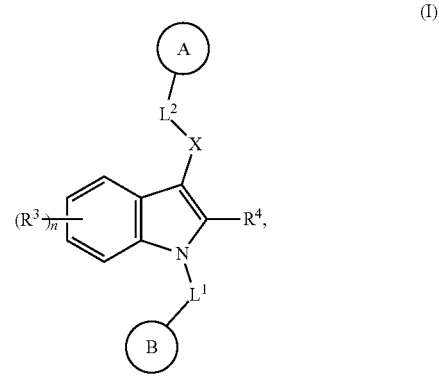

(I)

or a pharmaceutically acceptable salt thereof, wherein:

X is selected from S, O, and $C(R^5)_2$; wherein each $R^3$ is independently selected from H, $C_{1-3}$ alkyl, and $C_{1-3}$ haloalkyl;

$L^1$ is selected from a bond, $C(=O)$, $S(=O)$, $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;

$L^2$ is selected from a bond, $C(=O)$, $S(=O)$, $S(=O)_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, NO$_2$, and C$_{1-6}$ haloalkyl;

each R$^3$ is independently selected from halo, CN, NO$_2$, C$_{1-6}$ alkyl, C$_{1-6}$ haloalkyl, C$_{2-6}$ alkenyl, C$_{2-6}$ alkynyl, C$_{6-10}$ aryl, OR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)$_2$R$^{b1}$, NR$^{c1}$S(O)$_2$NR$^{c1}$R$^{d1}$, S(O)$_2$R$^{b1}$, and S(O)$_2$NR$^{c1}$R$^{d1}$; wherein said C$_{1-6}$ alkyl, $_{2-6}$ alkenyl, C$_{2-6}$ alkynyl, and C$_{6-10}$ aryl are each optionally substituted with 1, 2 or 3 substituents independently selected from halo, C$_{1-6}$ alkyl, C$_{1-6}$ haloalkyl, CN, NO$_2$, OR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)$_2$R$^{b1}$, NR$^{c1}$S(O)$_2$NR$^{c1}$R$^{d1}$, S(O)$_2$R$^{b1}$ and S(O)$_2$NR$^{c1}$R$^{d1}$;

n is an integer selected from 1, 2, 3, and 4; and at least one R$^3$ is selected from halo and C$_{1-6}$ haloalkyl;

ring A is adamantyl of formula:

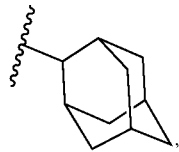 [SMILES: *C1C2CC3CC(C2)CC1C3]

which is optionally substituted with 1, 2, or 3 substituents independently selected from R$^2$;

ring B is selected from C$_{6-10}$ aryl, C$_{3-10}$ cycloalkyl, 5-10 membered heteroaryl, and 4-10 membered heterocycloalkyl, each of which is optionally substituted with 1, 2, or 3 substituents independently selected from R$^1$;

each R$^1$ is independently selected from halo, CN, NO$_2$, C$_{1-6}$ alkyl, C$_{1-6}$ haloalkyl, C$_{2-6}$ alkenyl, C$_{2-6}$ alkynyl, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, and C$_{2-6}$ alkynyl are each optionally substituted with 1, 2 or 3 substituents independently selected from halo, CN, NO$_2$, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)$_2$R$^{b2}$ and S(O)$_2$NR$^{c2}$R$^{d2}$;

each R$^2$ is independently selected from halo, CN, NO$_2$, C$_{1-6}$ alkyl, C$_{1-6}$ haloalkyl, C$_{2-6}$ alkenyl, C$_{2-6}$ alkynyl, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, and C$_{2-6}$ alkynyl are each optionally substituted with 1, 2 or 3 substituents independently selected from halo, CN, NO$_2$, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)$_2$R$^{b2}$ and S(O)$_2$NR$^{c2}$R$^{d2}$;

R$^4$ is selected from C(O)OR$^{a3}$ and C$_{1-3}$ alkylene-OR$^{a3}$;

each R$^{a1}$, R$^{b1}$, R$^{a2}$, R$^{b2}$, and R$^{a3}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene are optionally substituted with 1, 2, 3, 4, or 5 substituents independently selected from R$^g$;

each R$^{c1}$, R$^{d1}$, R$^{c2}$, and R$^{d2}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-10 membered heterocycloalkyl)-C$_{1-4}$ alkylene, C(O)OR$^{b7}$, C(O)NR$^{c7}$R$^{d7}$, C(O)OR$^{a7}$, NR$^{c7}$R$^{d7}$, S(O)R$^{b7}$, S(O)NR$^{c7}$R$^{d7}$, S(O)$_2$R$^{b7}$, and S(O)$_2$NR$^{c7}$R$^{d7}$; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene is optionally substituted with 1, 2, 3, 4, or 5 substituents independently selected from R$^g$;

each R$^{a7}$, R$^{b7}$, R$^{c7}$, and R$^{d7}$ is in dependently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-10 membered heterocycloalkyl)-C$_{1-4}$ alkylene and R$^g$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene is optionally substituted with 1, 2, 3, 4, or 5 substituents independently selected from R$^g$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from R$^g$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from R$^g$; and each R$^g$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkylene, HO-C$_{1-3}$ alkylene, C$_{6-10}$ aryl, C$_{6-10}$ aryloxy, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-10 membered heterocycloalkyl)-C$_{1-4}$ alkylene, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, $C_{1-6}$ alkylaminocarbonylamino, and di($C_{1-6}$ alkyl)aminocarbonylamino.

23. The compound of claim 22, wherein:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
ring B is selected from $C_{6-10}$ aryl and $C_{3-10}$ cycloalkyl;
each $R^1$ is independently selected from halo and $OR^{a2}$; and
each $R^2$ is independently selected from halo, $C_{1-6}$ alkyl, $C_{1-6}$ haloalkyl, $OR^{a2}$; and $C(O)OR^{a2}$.

24. The compound of claim 22, wherein:
X is selected from S, O and $CH_2$;
$L^1$ is selected from bond and $C_{1-6}$ alkylene;
$L^2$ is selected from bond and $C_{1-6}$ alkylene;
each $R^3$ is independently selected from halo, $C_{1-6}$ alkyl, $C_{1-6}$ haloalkyl, $C_{6-10}$ aryl and $OR^{a1}$;
n is 1 or 2; and at least one $R^3$ is selected from halo and $C_{1-6}$ haloalkyl;
ring B is selected from phenyl and adamantyl;
each $R^1$ is independently selected from halo, OH, and $C_{1-6}$ alkoxy; and
each $R^2$ is independently selected from halo, $C_{1-6}$ alkyl, $C_{1-6}$ haloalkyl, $C_{1-6}$ alkoxy, and C(O)OH.

25. A compound of Formula:

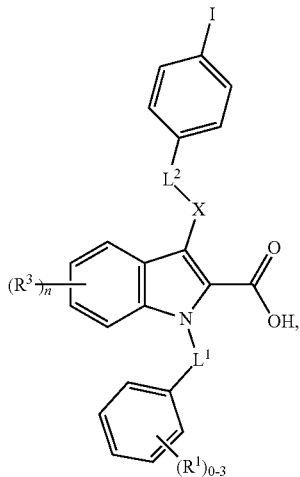

or a pharmaceutically acceptable salt thereof, wherein:
X is selected from S, O, and $C(R^5)_2$; wherein each $R^3$ is independently selected from H, $C_{1-3}$ alkyl, and $C_{1-3}$ haloalkyl;
$L^1$ is selected from a bond, C(=O), S(=O), S(=O)$_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;
$L^2$ is selected from a bond, C(=O), S(=O), S(=O)$_2$, $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, or 3 substituents independently selected from halo, CN, $NO_2$, and $C_{1-6}$ haloalkyl;
each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $C_{6-10}$ aryl, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $_{2-6}$ alkenyl, $C_{2-6}$ alkynyl, and $C_{6-10}$ aryl are each optionally substituted with 1, 2 or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;
n is an integer selected from 1, 2, 3, and 4; and at least one $R^3$ is selected from halo and $C_{1-6}$ haloalkyl;
each $R^1$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 substituents independently selected from halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;
each $R^{a1}$, $R^{b1}$, $R^{a2}$, and $R^{b2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;
each $R^{c1}$, $R^{d1}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, $C(O)OR^{b7}$, $C(O)NR^{c7}R^{d7}$, $C(O)OR^{a7}$, $NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;
each $R^{a7}$, $R^{b7}$, $R^{c7}$, and $R^{d7}$ is in dependently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO-$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

26. The compound of claim 25, wherein:

X is O;

$L^1$ is $C_{1-6}$ alkylene;

$L^2$ is selected from bond and $C_{1-6}$ alkylene; and each $R^1$ is independently selected from halo, OH, $C_{1-6}$ alkoxy; $C_{1-6}$ haloalkyl, and $C_{1-6}$ haloalkoxy.

27. A compound selected from any one of the following compounds:

| Structure | Compound No. |
|---|---|
| | 4 (analog 3) |
| 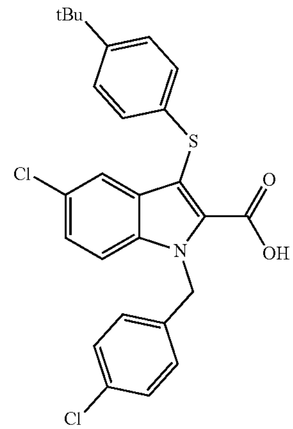 | 5 |
| 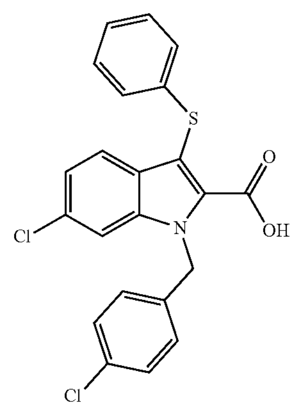 [SMILES: O=C(O)c1c(Sc2ccccc2)c2ccc(Cl)cc2n1Cc1ccc(Cl)cc1] | S9 (analog 2a) |
| 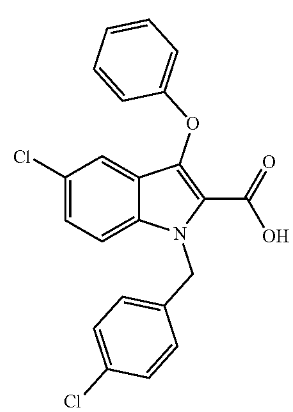 | 6 |

| Structure | Compound No. |
|---|---|
| 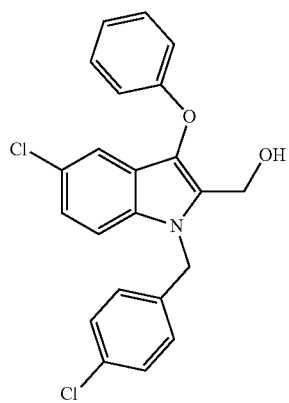 [SMILES: OCc1c(Oc2ccccc2)c2cc(Cl)ccc2n1Cc1ccc(Cl)cc1] | S13 |
| 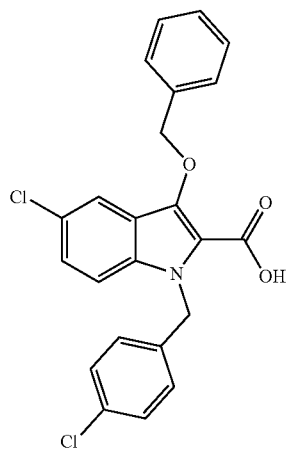 [SMILES: O=C(O)c1c(OCc2ccccc2)c2cc(Cl)ccc2n1Cc1ccc(Cl)cc1] | S15 |
| 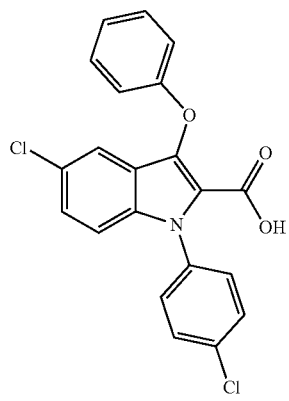 [SMILES: O=C(O)c1c(Oc2ccccc2)c2cc(Cl)ccc2n1-c1ccc(Cl)cc1] | S16 |
| Structure | Compound No. |
|---|---|
| 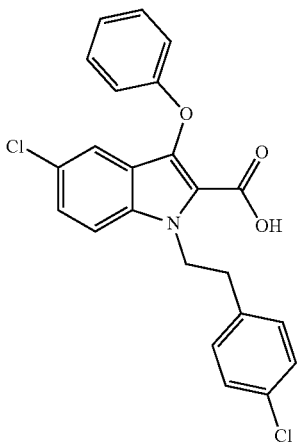 [SMILES: O=C(O)c1c(Oc2ccccc2)c2cc(Cl)ccc2n1CCc1ccc(Cl)cc1] | S17 |
| 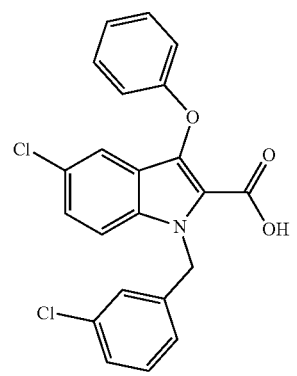 [SMILES: O=C(O)c1c(Oc2ccccc2)c2cc(Cl)ccc2n1Cc1cccc(Cl)c1] | S18 |
| 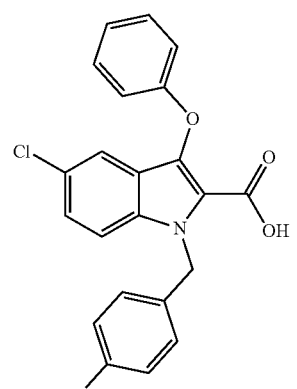 | S19 |
| 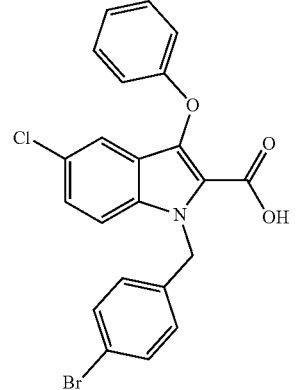 [SMILES: O=C(O)c1c(Oc2ccccc2)c2cc(Cl)ccc2n1Cc1ccc(Br)cc1] | S20 |

| Structure | Compound No. |
|---|---|
| 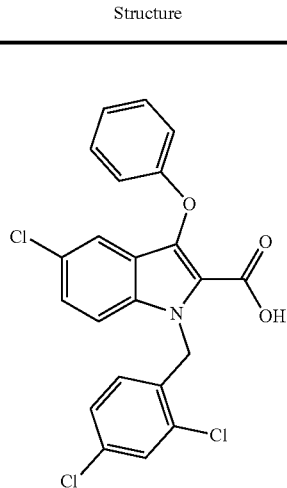 | S21 |
| 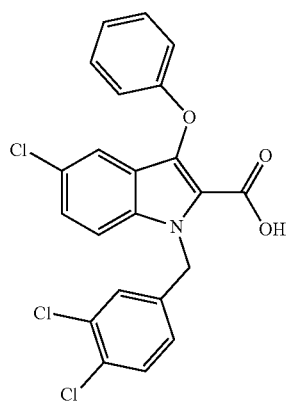 [SMILES: O=C(O)c1c(Oc2ccccc2)c2cc(Cl)ccc2n1Cc1ccc(Cl)c(Cl)c1] | S22 |
| 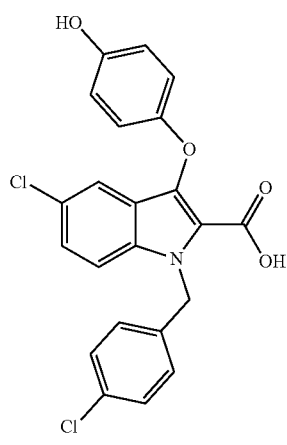 [SMILES: O=C(O)c1c(Oc2ccc(O)cc2)c2cc(Cl)ccc2n1Cc1ccc(Cl)cc1] | S22 |
| Structure | Compound No. |
|---|---|
| 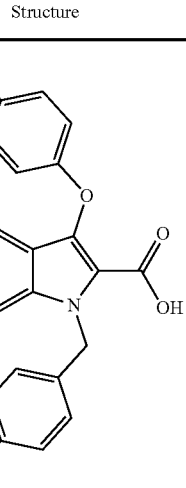 | S23 |
| | S24 |
| | S25 |

| Structure | Compound No. |
|---|---|
| 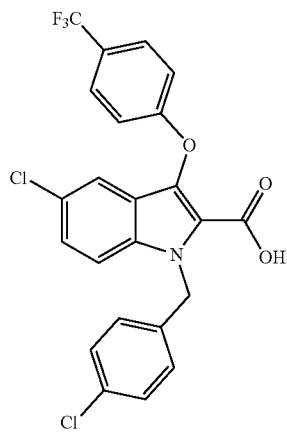 [SMILES: O=C(O)c1c(Oc2ccc(C(F)(F)F)cc2)c2cc(Cl)ccc2n1Cc1ccc(Cl)cc1] | S26 |
| 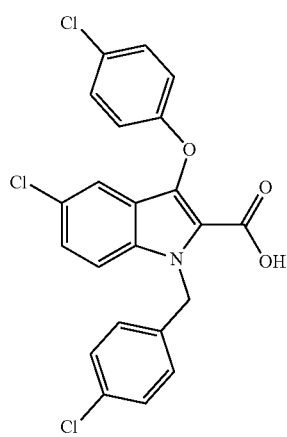 | 11 |
| 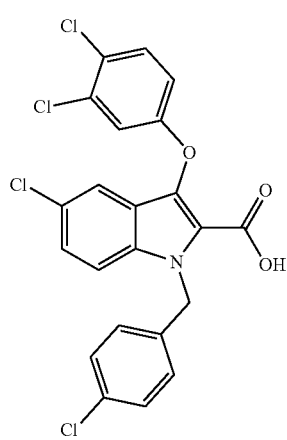 [SMILES: O=C(O)c1c(Oc2ccc(Cl)c(Cl)c2)c2cc(Cl)ccc2n1Cc1ccc(Cl)cc1] | 12 |
| Structure | Compound No. |
|---|---|
| 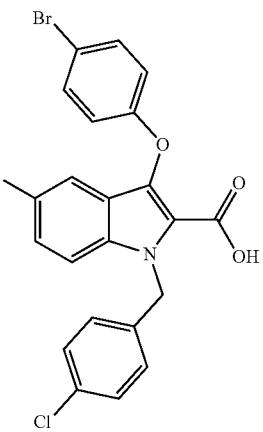 | 13 |
| 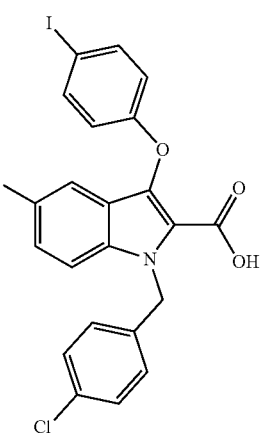 | 14 |
| 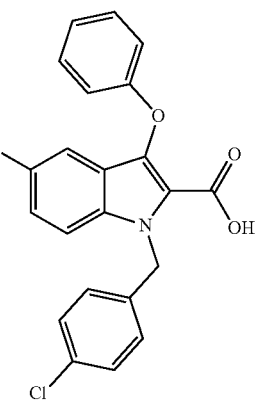 | S27 |

-continued

| Structure | Compound No. |
|---|---|
| | S28 |
| | S29 |
| | S30 | or a pharmaceutically acceptable salt thereof.

28. A compound selected from any one of the following compounds:

| Structure |
|---|
| |
| |
| |

| 189 -continued | 190 -continued |
|---|---|
| Structure | Structure |
| 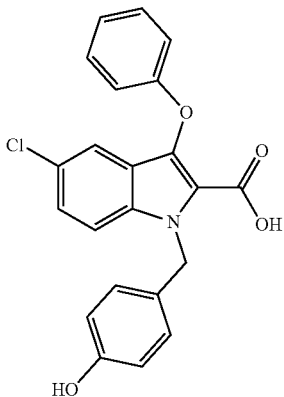 | 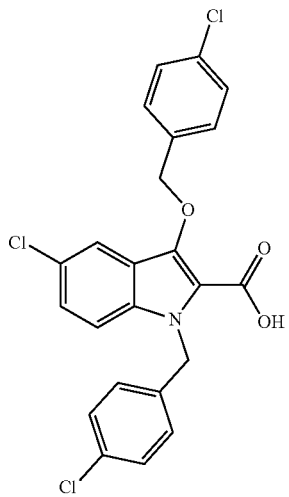 |
| 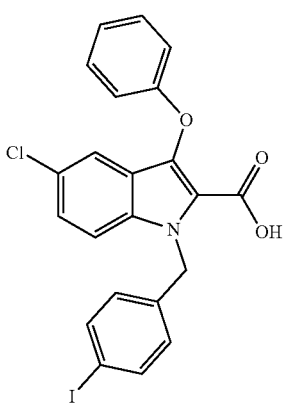 | 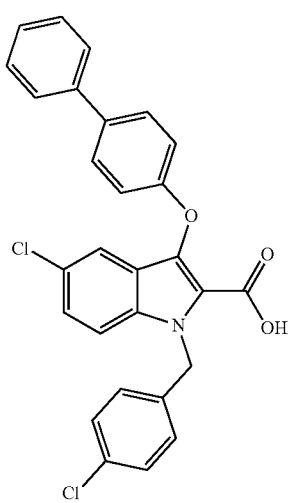 |
| 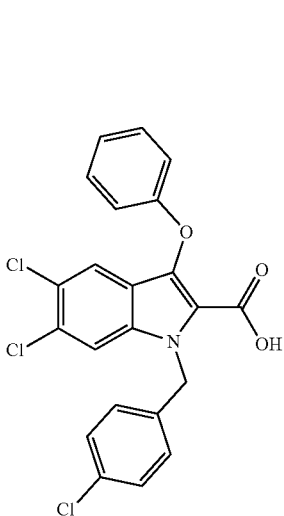 [SMILES: O=C(O)c1c(Oc2ccccc2)c2cc(Cl)c(Cl)cc2n1Cc1ccc(Cl)cc1] | 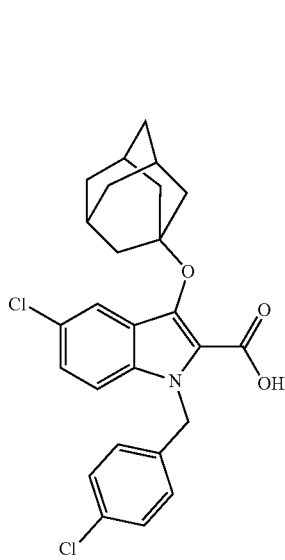 [SMILES: O=C(O)c1c(OC23CC4CC(CC(C4)C2)C3)c2cc(Cl)ccc2n1Cc1ccc(Cl)cc1] |

| Structure |
|---|
| 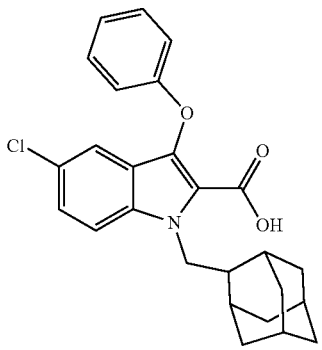 [SMILES: O=C(O)c1c(Oc2ccccc2)c2cc(Cl)ccc2n1CC1C2CC3CC(C2)CC1C3] | or a pharmaceutically acceptable salt thereof.

29. The compound of claim 25 having formula:

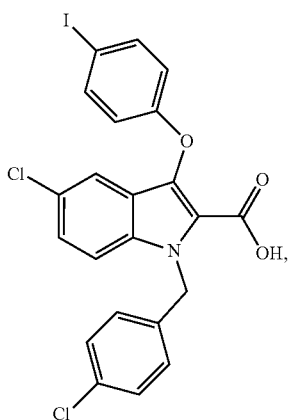 [SMILES: O=C(O)c1c(Oc2ccc(I)cc2)c2cc(Cl)ccc2n1Cc1ccc(Cl)cc1]

or a pharmaceutically acceptable salt thereof.

30. A pharmaceutical composition comprising a compound of claim 25, or a pharmaceutically acceptable salt thereof, and a pharmaceutically acceptable carrier.

31. The pharmaceutical composition of claim 25, comprising at least one additional antibiotic, or a pharmaceutically acceptable salt thereof.

32. The pharmaceutical composition of claim 31, wherein the antibiotic is selected from: a quinolone, β-lactam, a cephalosporin, a penicillin, a carbapenem, a lipopetide, an aminoglycoside, a glycopeptide, a macrolide, an ansamycin, a sulfonamide, a monobactam, oxazolidinone, lipopeptide, macrolide, and a cationic antimicrobial peptide (CAMP).

33. The pharmaceutical composition of claim 32, wherein the antibiotic is the aminogylcoside selected from: gentamicin, tobramycin, neomycin, kanamycin, and streptomycin, or a pharmaceutically acceptable salt thereof.

34. The pharmaceutical composition of claim 33, wherein the additional antibiotic is gentamicin, or a pharmaceutically acceptable salt thereof.

35. The method of claim 20, wherein ring B is selected from $C_{6-10}$ aryl and $C_{3-10}$ cycloalkyl.

36. The method of claim 20, wherein:

X is selected from S, O and $CH_2$;

$L^1$ is selected from bond and $C_{1-6}$ alkylene;

$L^2$ is selected from bond and $C_{1-6}$ alkylene;

each $R^3$ is independently selected from halo, $C_{1-6}$ alkyl, $C_{1-6}$ haloalkyl, $C_{6-10}$ aryl and $OR^{a1}$;

ring B is selected from $C_{6-10}$ aryl and $C_{3-10}$ cycloalkyl;

each $R^1$ is independently selected from halo and $OR^{a2}$; and each $R^2$ is independently selected from halo, $C_{1-6}$ alkyl, $C_{1-6}$ haloalkyl, $OR^{a2}$; and $C(O)OR^{a2}$.

37. The method of claim 20, wherein:

X is selected from S, O and $CH_2$;

$L^1$ is selected from bond and $C_{1-6}$ alkylene;

$L^2$ is selected from bond and $C_{1-6}$ alkylene;

each $R^3$ is independently selected fro as halo, $C_{1-6}$ alkyl, $C_{1-6}$ haloalkyl, $C_{6-10}$ aryl and $OR^{a1}$;

n is 1 or 2; and at least one $R^3$ is selected from halo and $C_{1-6}$ haloalkyl;

ring B is selected from phenyl and adamantyl;

each is independently selected from halo, OH, and $C_{1-6}$ alkoxy; and each $R^2$ is independently selected from halo, $C_{1-6}$ alkyl, $C_{1-6}$ haloalkyl, $C_{1-6}$ alkoxy, and C(O)OH.

38. A method of killing or inhibiting growth of bacteria, the method comprising contacting the bacteria with an effective amount of a compound selected from any one of the following compounds:

| Structure | Compound No. |
|---|---|
| 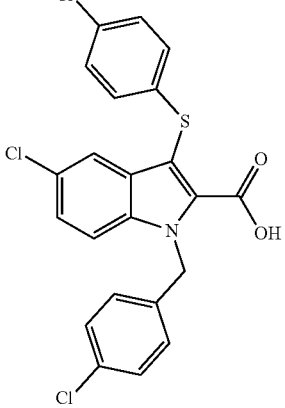 | 4 (analog 3) |
| 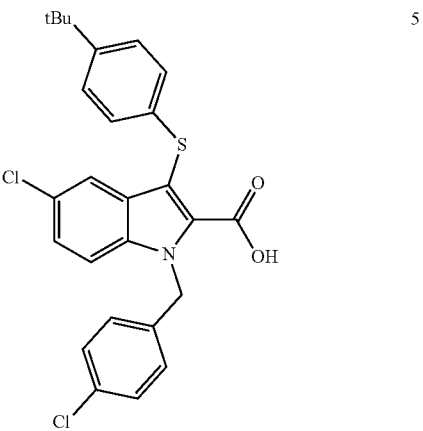 | 5 |

| Structure | Compound No. |
|---|---|
| 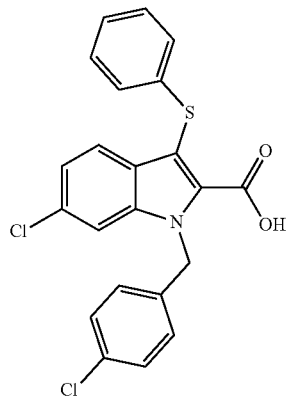 [SMILES: O=C(O)c1c(Sc2ccccc2)c2ccc(Cl)cc2n1Cc1ccc(Cl)cc1] | S9 (analog 2a) |
| 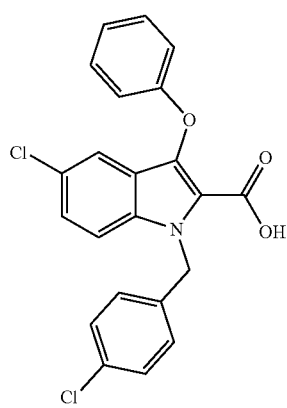 [SMILES: O=C(O)c1c(Oc2ccccc2)c2cc(Cl)ccc2n1Cc1ccc(Cl)cc1] | 6 |
| 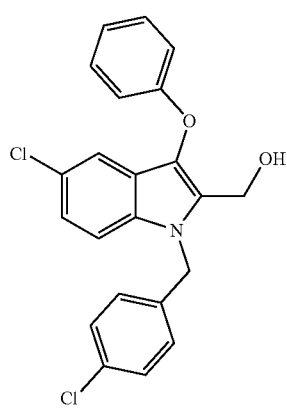 [SMILES: OCc1c(Oc2ccccc2)c2cc(Cl)ccc2n1Cc1ccc(Cl)cc1] | S13 |
| Structure | Compound No. |
|---|---|
| 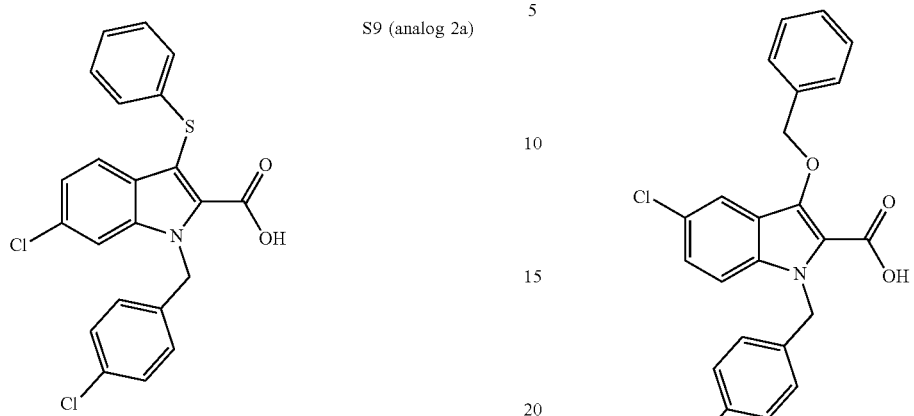 | S15 |
| 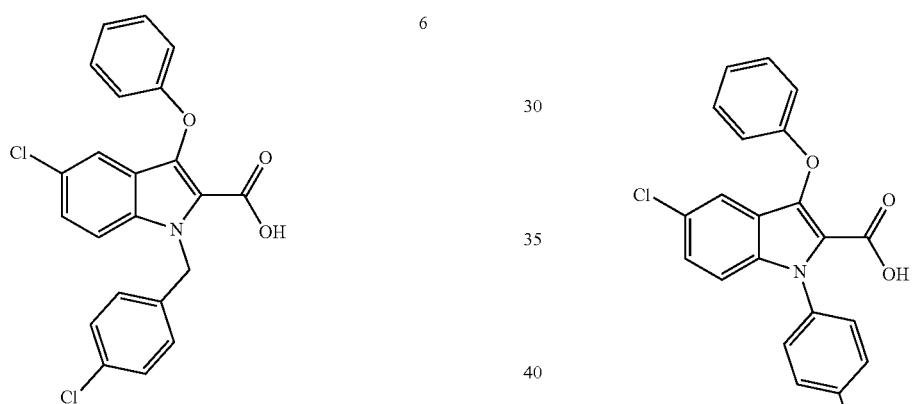 | S16 |
| 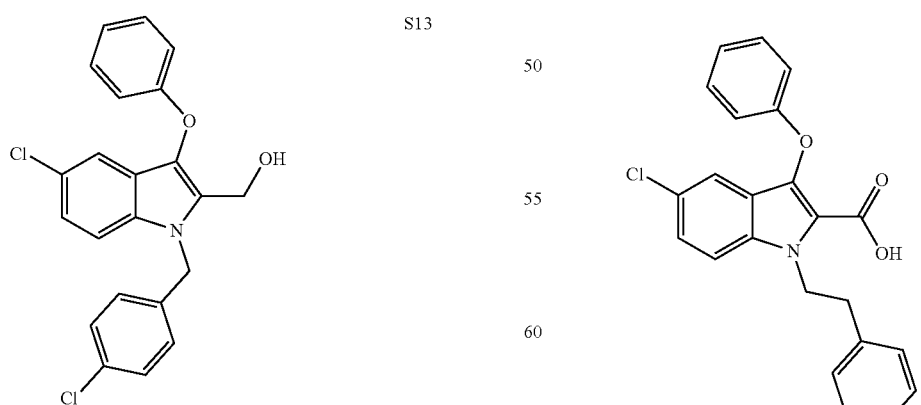 | S17 |

| Structure | Compound No. |
|---|---|
| 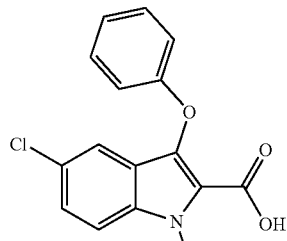 | S18 |
| 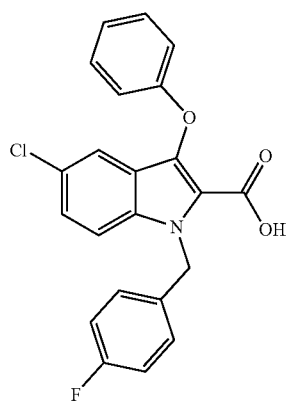 | S19 |
| 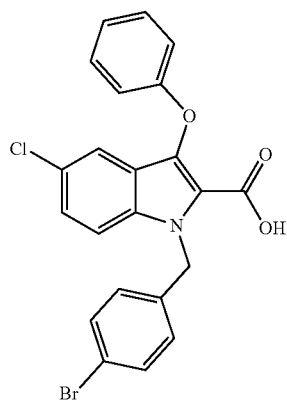 | S20 |
| 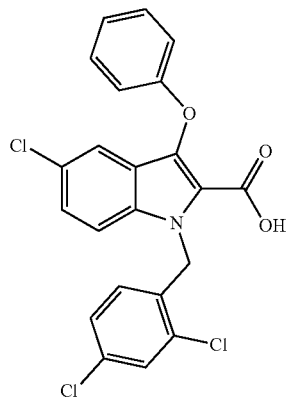 [SMILES: O=C(O)c1c(Oc2ccccc2)c2cc(Cl)ccc2n1Cc1ccc(Cl)cc1Cl] | S21 |
| Structure | Compound No. |
|---|---|
| 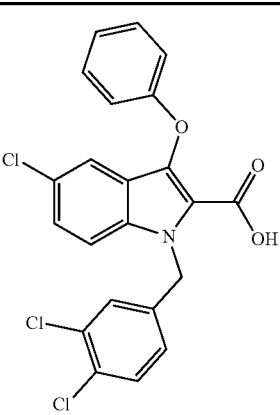 | 10 |
| 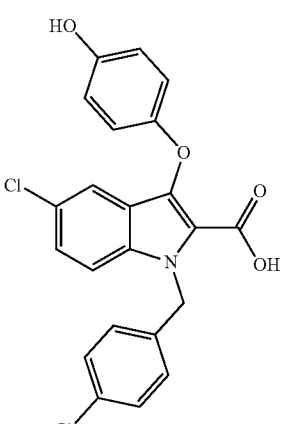 | S22 |
| 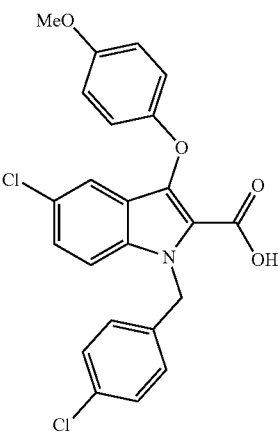 | S23 |

| Structure | Compound No. |
|---|---|
| 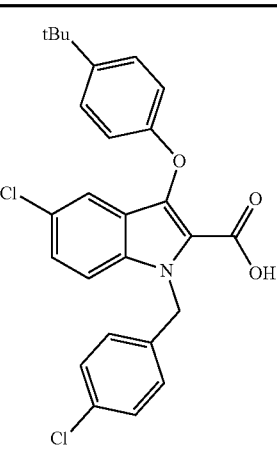 | S24 |
| 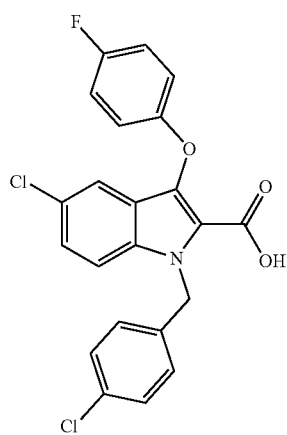 | S25 |
| 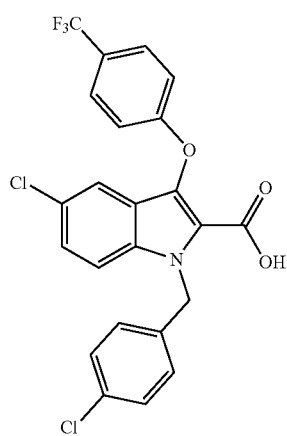 [SMILES: O=C(O)c1c(Oc2ccc(C(F)(F)F)cc2)c2cc(Cl)ccc2n1Cc1ccc(Cl)cc1] | S26 |
| Structure | Compound No. |
|---|---|
| 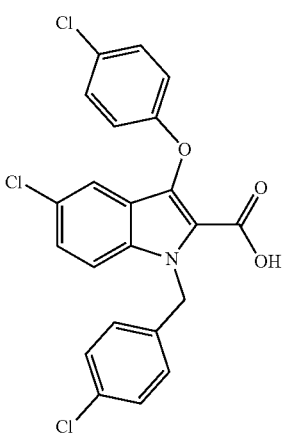 | 11 |
| 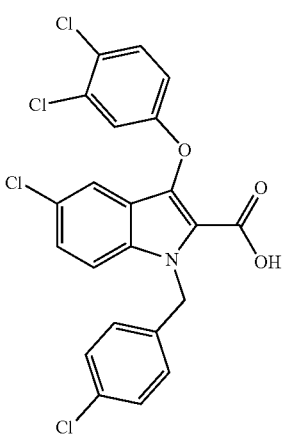 | 12 |
| 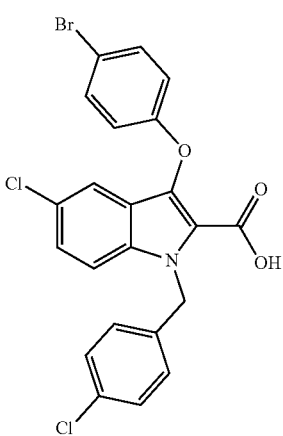 | 13 |

| Structure | Compound No. |
|---|---|
| 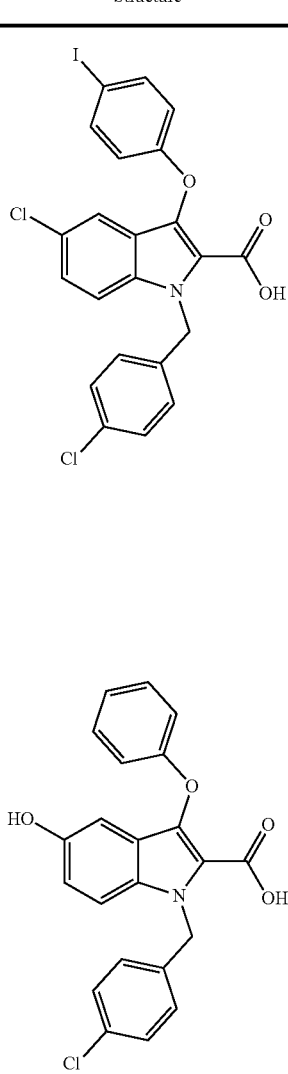 | 14 |
| | S27 |
| | S28 |
| Structure | Compound No. |
|---|---|
| 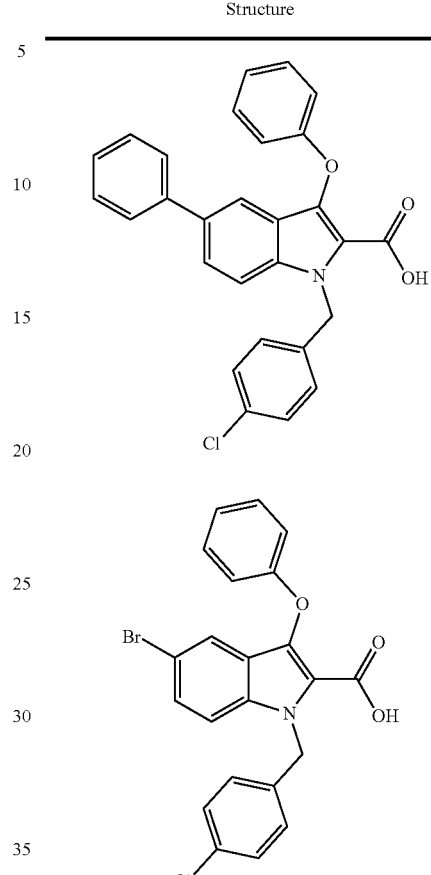 | S29 |
| | S30 |
or a pharmaceutically acceptable salt thereof.
39. A method of killing or inhibiting growth of bacteria, the method comprising contacting the bacteria with an effective amount of a compound selected from any one of the following compounds:
| Structure |
|---|
| 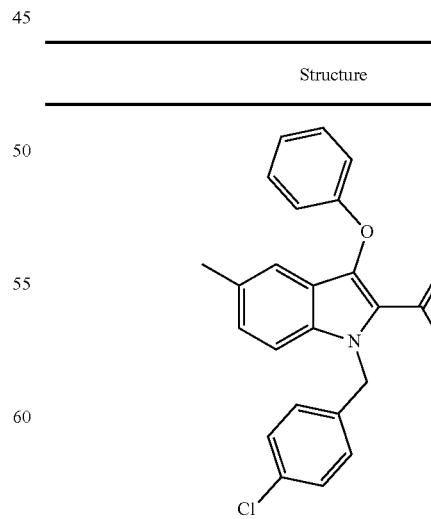 |

| 201 -continued | 202 -continued |
|---|---|
| Structure | Structure |
| 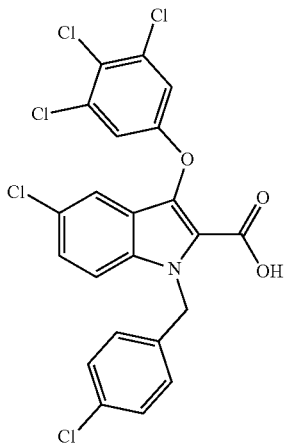 [SMILES: O=C(O)c1c(Oc2cc(Cl)c(Cl)c(Cl)c2)c2cc(Cl)ccc2n1Cc1ccc(Cl)cc1] | 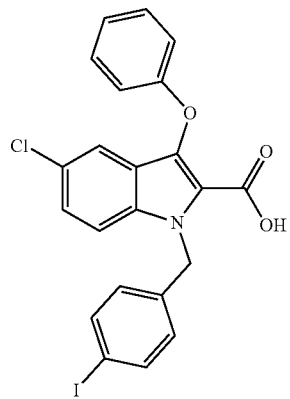 |
| 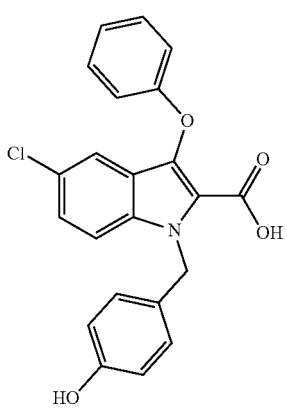 | 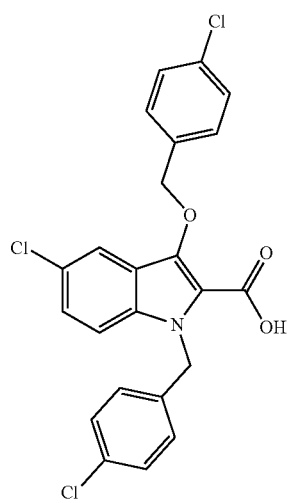 [SMILES: O=C(O)c1c(OCc2ccc(Cl)cc2)c2cc(Cl)ccc2n1Cc1ccc(Cl)cc1] |

-continued

Structure

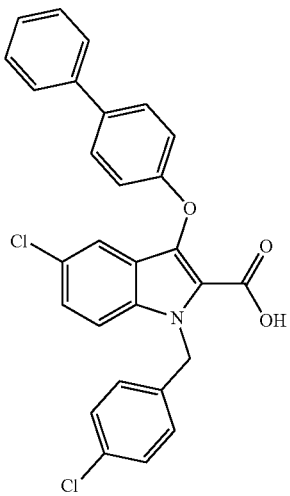 [SMILES: O=C(O)c1c(Oc2ccc(-c3ccccc3)cc2)c2cc(Cl)ccc2n1Cc1ccc(Cl)cc1]

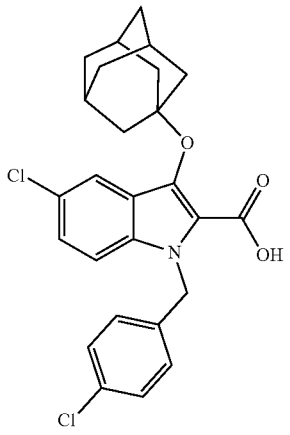 [SMILES: O=C(O)c1c(OC23CC4CC(CC(C4)C2)C3)c2cc(Cl)ccc2n1Cc1ccc(Cl)cc1]

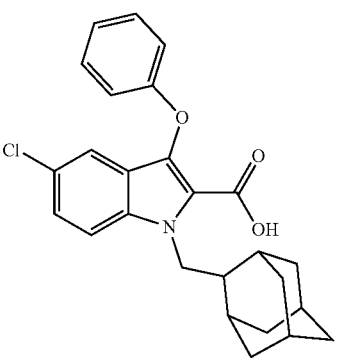 [SMILES: O=C(O)c1c(Oc2ccccc2)c2cc(Cl)ccc2n1CC1C2CC3CC(C2)CC1C3]

or a pharmaceutically acceptable salt thereof.

40. The method of claim 20, wherein the bacteria is a Gram-negative bacteria which is a member of a genus selected from: *Acinetobacter, Burkholderia, Acinetobacter, Burkholderia, Klebsiella, Pseudomonas,* and *Escherichia*.

41. The method of claim 20, wherein the bacteria is a Gram-positive bacteria which is a member of a genus selected from *Staphylococcus* (including *coagulase* negative and *coagulase* positive), *Streptococcus, Propionibacterium, Peptococcus, Enterococcus,* and *Bacillus*.

42. The method of claim 20, wherein the bacteria is resistant to one or more conventional antibiotic agents.

43. The method of claim 42, wherein the bacteria is selected from: methicillin-susceptible *S. aureus* (MSSA), methicillin-resistant *S. aureus* (MRSA), vancomycin-resistant *S. aureus* (VRSA), and coagulase negative staphylococci.

44. The pharmaceutical composition of claim 21, wherein ring B is selected from $C_{6-10}$ aryl and $C_{3-10}$ cycloalkyl.

45. The pharmaceutical composition of claim 21, wherein:

X is selected from S, O and $CH_2$;

$L^1$ is selected from bond and $C_{1-6}$ alkylene;

$L^2$ is selected from bond and $C_{1-6}$ alkylene;

each $R^3$ is independently selected from halo, $C_{1-6}$ alkyl, $C_{1-6}$ haloalkyl, $C_{6-10}$ aryl and $OR^{a1}$;

ring B is selected from $C_{6-10}$ aryl and $C_{3-10}$ cycloalkyl;

each $R^1$ is independently selected from halo and $OR^{a2}$; and each $R^2$ is independently selected from halo, $C_{1-6}$ alkyl, $C_{1-6}$ haloalkyl, $OR^{a2}$; and $C(O)OR^{a2}$.

46. The pharmaceutical composition of claim 21, wherein:

X is selected from S, O and $CH_2$;

$L^1$ is selected from bond and $C_{1-6}$ alkylene;

$L^2$ is selected from bond and $C_{1-6}$ alkylene;

each $R^3$ is independently selected from halo, $C_{1-6}$ alkyl, $C_{1-6}$ haloalkyl, $C_{6-10}$ aryl and $OR^{a1}$;

n is 1 or 2; and at least one $R^3$ is selected from halo and $C_{1-6}$ haloalkyl;

ring B is selected from phenyl and adamantyl;

each $R^1$ is independently selected from halo, OH, and $C_{1-6}$ alkoxy; and each $R^2$ is independently selected from halo, $C_{1-6}$ alkyl, $C_{1-6}$ haloalkyl, $C_{1-6}$ alkoxy, and C(O)OH.

47. A pharmaceutical composition comprising a compound selected from any one of the following compounds:

| Structure | Compound No. |
|---|---|
| 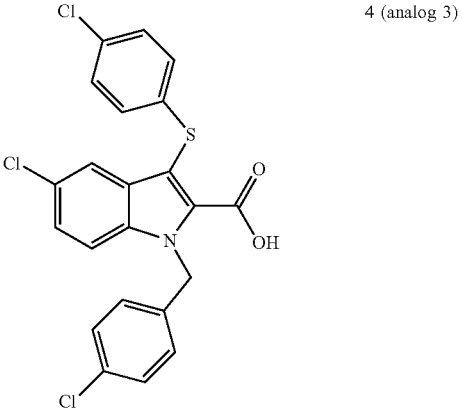 | 4 (analog 3) |

| Structure | Compound No. |
|---|---|
| 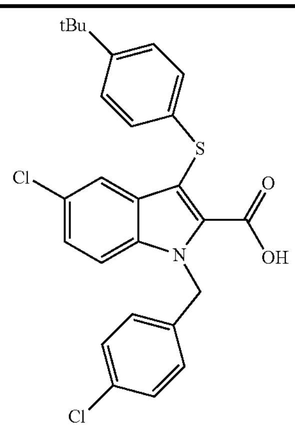 | 5 |
| 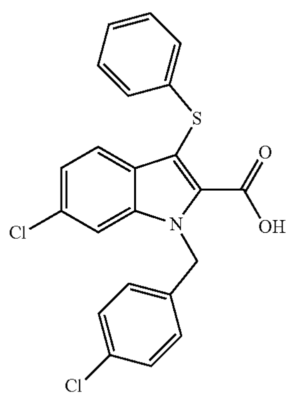 [SMILES: O=C(O)c1c(Sc2ccccc2)c2ccc(Cl)cc2n1Cc1ccc(Cl)cc1] | S9 (analog 2a) |
| 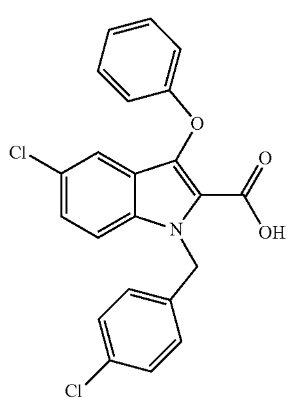 [SMILES: O=C(O)c1c(Oc2ccccc2)c2cc(Cl)ccc2n1Cc1ccc(Cl)cc1] | 6 |
| 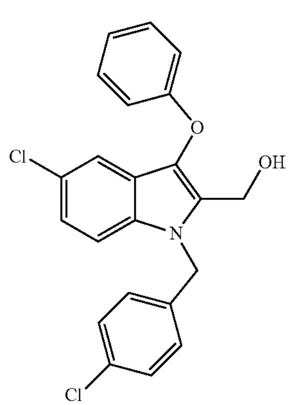 [SMILES: OCc1c(Oc2ccccc2)c2cc(Cl)ccc2n1Cc1ccc(Cl)cc1] | S13 |

| Structure | Compound No. |
|---|---|
| | S15 |
| | S16 |
| | S17 |

| Structure | Compound No. |
|---|---|
| 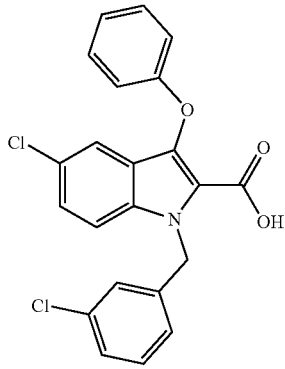 [SMILES: O=C(O)c1c(Oc2ccccc2)c2cc(Cl)ccc2n1Cc1cccc(Cl)c1] | S18 |
| 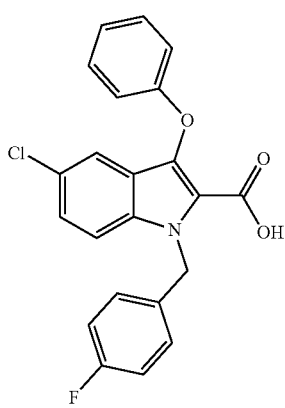 | S19 |
| 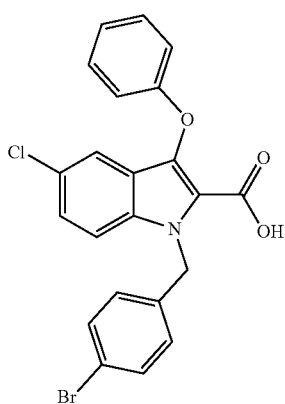 | S20 |
| 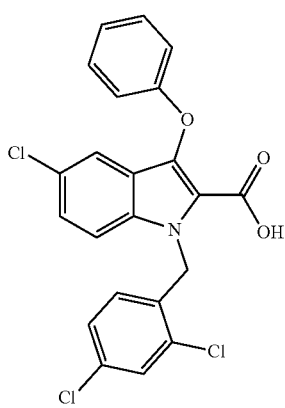 [SMILES: O=C(O)c1c(Oc2ccccc2)c2cc(Cl)ccc2n1Cc1ccc(Cl)cc1Cl] | S21 |
| Structure | Compound No. |
|---|---|
| 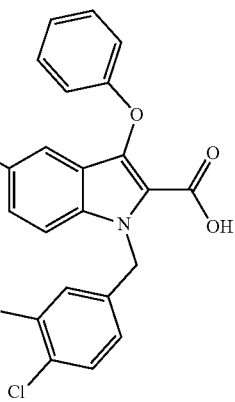 | 10 |
| 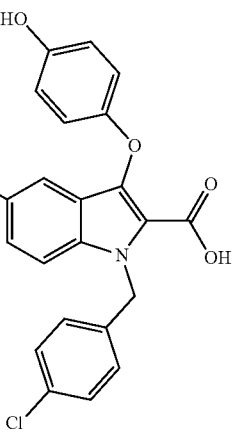 | S22 |
| 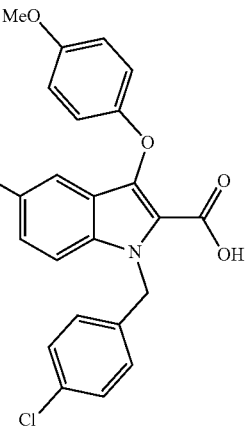 | S23 |

| Structure | Compound No. |
|---|---|
| (structure) | S24 |
| (structure) | S25 |
| (structure) | S26 |

| Structure | Compound No. |
|---|---|
| (structure) | 11 |
| (structure) | 12 |
| (structure) | 13 |

| Structure | Compound No. |
|---|---|
| 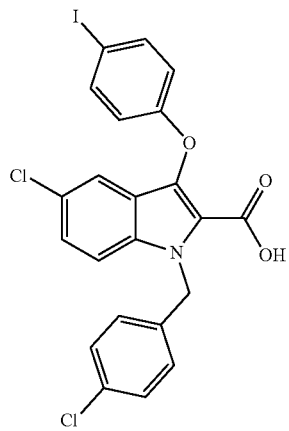 [SMILES: O=C(O)c1c(Oc2ccc(I)cc2)c2cc(Cl)ccc2n1Cc1ccc(Cl)cc1] | 14 |
| 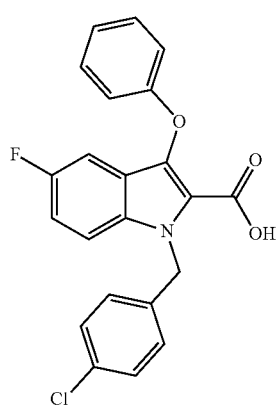 [SMILES: O=C(O)c1c(Oc2ccccc2)c2cc(F)ccc2n1Cc1ccc(Cl)cc1] | S27 |
|  | S28 |
| Structure | Compound No. |
|---|---|
| 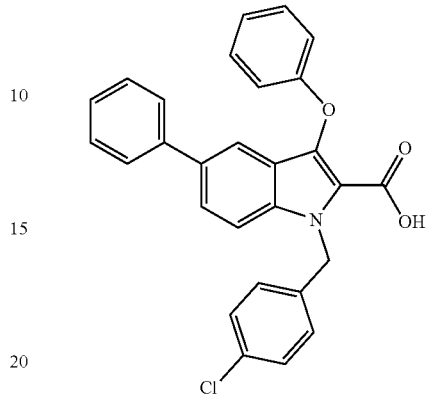 | S29 |
| 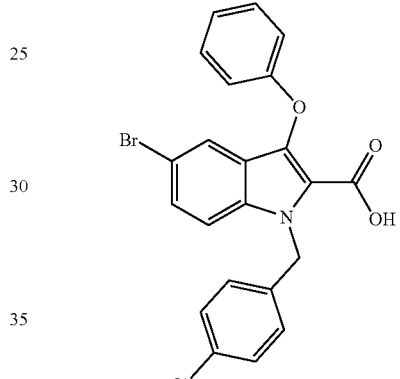 | S30 |
or a pharmaceutically acceptable salt thereof,
(ii) at least one additional antibiotic, or a pharmaceutically acceptable salt thereof; and
(iii) a pharmaceutically acceptable carrier.
48. A pharmaceutical composition comprising a compound selected from any one of the following compounds:
| Structure |
|---|
| 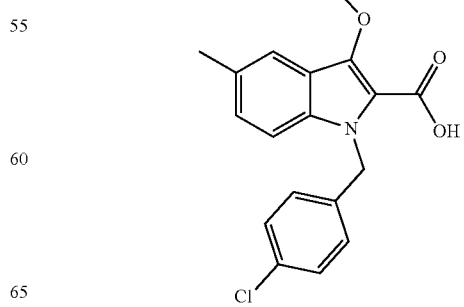 |

| 213 -continued | 214 -continued |
|---|---|
| Structure | Structure |
| 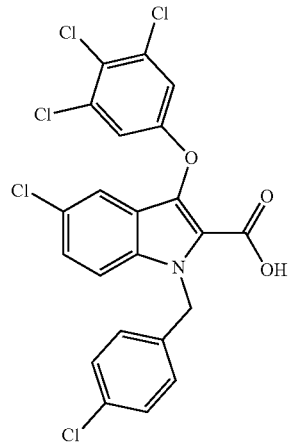 [SMILES: O=C(O)c1c(Oc2cc(Cl)c(Cl)c(Cl)c2)c2cc(Cl)ccc2n1Cc1ccc(Cl)cc1] | 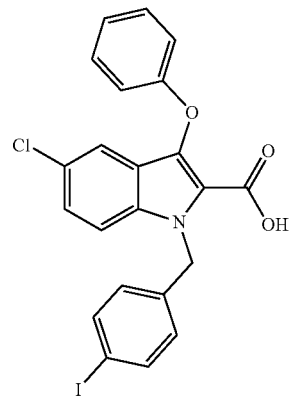 |
| 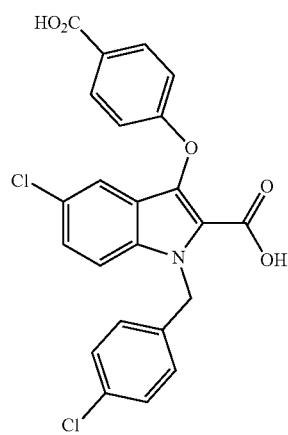 [SMILES: O=C(O)c1ccc(Oc2c(C(=O)O)n(Cc3ccc(Cl)cc3)c3ccc(Cl)cc23)cc1] | 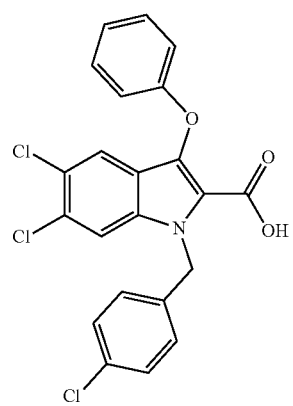 |
| 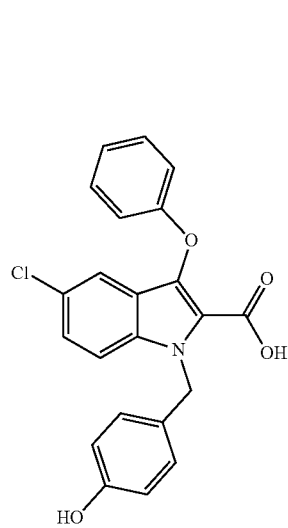 [SMILES: O=C(O)c1c(Oc2ccccc2)c2cc(Cl)ccc2n1Cc1ccc(O)cc1] | 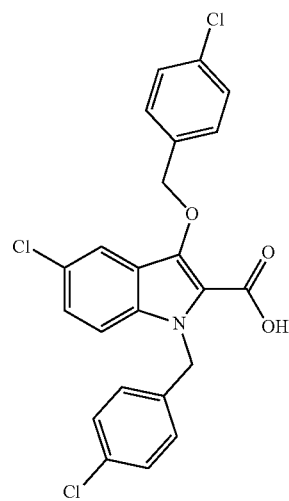 [SMILES: O=C(O)c1c(OCc2ccc(Cl)cc2)c2cc(Cl)ccc2n1Cc1ccc(Cl)cc1] |

| Structure | | Structure |
|---|---|---|
| 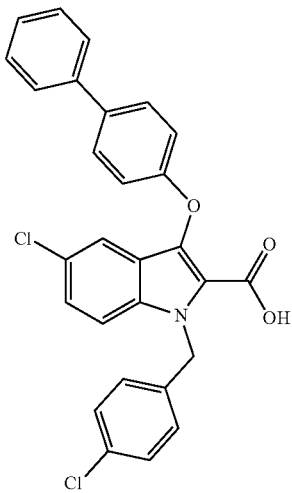 [SMILES: O=C(O)c1c(Oc2ccc(-c3ccccc3)cc2)c2cc(Cl)ccc2n1Cc1ccc(Cl)cc1]<br><br>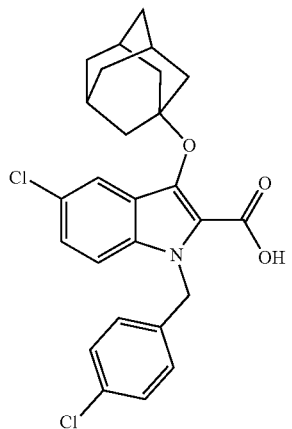 [SMILES: O=C(O)c1c(OC23CC4CC(CC(C4)C2)C3)c2cc(Cl)ccc2n1Cc1ccc(Cl)cc1] | 5<br><br>10<br><br>15 | 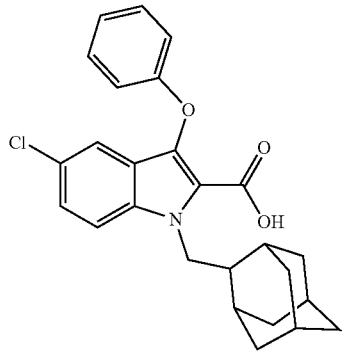 [SMILES: O=C(O)c1c(Oc2ccccc2)c2cc(Cl)ccc2n1CC1C2CC3CC(C2)CC1C3] | or a pharmaceutically acceptable salt thereof, (ii) at least one additional antibiotic, or a pharmaceutically acceptable salt thereof; and (iii) a pharmaceutically acceptable carrier.

49. The pharmaceutical composition of claim 21, wherein the antibiotic is selected from: a quinolone, a β-lactam, a cephalosporin, a penicillin, a carbapenem, a lipopetide, aminoglycoside, a glycopeptide, a macrolide, an ansamycin, a sulfonamide, a monobactam, oxazolidinone, lipopeptide, macrolide, and a cationic antimicrobial peptide (CAMP).

50. The pharmaceutical composition of claim 49, wherein the antibiotic is the aminogylcoside selected from: gentamicin, tobramycin, neomycin, kanamycin, and streptomycin, or a pharmaceutically acceptable salt thereof.

51. The pharmaceutical composition of claim 50, wherein the antibiotic is gentamicin, or a pharmaceutically acceptable salt thereof.

\* \* \* \* \*

UNITED STATES PATENT AND TRADEMARK OFFICE
CERTIFICATE OF CORRECTION

PATENT NO.       : 11,690,824 B2
APPLICATION NO.  : 17/046463
DATED            : July 4, 2023
INVENTOR(S)      : Frederick M. Ausubel et al.

It is certified that error appears in the above-identified patent and that said Letters Patent is hereby corrected as shown below:

In the Claims

In Column 155, Lines 4-9 (approx.), Claim 1, delete " 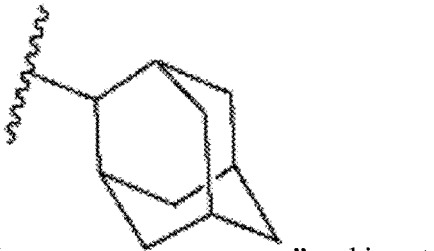 " and insert 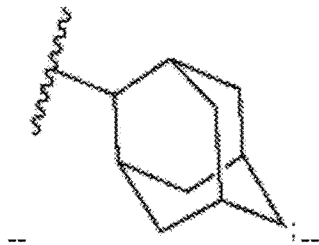 --

In Column 155, Line 45, Claim 1, before "$R^{a1}$," insert -- each --

In Column 155, Line 65, Claim 1, delete "$C(O)OR^{b7}$," and insert -- $C(O)R^{b7}$, --

In Column 156, Line 8, Claim 1, delete "in dependently" and insert -- independently --

In Column 156, Line 21, Claim 1, before "is" insert -- alkylene --

In Column 156, Line 61, Claim 3, delete "$OR^{a2}$," and insert -- $OR^{a2}$; --

In Column 168, Line 40, Claim 7, delete "Barkholderia, Kilebsiella," and insert -- Burkholderia, Klebsiella, --

Signed and Sealed this
Twenty-sixth Day of December, 2023

Katherine Kelly Vidal
*Director of the United States Patent and Trademark Office*

CERTIFICATE OF CORRECTION (continued)

In Column 168, Line 56, Claim 9, delete "ciprofloxacim." and insert -- ciprofloxacin. --

In Column 169, Line 6, Claim 15, before "β-lactam," insert -- a --

In Column 169, Line 7, Claim 15, delete "lipopetide," and insert -- lipopeptide, --

In Column 169, Line 12, Claim 16, delete "aminogylcoside" and insert -- aminoglycoside --

In Column 169, Line 15 (approx.), Claim 17, delete "antibiotic," and insert -- antibiotic --

In Column 169, Line 49, Claim 20, delete "$R^3$" and insert -- $R^5$ --

In Column 170, Line 3, Claim 20, delete "$_{2-6}$ alkenyl," and insert -- $C_{2-6}$ alkenyl, --

In Column 170, Line 15-21 (approx.), Claim 20, delete " 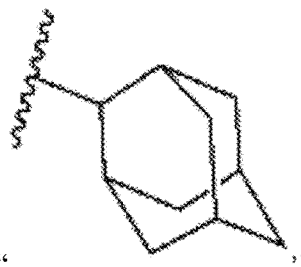 " and insert -- 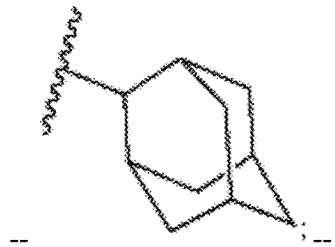 --

In Column 170, Line 52, Claim 20, delete "$R^{c2}R^{d2}$," and insert -- $NR^{c2}R^{d2}$, --

In Column 170, Line 56, Claim 20, before "$R^{a1}$," insert -- each --

In Column 171, Line 10, Claim 20, delete "$C(O)OR^{b7}$," and insert -- $C(O)R^{b7}$ --

In Column 171, Line 20 (approx.), Claim 20, delete "in dependently" and insert -- independently --

In Column 171, Line 36 (approx.), Claim 20, before "is" insert -- alkylene --

In Column 172, Line 22, Claim 21, delete "$R^3$" and insert -- $R^5$ --

In Column 172, Line 43, Claim 21, delete "$_{2-6}$ alkenyl," and insert -- $C_{2-6}$ alkenyl, --

In Column 172, Lines 55-60 (approx.), Claim 21, delete " 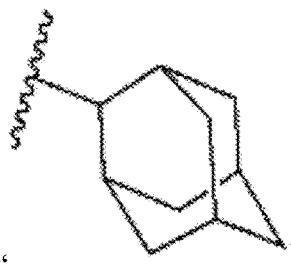 " and insert
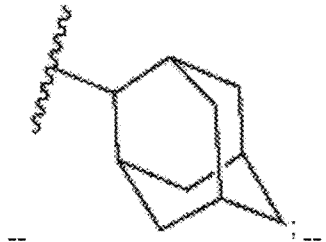 --

In Column 173, Line 28, Claim 21, before "$R^{a1}$," insert -- each --

In Column 173, Line 48, Claim 21, delete "$C(O)OR^{b7}$," and insert -- $C(O)R^{b7}$, --

In Column 173, Line 58, Claim 21, delete "in dependently" and insert -- independently --

In Column 174, Line 56, Claim 22, delete "$R^3$" and insert -- $R^5$ --

In Column 175, Line 10 (approx.), Claim 22, delete "$_{2-6}$ alkenyl," and insert -- $C_{2-6}$ alkenyl, --

In Column 175, Lines 23-29 (approx.), Claim 22, delete " 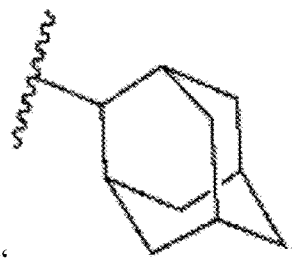 " and insert
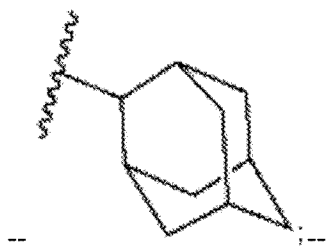 --

In Column 176, Line 19, Claim 22, delete "$C(O)OR^{b7}$," and insert -- $C(O)R^{b7}$ --

In Column 176, Line 29, Claim 22, delete "in dependently" and insert -- independently --

In Column 177, Line 51, Claim 25, delete "$R^3$" and insert -- $R^5$ --

CERTIFICATE OF CORRECTION (continued)

U.S. Pat. No. 11,690,824 B2

In Column 178, Line 5, Claim 25, delete "$_{2-6}$ alkenyl," and insert -- $C_{2-6}$ alkenyl, --

In Column 178, Line 49, Claim 25, delete "C(O)OR$^{b7}$," and insert -- C(O)R$^{b7}$, --

In Column 178, Line 59, Claim 25, delete "in dependently" and insert -- independently --

In Column 191, Line 48, Claim 32, before "β-lactam," insert -- a --

In Column 191, Line 49, Claim 32, delete "lipopetide," and insert -- lipopeptide, --

In Column 191, Line 54, Claim 33, delete "aminogylcoside" and insert -- aminoglycoside --

In Column 192, Line 12, Claim 37, delete "fro as" and insert -- from --

In Column 192, Line 19, Claim 37, after "each" insert -- R$^1$ --

In Column 203, Lines 58-59 (approx.), Claim 40, delete "Acinetobacter, Burkholderia, Acinetobacter, Burkholderia," and insert -- Acinetobacter, Burkholderia, --

In Column 203, Line 66, Claim 42, after "of" insert -- claim --

In Column 204, Line 12, Claim 45, delete "C$_{106}$" and insert -- C$_{1-6}$ --

In Column 216, Line 28, Claim 49, delete "lipopetide," and insert -- lipopeptide, --

In Column 216, Line 29, Claim 49, before "aminoglycoside," insert -- an --

In Column 216, Line 33, Claim 50, delete "aminogylcoside" and insert -- aminoglycoside --